US012690387B2

(12) United States Patent
Kim et al.

(10) Patent No.: US 12,690,387 B2
(45) Date of Patent: Jul. 21, 2026

(54) ANTHRACENE COMPOUND AND ORGANIC LIGHT-EMITTING DEVICE COMPRISING SAME

(71) Applicant: SFC CO., LTD., Cheongju-si (KR)

(72) Inventors: Hee-dae Kim, Cheongju-si (KR); Seok-bae Park, Cheongju-si (KR); Dong Myung Park, Cheongju-si (KR); Seongeun Woo, Cheongju-si (KR); Soo Kyung Kang, Cheongju-si (KR)

(73) Assignee: SFC CO., LTD., Cheongju-si (KR)

( * ) Notice: Subject to any disclaimer, the term of this patent is extended or adjusted under 35 U.S.C. 154(b) by 967 days.

(21) Appl. No.: 17/915,457

(22) PCT Filed: Apr. 8, 2021

(86) PCT No.: PCT/KR2021/004452
§ 371 (c)(1),
(2) Date: Sep. 28, 2022

(87) PCT Pub. No.: WO2021/206488
PCT Pub. Date: Oct. 14, 2021

(65) Prior Publication Data

US 2023/0143961 A1 May 11, 2023

(30) Foreign Application Priority Data

Apr. 9, 2020 (KR) ........................ 10-2020-0043559

(51) Int. Cl.
*H10K 85/60* (2023.01)
*C07D 307/79* (2006.01)
(Continued)

(52) U.S. Cl.
CPC ....... *H10K 85/6574* (2023.02); *C07D 307/79* (2013.01); *C07D 307/91* (2013.01); *H10K 2101/20* (2023.02)

(58) Field of Classification Search
CPC ............. H10K 85/615; H10K 85/6574; H10K 85/6576; C07D 333/54; C07D 307/79
See application file for complete search history.

(56) References Cited

U.S. PATENT DOCUMENTS

2011/0121269 A1* 5/2011 Lecloux .................. C07C 15/28
564/426
2021/0013418 A1* 1/2021 Kim ..................... H10K 85/626
2022/0162222 A1* 5/2022 Vo ........................ C07D 307/77

FOREIGN PATENT DOCUMENTS

CN 108178750 A 6/2018
JP H0812600 A 1/1996
(Continued)

OTHER PUBLICATIONS

The extended European search report of EP 21 78 5438, May 31, 2024.
(Continued)

*Primary Examiner* — Vu A Nguyen
(74) *Attorney, Agent, or Firm* — STIP Law Group, LLC

(57) ABSTRACT

Provided are an anthracene compound represented by Chemical Formula A and an organic light-emitting diode comprising the same. The anthracene compound includes at least one deuterium atom and is useful as a host material in a light-emitting laver, thereby enabling an organic light-emitting diode exhibiting improved device characteristics including low driving voltage and high luminous efficiency.
(Continued)

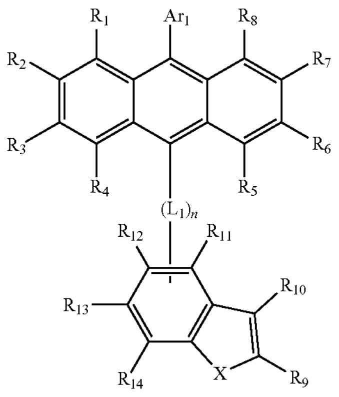

15 Claims, 1 Drawing Sheet

(51) Int. Cl.
*C07D 307/91* (2006.01)
*H10K 101/20* (2023.01)

(56) References Cited

FOREIGN PATENT DOCUMENTS

| | | | | | |
|---|---|---|---|---|---|
| JP | 5608978 | | | 10/2014 | |
| KR | 20070034430 | A | | 3/2007 | |
| KR | 20120135501 | A | * | 12/2012 | ........... H10K 85/615 |
| KR | 20140076170 | A | * | 6/2014 | ........... H10K 85/633 |
| KR | 20160018332 | A | | 2/2016 | |
| KR | 20190056338 | A | * | 5/2019 | ............. C07C 15/14 |
| WO | WO2021021840 | A1 | | 2/2021 | |

OTHER PUBLICATIONS

International search report of PCT/KR2021/004452, Jul. 29, 2021, English translation.

* cited by examiner

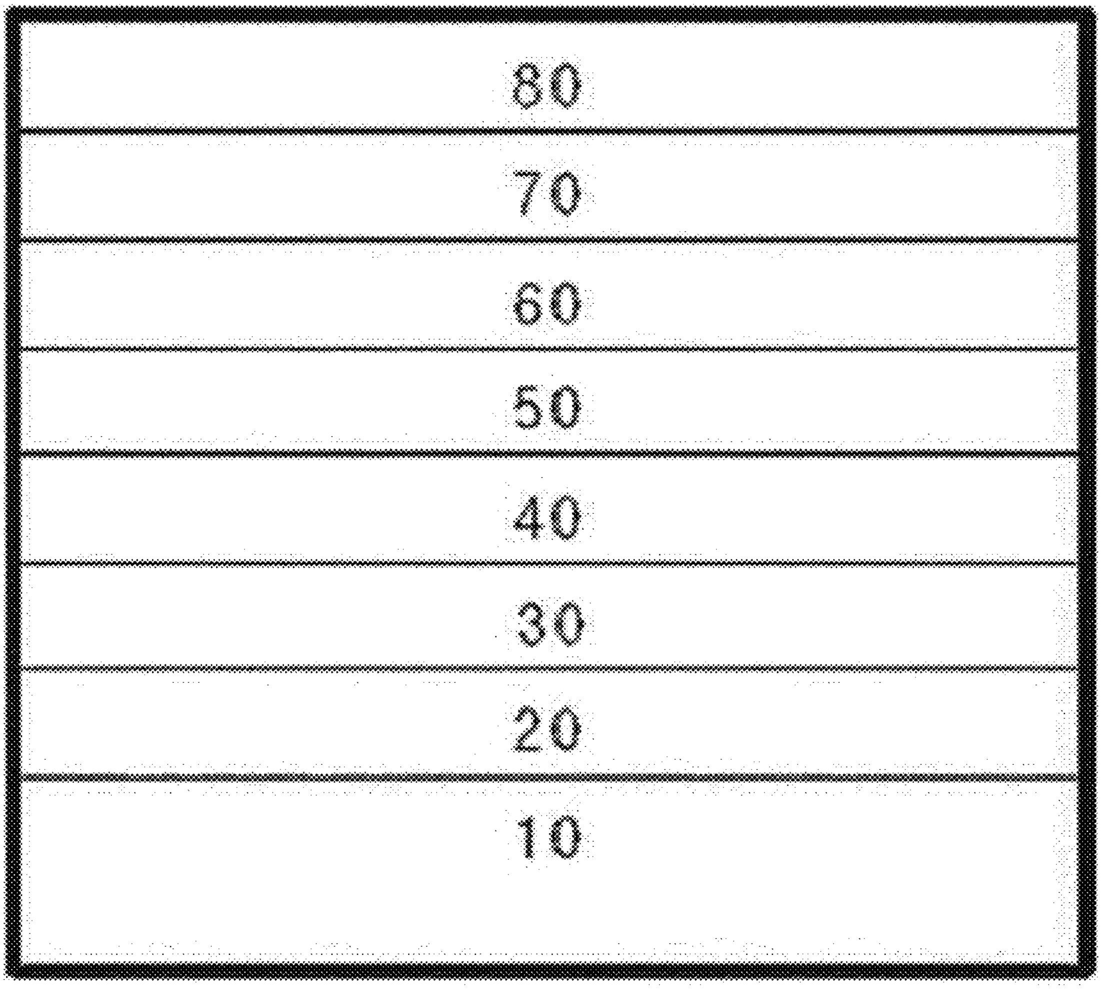
80
70
60
50
40
30
20
10

ANTHRACENE COMPOUND AND ORGANIC LIGHT-EMITTING DEVICE COMPRISING SAME

CROSS-REFERENCE TO RELATED APPLICATIONS

This application is the U.S. National Phase under 35 U.S.C. § 371 of International Application No. PCT/KR2021/004452 filed on Apr. 8, 2021, which in turn claims the benefit of Korean Application No. 10-2020-0043559 filed on Apr. 9, 2020, the disclosures of which are incorporated by reference into the present application.

TECHNICAL FIELD

The present disclosure relates to a novel anthracene compound useful for an organic light-emitting diode and, more particularly, to a novel anthracene compound that can be used as a host material in an organic light-emitting diode and allow for excellent diode characteristics including high luminous efficiency and low driving voltage, and an organic light-emitting diode including the anthracene compound.

BACKGROUND ART

Organic light-emitting diodes, based on self-luminescence, exhibit the advantages of having a wide viewing angle, excellent contrast, fast response time, high brightness, and excellent driving voltage and response rate characteristics and of allowing for a polychromic display.

A typical organic light-emitting diode includes a positive electrode (anode) and a negative electrode (cathode), facing each other, with an organic emissive layer disposed therebetween.

As to the general structure of the organic light-emitting diode, a hole transport layer, a light-emitting layer, an electron transport layer, and a cathode are formed in that order on an anode. Here, all of the hole transport layer, the light-emitting layer, and the electron transport layer are organic films comprising organic compounds.

An organic light-emitting diode having such a structure operates as follows: when a voltage is applied between the anode and the cathode, the anode injects holes which are then transferred to the light-emitting layer via the hole transport layer while electrons injected from the cathode move to the light-emitting layer via the electron transport layer. In the luminescent zone, the carriers such as holes and electrons recombine to produce an exciton. When the exciton returns to the ground state from the excited state, the molecule of the light-emitting layer emits light.

Materials used as organic layers in OLEDs may be divided according to functions into luminescent materials and charge transport materials, for example, a hole injection material, a hole transport material, an electron transport material, and an electron injection material and, as needed, further into an electron-blocking material or a hole-blocking material.

As for the luminescent materials, there are two main families of OLED: those based on small molecules and those employing polymers. The light-emitting mechanism forms the basis of classification of luminescent materials as fluorescent and phosphorescent materials, which use excitons in singlet and triplet states, respectively.

When a single material is employed as the luminescent material, intermolecular actions cause the maximum luminescence wavelength to shift toward a longer wavelength, resulting in a reduction in color purity and luminous efficiency due to light attenuation. In this regard, a host-dopant system may be used as a luminescent material so as to increase the color purity and the luminous efficiency through energy transfer.

This is based on the principle whereby, when a dopant which is smaller in energy band gap than a host forming a light-emitting layer is added in a small amount to the light-emitting layer, excitons are generated from the light-emitting layer and transported to the dopant, emitting light at high efficiency. Here, light with desired wavelengths can be obtained depending on the kind of the dopant because the wavelength of the host moves to the wavelength range of the dopant.

With regard to related art pertaining to the use of host compounds, reference may be made to Japanese Patent No. 1996-012600 A (Jan. 15, 1996), which discloses an organic light-emitting diode employing a phenyl anthracene derivative as a luminous material and to Japanese Patent No. 5608978 (Oct. 22, 2014), which describes an organic light-emitting diode comprising a luminescent medium layer containing an anthracene derivative in which an anthracene moiety has a dibenzofuran moiety as a substituent at a terminal position thereof.

Despite preparation of various kinds of compounds including the related art, there is still a continued need to develop organic layer materials that are capable of driving OLEDs at a lower voltage than ever and guarantee that OLEDs retain high efficiency characteristics.

DISCLOSURE

Technical Problem

Therefore, an aspect of the present disclosure is to provide an anthracene compound having a novel structure which can be used as a host material in a light-emitting layer of an organic light-emitting diode.

In addition, another aspect of the present disclosure is to provide an organic light-emitting diode (OLED) having the anthracene compound applied as a host material therein and exhibiting excellent diode characteristics including high luminous efficiency and low-voltage driving.

Technical Solution

In order to accomplish the purposes, the present disclosure provides an anthracene compound represented by the following Chemical Formula A:

[Chemical Formula A]

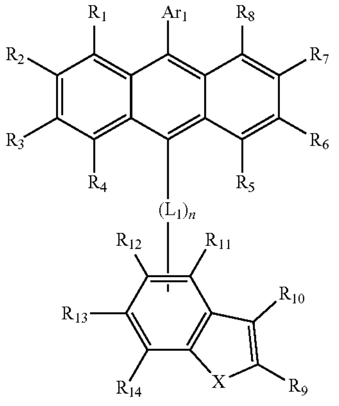

wherein, $Ar_1$ is a substituted or unsubstituted aryl of 6 to 50 carbon atoms or a substituted or unsubstituted heteroaryl of 2 to 50 carbon atoms, $R_1$ to $R_8$ and $R_{11}$ to $R_{14}$, which are same or different, are each independently selected from a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkyl thioxy of 1 to 30 carbon atoms, a substituted or unsubstituted aryl thioxy of 6 to 30 carbon atoms, a substituted or unsubstituted alkyl amine of 1 to 30 carbon atoms, a substituted or unsubstituted aryl amine of 6 to 30 carbon atoms, a substituted or unsubstituted alkylsilyl of 1 to 30 carbon atoms, a substituted or unsubstituted arylsilyl of 6 to 30 carbon atoms, a cyano, a nitro, and a halogen, one of $R_{11}$ to $R_{14}$ being a single bond to $L_1$, $R_9$ is any one selected from a hydrogen atom, a deuterium atom, a substituted or unsubstituted alkyl of 1 to 30 carbon atoms, a substituted or unsubstituted cycloalkyl of 3 to 20 carbon atoms, a substituted or unsubstituted aryl of 6 to 50 carbon atoms, and a substituted or unsubstituted heteroaryl of 2 to 50 carbon atoms, $R_{10}$ is a hydrogen atom or a deuterium atom, X is an oxygen atom (O) or a sulfur atom (S), $L_1$, which functions as a linker, is a single bond or any one selected from a substituted or unsubstituted arylene of 6 to 20 carbon atoms, or a substituted or unsubstituted heteroarylene of 2 to 20 carbon atoms, and n is an integer of 1 to 3 wherein when n is 2 or more, the corresponding $L_1$'s are same or different, wherein the term "substituted" in the expression "substituted or unsubstituted" used for compounds of Chemical Formula A means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, cycloalkyl of 3 to 30 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, an alkylaryl of 7 to 24 carbon atoms, a heteroalkyl of 2 to 24 carbon atoms, a heteroarylalkyl of 2 to 24 carbon atoms, an alkoxy of 1 to 24 carbon atoms, an alkylamino of 1 to 24 carbon atoms, a diarylamino of 12 to 24 carbon atoms, a diheteroarylamino of 2 to 24 carbon atoms, an aryl(heteroaryl)amino of 7 to 24 carbon atoms, an alkylsilyl of 1 to 24 carbon atoms, an arylsilyl of 6 to 24 carbon atoms, an aryloxy of 6 to 24 carbon atoms, and an arylthionyl of 6 to 24 carbon atoms.

Advantageous Effects

When used as a host material, the novel anthracene compound according to the present disclosure allows for the provision of an organic light-emitting diode that can be driven at a lower voltage with improved luminous efficiency, compared to conventional organic light-emitting diodes.

BRIEF DESCRIPTION OF THE DRAWING

FIGURE is a schematic diagram of an organic light-emitting diode according to some embodiments of the present disclosure.

BEST MODE FOR CARRYING OUT THE INVENTION

Below, a detailed description will be given of the present disclosure. In each drawing of the present disclosure, sizes or scales of components may be enlarged or reduced from their actual sizes or scales for better illustration, and known components may not be depicted therein to clearly show features of the present disclosure. Therefore, the present disclosure is not limited to the drawings.

In drawings, for convenience of description, sizes of components may be exaggerated for clarity. For example, since sizes and thicknesses of components in drawings are arbitrarily shown for convenience of description, the sizes and thicknesses are not limited thereto. Furthermore, throughout the description, the terms "on" and "over" are used to refer to the relative positioning, and mean not only that one component or layer is directly disposed on another component or layer but also that one component or layer is indirectly disposed on another component or layer with a further component or layer being interposed therebetween. Also, spatially relative terms, such as "below", "beneath", "lower", and "between" may be used herein for ease of description to refer to the relative positioning.

Throughout the specification, when a portion may "include" a certain constituent element, unless explicitly described to the contrary, it may not be construed to exclude another constituent element but may be construed to further include other constituent elements. Further, throughout the specification, the word "on" means positioning on or below the object portion, but does not essentially mean positioning on the lower side of the object portion based on a gravity direction.

The present disclosure provides an anthracene compound represented by the following Chemical Formula A:

[Chemial Formula A]

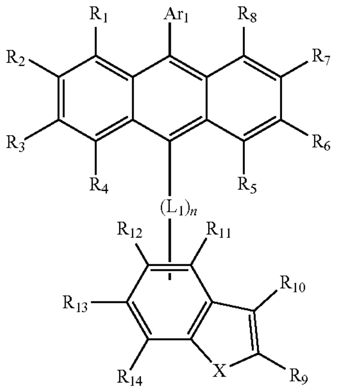

wherein, $Ar_1$ is a substituted or unsubstituted aryl of 6 to 50 carbon atoms or a substituted or unsubstituted heteroaryl of 2 to 50 carbon atoms, $R_1$ to $R_8$ and $R_{11}$ to $R_{14}$, which are same or different, are each independently selected from a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkyl thioxy of 1 to 30 carbon atoms, a substituted or unsubstituted aryl thioxy of 6 to 30 carbon atoms, a substituted or unsubstituted alkyl amine of 1 to 30 carbon atoms, a substituted or unsubstituted aryl amine of 6 to 30 carbon atoms, a substituted or unsubstituted alkylsilyl of 1 to 30 carbon atoms, a substituted or unsubstituted arylsilyl of 6 to 30 carbon atoms, a cyano, a nitro, and a halogen, one of $R_{11}$ to $R_{14}$ being a single bond to $L_1$, $R_9$ is any one selected from a hydrogen atom, a deuterium atom, a substituted or unsubstituted alkyl of 1 to 30 carbon atoms, a substituted or unsubstituted cycloalkyl of 3 to 30 carbon atoms, a substituted or unsubstituted aryl of 6 to 50 carbon atoms, and a substituted or unsubstituted heteroaryl of 2 to 50 carbon atoms, $R_{10}$ is a hydrogen atom or a deuterium atom, X is an oxygen atom (O) or a sulfur atom (S), $L_1$, which functions as a linker, is a single bond or any one selected from a substituted or unsubstituted arylene of 6 to 20 carbon atoms, or a substituted or unsubstituted heteroarylene of 2 to 20 carbon atoms, n is an integer of 1 to 3 wherein when n is 2 or more, the corresponding $L_1$'s are same or different, wherein, the term "substituted" in the expression "substituted or unsubstituted" used for compounds of Chemical Formula A means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, cycloalkyl of 3 to 30 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, an alkylaryl of 7 to 24 carbon atoms, a heteroalkyl of 2 to 24 carbon atoms, a heteroarylalkyl of 2 to 24 carbon atoms, an alkoxy of 1 to 24 carbon atoms, an alkylamino of 1 to 24 carbon atoms, a diarylamino of 12 to 24 carbon atoms, a diheteroarylamino of 2 to 24 carbon atoms, an aryl(heteroaryl)amino of 7 to 24 carbon atoms, an alkylsilyl of 1 to 24 carbon atoms, an arylsilyl of 6 to 24 carbon atoms, an aryloxy of 6 to 24 carbon atoms, and an arylthionyl of 6 to 24 carbon atoms.

The expression indicating the number of carbon atoms, such as "a substituted or unsubstituted alkyl of 1 to 30 carbon atoms", "a substituted or unsubstituted aryl of 5 to 50 carbon atoms", etc. means the total number of carbon atoms of, for example, the alkyl or aryl radical or moiety alone, exclusive of the number of carbon atoms of substituents attached thereto. For instance, a phenyl group with a butyl at the para position falls within the scope of an aryl of 6 carbon atoms, even though it is substituted with a butyl radical of 4 carbon atoms.

As used herein, the term "aryl" means an organic radical derived from an aromatic hydrocarbon by removing one hydrogen that is bonded to the aromatic hydrocarbon. The aromatic system may include a fused ring that is formed by adjacent substituents on the aryl radical.

Concrete examples of the aryl include phenyl, o-biphenyl, m-biphenyl, p-biphenyl, o-terphenyl, m-terphenyl, p-terphenyl, naphthyl, anthryl, phenanthryl, pyrenyl, indenyl, fluorenyl, tetrahydronaphthyl, perylenyl, chrysenyl, naphthacenyl, and fluoranthenyl. At least one hydrogen atom of the aryl may be substituted by a deuterium atom, a halogen atom, a hydroxy, a nitro, a cyano, a silyl, an amino ($-NH_2$, $-NH(R)$, $-N(R')(R'')$ wherein R' and R" are each independently an alkyl of 1 to 10 carbon atoms, in this case, called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 1 to 24 carbon atoms, an alkynyl of 1 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms, or a heteroarylalkyl of 2 to 24 carbon atoms.

The term "heteroaryl substituent" used in the compound of the present disclosure refers to a hetero aromatic radical of 2 to 24 carbon atoms, bearing 1 to 3 heteroatoms selected from among N, O, P, Si, S, Ge, Se, and Te. In the aromatic radical, two or more rings may be fused. One or more hydrogen atoms on the heteroaryl may be substituted by the same substituents as on the aryl.

In addition, the term "heteroaromatic ring", as used herein, refers to an aromatic hydrocarbon ring bearing at least one heteroatom as aromatic ring member. In the heteroaromatic ring, one to three carbon atoms of the aromatic hydrocarbon may be substituted by at least one selected particularly from N, O, P, Si, S, Ge, Se, and Te.

As used herein, the term "alkyl" refers to an alkane missing one hydrogen atom and includes linear or branched structures. Examples of the alkyl substituent useful in the present disclosure include methyl, ethyl, propyl, isopropyl, isobutyl, sec-butyl, tert-butyl, pentyl, isoamyl, and hexyl. At least one hydrogen atom of the alkyl may be substituted by the same substituent as in the aryl.

The term "cyclo" as used in substituents of the present disclosure, such as cycloalkyl, cycloalkoxy, etc., refers to a structure responsible for a mono- or polycyclic ring of saturated hydrocarbons. Concrete examples of cycloalkyl radicals include cyclopropyl, cyclobutyl, cyclopentyl, cyclohexyl, methylcyclopentyl, methylcyclohexyl, ethylcyclopentyl, ethylcyclohexyl, adamantyl, dicyclopentadienyl, decahydronaphthyl, norbornyl, bornyl, and isobornyl. One or more hydrogen atoms on the cycloalkyl may be substituted by the same The term "alkoxy" as used in the compounds of the present disclosure refers to an alkyl or cycloalkyl singularly bonded to oxygen. Concrete examples of the alkoxy include methoxy, ethoxy, propoxy, isobutoxy, sec-butoxy, pentoxy, iso-amyloxy, hexyloxy, cyclobutyloxy, cyclopentyloxy, adamantyloxy, dicyclopentyloxy, bornyloxy, and isobornyloxy. One or more hydrogen atoms on the alkoxy may be substituted by the same substituents as on the aryl.

Concrete examples of the arylalkyl used in the compounds of the present disclosure include phenylmethyl(benzyl), phenylethyl, phenylpropyl, naphthylmethyl, and naphthylethyl. One or more hydrogen atoms on the arylalkyl may be substituted by the same substituents as on the aryl.

Concrete examples of the silyl radicals used in the compounds of the present disclosure include trimethylsilyl, triethylsilyl, triphenylsilyl, trimethoxysilyl, dimethoxyphenylsilyl, diphenylmethylsilyl, diphenylvinlysilyl, methylcyclobutylsilyl, and dimethyl furylsilyl. One or more hydrogen atoms on the silyl may be substituted by the same substituents as on the aryl.

As used herein, the term "alkenyl" refers to an unsaturated hydrocarbon group that contains a carbon-carbon double bond between two carbon atoms and the term "alkynyl" refers to an unsaturated hydrocarbon group that contains a carbon-carbon triple bond between two carbon atoms.

As used herein, the term "alkylene" refers to an organic aliphatic radical regarded as derived from a linear or branched saturated hydrocarbon alkane by removal of two hydrogen atoms from different carbon atoms. Concrete examples of the alkylene include methylene, ethylene, propylene, isopropylene, isobutylene, sec-butylene, tert-butylene, pentylene, iso-amylene, hexylene, and so on. One or more hydrogen atoms on the alkylene may be substituted by the same substituents as on the aryl.

Furthermore, as used herein, the term "diarylamino" refers to an amine radical having two identical or different aryl groups bonded to the nitrogen atom thereof, the term "diheteroarylamino" refers to an amine radical having two identical or different heteroaryl groups bonded to the nitrogen atom thereof, and the term "aryl(heteroaryl)amino" refers to an amine radical having an aryl group and a heteroarylgroup both bonded to the nitrogen atom thereof.

As more particular examples accounting for the term "substituted" in the expression "substituted or unsubstituted" used for compounds of Chemical Formula A, the compounds may be substituted by at least one substituent selected from the group consisting of a deuterium atom, a cyano, a halogen, a hydroxy, a nitro, an alkyl of 1 to 12 carbon atoms, a halogenated alkyl of 1 to 12 carbon atoms, an alkenyl of 2 to 12 carbon atoms, an alkynyl of 2 to 12 carbon atoms, a cycloalkyl of 3 to 12 carbon atoms, a heteroalkyl of 1 to 12 carbon atoms, an aryl of 6 to 18 carbon atoms, an arylalkyl of 7 to 20 carbon atoms, an alkylaryl of 7 to 20 carbon atoms, a heteroaryl of 2 to 18 carbon atoms, a heteroarylalkyl of 2 to 18 carbon atoms, an alkoxy of 1 to 12 carbon atoms, an alkylamino of 1 to 12 carbon atoms, a diarylamino of 12 to 18 carbon atoms, a diheteroarylamino of 2 to 18 carbon atoms, an aryl(heteroaryl)amino of 7 to 18 carbon atoms, an alkylsilyl of 1 to 12 carbon atoms, an arylsilyl of 6 to 18 carbon atoms, an aryloxy of 6 to 18 carbon atoms, and an arylthionyl of 6 to 18 carbon atoms.

The anthracene compound represented by Chemical Formula A according to the present disclosure is characterized by the structure in which the anthracene ring moiety has a substituted or unsubstituted aryl of 6 to 50 carbon atoms or a substituted or unsubstituted heteroaryl of 2 to 50 carbon atoms as the substituent ($Ar_1$) on the carbon atom at position 9 thereof, and any one selected from a single bond, a substituted or unsubstituted arylene of 6 to 20 carbon atoms, a substituted or unsubstituted heteroarylene of 2 to 20 carbon atoms as the linker ($L_1$) on the carbon atom at position 10, and the linker ($L_1$) is bonded to any one of the substituents $R_{11}$ to $R_{14}$ on the aromatic ring represented by the following structural formula A or B wherein the substituent $R_{10}$ on the unsaturated pentagonal ring is a hydrogen atom or a deuterium atom.

[Structural Formula A]

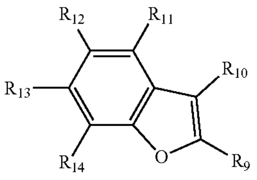

[Structural Formula B]

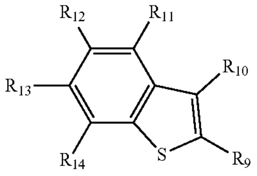

That is, any one of the substituents $R_{11}$ to $R_{14}$ in the Structural Formulas A and B is a single bond to the linker $L_1$.

In an embodiment according to the present disclosure, the substituent $R_{11}$ or $R_{12}$ in Structural Formulas A and B may be a single bond to the linker $L_1$. In this case, the anthracene compound represented by Chemical formula A according to the present disclosure may be an anthracene compound represented by the following [Chemical Formula A-1] or [Chemical Formula A-2]:

[Chemical Formula A-1]

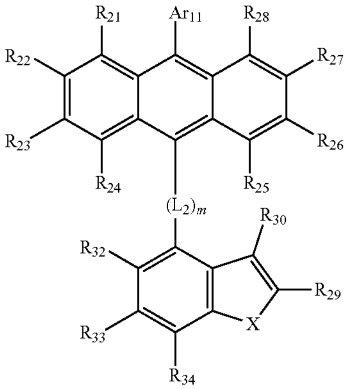

[Chemical Formula A-2]

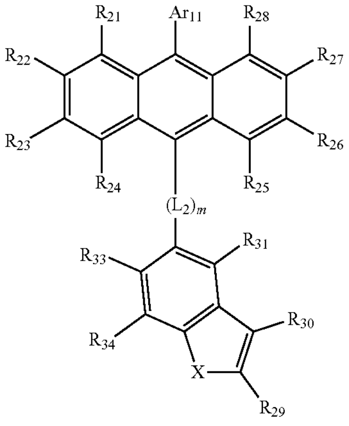

wherein, $Ar_{11}$ is a substituted or unsubstituted aryl of 6 to 18 carbon atoms or a substituted or unsubstituted heteroaryl of 2 to 18 carbon atoms, $R_{21}$ to $R_{28}$ and $R_{31}$ to $R_{34}$, which are same or different, are each independently any one selected from a hydrogen atom, a deuterium atom, a substituted or unsubstituted alkyl of 1 to 15 carbon atoms, a substituted or unsubstituted cycloalkyl of 3 to 15 carbon atoms, a substituted or unsubstituted aryl of 6 to 18 carbon atoms, a substituted or unsubstituted heteroaryl of 2 to 18 carbon atoms, a substituted or unsubstituted alkylsilyl of 1 to 15 carbon atoms, a substituted or unsubstituted arylsilyl of 6 to 18 carbon atoms, a cyano, a nitro, and a halogen, $R_{29}$ is any one selected from a hydrogen atom, a deuterium atom, a substituted or unsubstituted alkyl of 1 to 15 carbon atoms, a substituted or unsubstituted cycloalkyl of 3 to 15 carbon atoms, a substituted or unsubstituted aryl of 6 to 18 carbon atoms, and a substituted or unsubstituted heteroaryl of 2 to 18 carbon atoms, $R_{30}$ is a hydrogen atom or a deuterium atom, X is an oxygen atom (O) or a sulfur atom (S), $L_2$ is a single bond or any one selected from a substituted or unsubstituted arylene of 6 to 20 carbon atoms and or a substituted or unsubstituted heteroarylene of 2 to 20 carbon atoms, and m is an integer of 1 to 3 wherein when m is 2 or higher, the corresponding $L_2$'s are same or different, wherein the term “substituted” in the expression “substituted or unsubstituted” is as defined above.

In an embodiment, the substituents $R_1$ to $R_8$ in Chemical Formula A, which are same or different, may each be independently a hydrogen atom or a deuterium atom.

The anthracene compound of Chemical Formula A in which at least one of the substituents $R_1$ to $R_8$ is a deuterium atom may exhibit a longer lifespan, compared to the antracene compound with the substituents being all hydrogen atoms.

In an embodiment, the substituent $Ar_1$ in Chemical Formula A may be a substituted or unsubstituted aryl of 6 to 18 carbon atoms. In this regard, the $Ar_1$ in Chemical Formula A may be an aryl of 6 to 18 carbon atoms having as a substituent thereon any one selected from a deuterium atom, a phenyl, and a naphthyl or having no substituents thereon.

In addition, when the substituent $Ar_1$ is a substituted or unsubstituted aryl of 6 to 18 carbon atoms, it may be a substituted or unsubstituted phenyl, a substituted or unsubstituted naphthyl, a substituted or unsubstituted biphenyl, a substituted or unsubstituted anthracenyl, a substituted or unsubstituted phenantrenyl, and a substituted or unsubstituted fluorenyl.

In a particular embodiment according to the present disclosure, the linker $L_1$ in Chemical Formula A may be a single bond or a substituted or unsubstituted arylene of 6 to 18 carbon atoms.

Moreover, in a particular embodiment according to the present disclosure, the linker $L_1$ in Chemical Formula A may be a single bond or any one selected from the compounds represented by the following Structural Formulas 11 to 17:

[Structural Formula 11]

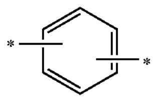

[Structural Formula 12]

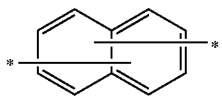

-continued

[Structural Formula 13]

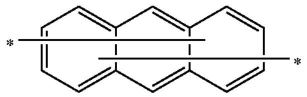

[Structural Formula 14]

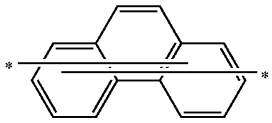

[Structural Formula 15]

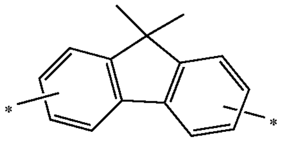

[Structural Formula 16]

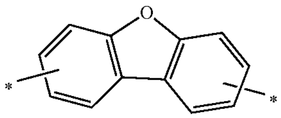

[Structural Formula 17]

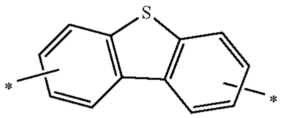

In the linker $L_1$, each of the unsubstituted carbon atoms of the aromatic ring moiety may be bound with a hydrogen atom or a deuterium atom.

In Structural Formulas 11 to 17, *- refers to a site which is linked to the carbon atom at position 10 in the anthracene ring moiety or any one of the substituents $R_{11}$ to $R_{14}$ in Chemical Formula A.

In an embodiment according to the present disclosure, the substituent $R_9$ in Chemical Formula A may be a substituted or unsubstituted aryl of 6 to 18 carbon atoms or a substituted or unsubstituted heteroaryl of 2 to 18 carbon atoms. In this regard, the substituent $R_9$ may be preferably any one selected from a substituted or unsubstituted phenyl, a substituted or unsubstituted naphthyl, a substituted or unsubstituted biphenyl, a substituted or unsubstituted anthracenyl, a substituted or unsubstituted phenanthrenyl, a substituted or unsubstituted fluorenyl, a substituted or unsubstituted benzofuran, a substituted or unsubstituted benzothiophene, a substituted or unsubstituted dibenzofuran, and a substituted or unsubstituted dibenzothiophene.

In addition, the anthracene compound represented by Chemical Formula A according to the present disclosure may include at least one a deuterium atom. Here, the deuterium atom may be positioned on at least one carbon atom of substituted for a hydrogen atom positioned, instead of a hydrogen atom, on at least one selected from the anthracene moiety including $R_1$ to R8, the substituent $Ar_1$ moiety, the linker $L_1$, and the hetero ring moiety including $R_9$ to $R_{14}$.

More specifically, the anthracene compound represented by Chemical Formula A may be any one selected from the following [Compound 1] to [Compound 111]:

[Compound 1]
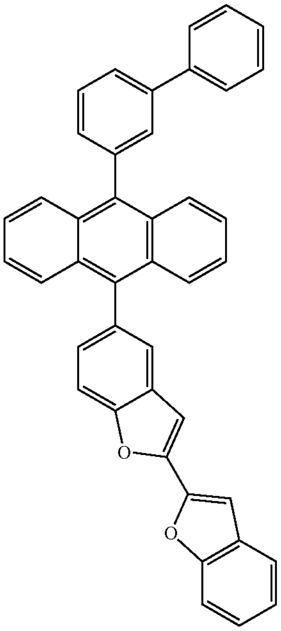
[Compound 2]
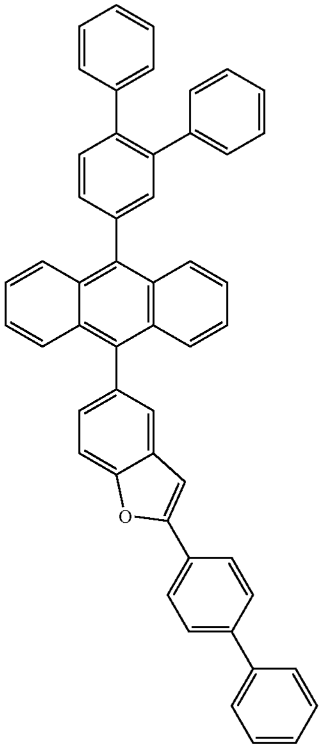
-continued
[Compound 3]
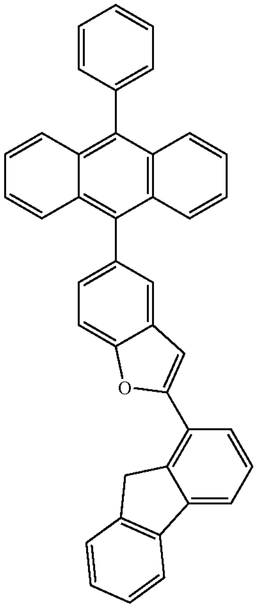
[Compound 4]
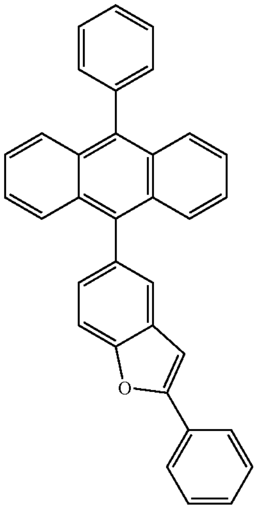
[Compound 5]
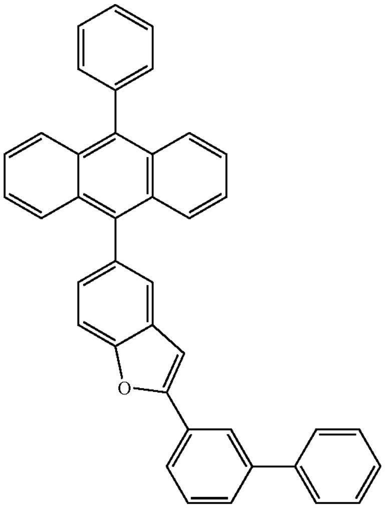

-continued
[Compound 6]
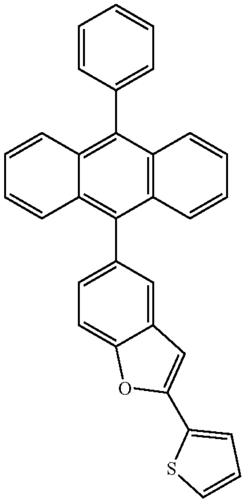
[Compound 7]
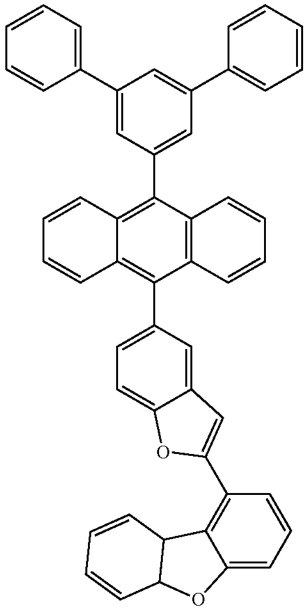
-continued
[Compound 8]
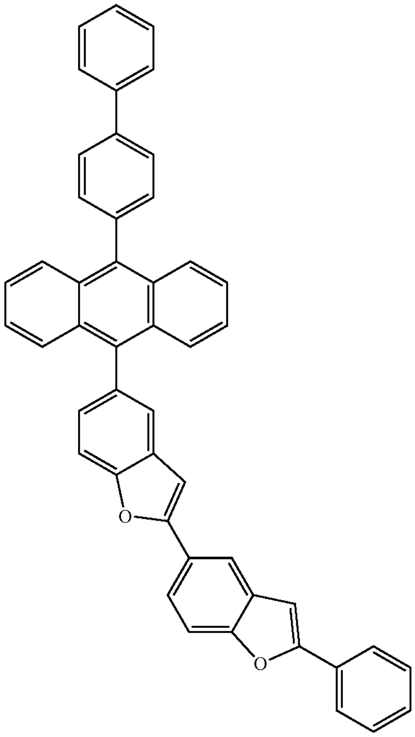
[Compound 9]
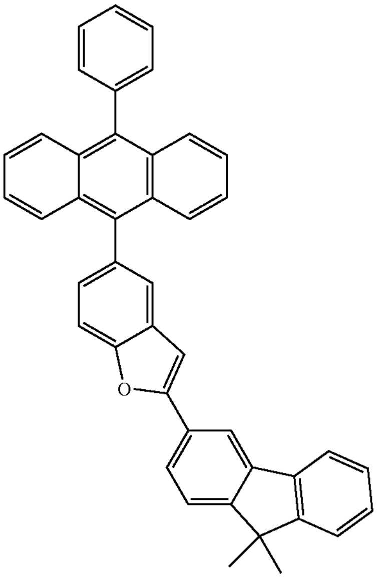

-continued
[Compound 10]
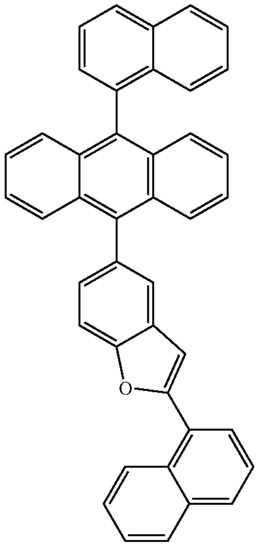
[Compound 11]
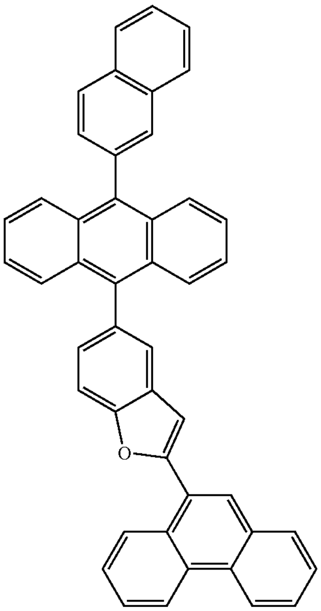
[Compound 12]
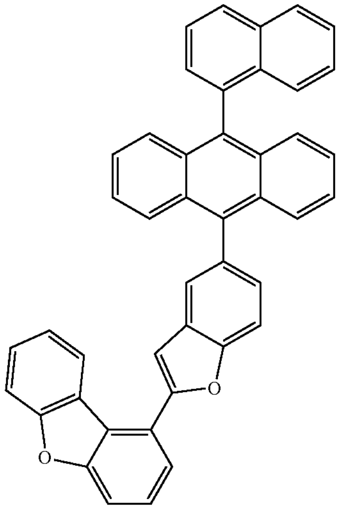
-continued
[Compound 13]
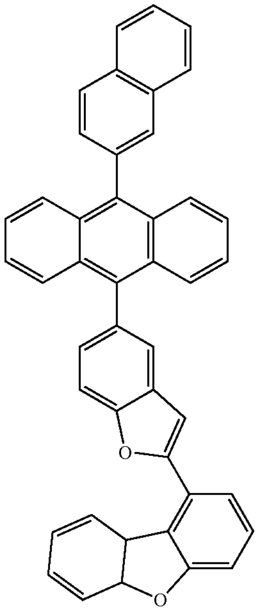
[Compound 14]
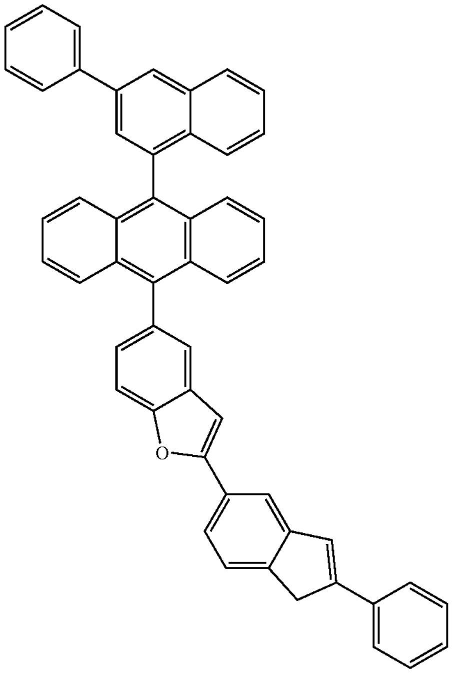

-continued
[Compound 15]
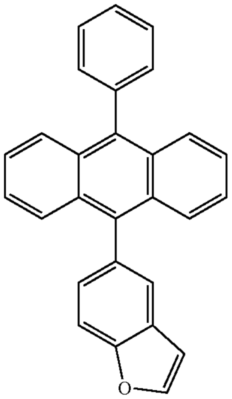
[Compound 16]
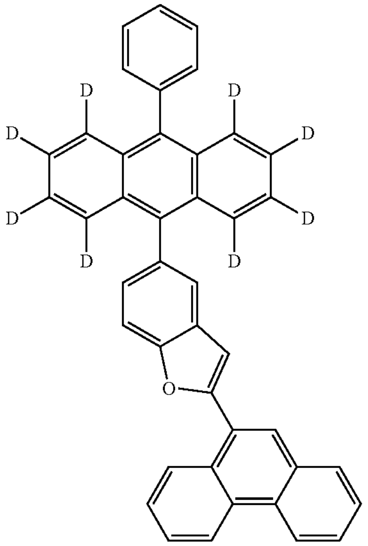
[Compound 17]
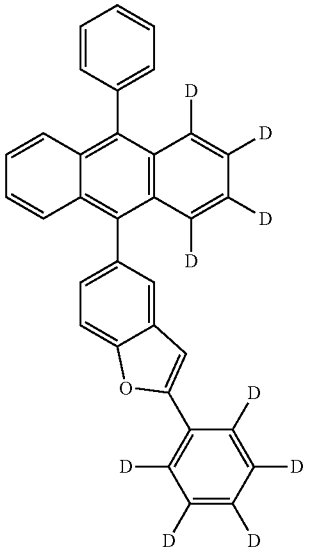
-continued
[Compound 18]
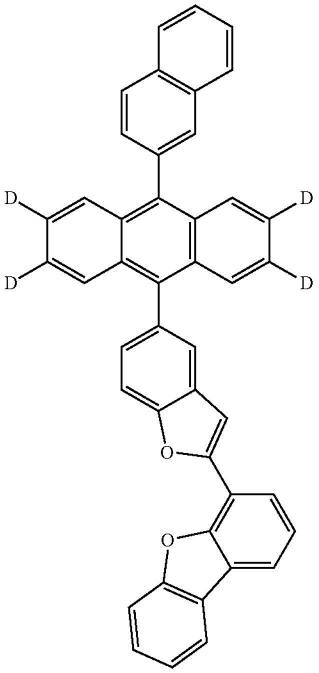
[Compound 19]
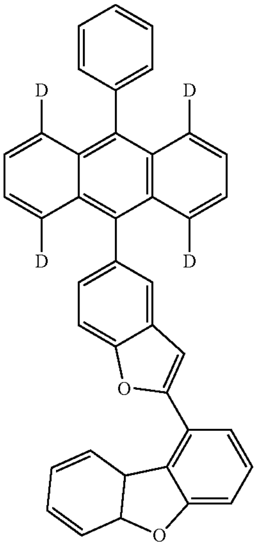

-continued
[Compound 20]
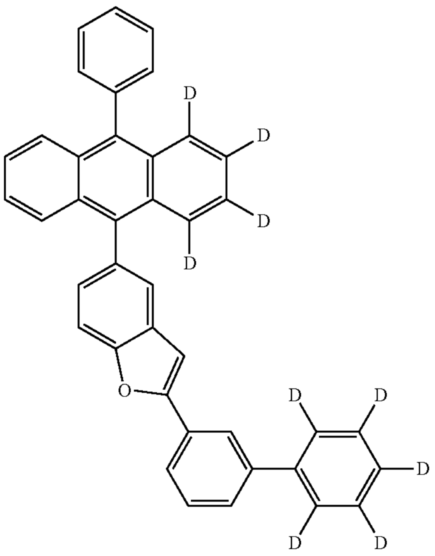
[Compound 21]
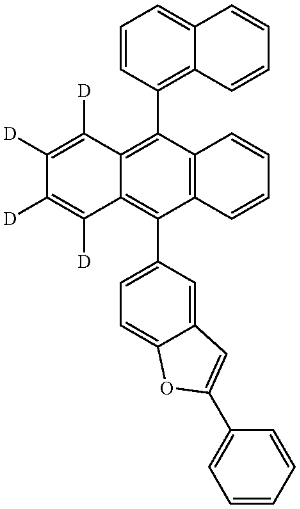
[Compound 22]
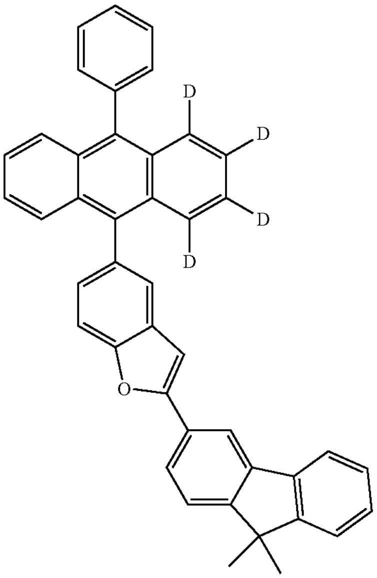
-continued
[Compound 23]
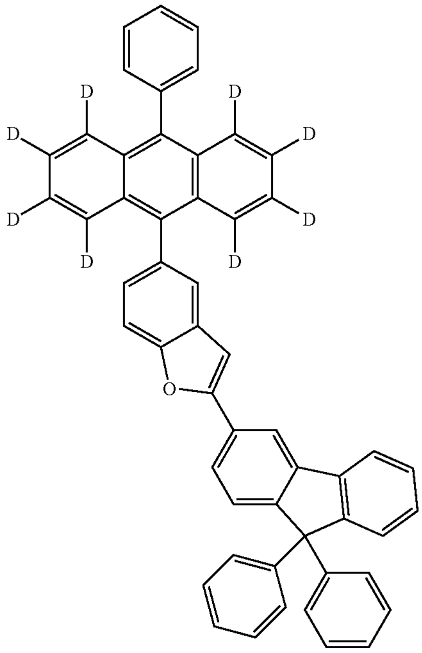
[Compound 24]
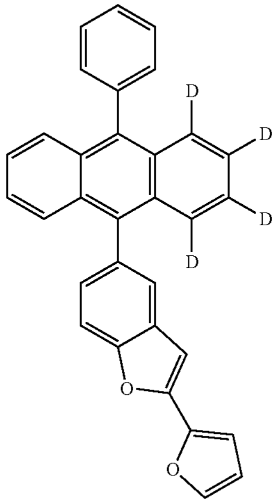

-continued
[Compound 25]
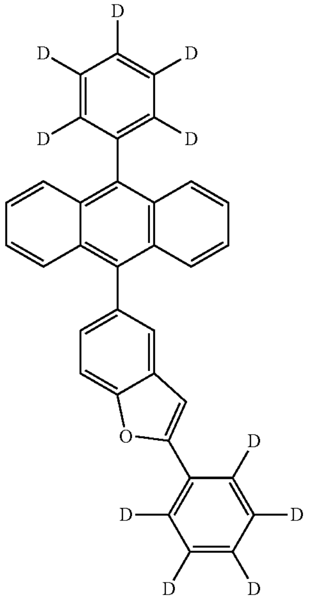
[Compound 26]
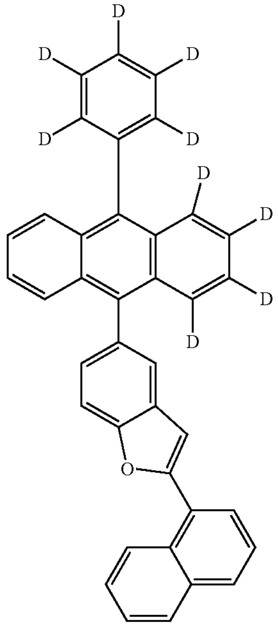
-continued
[Compound 27]
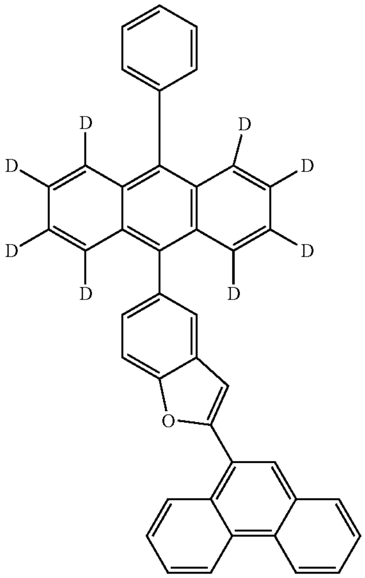
[Compound 28]
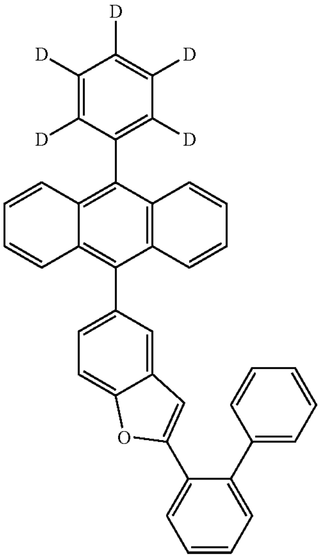

[Compound 29]
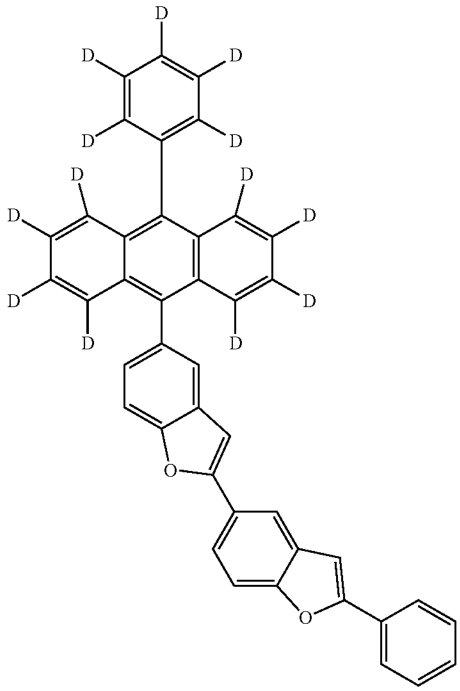
[Compound 30]
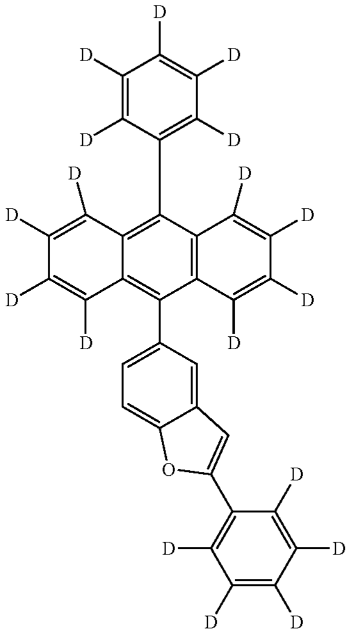
[Compound 31]
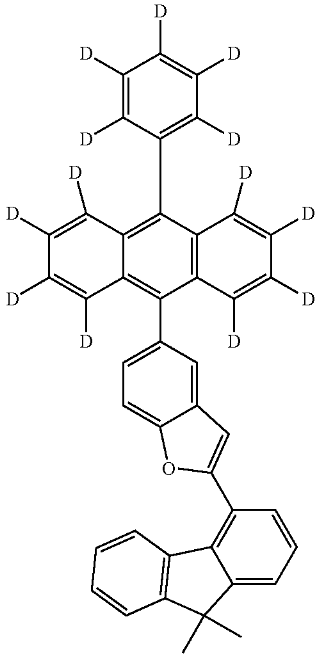
[Compound 32]
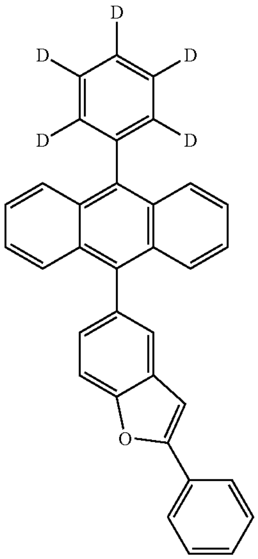

-continued
[Compound 33]
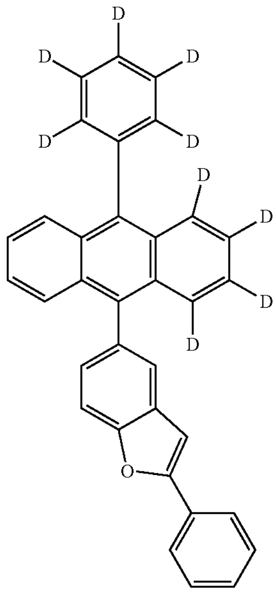
[Compound 34]
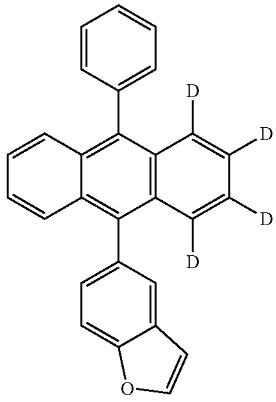
[Compound 35]
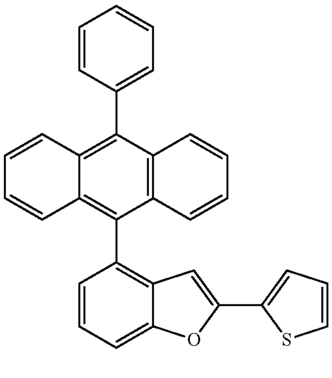
-continued
[Compound 36]
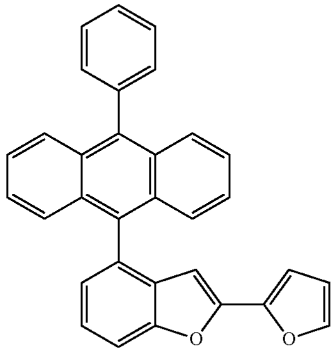
[Compound 37]
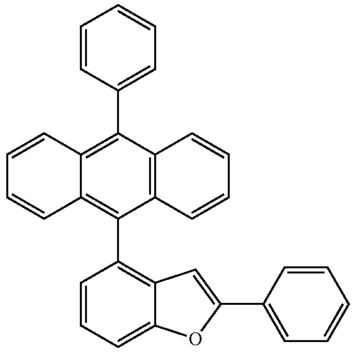
[Compound 38]
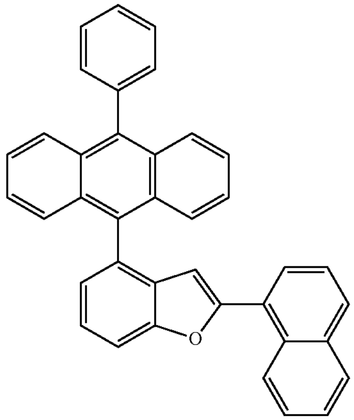
[Compound 39]
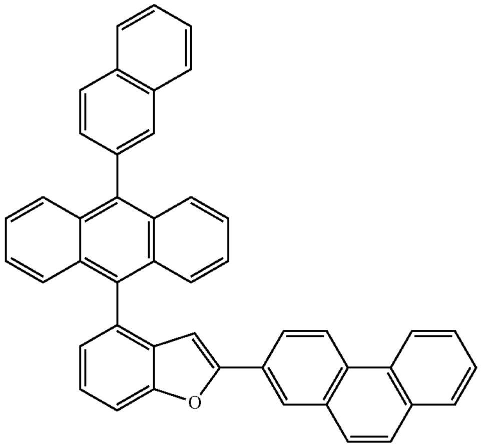

-continued
[Compound 40]
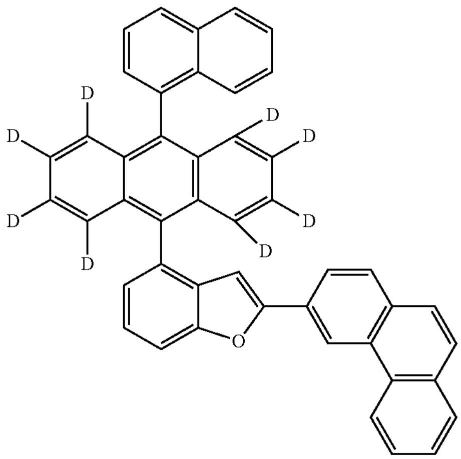
[Compound 41]
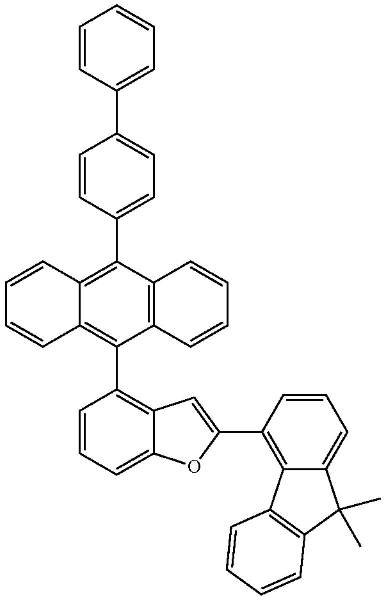
[Compound 42]
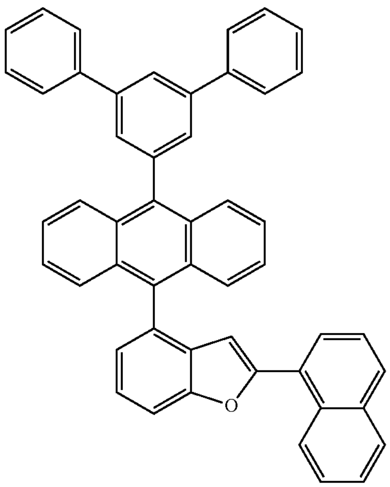
-continued
[Compound 43]
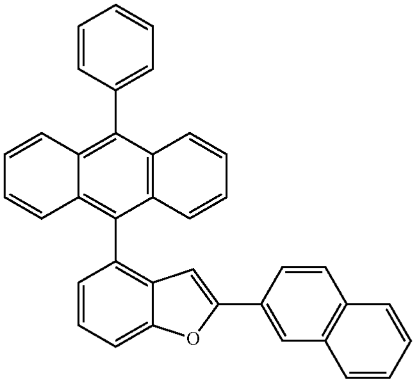
[Compound 44]
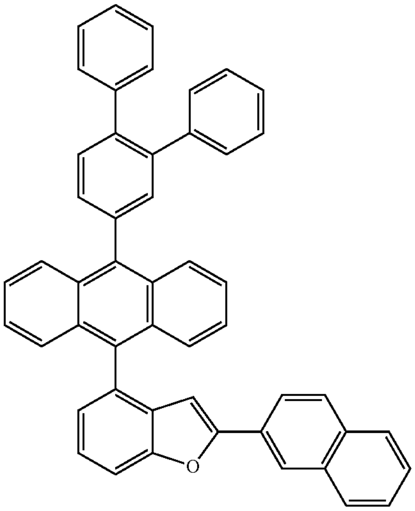
[Compound 45]
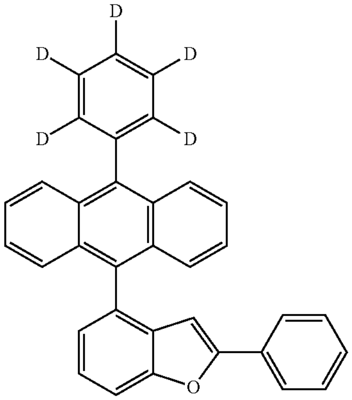

-continued
[Compound 46]
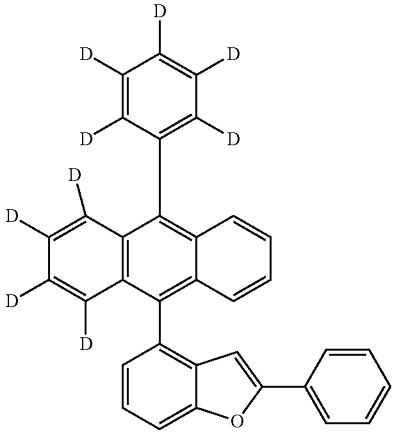
[Compound 47]
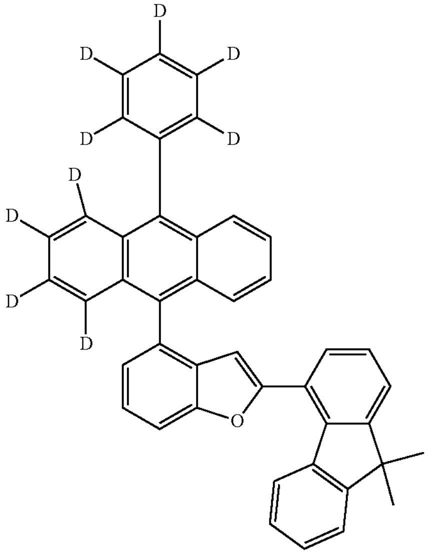
[Compound 48]
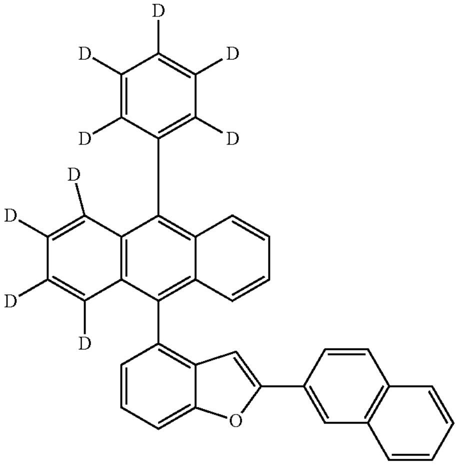
-continued
[Compound 49
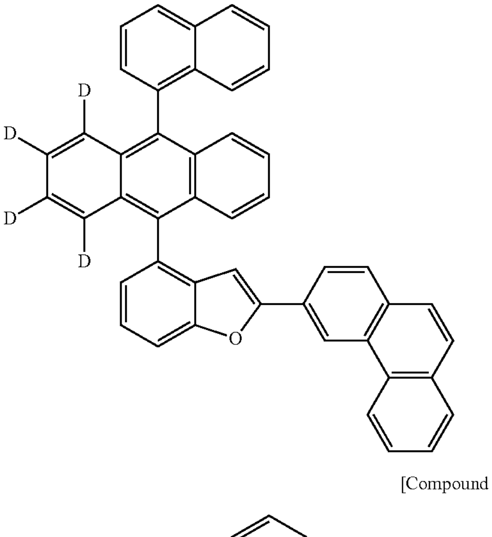
[Compound 50]
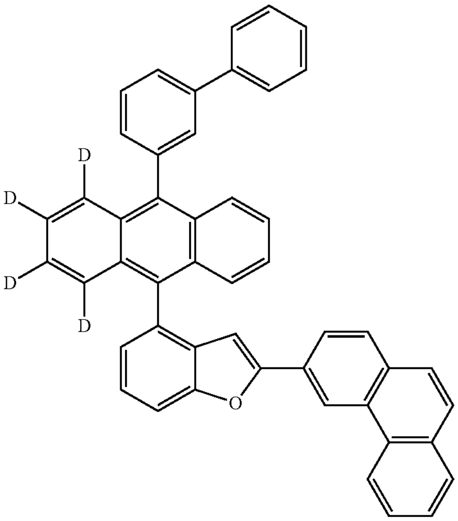
[Compound 51]
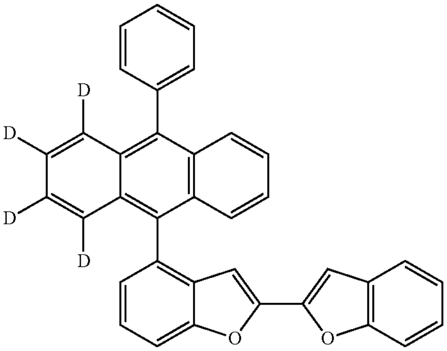

-continued
[Compound 52]
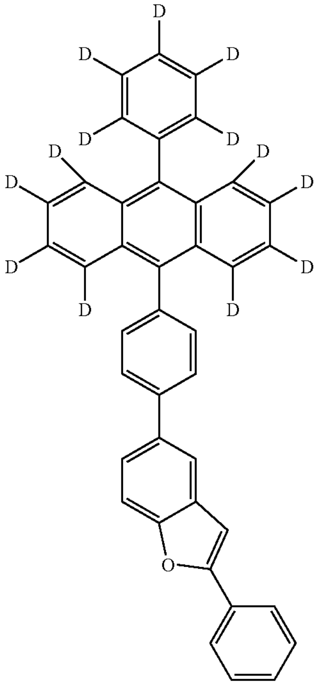
[Compound 53]
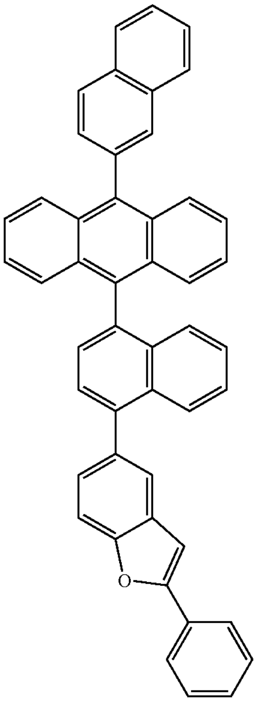
-continued
[Compound 54]
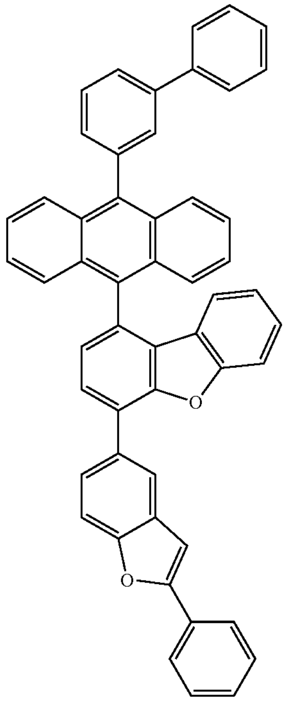
[Compound 55]
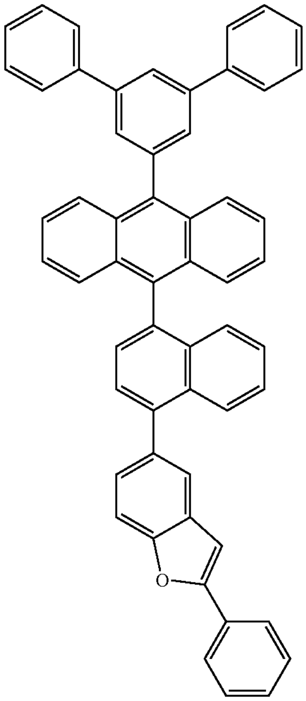

-continued
[Compound 56]
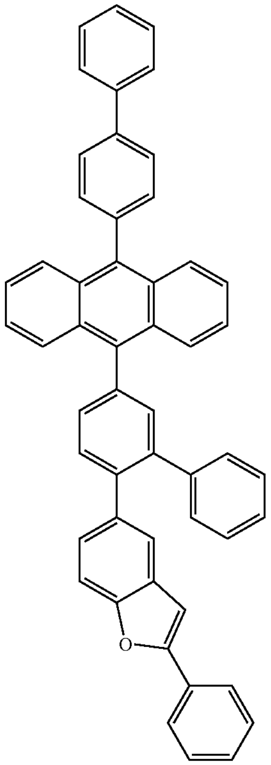
[Compound 57]
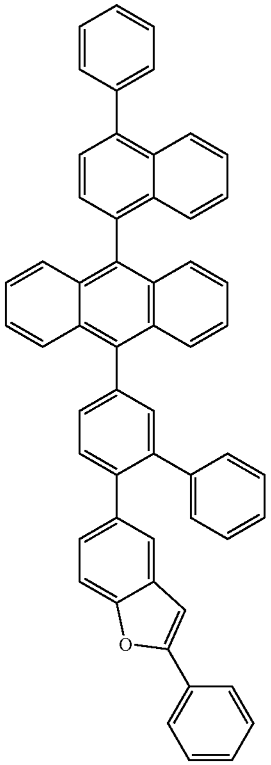
-continued
[Compound 58]
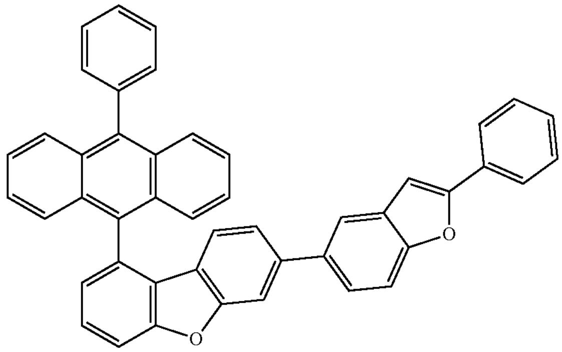
[Compound 59]
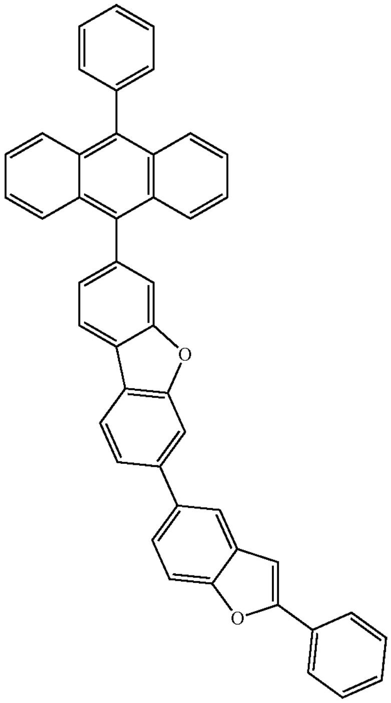
[Compound 60]
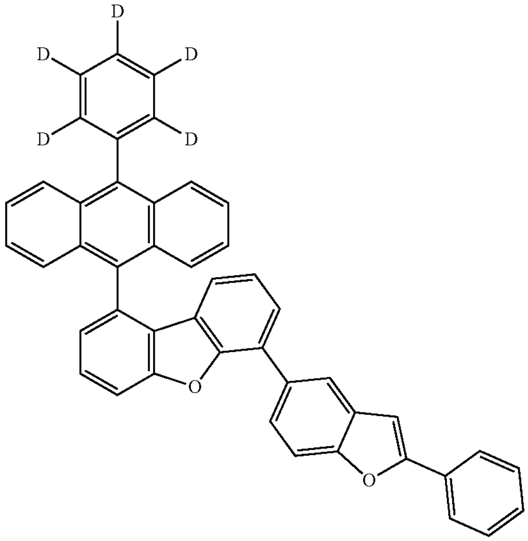

-continued
[Compound 61]
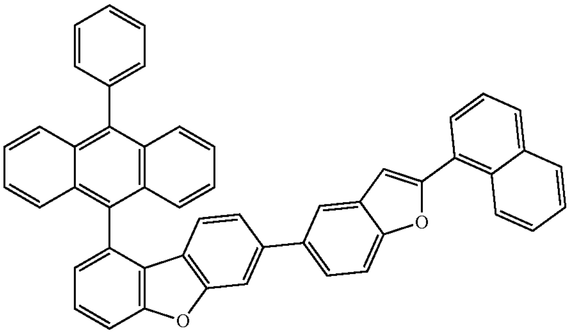
[Compound 62]
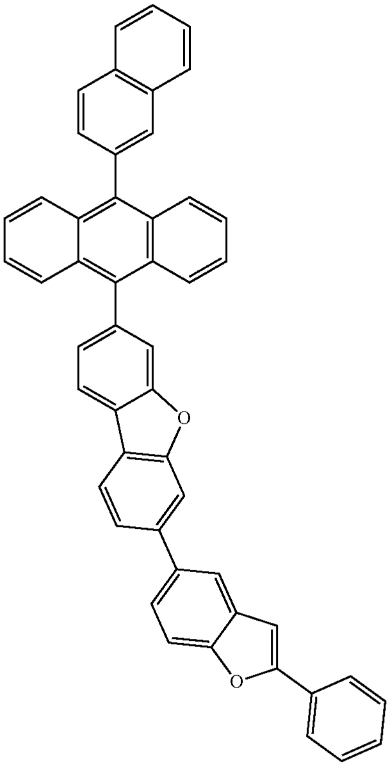
[Compound 63]
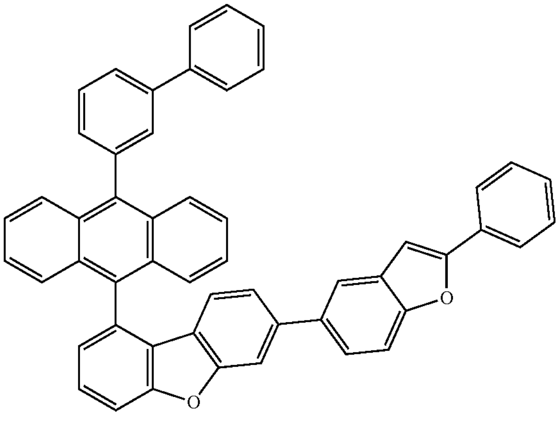
-continued
[Compound 64]
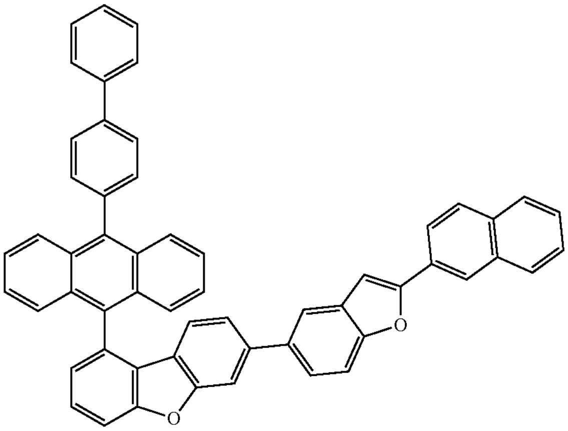
[Compound 65]
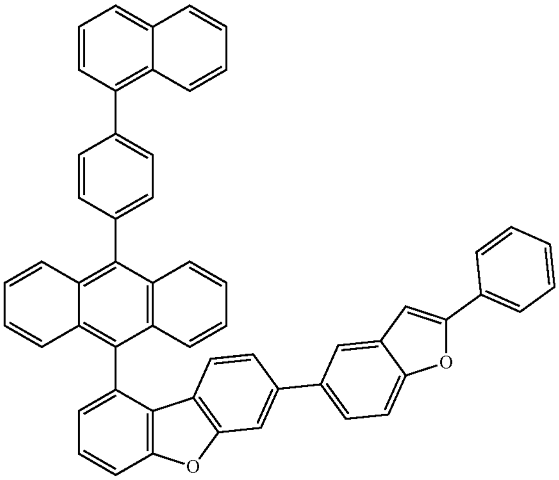

-continued
[Compound 66]
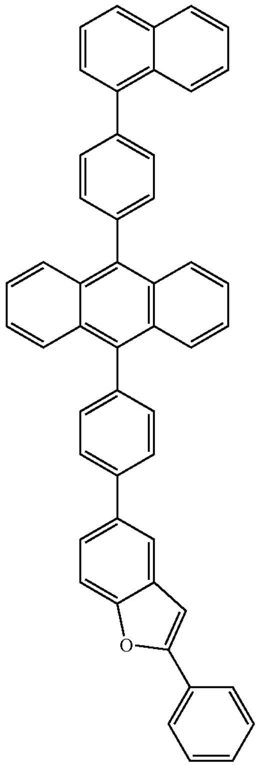
[Compound 67]
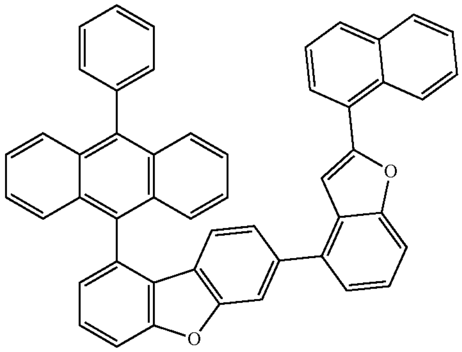
[Compound 68]
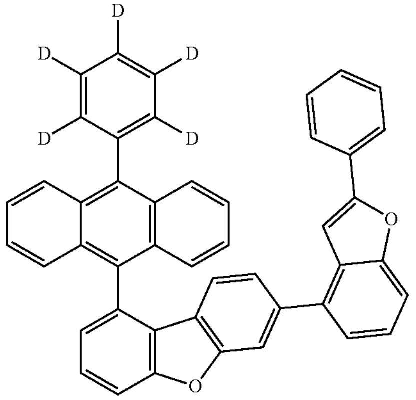
-continued
[Compound 69]
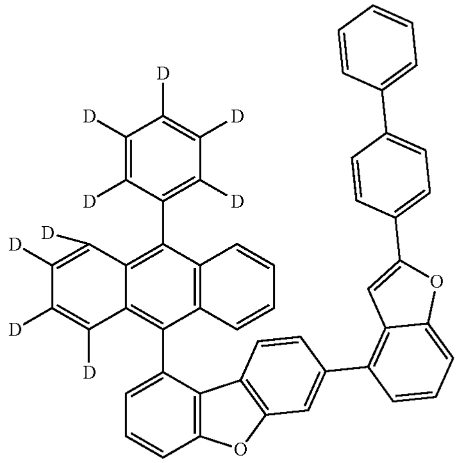
[Compound 70]
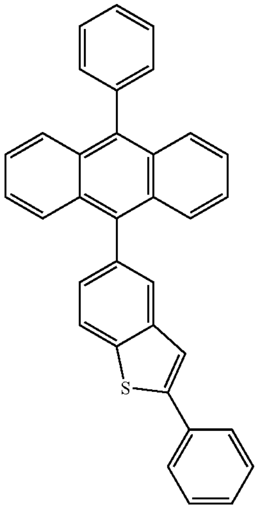
[Compound 71]
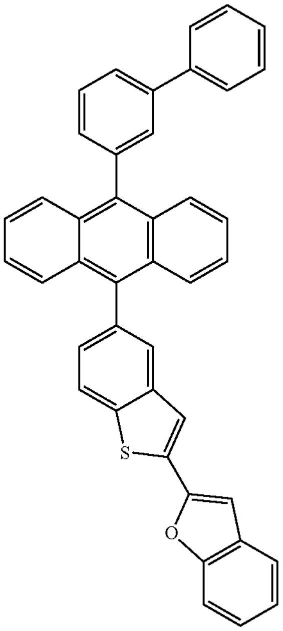

-continued
[Compoound 72]
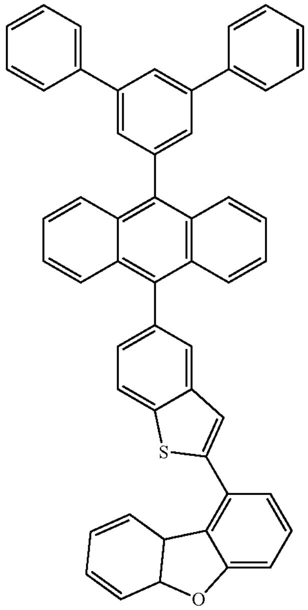
[Compound 73]
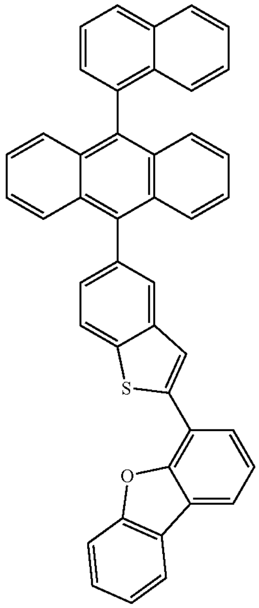
-continued
[Compound 74]
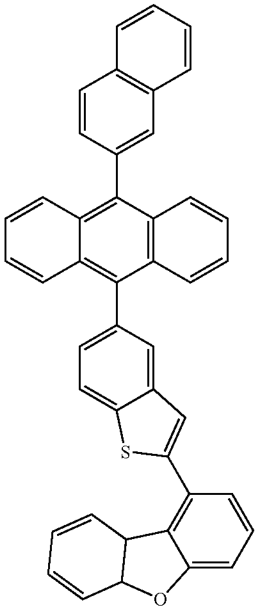
[Compound 75]
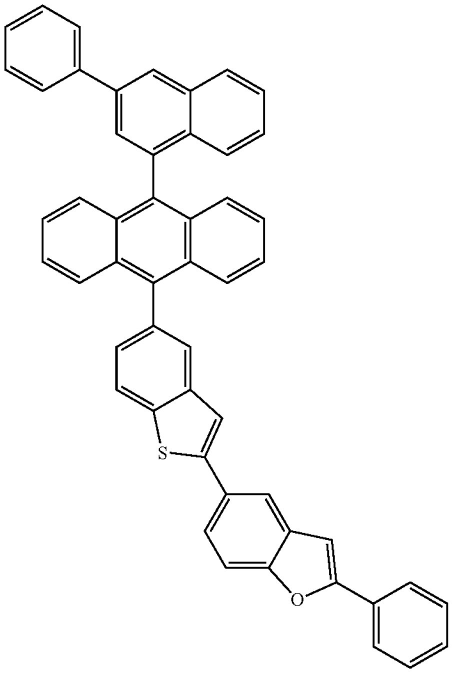

-continued
[Compound 76]
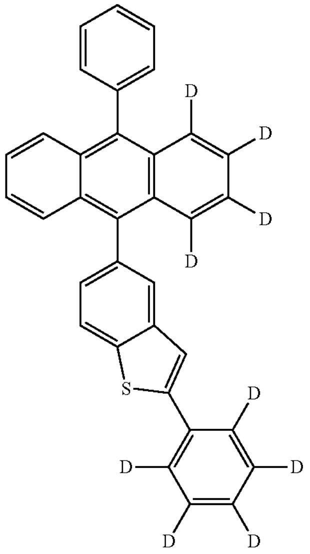
[Compound 77]
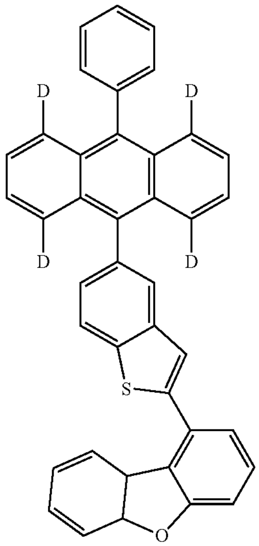
[Compound 78]
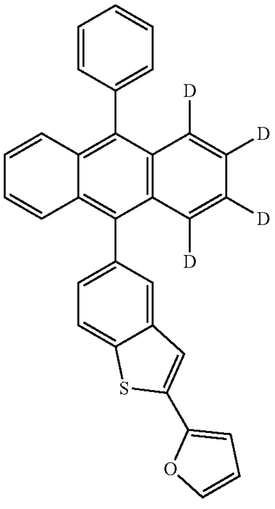
-continued
[Compound 79]
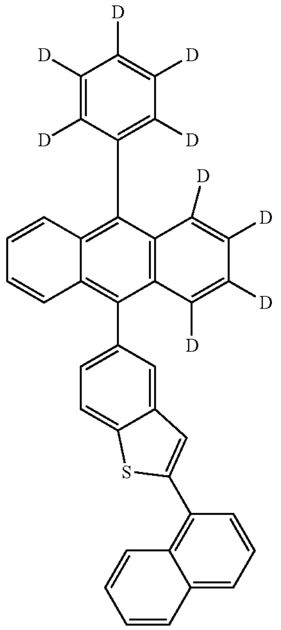
[Compound 80]
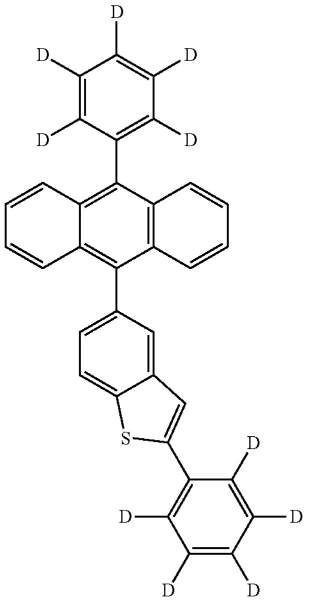

-continued
[Compound 81]
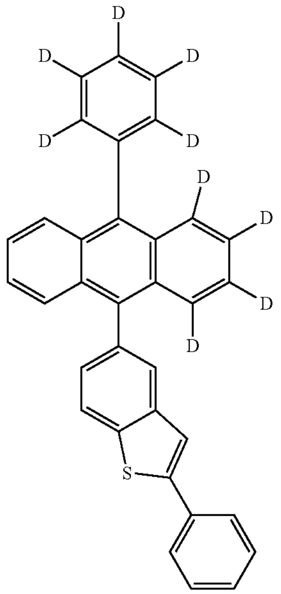
[Compound 82]
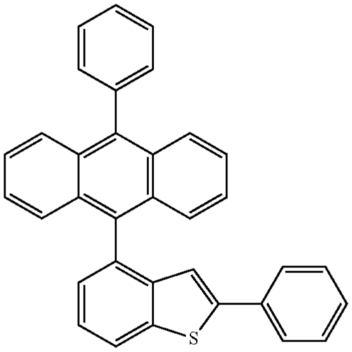
[Compound 83]
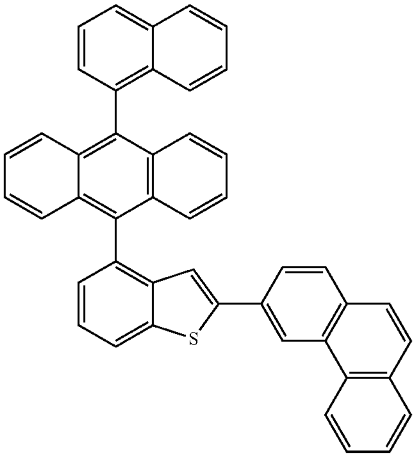
-continued
[Compound 84]
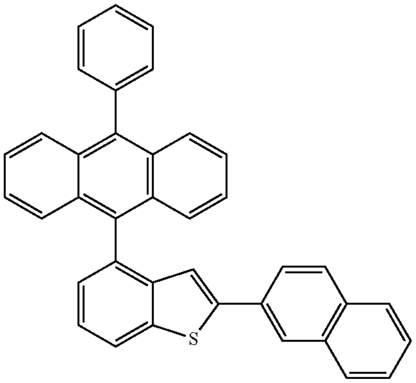
[Compound 85]
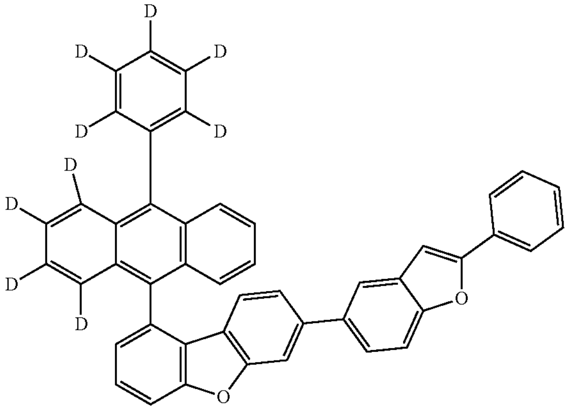
[Compound 86]
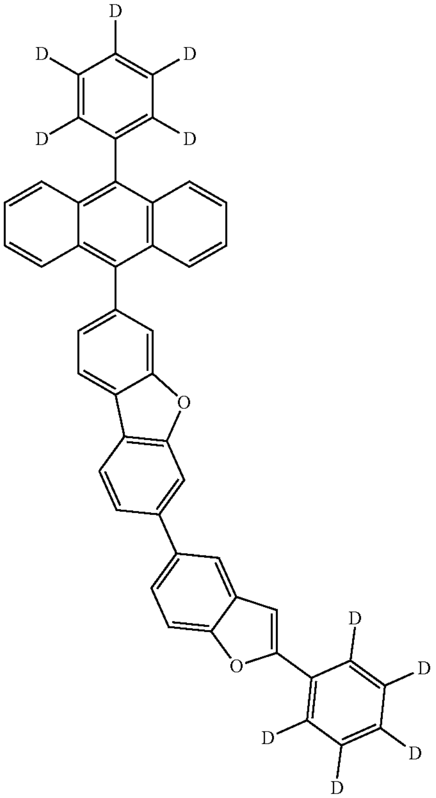

-continued
[Compound 87]
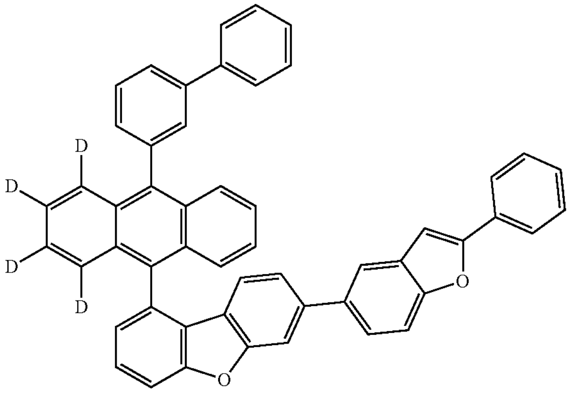
[Compound 88]
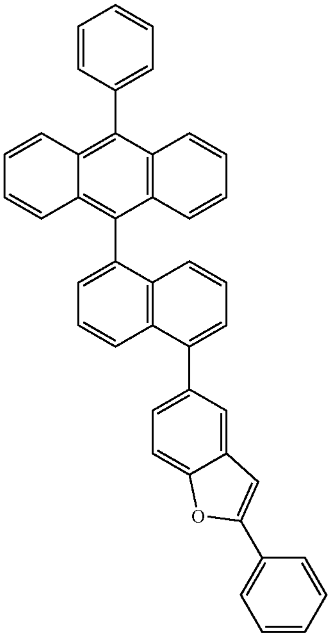
-continued
[Compound 89]
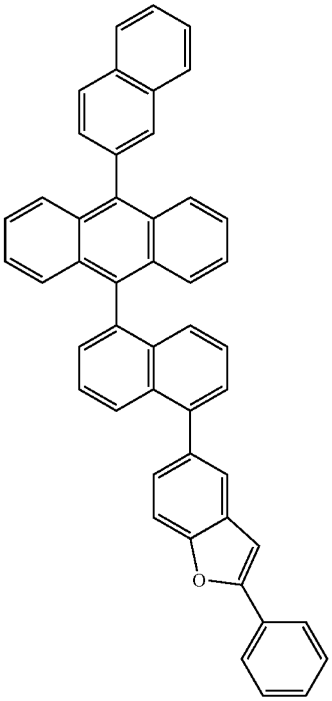
[Compound 90]
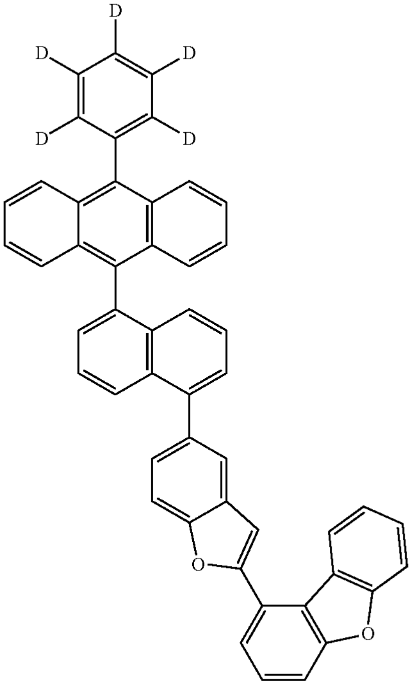

-continued
[Compound 91]
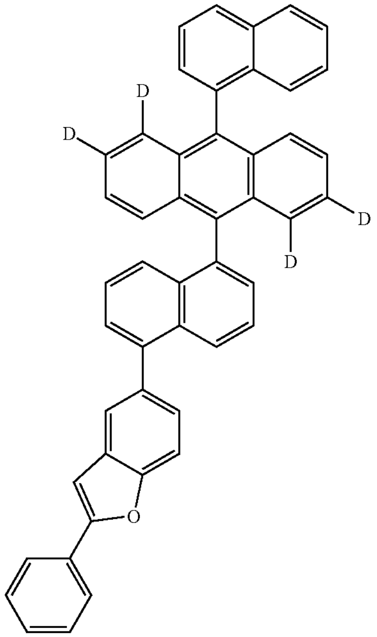
[Compound 92]
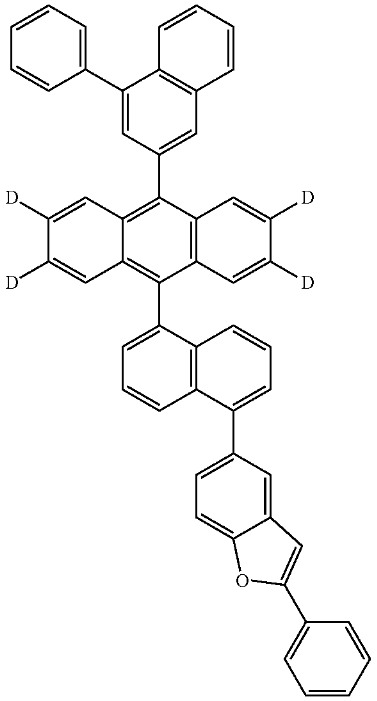
-continued
[Compound 93]
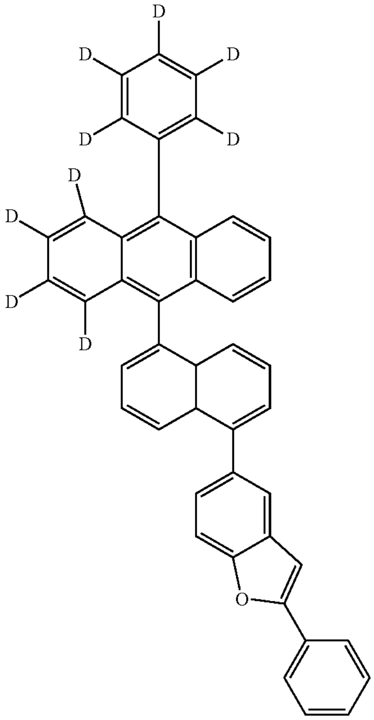
[Compound 94]
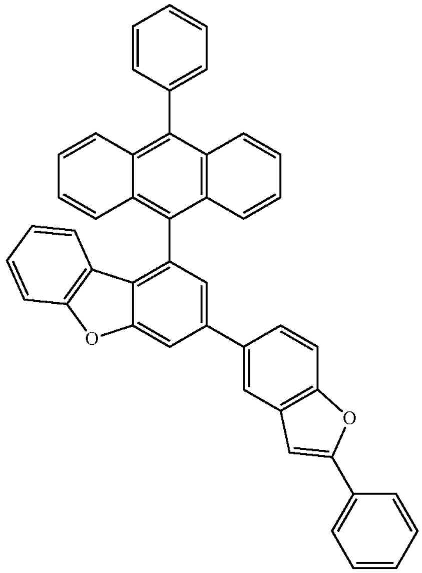

-continued
[Compound 95]
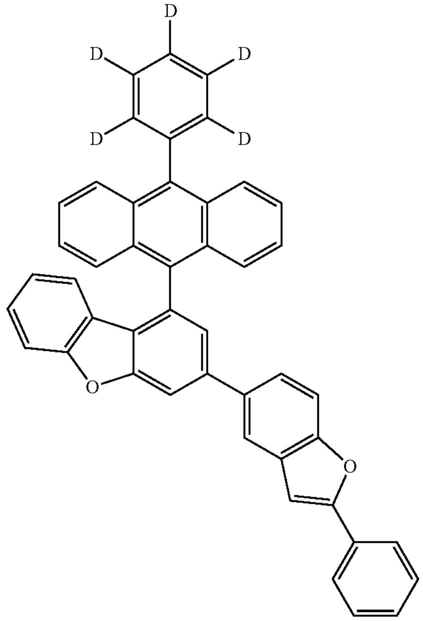
[Compound 96]
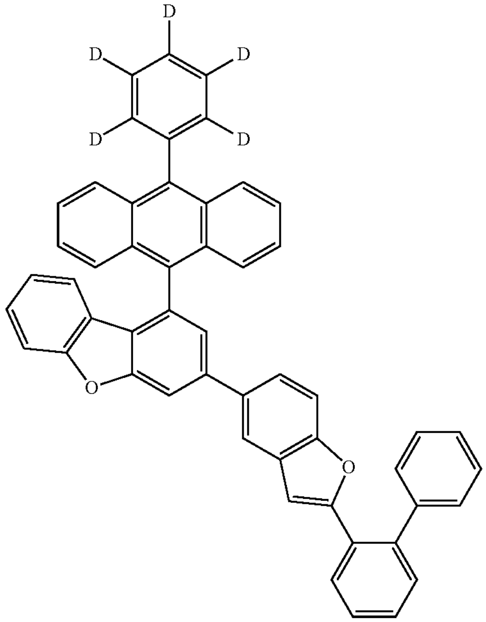
-continued
[Compound 97]
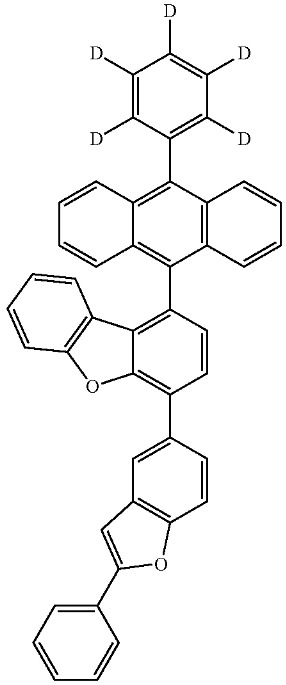
[Compound 98]
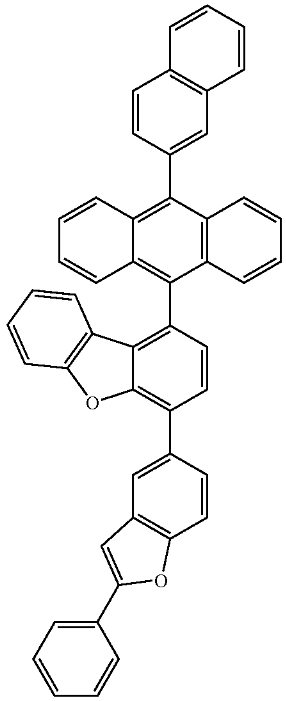

-continued
[Compound 99]
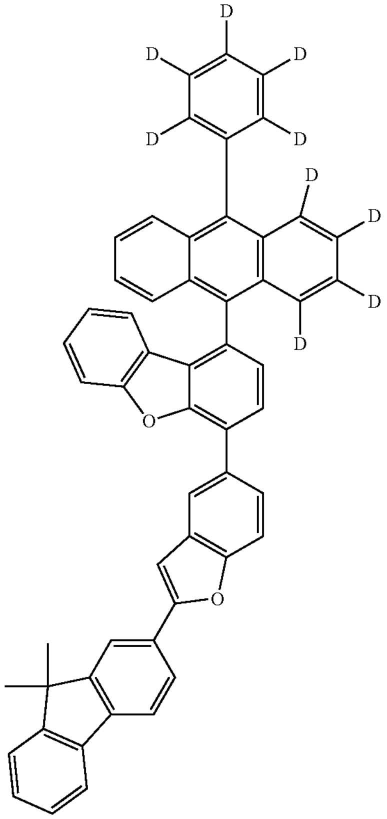
[Compound 100]
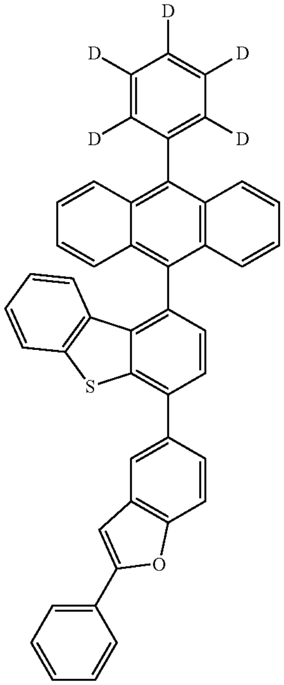
-continued
[Compound 101]
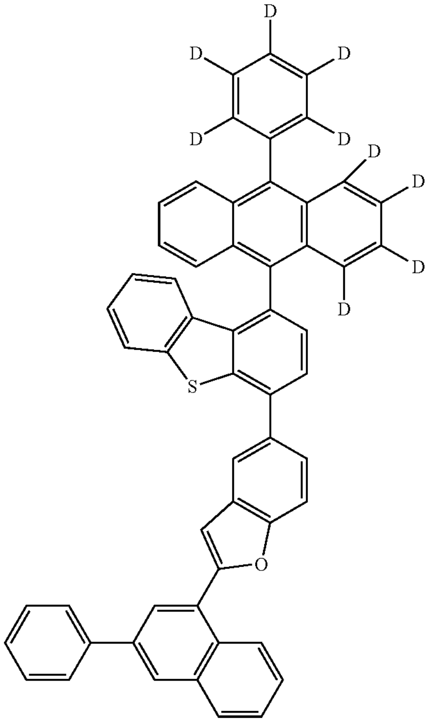
[Compound 102]
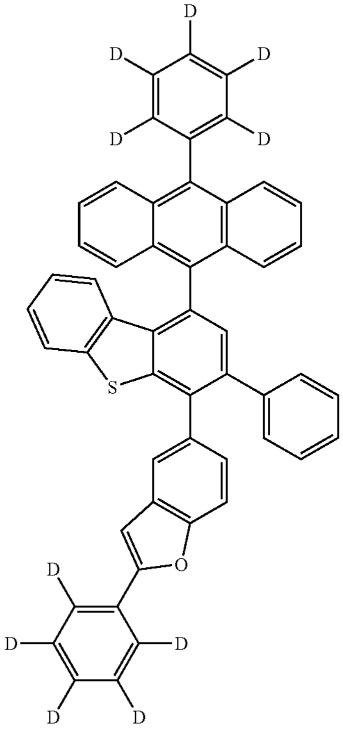

-continued
[Compound 103]
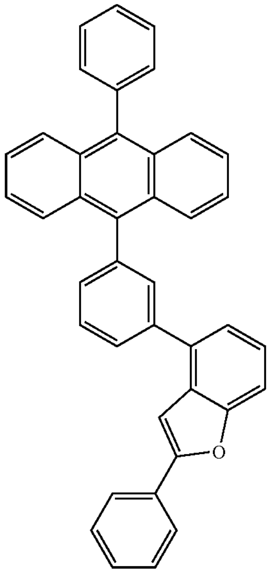
[Compound 104]
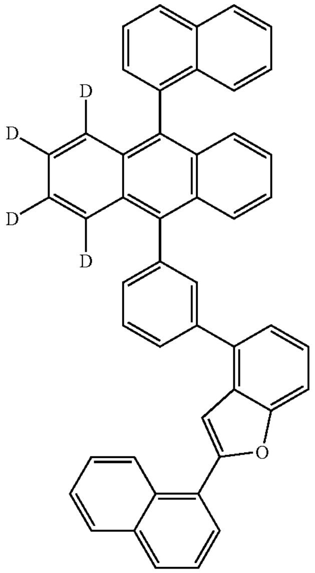
-continued
[Compound 105]
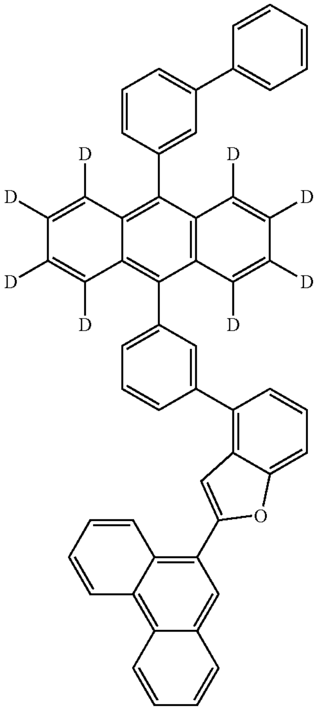
[Compound 106]
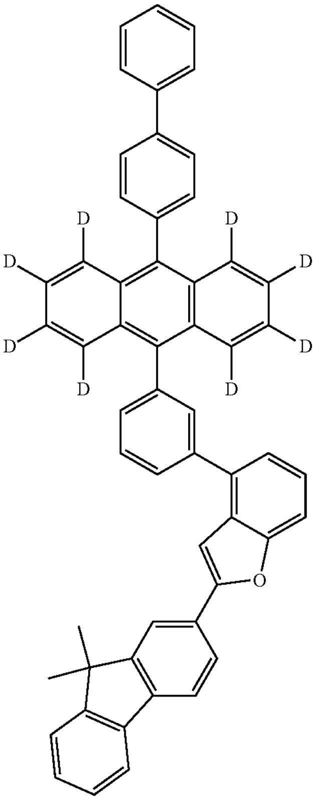

-continued
[Compound 107]
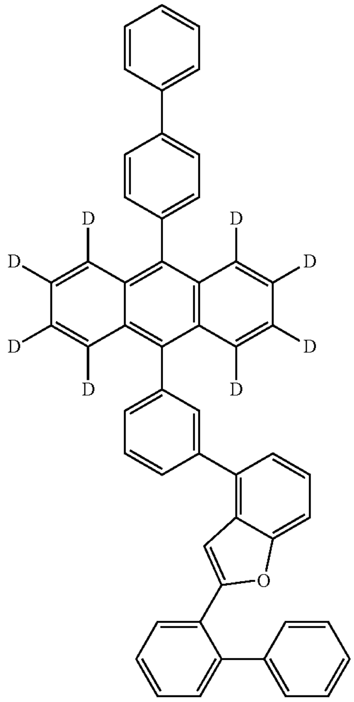
[Compound 108]
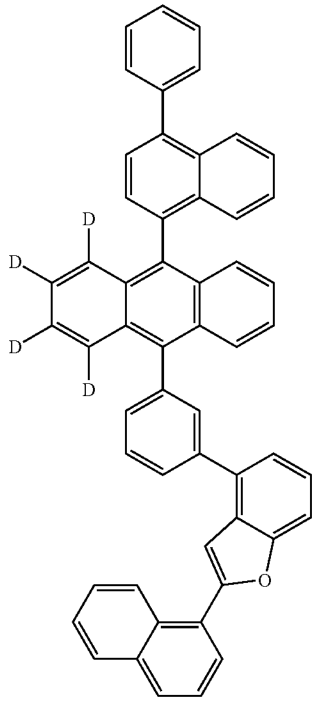
-continued
[Compound 109]
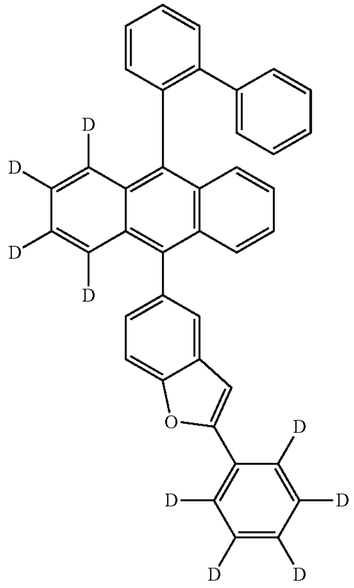
[Compound 110]
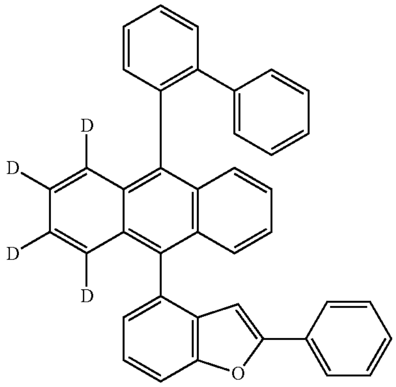
[Compound 111]
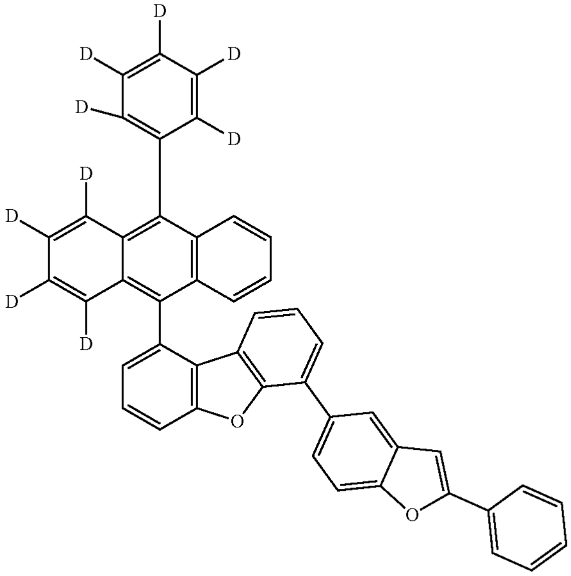
In particular some embodiments thereof, the present disclosure provides an organic light-emitting diode including:

a first electrode; a second electrode facing the second electrode; and an organic layer interposed between the first electrode and the second electrode, wherein the organic layer includes an anthracene compound represented by Chemical Formula A.

Throughout the description of the present disclosure, the phrase "(an organic layer) includes at least one organic compound" may be construed to mean that "(an organic layer) may include a single organic compound species or two or more difference species of organic compounds falling within the scope of the present disclosure".

In this regard, the organic light-emitting diode according to the present disclosure may include at least one of a hole injection layer, a hole transport layer, a functional layer capable of both hole injection and hole transport, an electron blocking layer, a light emitting layer, an electron transport layer, an electron injection layer, and a capping layer.

In more particular embodiments of the present disclosure, the organic layer disposed between the first electrode and the second electrode includes a light-emitting layer composed of a host and a dopant, wherein the anthracene compound represented by Chemical Formula A serves as the host.

When the anthracene compound represented by Chemical Formula A is used as a host in the light emitting layer of the present disclosure, a dopant used in the light emitting layer may be any one compound represented by one selected from Chemical Formulas D1 to D8:

[Chemical Formula D1]

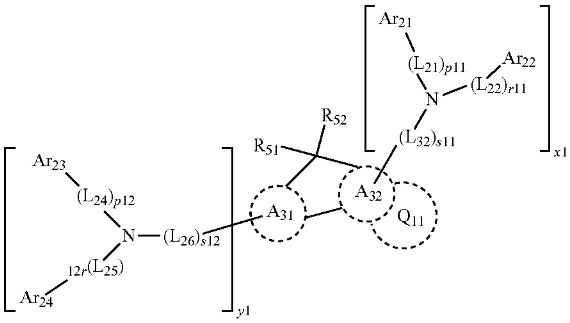

Q11:

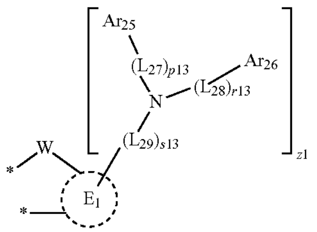

-continued

[Chemical Formula D2]

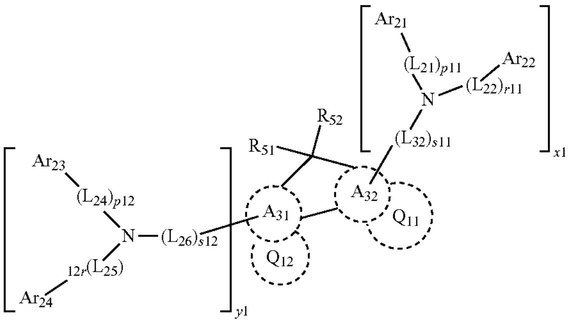

Q11:

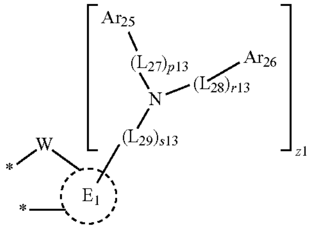

Q12:

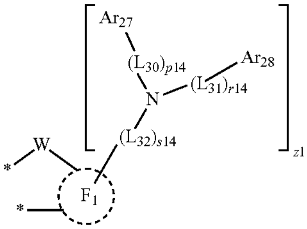

wherein, $A_{31}$, $A_{32}$, $E_1$, and $F_1$ may be same or different and are each independently a substituted or unsubstituted aromatic hydrocarbon ring of 6 to 50 carbon atoms, or a substituted or unsubstituted heteroaromatic ring of 2 to 40 carbon atoms wherein two adjacent carbon atoms of the aromatic ring $A_{31}$ and two adjacent carbon atoms of the aromatic ring $A_{32}$ form a 5-membered fused ring together with a carbon atom to which substituents $R_{51}$ and $R_{52}$ are bonded;

linkers $L_{21}$ to $L_{32}$ may be same or different, and are each independently selected from among a single bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

W is any one selected from among N—$R_{53}$, $CR_{54}R_{55}$, $SiR_{56}R_{57}$, $GeR_{58}R_{59}$, O, S, and Se;

$R_{51}$ to $R_{59}$, and $Ar_{21}$ to $Ar_{28}$ may be same or different, and are each independently any one selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxyl of 1 to 30 carbon atoms, a substituted or unsubstituted aryloxyl of 6 to 30 carbon atoms, a substituted or unsubstituted alkylthioxy of 1 to 30 carbon atoms, a substituted or unsubstituted arylthoxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a substituted or unsubstituted alkylgermyl of 1 to 30 carbon atoms, a substituted or unsubstituted arylgermyl of 1 to 30 carbon atoms a cyano, a nitro, and a halogen, with a proviso that $R_{51}$ and $R_{52}$ together may form a mono- or polycyclic aliphatic or aromatic ring that may be a heterocyclic ring bearing a heteroatom selected from among N, O, P, Si, S, Ge, Se, and Te as a ring member;

p11 to p14, $r_{11}$ to $r_{14}$, and s11 to s14 are each independently an integer of 1 to 3, with a proviso that when any of them is 2 or greater, the corresponding respective linkers $L_{21}$'s to $L_{32}$'s may be same or different;

$x_1$ is an integer of 1 or 2, and $Y_1$ and $z_1$ may be same or different and are each independently an integer of 0 to 3;

$Ar_{21}$ may form a ring with $Ar_{22}$, $Ar_{23}$ may form a ring with $Ar_{24}$, $Ar_{25}$ may form a ring with $Ar_{26}$, and $Ar_{27}$ may form a ring with $Ar_{28}$;

two adjacent carbon atoms of the $A_{32}$ ring moiety of Chemical Formula D1 occupy respective positions * of Structural Formula $Q_{11}$ to form a fused ring, and two adjacent carbon atoms of the $A_{31}$ ring moiety of Chemical Formula D2 occupy respective positions * of structural Formula $Q_{12}$ to form a fused ring, and two adjacent carbon atoms of the $A_{32}$ ring moiety of Chemical Formula D2 occupy respective positions * of structural Formula $Q_{11}$ to form a fused ring:

[Chemical Formula D3] 30

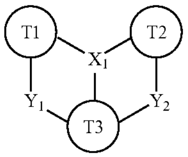

wherein, $X_1$ is any one selected from B, P, and P═O,

T1 to T3, which are same or different, are each independently a substituted or unsubstituted aromatic hydrocarbon ring of 6 to 50 carbon atoms, or a substituted or unsubstituted heteroaromatic ring of 2 to 40 carbon atoms;

$Y_1$ is any one selected from among N—$R_{61}$, $CR_{62}R_{63}$, O, S, and $SiR_{64}R_{65}$;

$Y_2$ is any one selected from among N—$R_{66}$, $CR_{67}R_{68}$, O, S, $SiR_{69}R_{70}$;

wherein $R_{61}$ to $R_{70}$, which may be same or different, are each independently any one selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a cyano, and a halogen and wherein at least one of R61 to R70 may be connected to at least one of T1 to T3 to form an additional mono- or polycyclic aliphatic or aromatic ring;

[Chemical Formula D4]

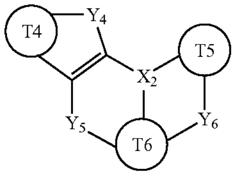

[Chemical Formula D5]

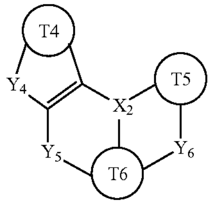

wherein, $X_2$ is any one selected from among B, P, and P═O,

T4 to T6 are as defined for T1 to T3 in Chemical Formula D3, $Y_4$ to $Y_6$ are as defined for $Y_1$ to $Y_2$ in Chemical Formula D3;

[Xhemical Formula D6]

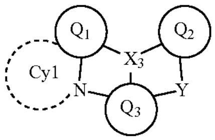

[Chemical Formula D7]

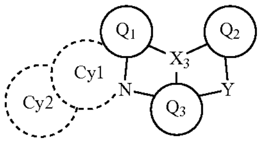

[Chemical Formula D8]

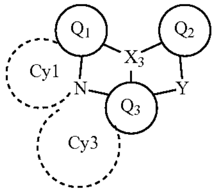

wherein, $Q_1$ to $Q_3$, which may be same or different, are each independently a substituted or unsubstituted aromatic hydrocarbon ring of 6 to 50 carbon atoms, or a substituted or unsubstituted heteroaromatic ring of 2 to 50 carbon atoms, Y is any one selected from N—$R_{73}$, $CR_{74}R_{75}$, O, S, and Se, $X_3$ is any one selected from B, P, and P═O, $R_{73}$ to $R_{75}$, which may be same or different, are each independently any one selected from a hydrogen atom, a deuterium atom, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkoxyl of 1 to 30 carbon atoms, a substituted or unsubstituted aryloxyl of 6 to 30 carbon atoms, a substituted or unsubstituted alkylthioxy of 1 to 30 carbon atoms, a substituted or unsubstituted arylthoxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a nitro, a cyano, and a halogen, and $R_{73}$ to $R_{75}$ may each be connected to the Q2 or $Q_3$ ring moiety to form an additional mono- or polycyclic aliphatic or aromatic, $R_{74}$ and $R_{75}$ may be connected to each other to form an additional mono- or polycyclic aliphatic or aromatic ring, the ring formed by Cy1 is a substituted or unsubstituted alkylene of 1 to 10 carbon atoms, except for the nitrogen (N) atom, the aromatic carbon atom of $Q_1$ to which the nitrogen (N) atom is connected, and the aromatic carbon atom of $Q_1$ to which Cy1 is to bond, Cy2 in Chemical Formula D7 forms a saturated hydrocarbon ring added to Cy1 wherein the ring formed by Cy2 is a substituted or unsubstituted alkylene of 1 to 10 carbon atoms, except for the carbon atoms included in Cy1, and the ring formed by Cy3 in Chemical Formula D8 is a substituted or unsubstituted alkylene of 1 to 10 carbon atoms, except for the aromatic carbon atom of $Q_3$ to which Cy3 is to bond, the aromatic carbon atom of $Q_3$ to which the nitrogen (N) atom is connected, the nitrogen (N) atom, and the carbon atom of Cy1 to which the nitrogen (N) atom is connected, wherein the term "substituted" in the expression "substituted or unsubstituted" used for compounds of Chemical Formulas D1 to D8 means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, a cycloalkyl of 3 to 30 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, an alkylaryl of 7 to 24 carbon atoms, a heteroaryl of 2 to 24 carbon atoms, a heteroarylalkyl of 2 to 24 carbon atoms, al alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

In Chemical Formulas D6 to D8, "Cy1" is linked to the nitrogen (N) atom and an aromatic carbon atom of the $Q_1$ ring to form a ring with the nitrogen (N) atom, the aromatic carbon atom of the $Q_1$ ring to which the nitrogen (N) atom is boned, and the aromatic carbon atom of the $Q_1$ ring to which Cy1 is to bond, and the ring formed by Cy1 may be a substituted or unsubstituted alkylene of 1 to 10 carbon atoms, particularly a substituted or unsubstituted alkylene of 2 to 7 carbon atoms, and more particularly a substituted or unsubstituted alkylene of 2 to 5 carbon atoms, except for the nitrogen (N) atom, the aromatic carbon atom of $Q_1$ to which the nitrogen (N) atom is bonded, and the aromatic carbon atom of $Q_1$ to which Cy1 is to bond.

In addition, the ring formed by "Cy2" in Chemical Formula D7 is a substituted or unsubstituted alkylene of 1 to 10 carbon atoms, particularly a substituted or unsubstituted alkylene of 2 to 7 carbon atoms, and more particularly a substituted or unsubstituted alkylene of 2 to 5 carbon atoms, except for the carbon atoms shared by Cy1.

Turning to 'Cy3' in Chemical Formula D8, it is linked to both the carbon atom boned to the nitrogen atom in Cy1 and the aromatic carbon atom of $Q_3$ ring to which Cy3 is to bond so as to form a fused ring with the aromatic carbon atom of $Q_3$ ring to which Cy3 is to bond, the nitrogen (N) atom, and the carbon atom of Cy1 to which the nitrogen (N) atom is bonded, and the ring formed by Cy3 is a substituted or unsubstituted alkylene of 1 to 10 carbon atoms, particularly a substituted or unsubstituted alkylene of 2 to 7 carbon atoms, and more particularly a substituted or unsubstituted alkylene of 2 to 5 carbon atoms, except for the aromatic carbon atom of $Q_3$ to which Cy3 is to bond, the aromatic carbon atom of $Q_3$ to which the nitrogen (N) atom is bonded, the nitrogen (N) atom, and the carbon atom of Cy1 to which the nitrogen (N) atom is bonded.

Among the dopant compounds according to the present disclosure, the boron compounds represented by Chemical Formulas D3 to D8 may have, on the aromatic hydrocarbon rings or heteroaromatic rings of T1 to T6 or on the aromatic hydrocarbon rings or heteroaromatic rings of $Q_1$ to $Q_3$, a substituent selected from a deuterium atom, an alkyl of 1 to 24 carbon atoms, an aryl of 6 to 24 carbon atoms, an alkylamino of 1 to 24 carbon atoms, an arylamino of 6 to 24 carbon atoms, wherein the alkyl radicals or the aryl radicals in the alkylamino of 1 to 24 carbon atoms and the arylamino of 6 to 24 carbon atoms on the rings may be linked to each other, and particularly a substituent selected from an alkyl of 1 to 12 carbon atoms, an aryl of 6 to 18 carbon atoms, an alkylamino of 1 to 12 carbon atoms, and an arylamino of 6 to 18 carbon atoms wherein the alkyl radicals or aryl radicals in the alkylamino of 1 to 12 carbon atoms and the arylamino of 6 to 18 carbon atoms on the rings may be linked to each other.

Concrete examples of the dopant compounds of Chemical Formulas D1 and D2 used in the light-emitting layer include the compounds of the following <Chemical Formula d1> to <Chemical Formula d240>:

<Chemical Formula d1>

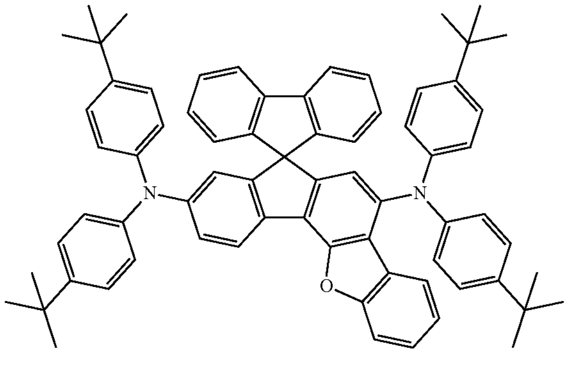

-continued
<Chemical Formula d2>
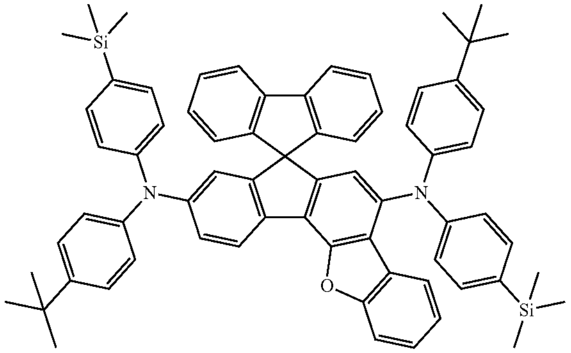
<Chemical Formula d3>
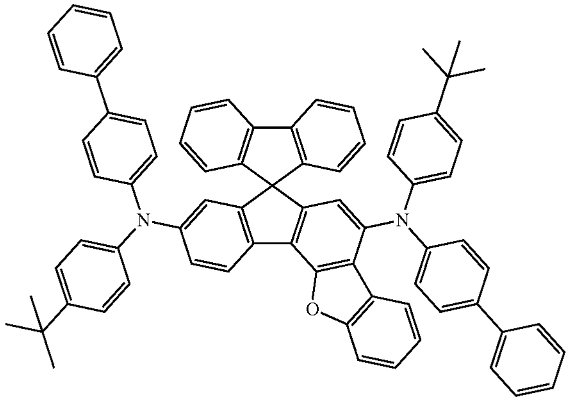
<Chemical Formula d4>
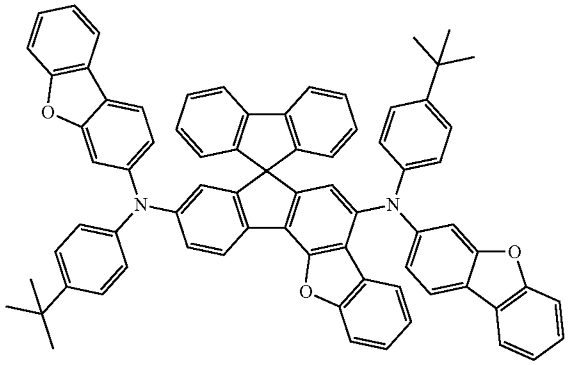
<Chemical Formula d5>
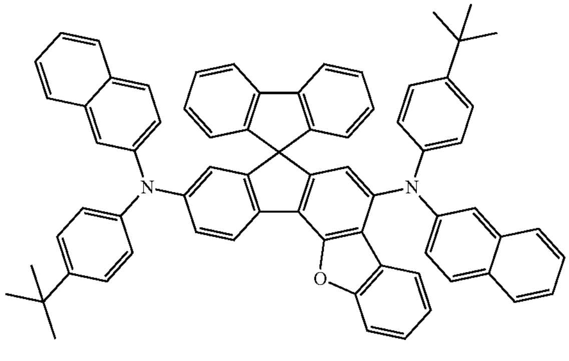
-continued
<Chemical Formula d6>
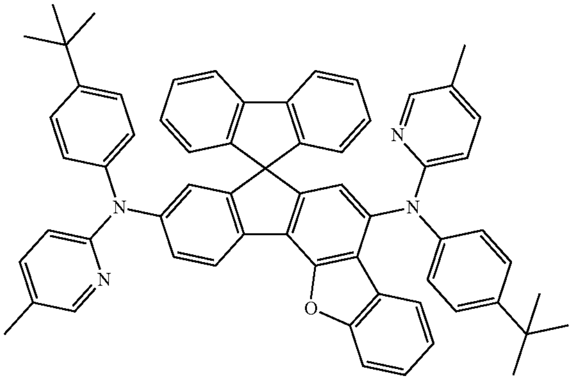
<Chemical Formula d7>
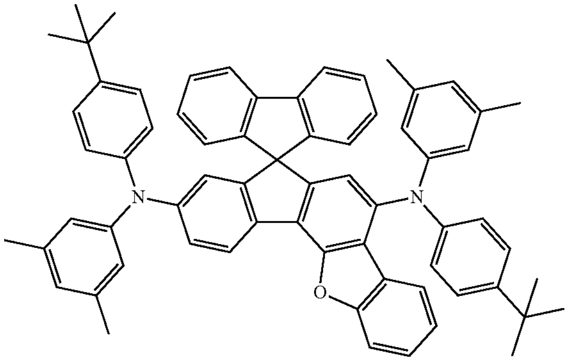
<Chemical Formula d8>
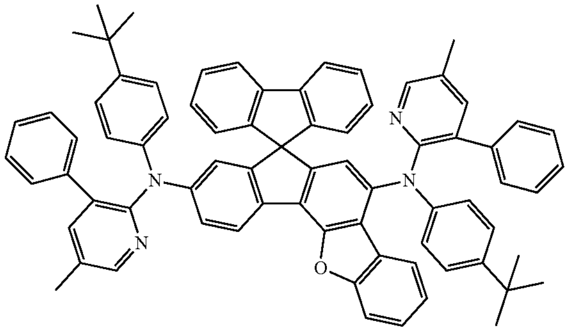
<Chemical Formula d9>
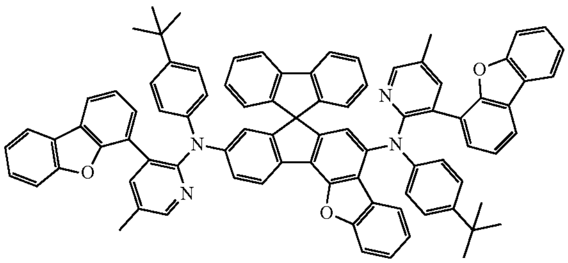

-continued
<Chemical Formula d10>
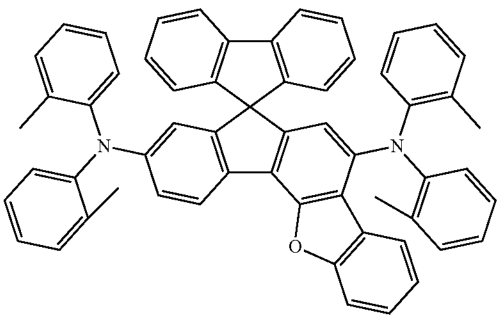
<Chemical Formula d11>
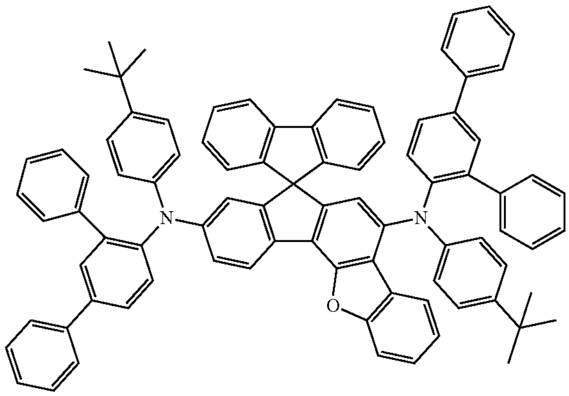
<Chemical Formula d12>
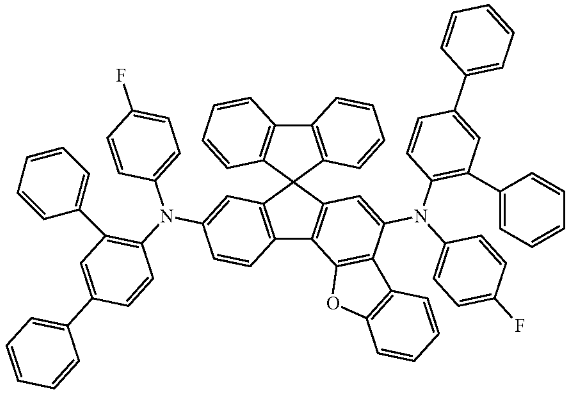
<Chemical Formula d13>
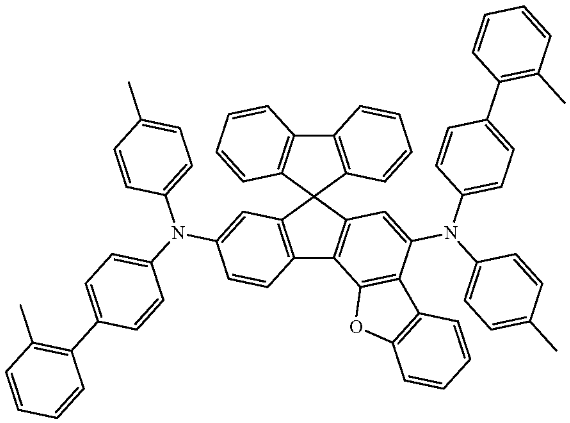
-continued
<Chemical Formula d14>
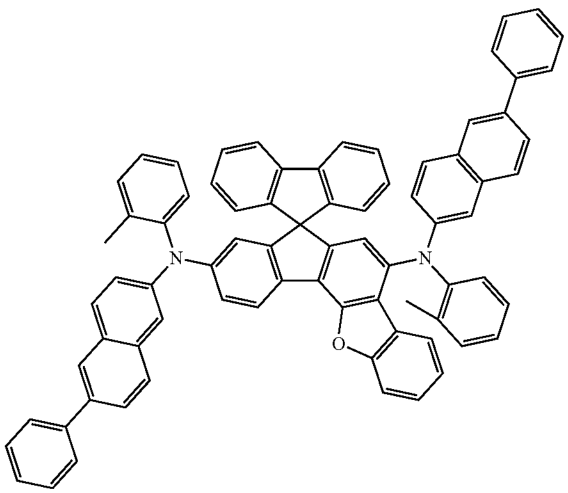
<Chemical Formula d15>
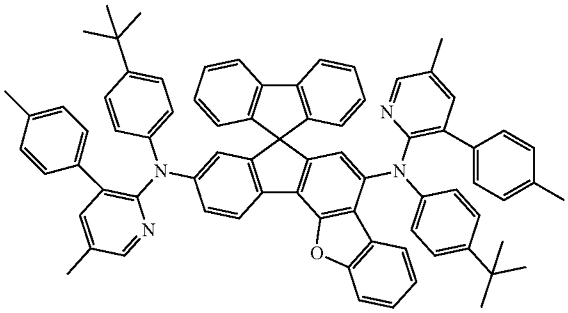
<Chemical Formula d16>
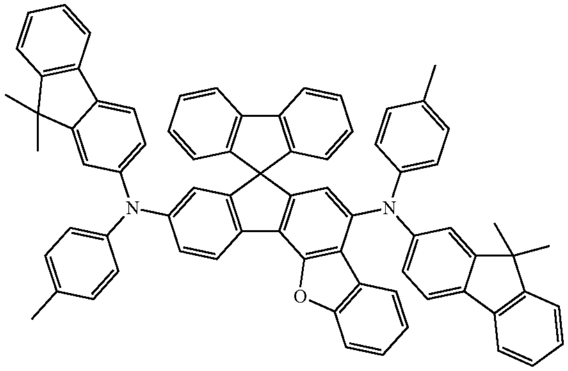
<Chemical Formula d17>
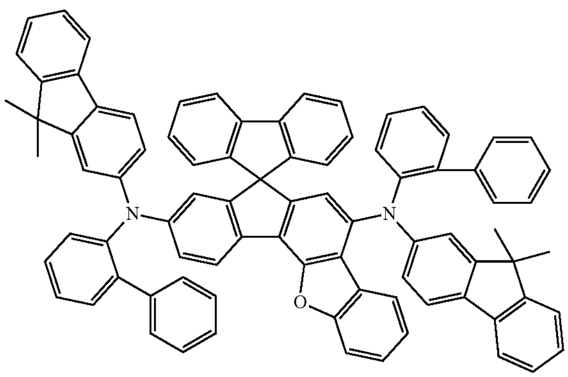

-continued
<Chemical Formula d18>
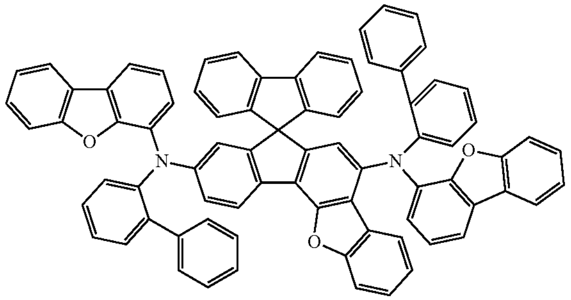
<Chemical Formula d19>
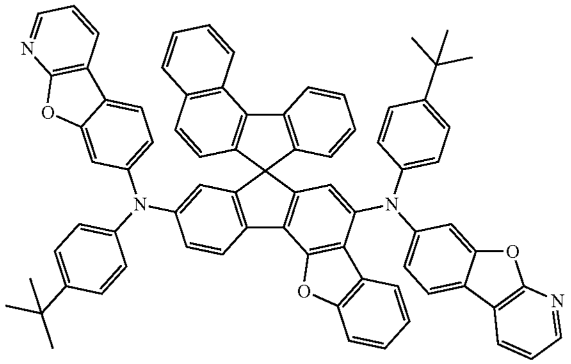
<Chemical Formula d20>
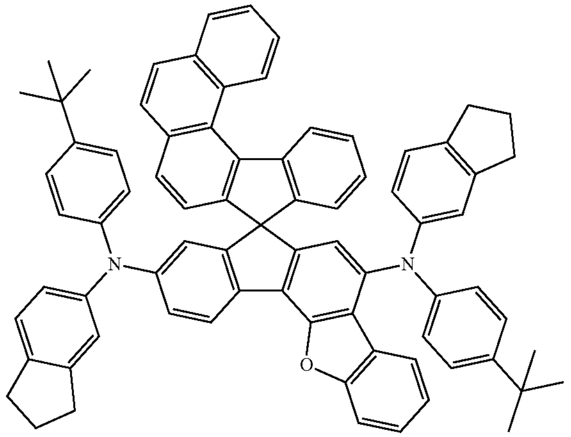
<Chemical Formula d21>
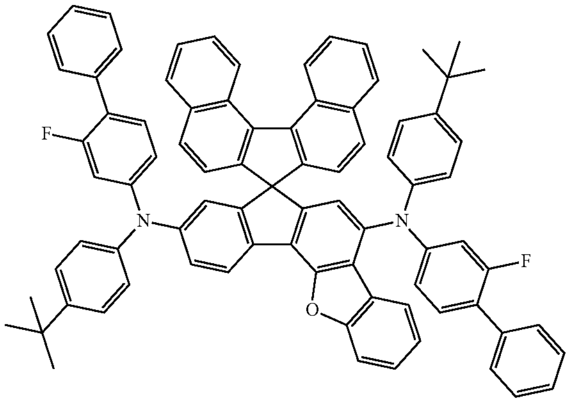
-continued
<Chemical Formula d22>
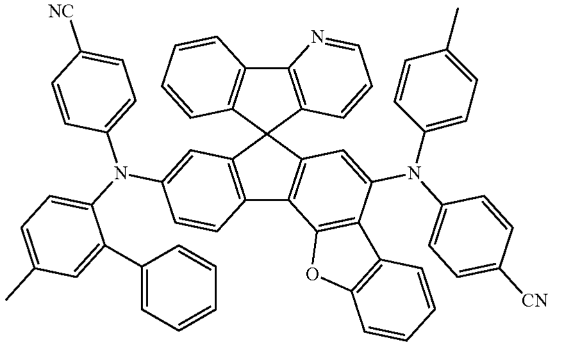
<Chemical Formula d23>
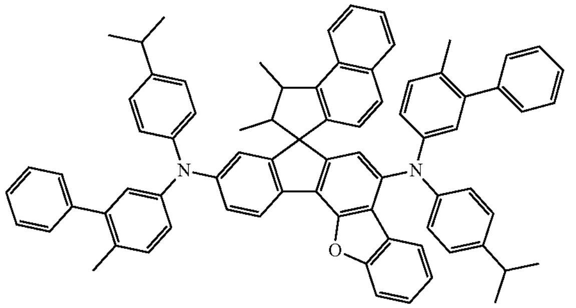
<Chemical Formula d24>
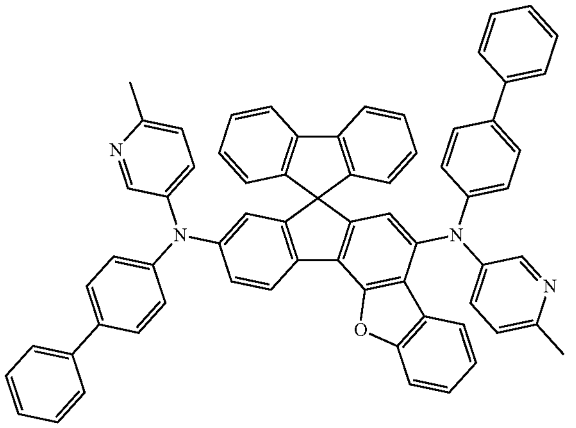
<Chemical Formula d25>
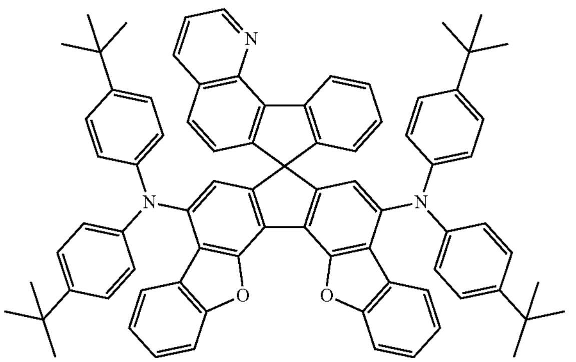

-continued
<Chemical Formula d26>
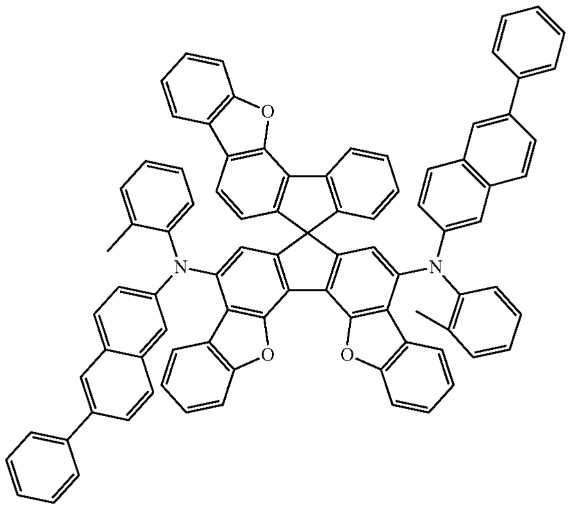
<Chemical Formula d27>
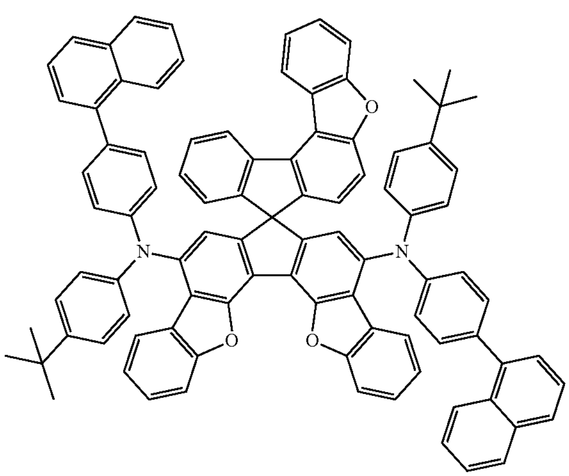
<Chemical Formula d28>
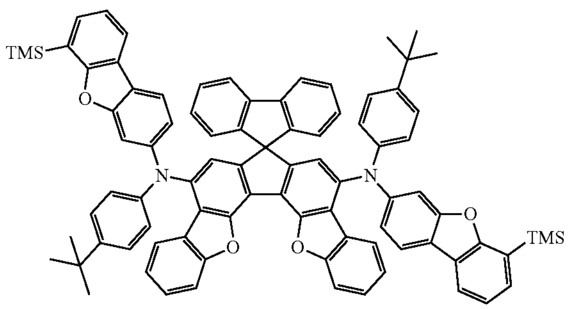
<Chemical Formula d29>
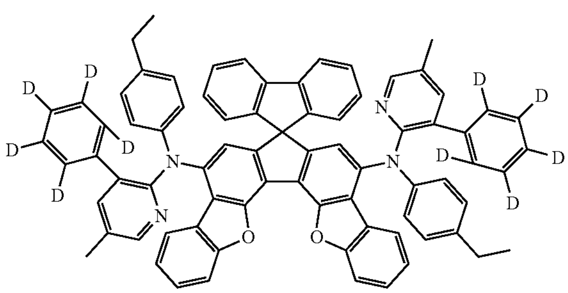
-continued
<Chemical Formula d30>
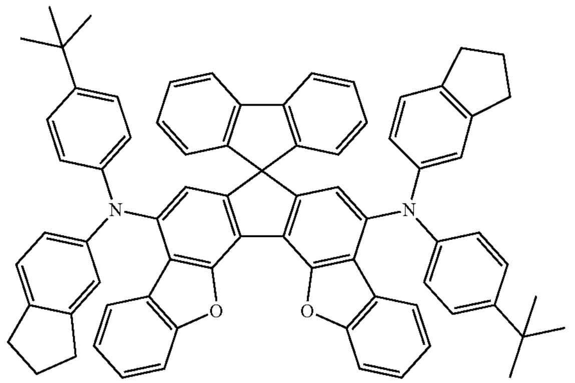
<Chemical Formula d31>
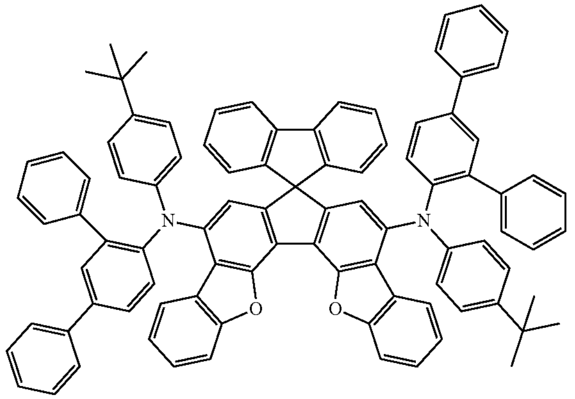
<Chemical Formula d32>
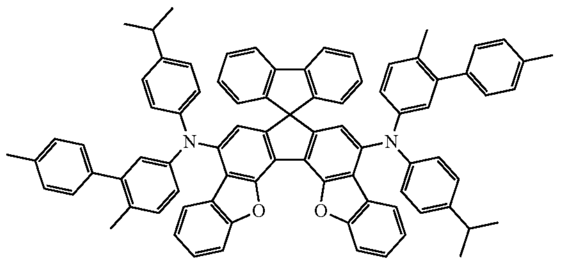
<Chemical Formula d33>
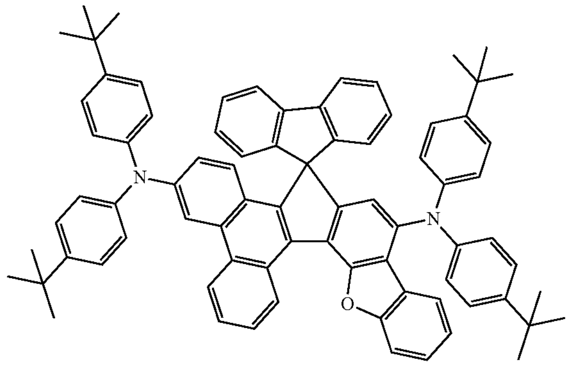

-continued
<Chemical Formula d34>
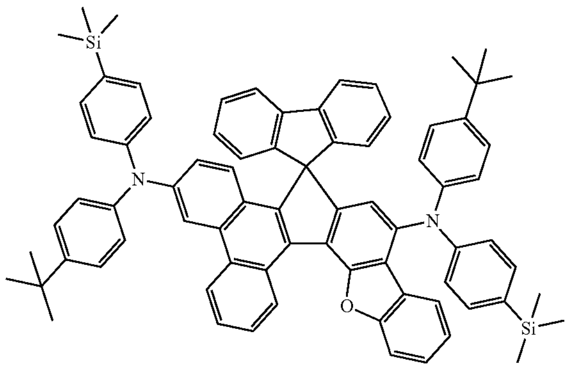
<Chemical Formula d35>
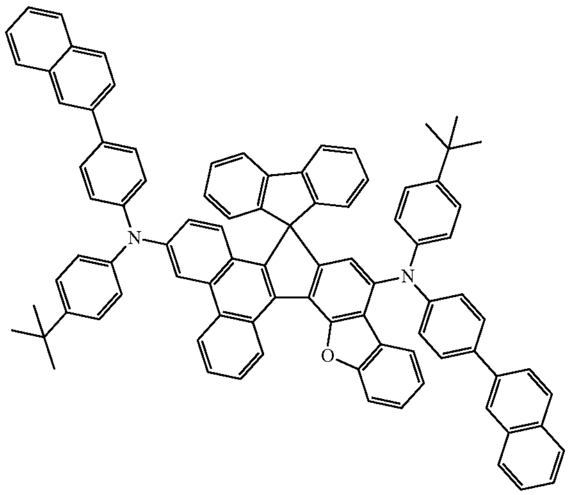
<Chemical Formula d36>
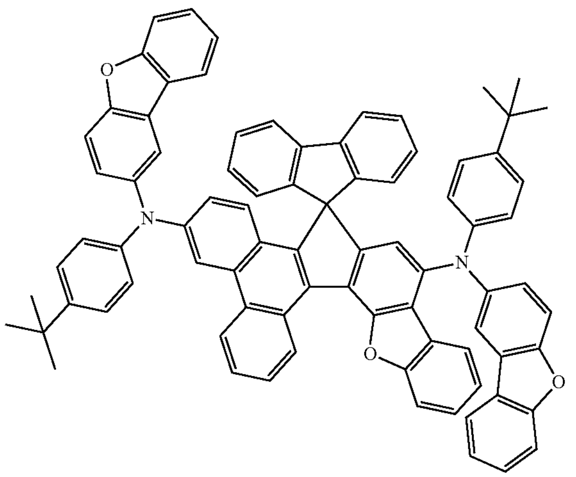
-continued
<Chemical Formula d37>
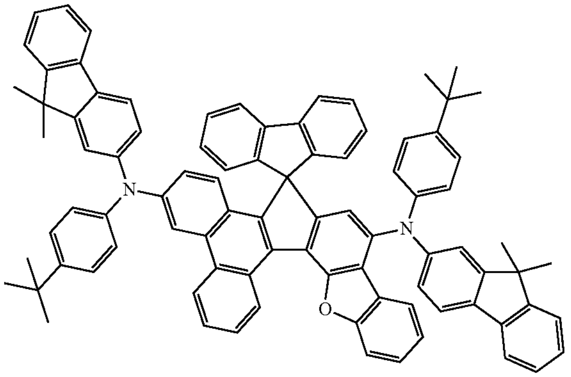
<Chemical Formula d38>
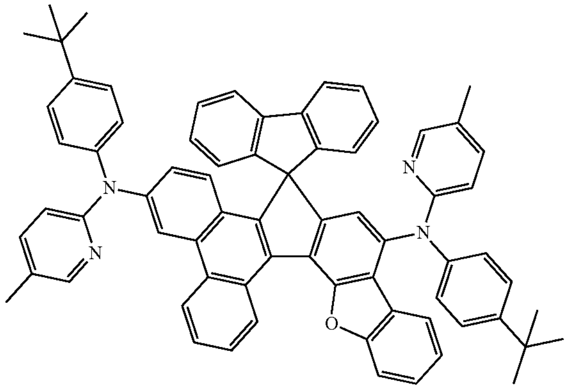
<Chemical Formula d39>
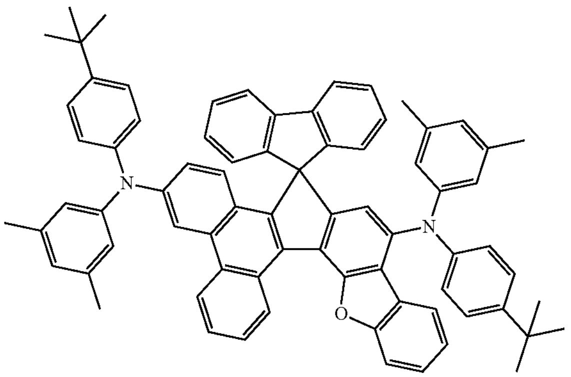
<Chemical Formula d40>
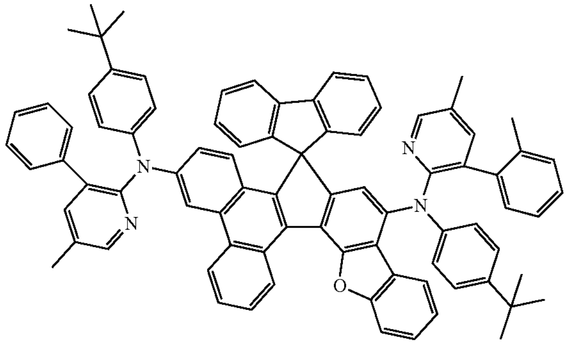

-continued
<Chemical Formula d41>
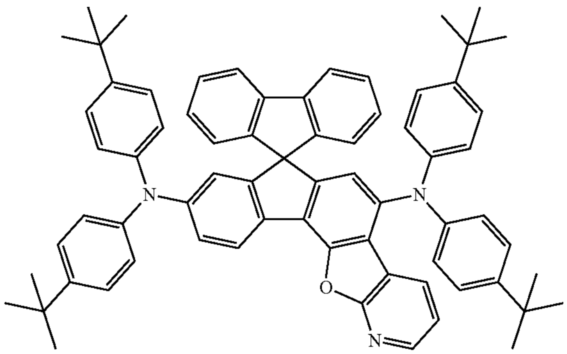
<Chemical Formula d42>
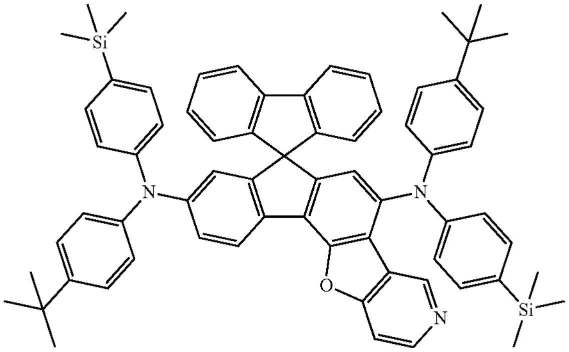
<Chemical Formula d43>
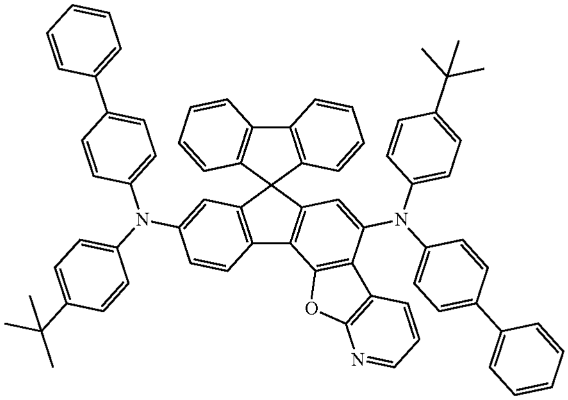
<Chemical Formula d44>
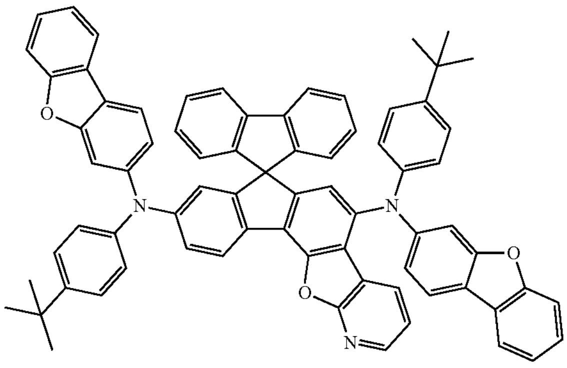
-continued
<Chemical Formula d45>
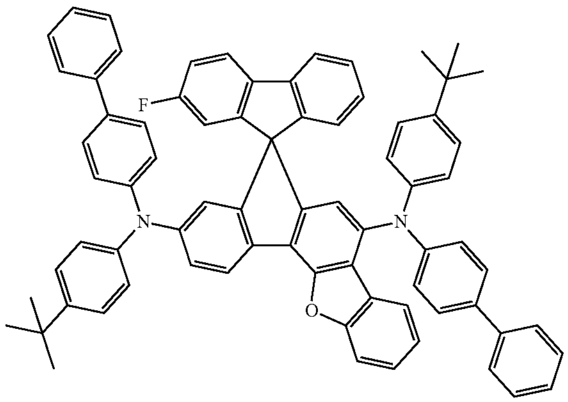
<Chemical Formula d46>
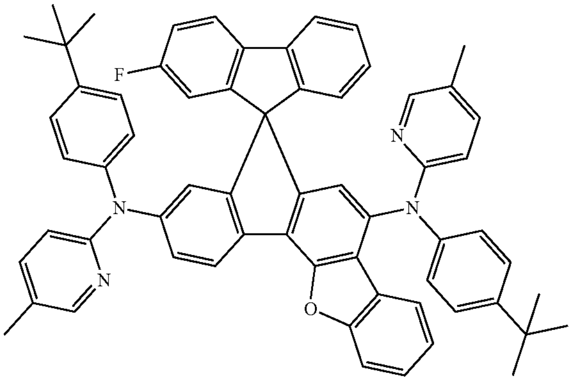
<Chemical Formula d47>
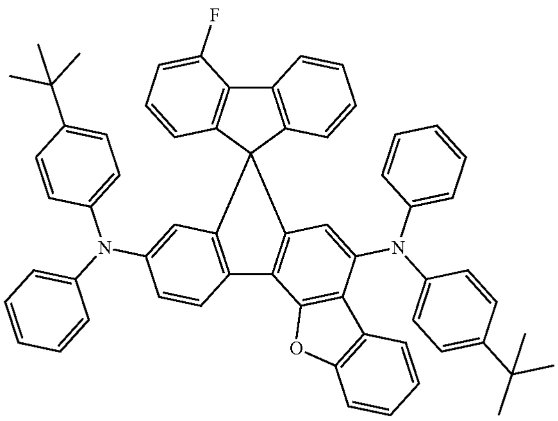
<Chemical Formula d48>
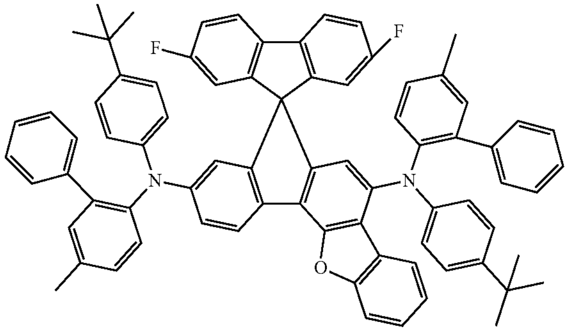

-continued
<Chemical Formula d49>
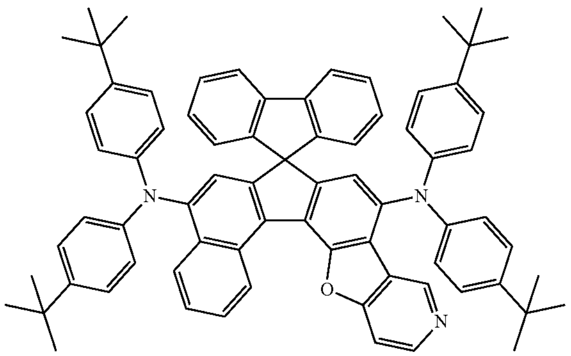
<Chemical Formula d50>
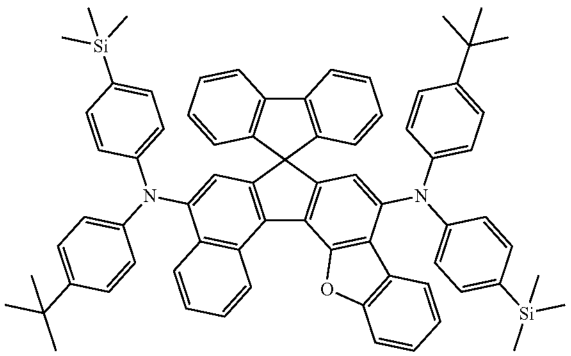
<Chemical Formula d51>
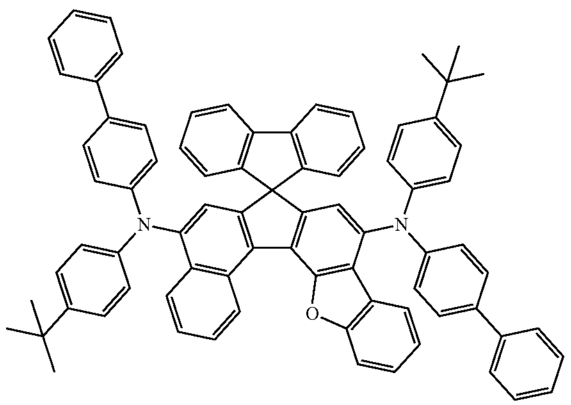
<Chemical Formula d52>
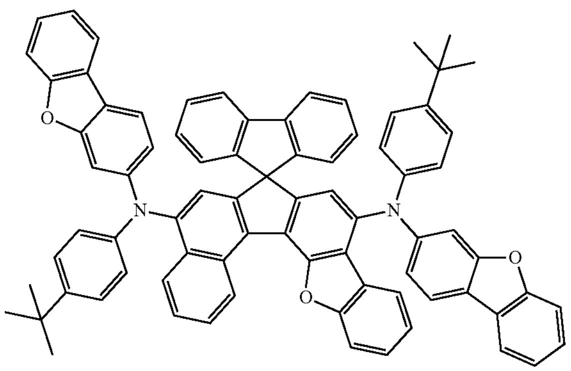
-continued
<Chemical Formula d53>
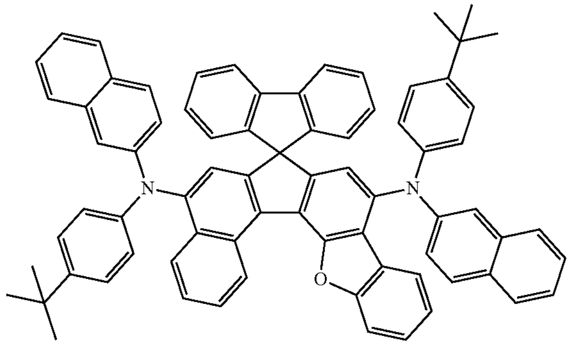
<Chemical Formula d54>
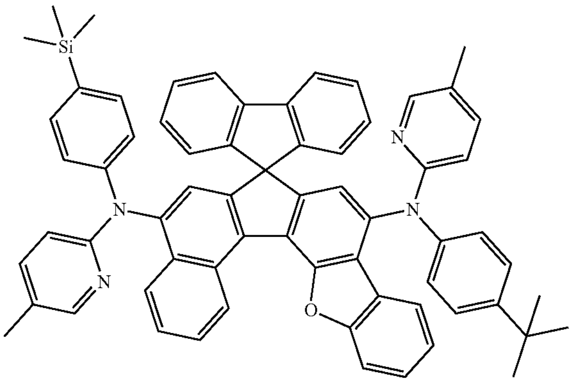
<Chemical Formula d55>
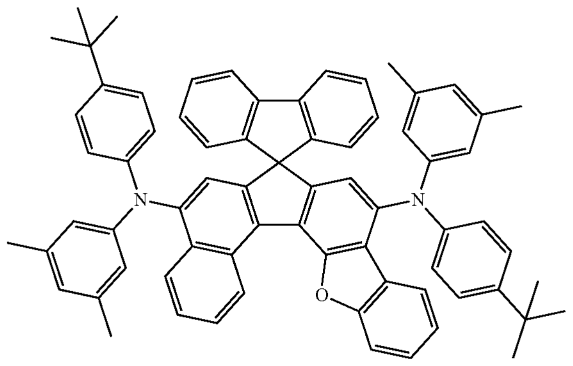
<Chemical Formula d56>
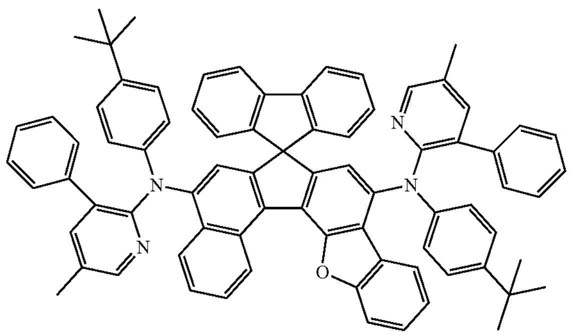

-continued
<Chemical Formula d57>
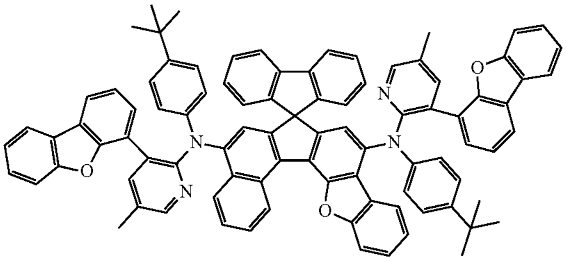
<Chemical Formula d58>
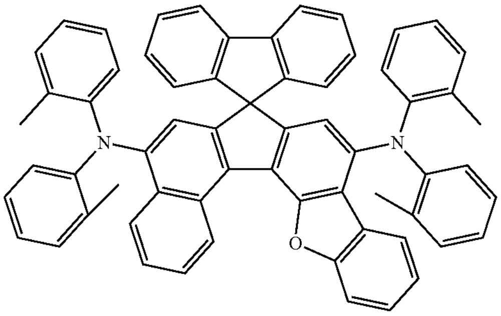
<Chemical Formula d59>
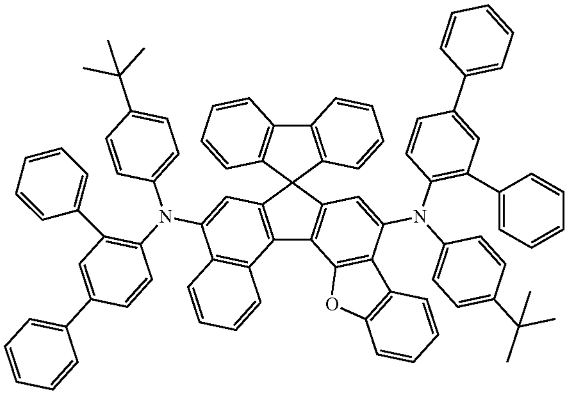
<Chemical Formula d60>
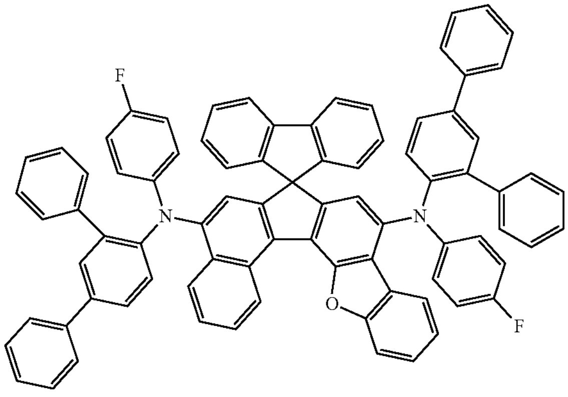
-continued
<Chemical Formula d61>
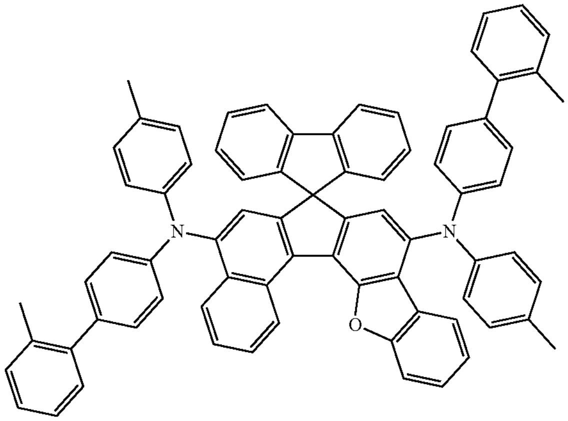
<Chemical Formula d62>
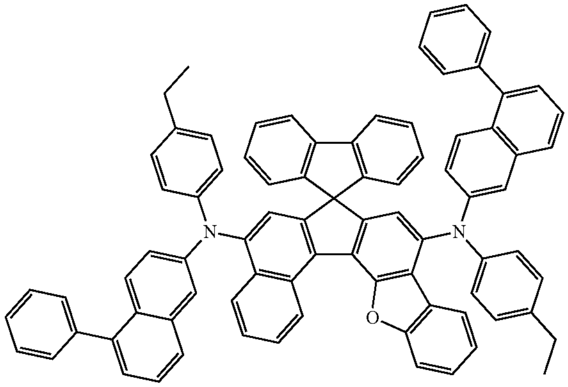
<Chemical Formula d63>
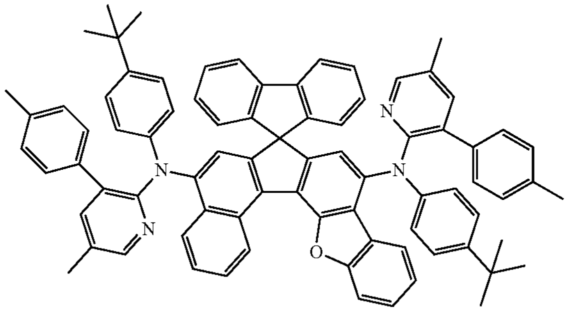
<Chemical Formula d64>
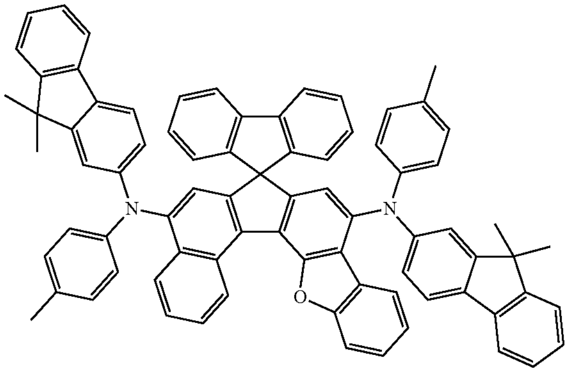

-continued
<Chemical Formula d65>
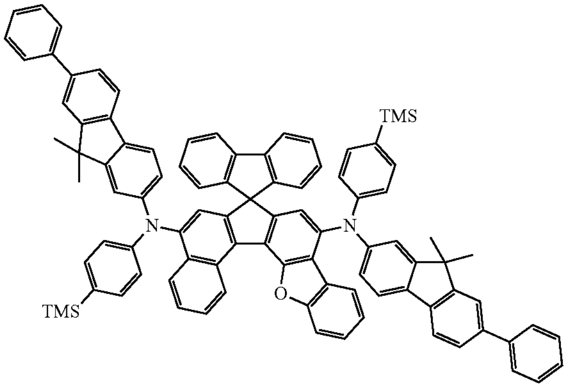
<Chemical Formula d66>
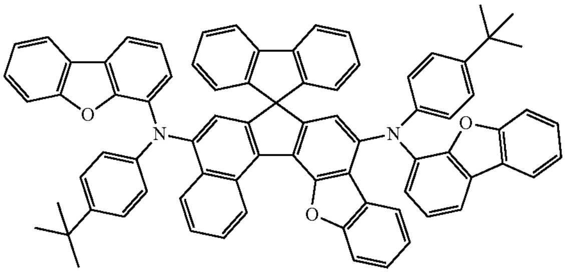
<Chemical Formula d67>
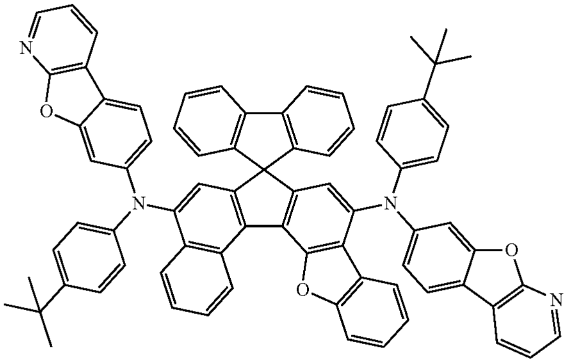
<Chemical Formula d68>
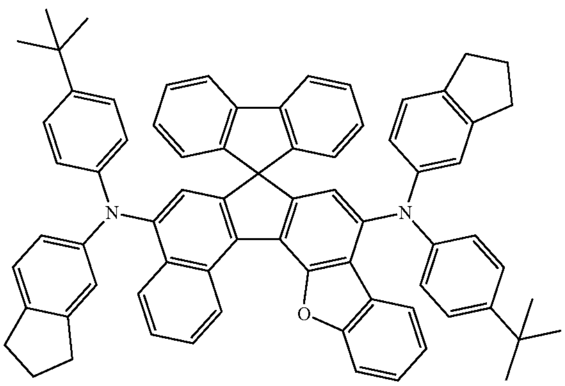
-continued
<Chemical Formula d69>
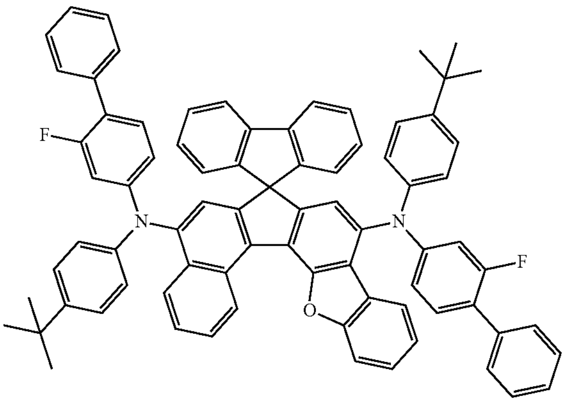
<Chemical Formula d70>
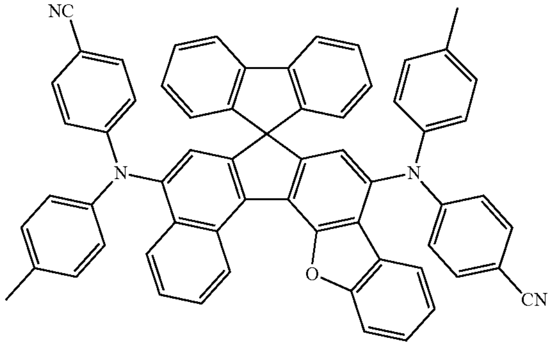
<Chemical Formula d71>
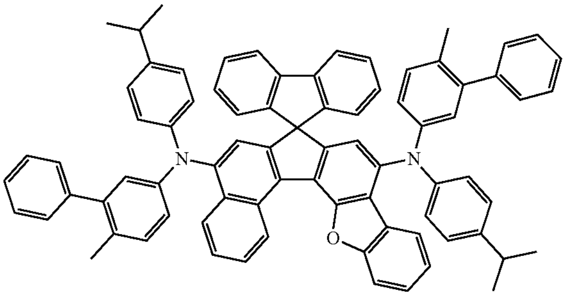
<Chemical Formula d72>
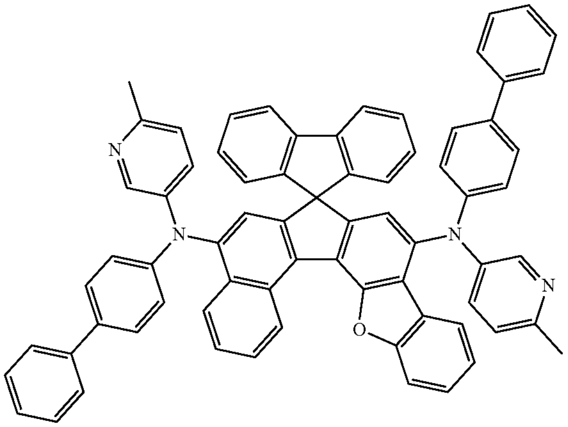

-continued
<Chemical Formula d73>
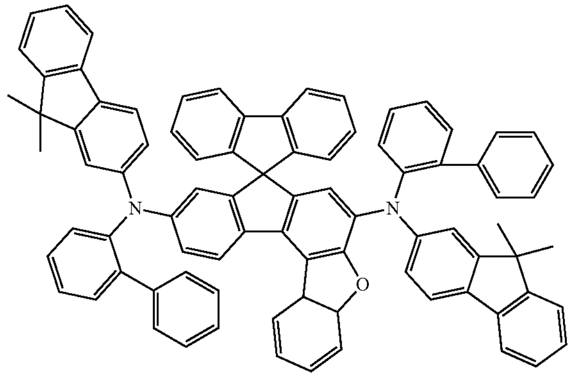
<Chemical Formula d74>
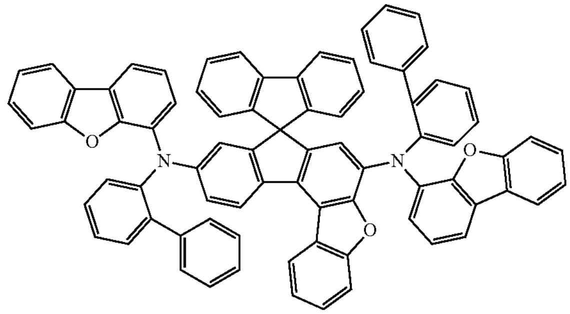
<Chemical Formula d75>
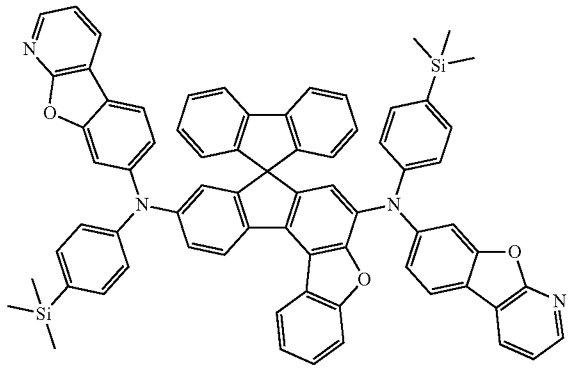
<Chemical Formula d76>
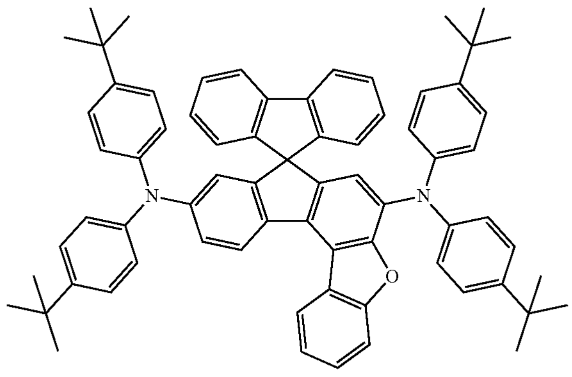
-continued
<Chemical Formula d77>
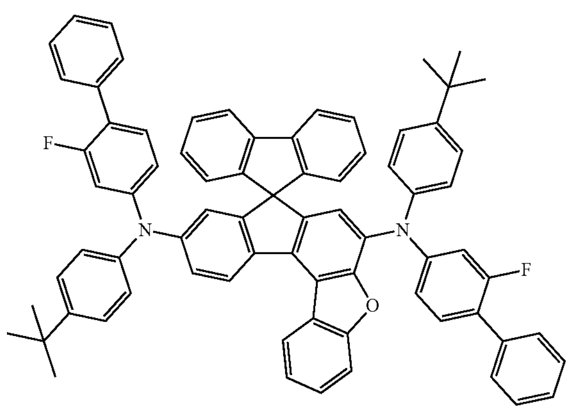
<Chemical Formula d78>
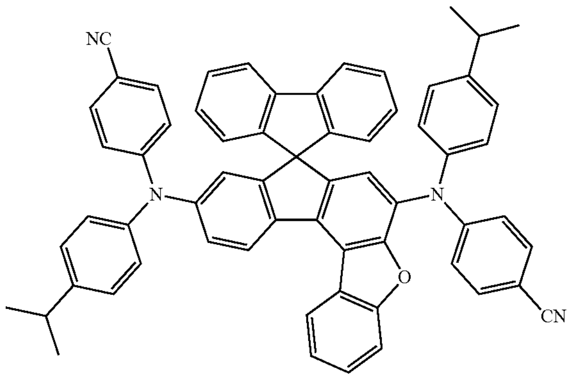
<Chemical Formula d79>
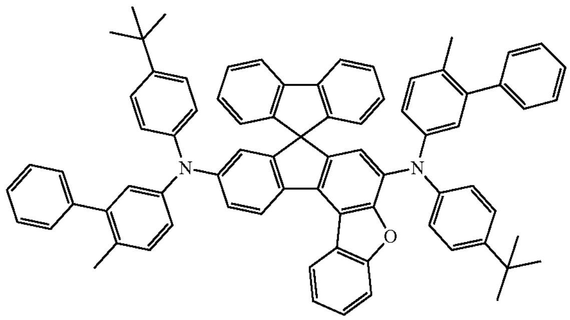
<Chemical Formula d80>
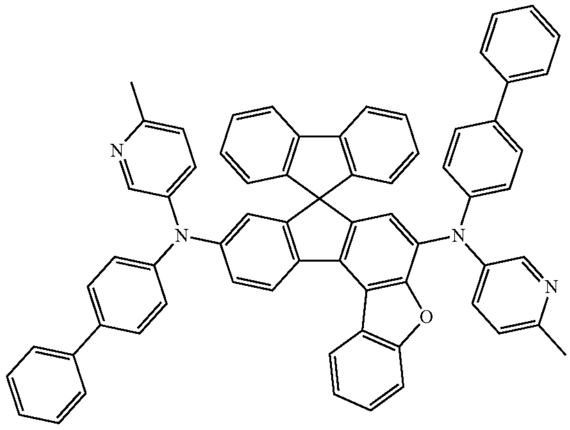

-continued
<Chemical Formula d81>
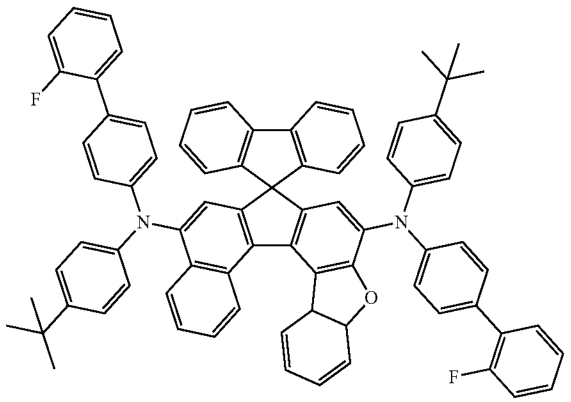
<Chemical Formula d82>
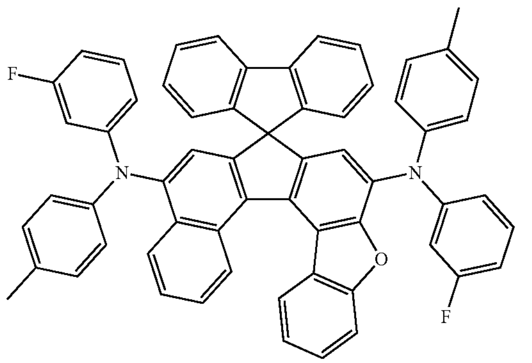
<Chemical Formula d83>
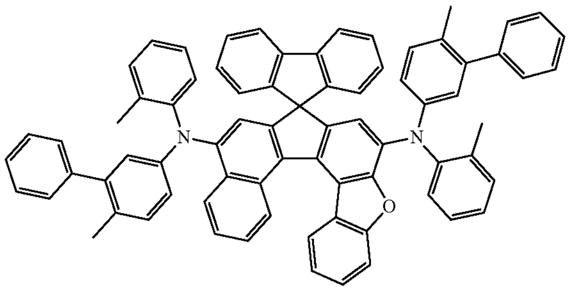
<Chemical Formula d84>
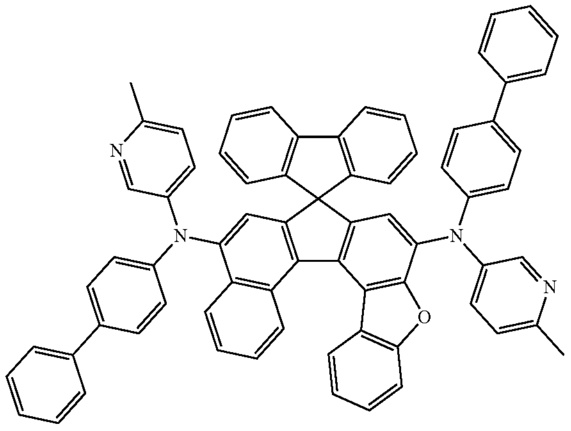
-continued
<Chemical Formula d85>
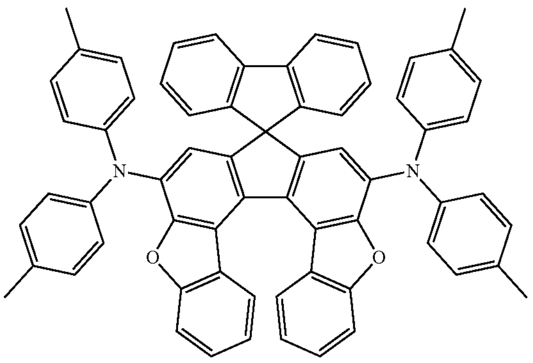
<Chemical Formula d86>
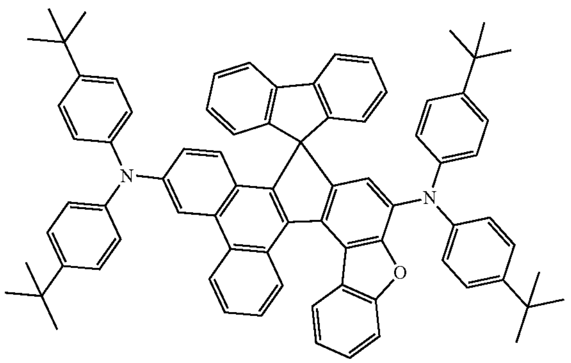
<Chemical Formula d87>
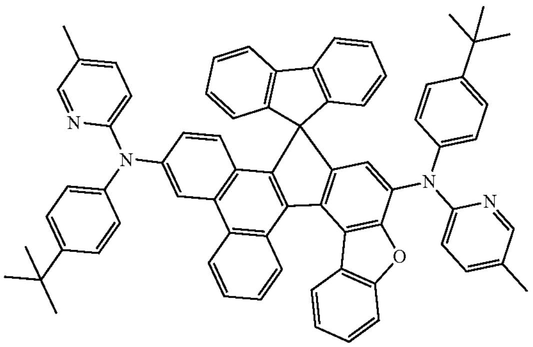
<Chemical Formula d88>
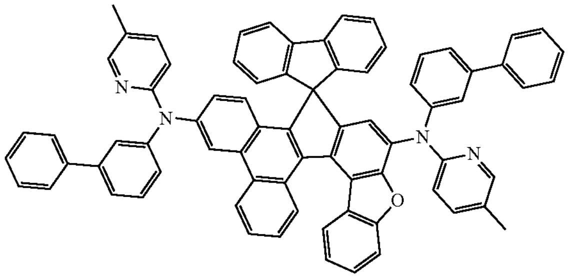

-continued
<Chemical Formula d89>
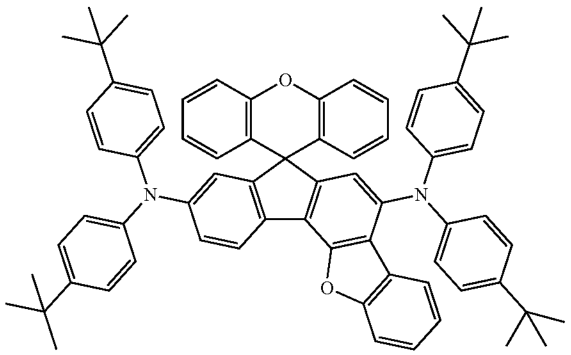
<Chemical Formula d90>
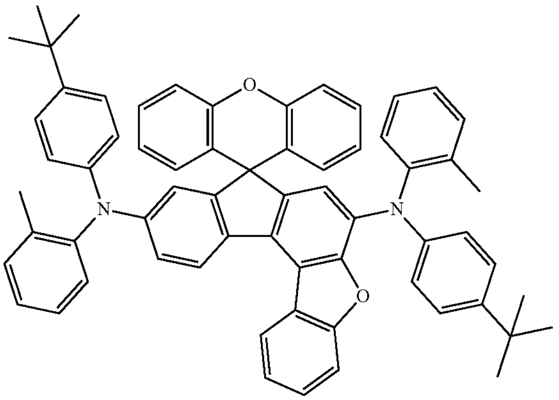
<Chemical Formula d91>
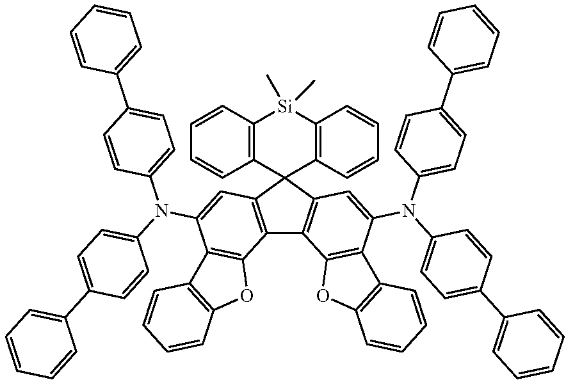
<Chemical Formula d92>
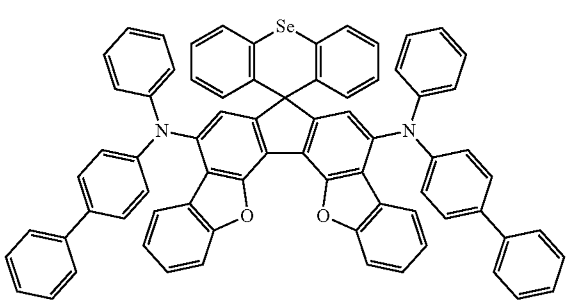
-continued
<Chemical Formula d93>
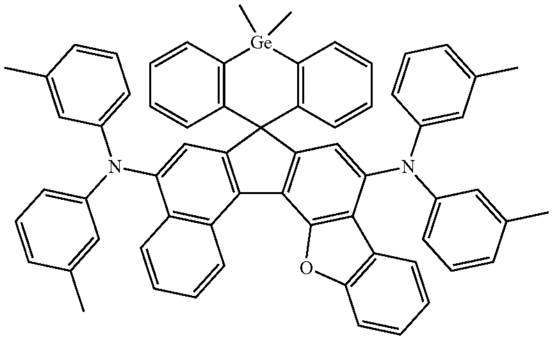
<Chemical Formula d94>
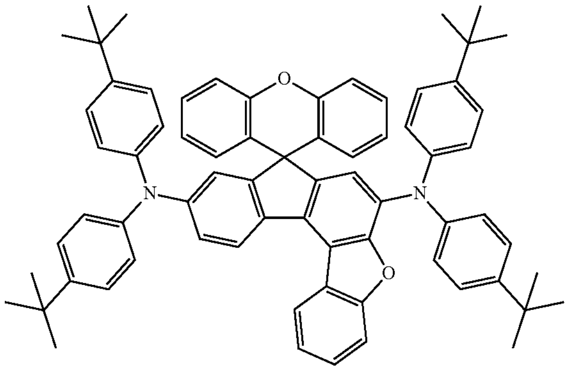
<Chemical Formula d95>
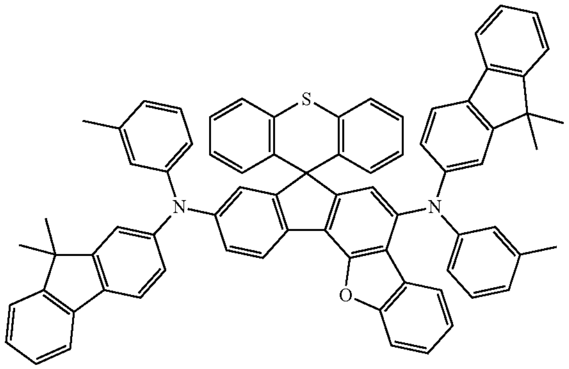
<Chemical Formula d96>
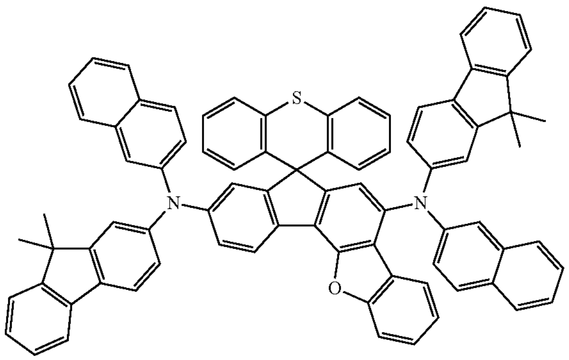

-continued
<Chemical Formula d97>
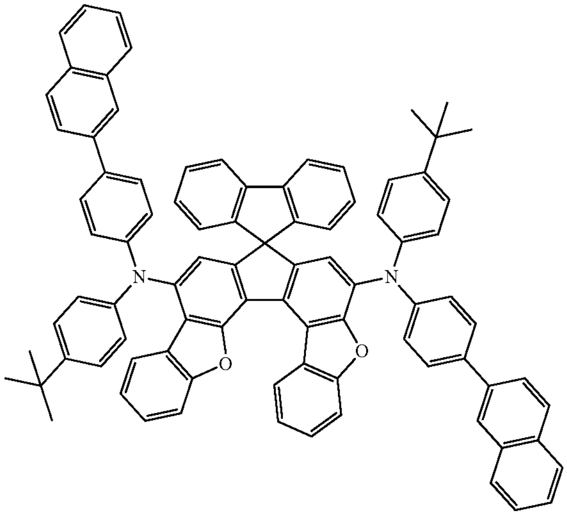
<Chemical Formula d98>
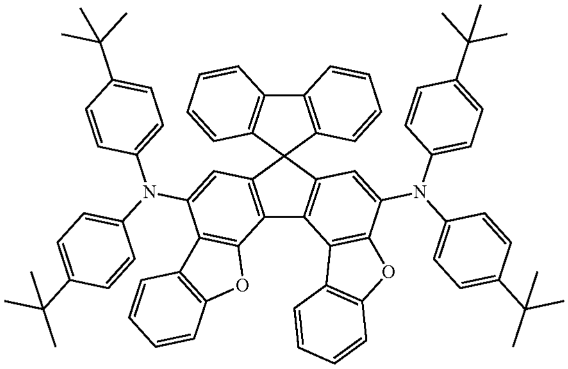
<Chemical Formula d99>
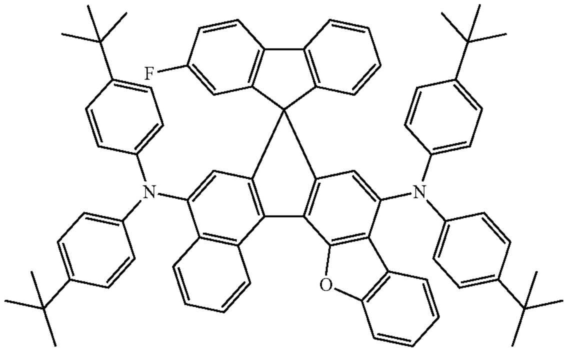
-continued
<Chemical Formula d100>
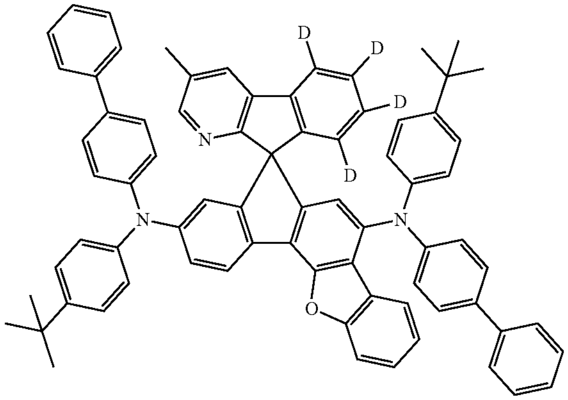
<Chemical Formula d101>
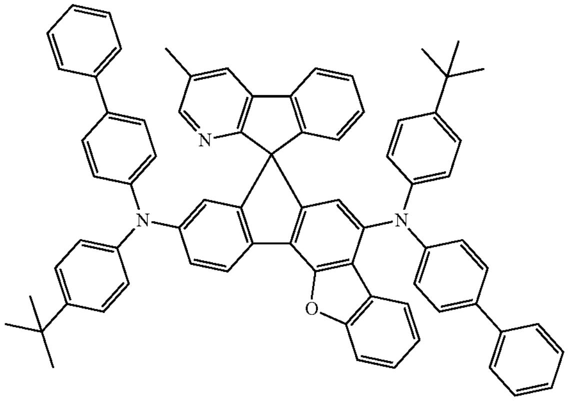
<Chemical Formula d102>
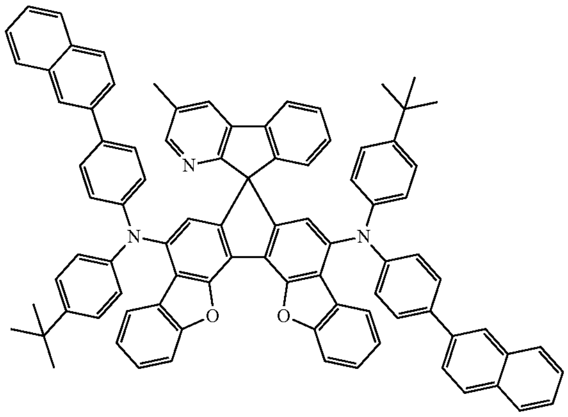

-continued
<Chemical Formula d103>
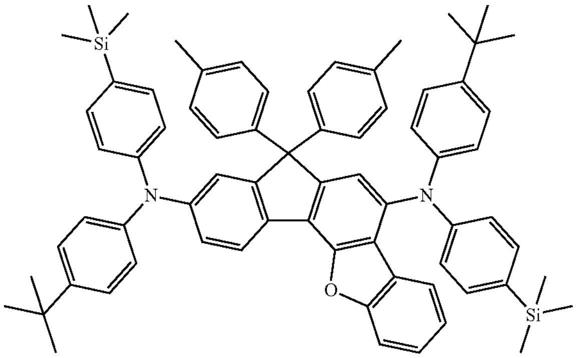
<Chemical Formula d104>
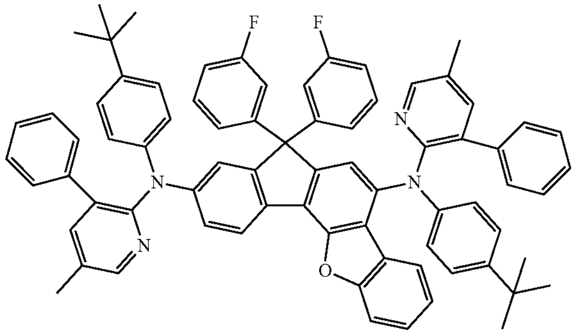
<Chemical Formula d105>
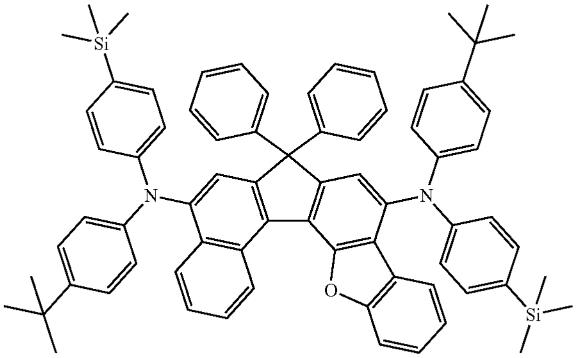
<Chemical Formula d106>
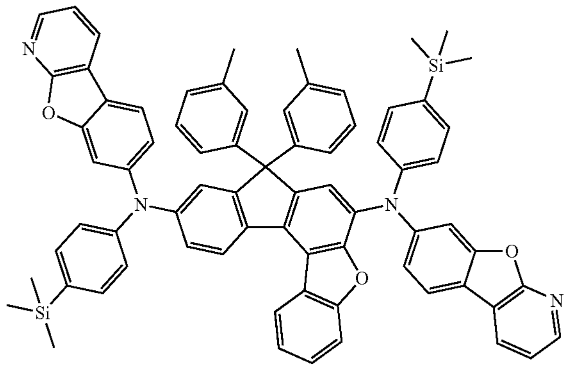
-continued
<Chemical Formula d107>
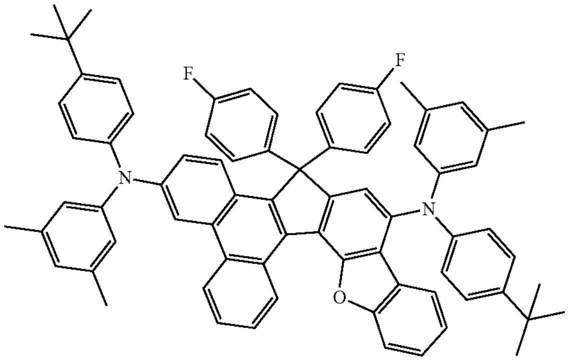
<Chemical Formula d108>
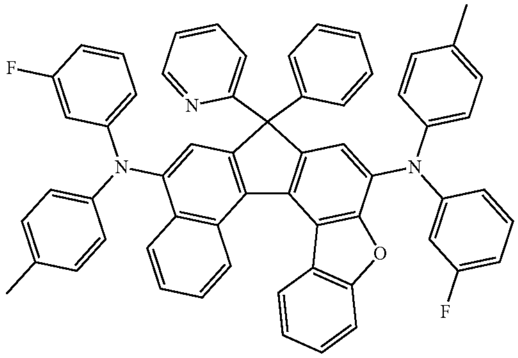
<Chemical Formula d109>
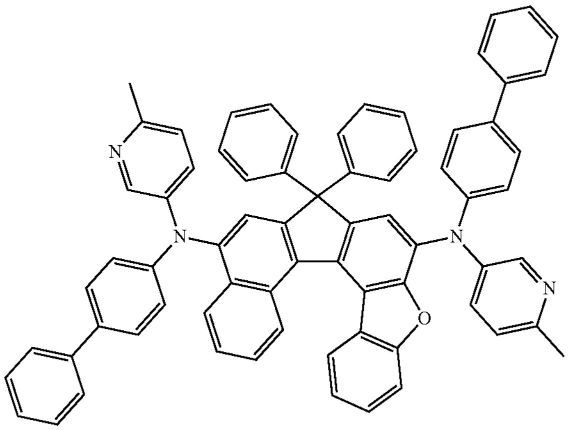
<Chemical Formula d110>
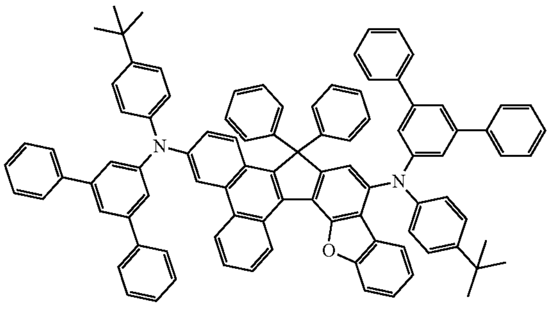

-continued
<Chemical Formula d111>
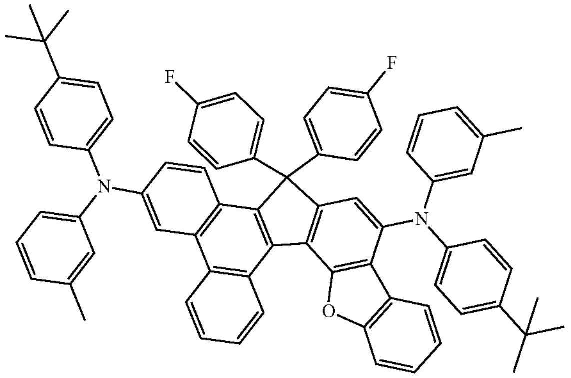
<Chemical Formula d112>
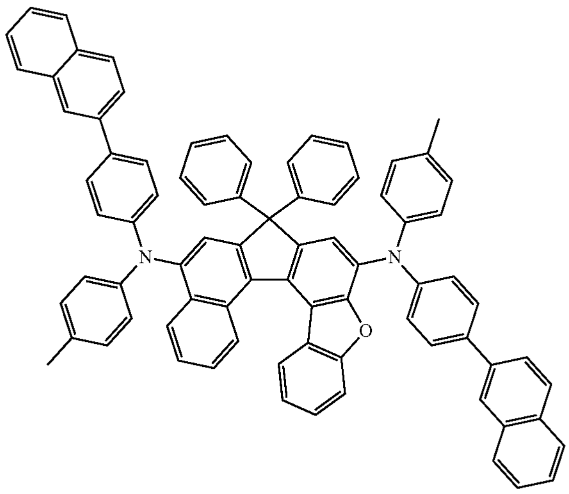
<Chemical Formula d113>
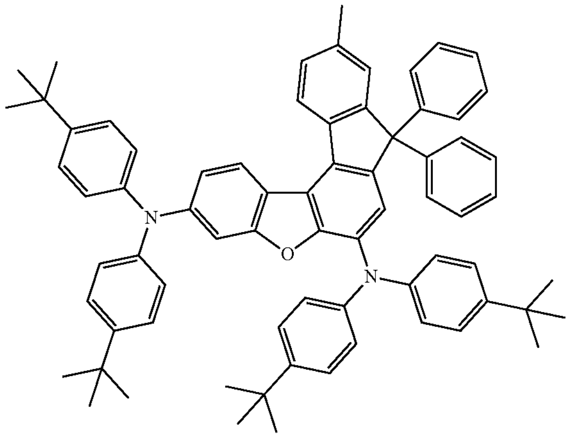
-continued
<Chemical Formula d114>
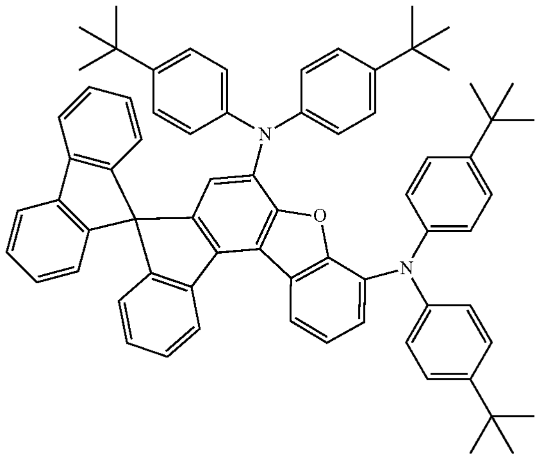
<Chemical Formula d115>
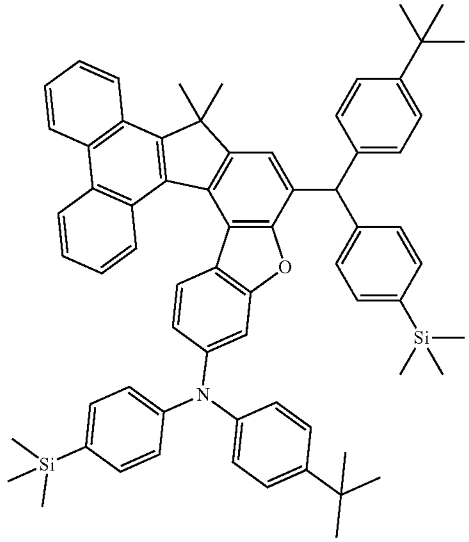
<Chemical Formula d116>
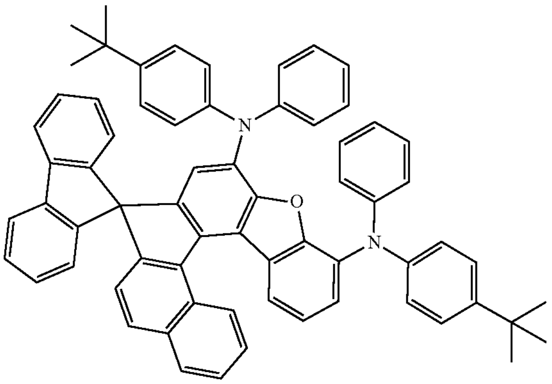

-continued
<Chemical Formula d117>
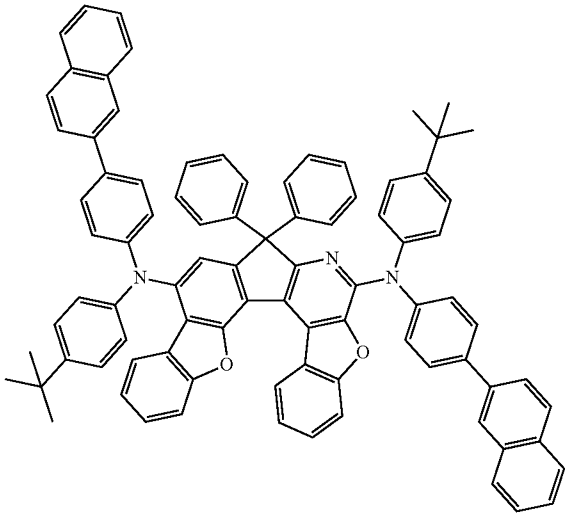
<Chemical Formula d118>
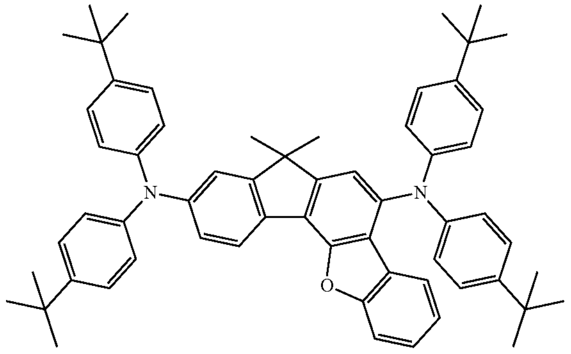
<Chemical Formula d119>
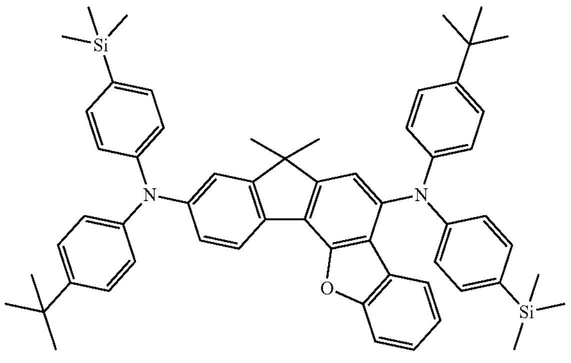
-continued
<Chemical Formula d120>
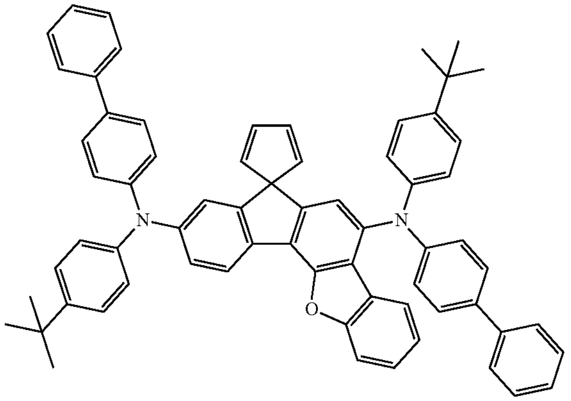
<Chemical Formula d121>
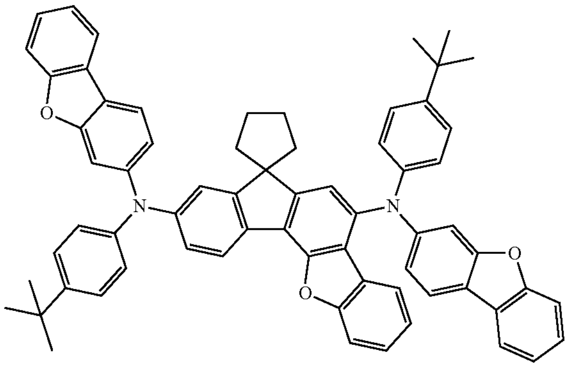
<Chemical Formula d122>
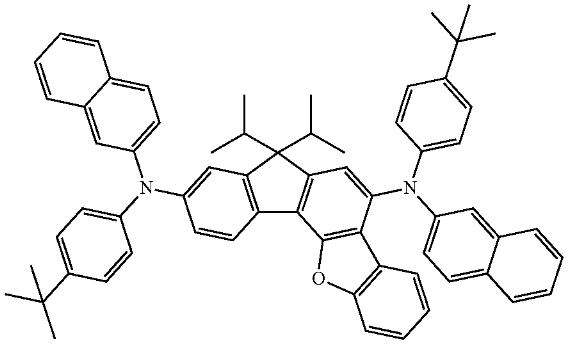
<Chemical Formula d123>
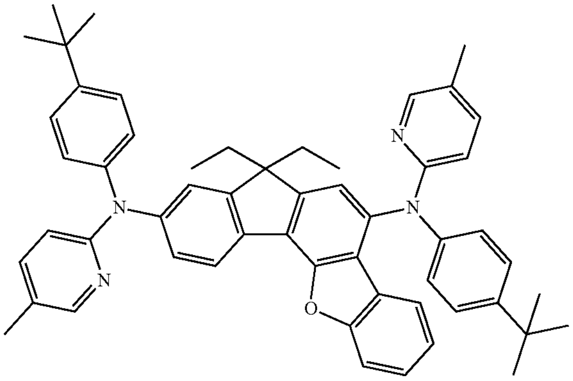

<Chemical Formula d124>
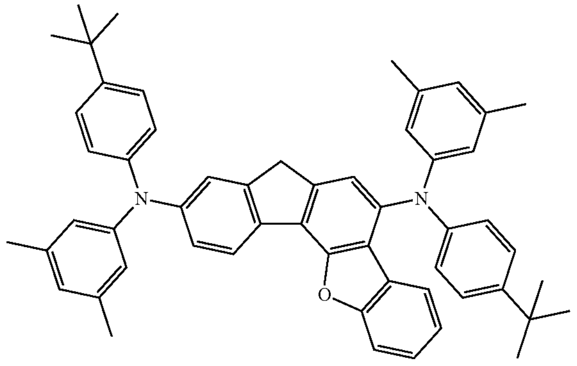
<Chemical Formula d124>
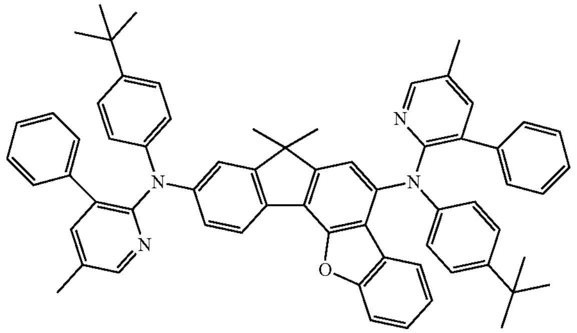
<Chemical Formula d126>
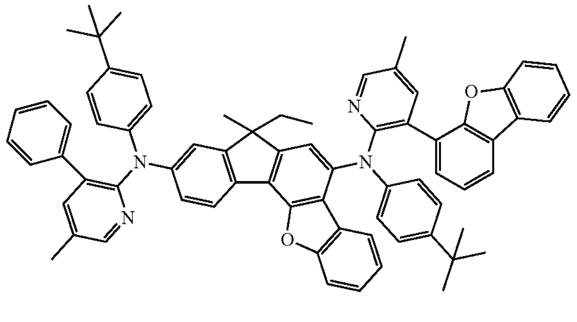
<Chemical Formula d127>
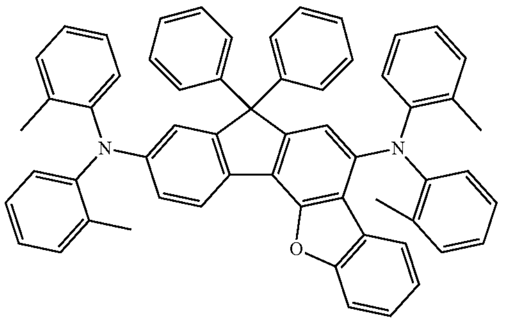
-continued
<Chemical Formula d128>
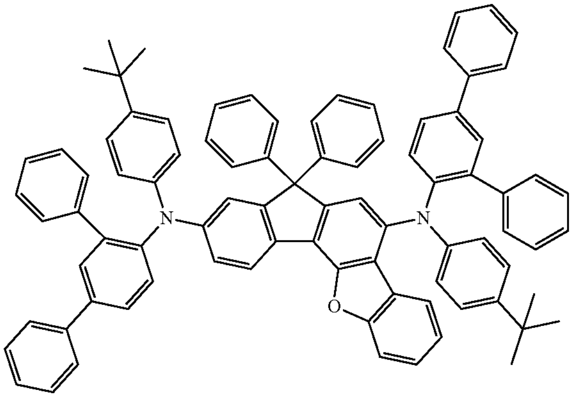
<Chemical Formula d129>
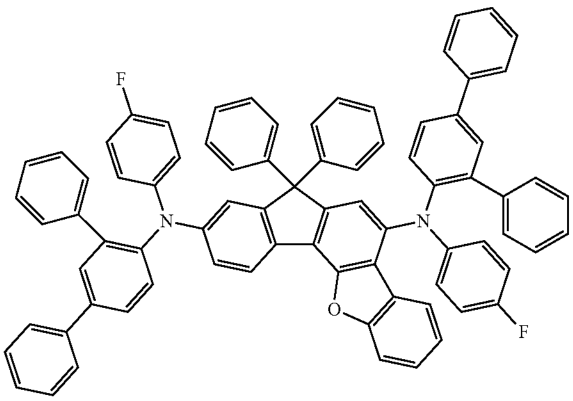
<Chemical Formula d130>
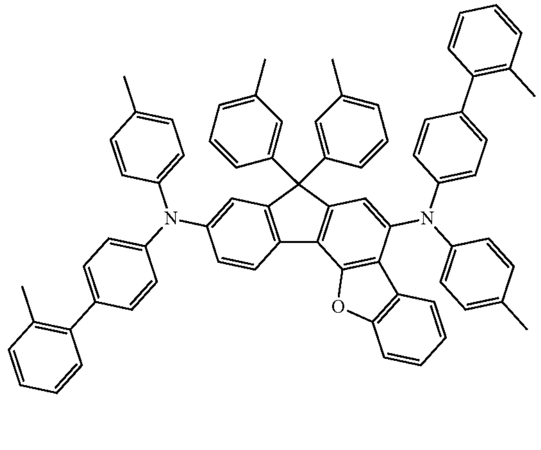

-continued
<Chemical Formula d131>
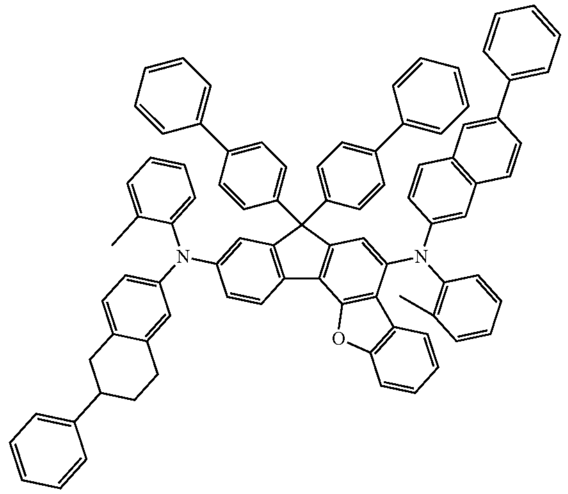
<Chemical Formula d132>
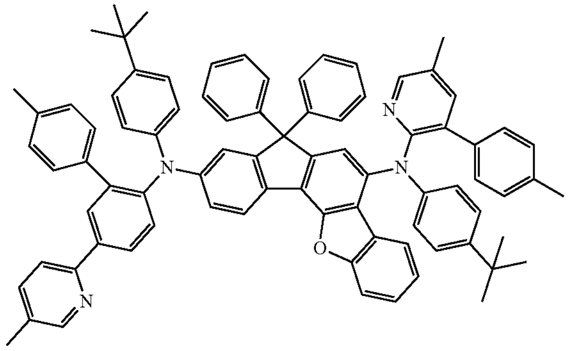
<Chemical Formula d133>
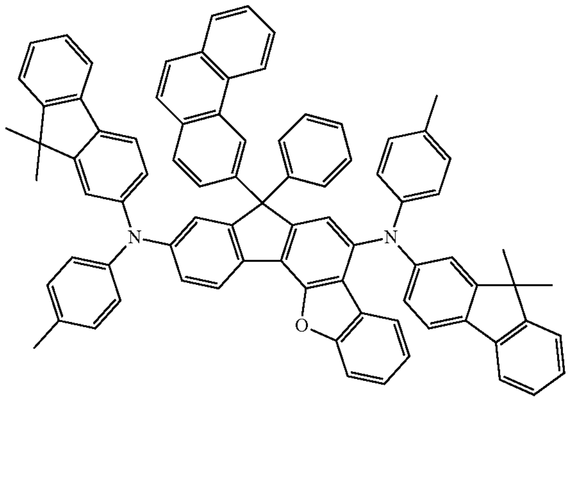
-continued
<Chemical Formula d134>
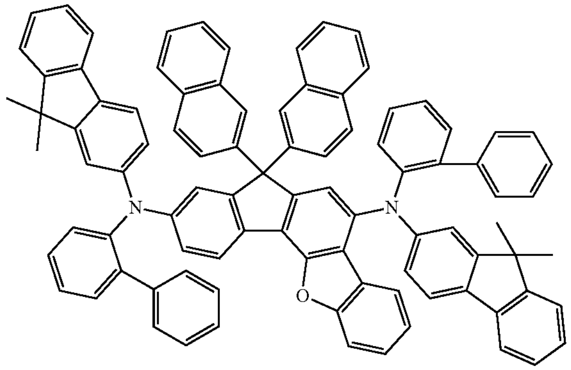
<Chemical Formula d135>
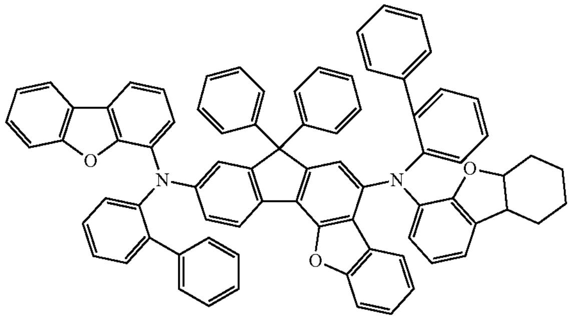
<Chemical Formula d136>
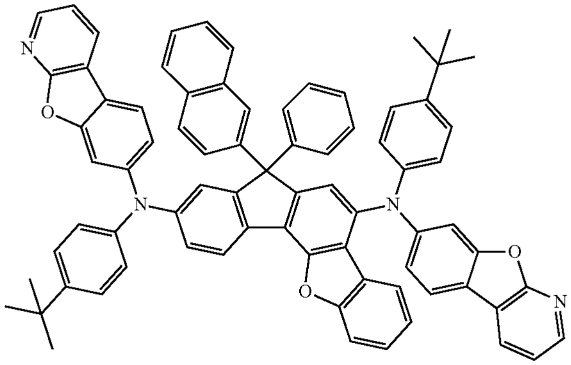
<Chemical Formula d137>
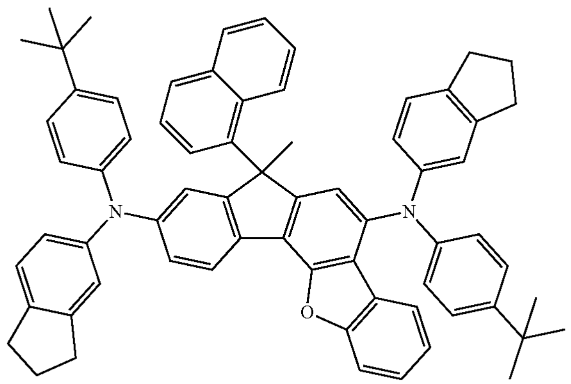

-continued
<Chemical Formula d138>
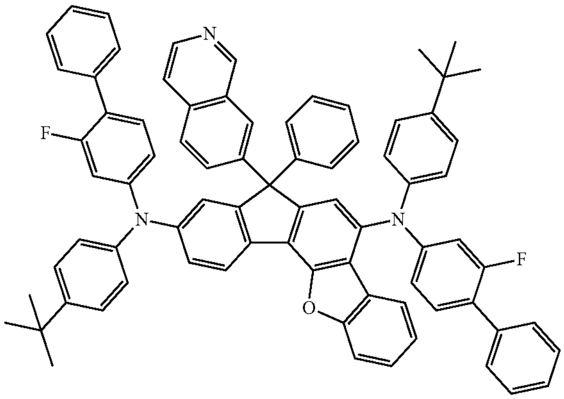
<Chemical Formula d139>
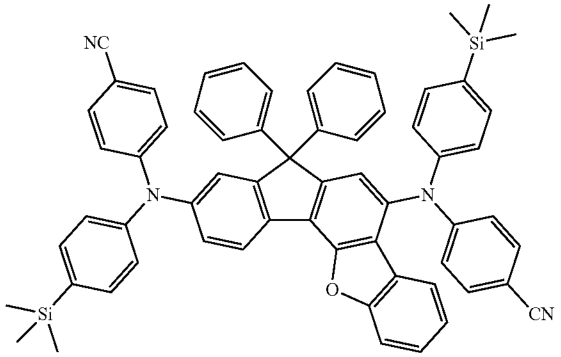
<Chemical Formula d140>
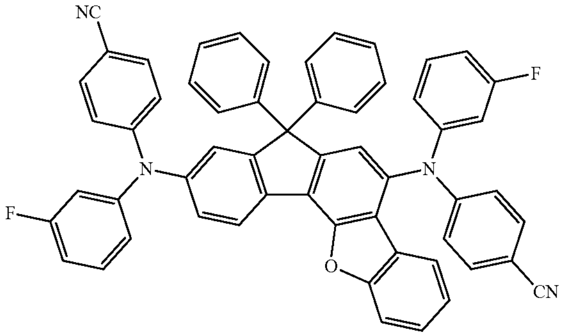
<Chemical Formula d141>
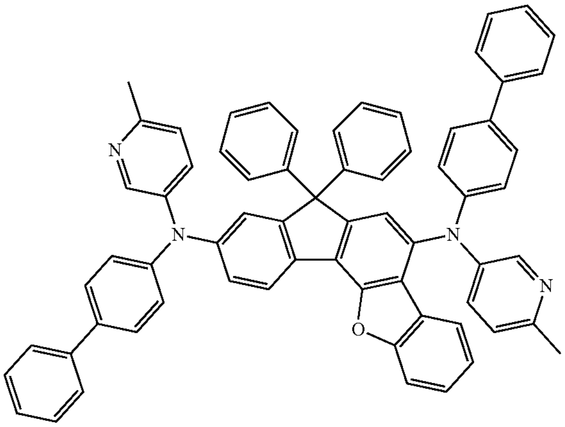
-continued
<Chemical Formula d142>
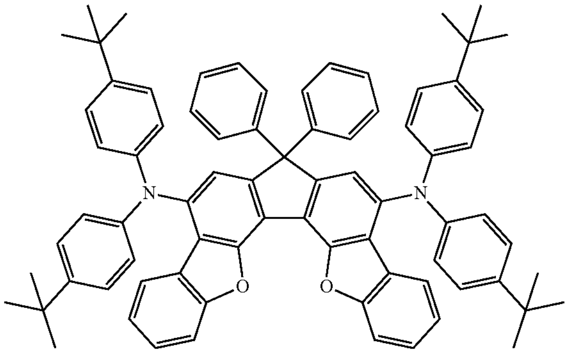
<Chemical Formula d143>
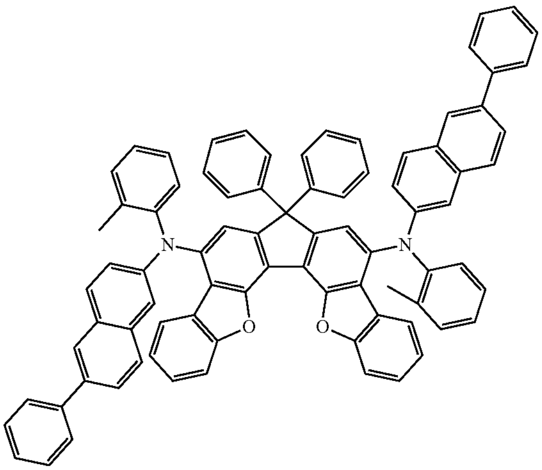
<Chemical Formula d144>
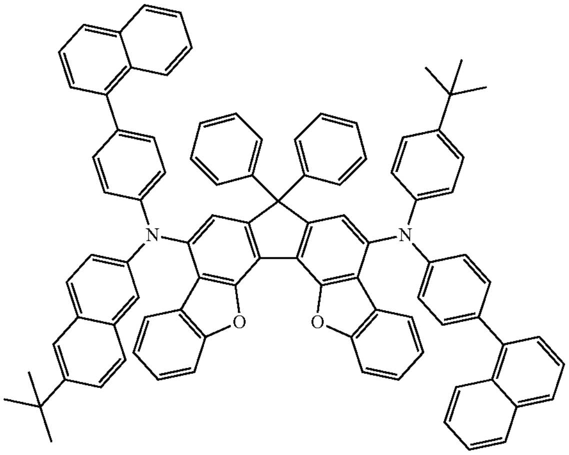

-continued
<Chemical Formula d145>
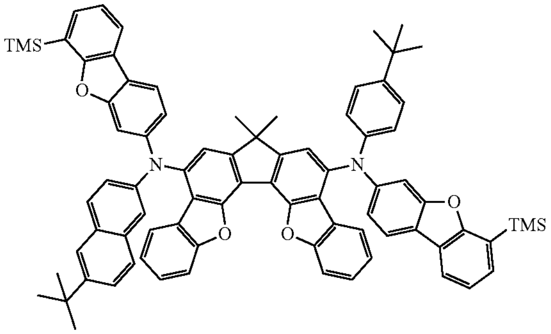
<Chemical Formula d146>
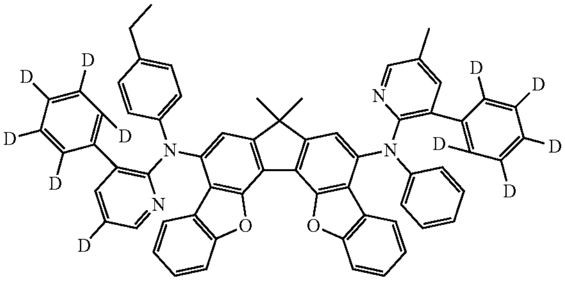
<Chemical Formula d147>
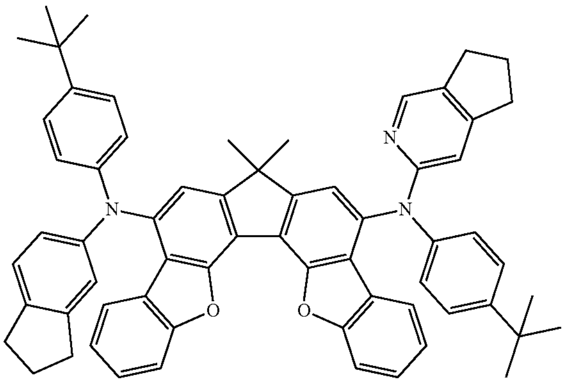
<Chemical Formula d148>
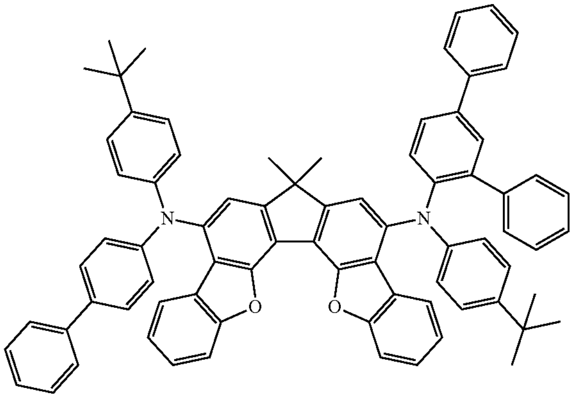
-continued
<Chemical Formula d149>
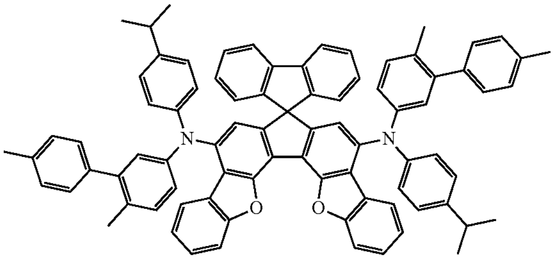
<Chemical Formula d150>
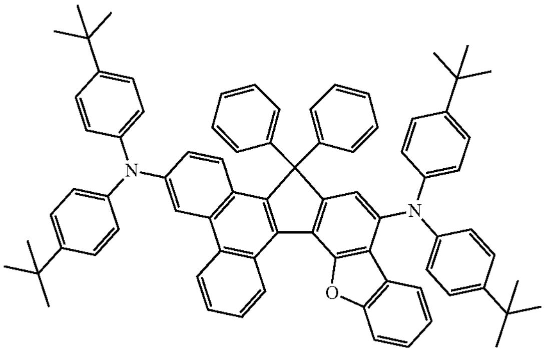
<Chemical Formula d151>
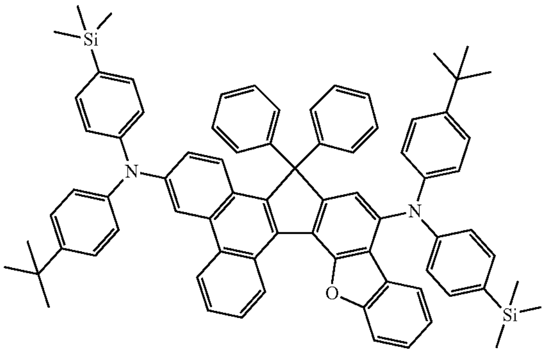
<Chemical Formula d152>
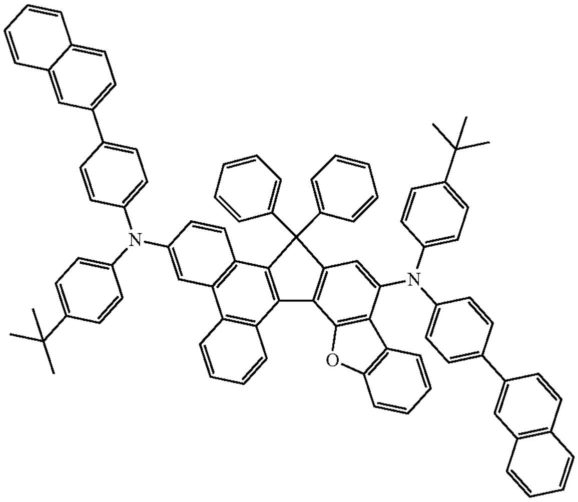

-continued
<Chemical Formula d153>
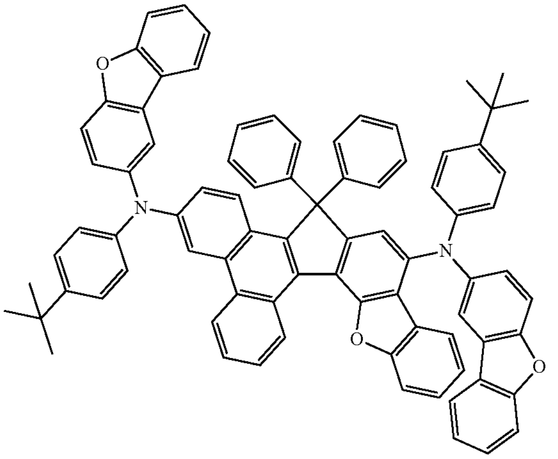
<Chemical Formula d154>
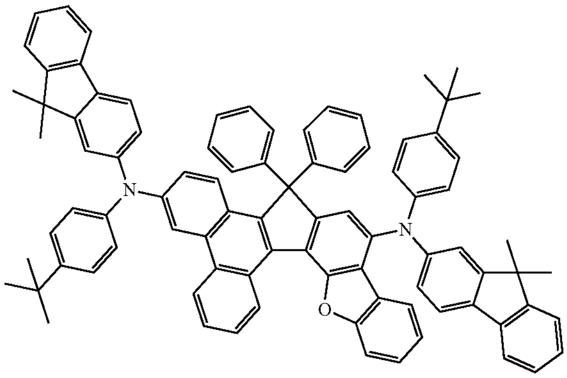
<Chemical Formula d155>
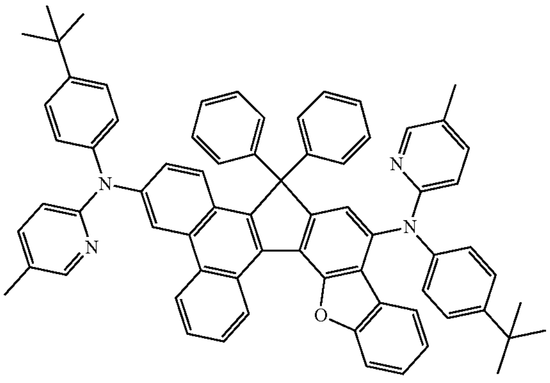
-continued
<Chemical Formula d156>
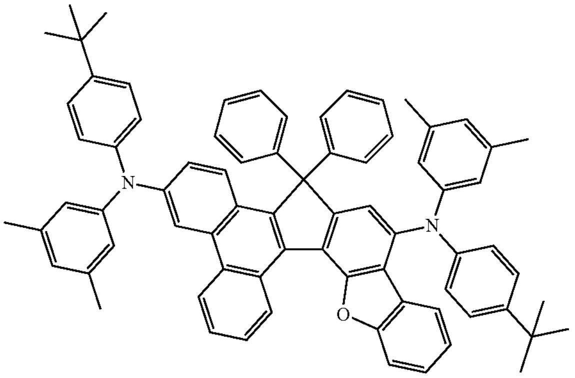
<Chemical Formula d157>
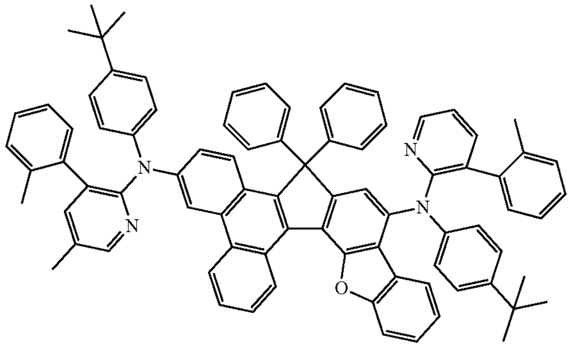
<Chemical Formula d158>
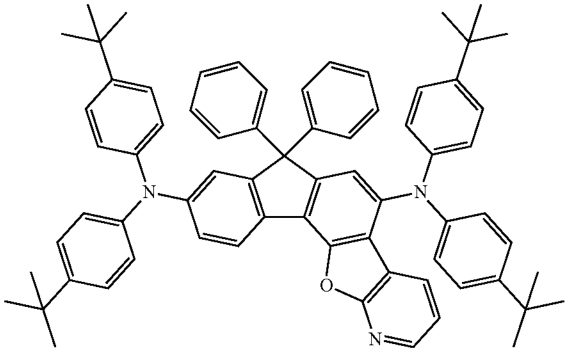
<Chemical Formula d159>
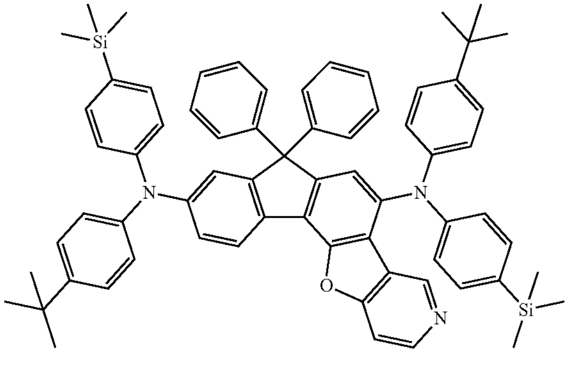

-continued
<Chemical Formula d160>
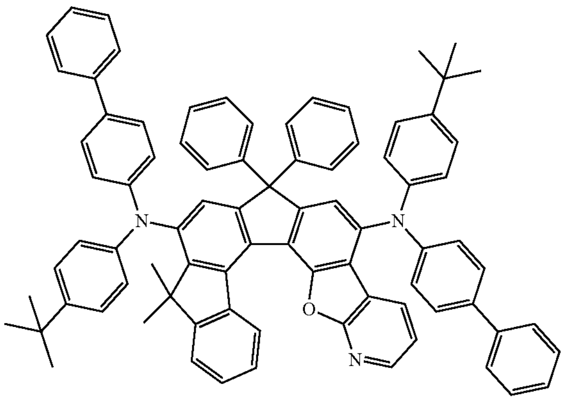
<Chemical Formula d161>
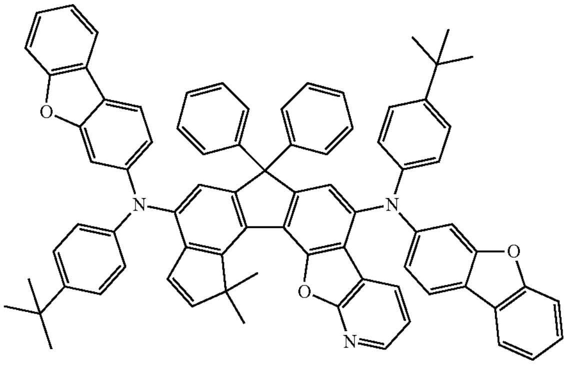
<Chemical Formula d162>
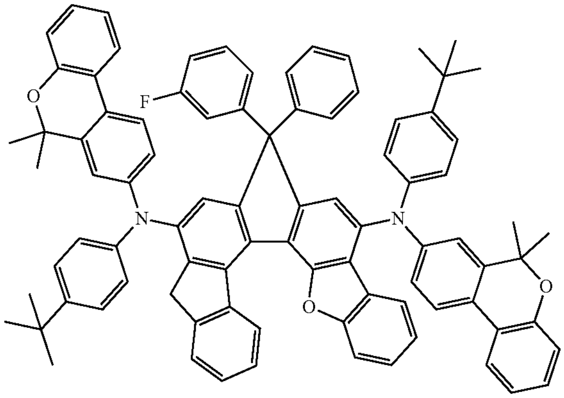
<Chemical Formula d163>
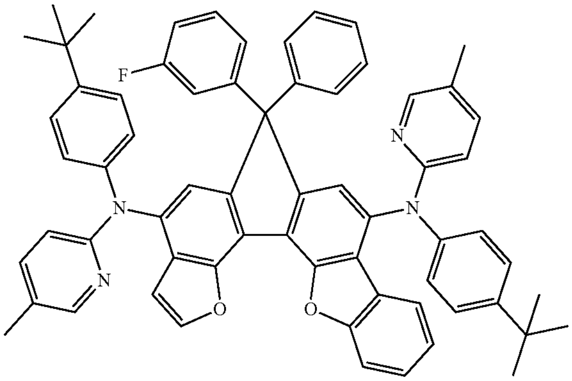
-continued
<Chemical Formula d164>
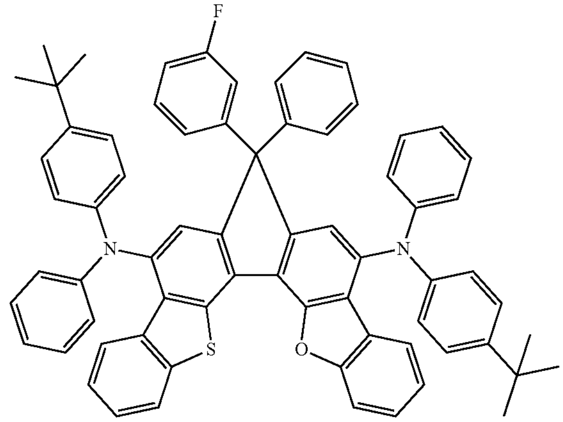
<Chemical Formula d165>
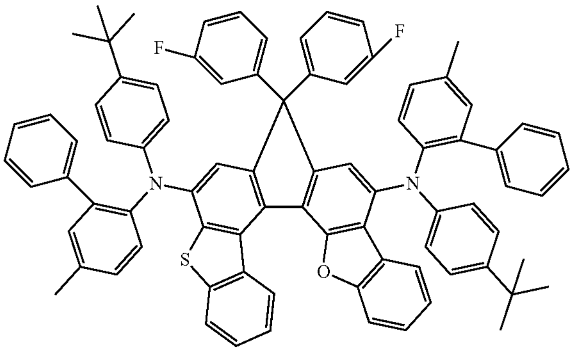
<Chemical Formula d166>
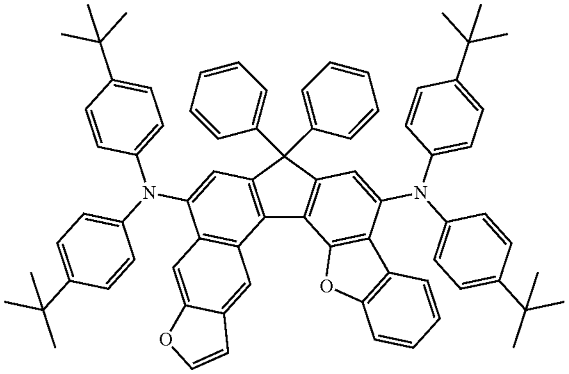
<Chemical Formula d167>
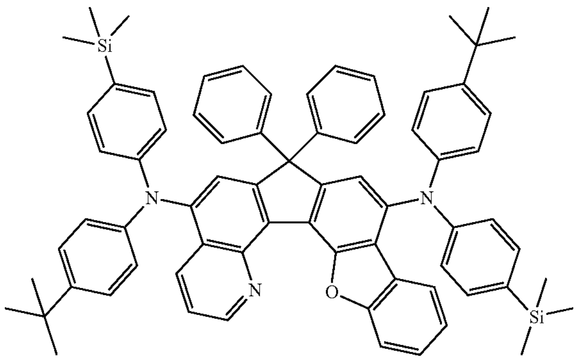

-continued
<Chemical Formula d168>
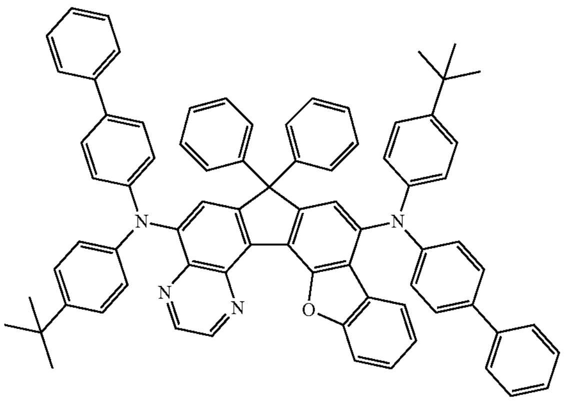
<Chemical Formula d169>
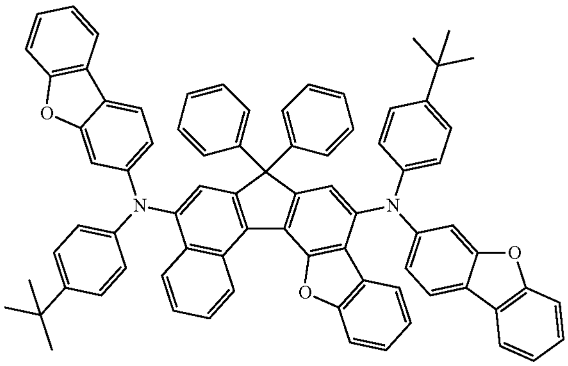
<Chemical Formula d170>
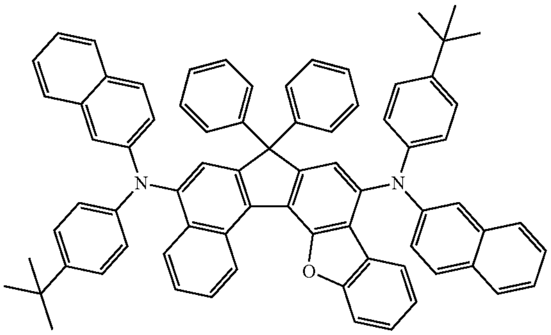
<Chemical Formula d171>
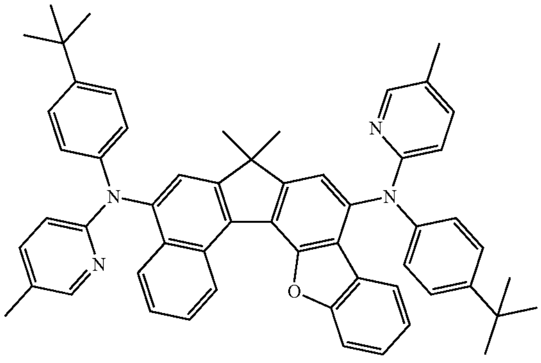
-continued
<Chemical Formula d172>
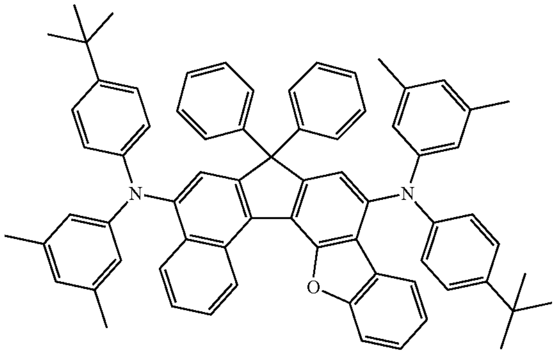
<Chemical Formula d173>
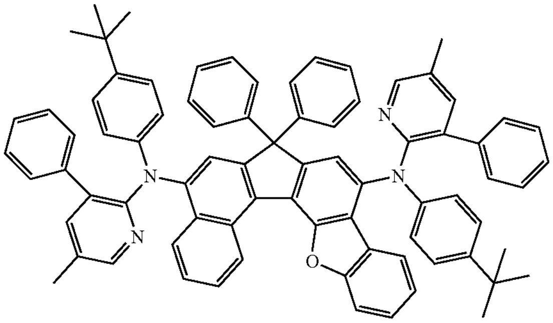
<Chemical Formula d174>
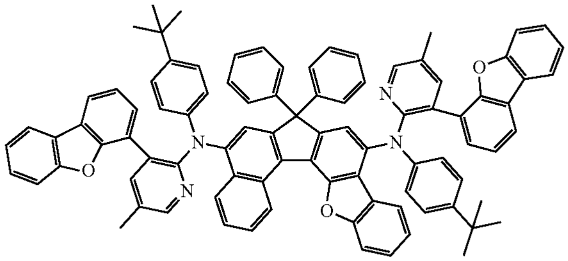
<Chemical Formula d175>
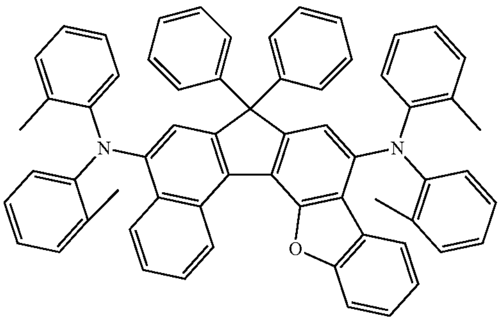

-continued
<Chemical Formula d176>
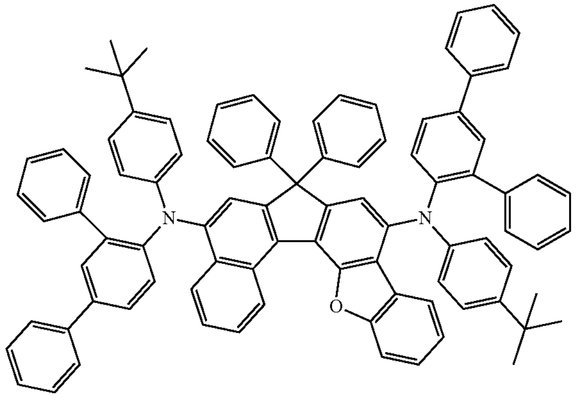
<Chemical Formula d177>
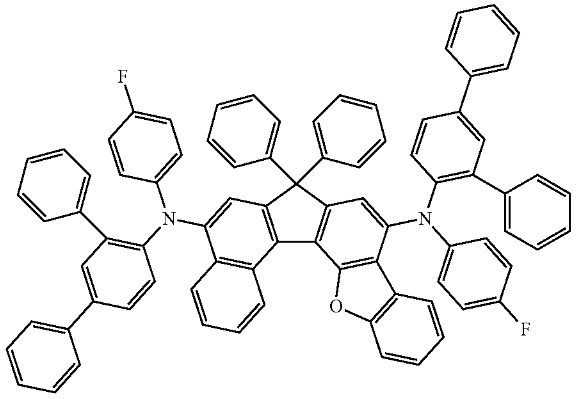
<Chemical Formula d178>
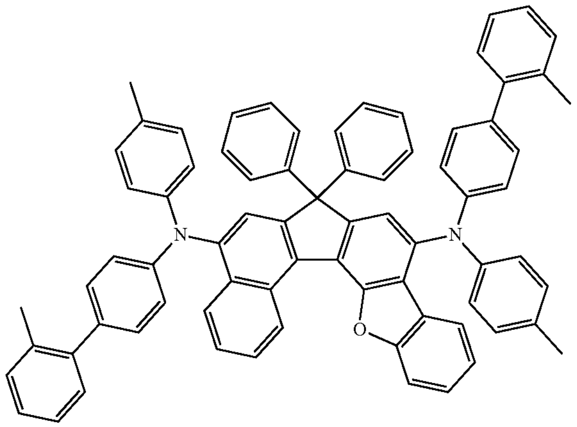
-continued
<Chemical Formula d179>
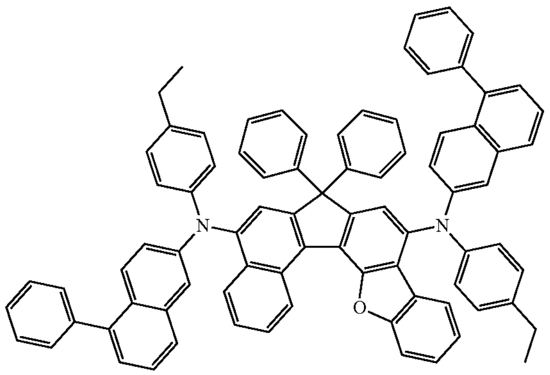
<Chemical Formula d180>
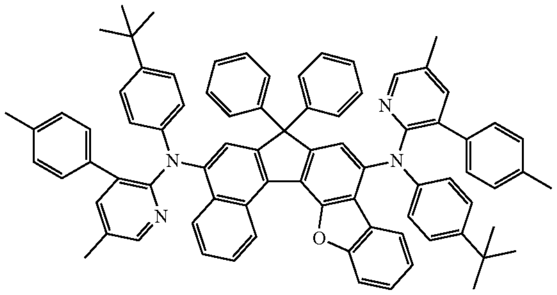
<Chemical Formula d181>
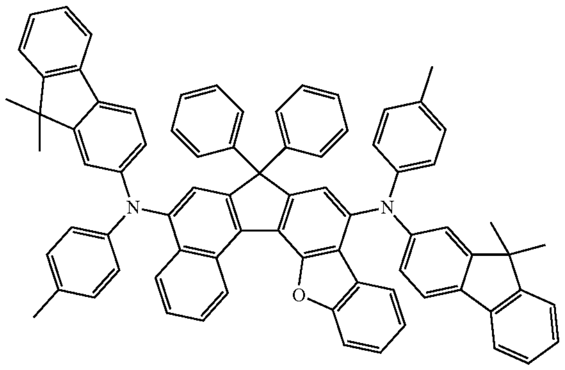
<Chemical Formula d182>
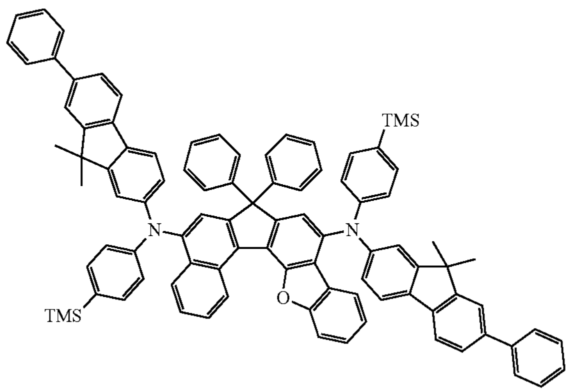

-continued
<Chemical Formula d183>
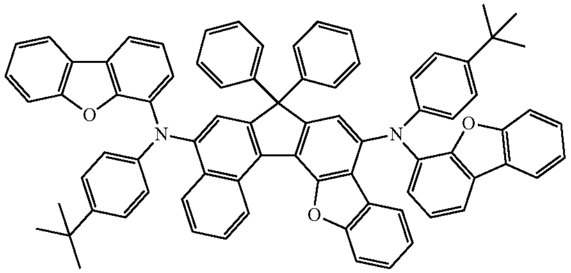
<Chemical Formula d184>
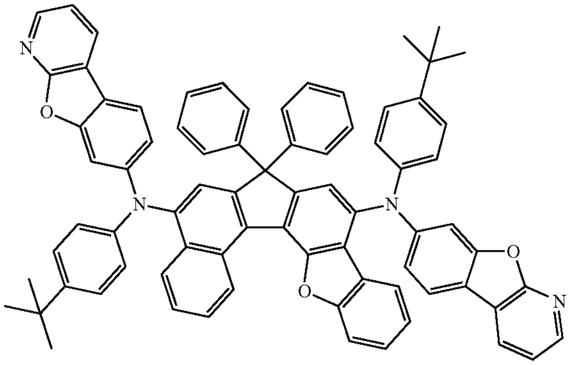
<Chemical Formula d185>
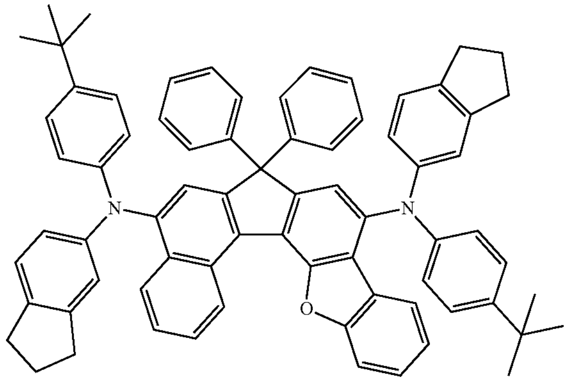
<Chemical Formula d186>
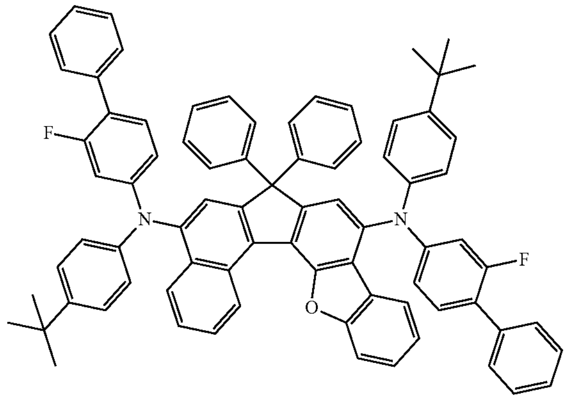
-continued
<Chemical Formula d187>
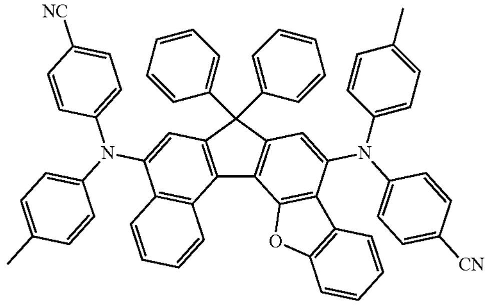
<Chemical Formula d188>
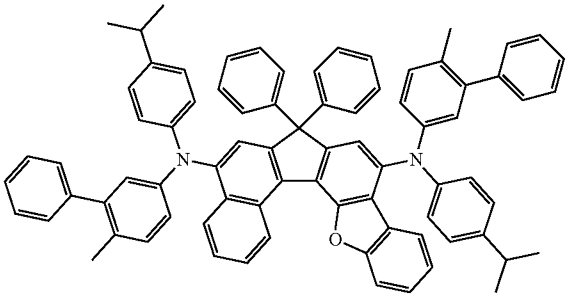
<Chemical Formula d189>
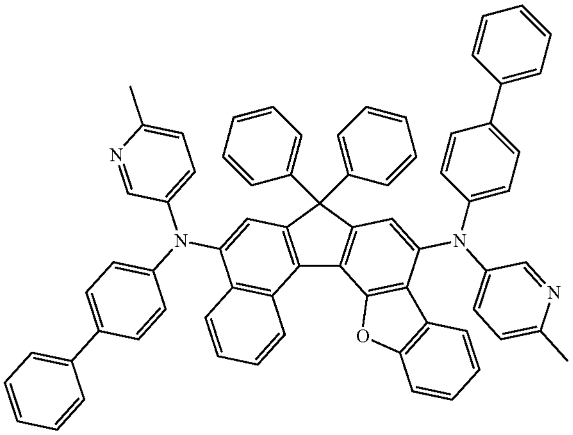
<Chemical Formula d190>
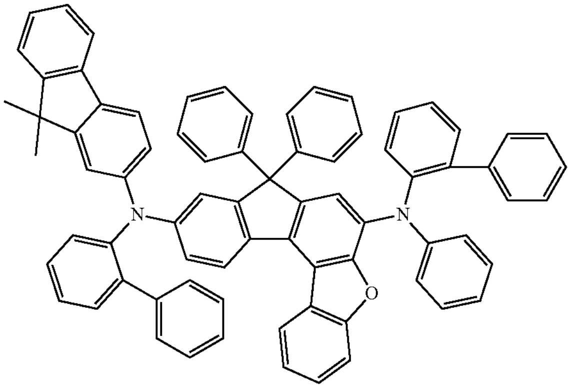

-continued
<Chemical Formual d191>
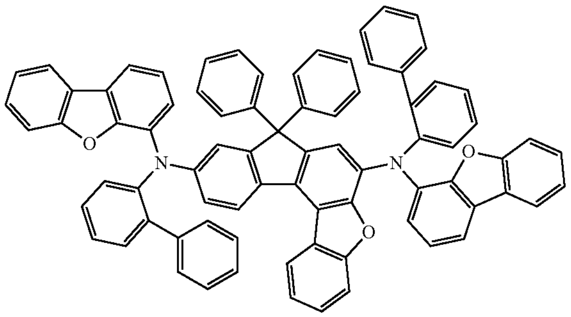
<Chemical Formula d192>
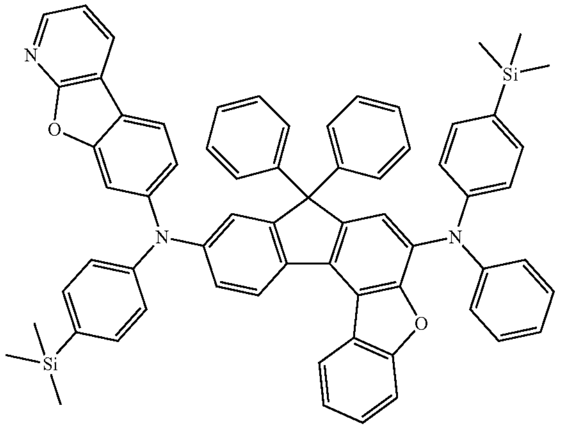
<Chemical Formula d193>
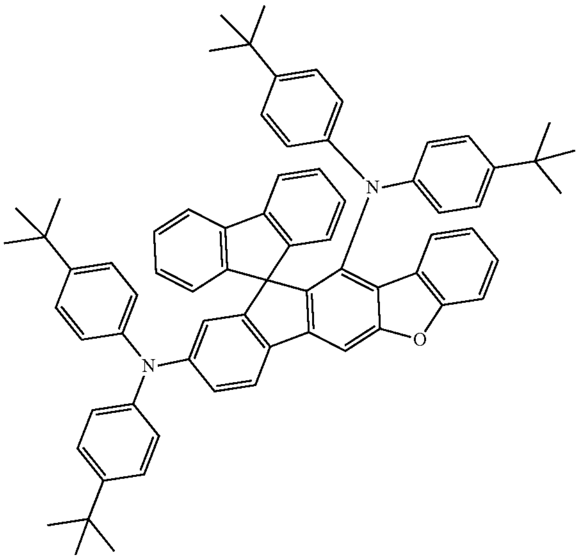
-continued
<Chemical Formula d194>
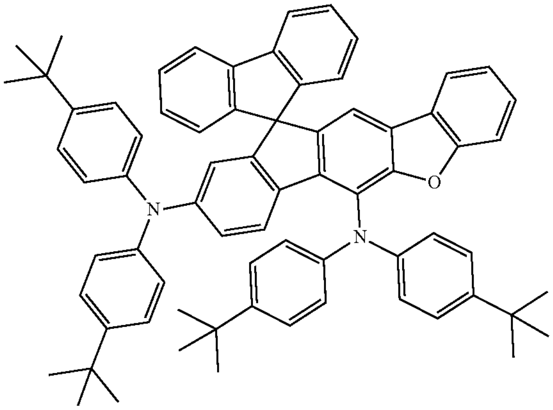
<Chemical Formula d195>
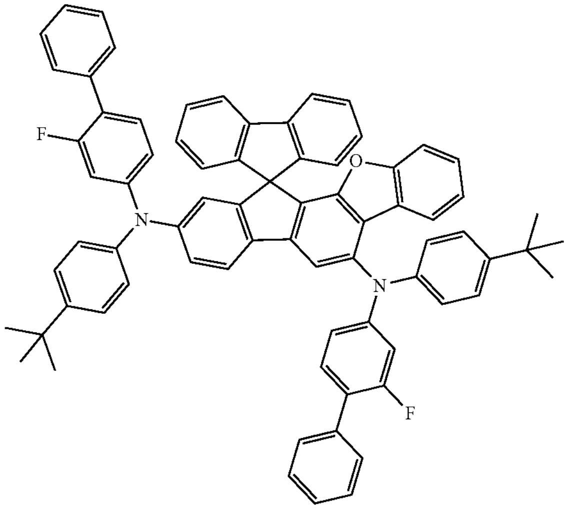
<Chemical Formula d196>
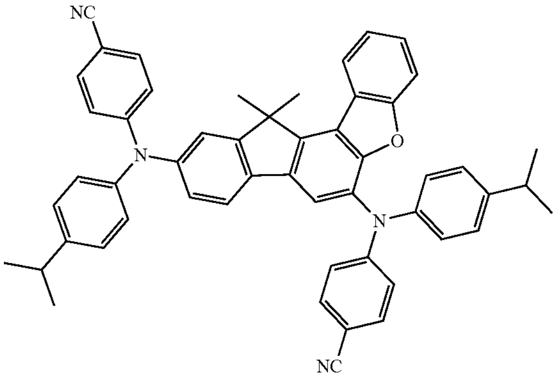

<Chemical Formula d197>
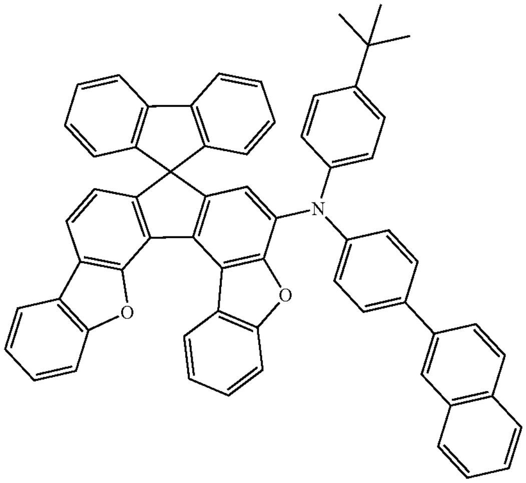
<Chemical Formula d198>
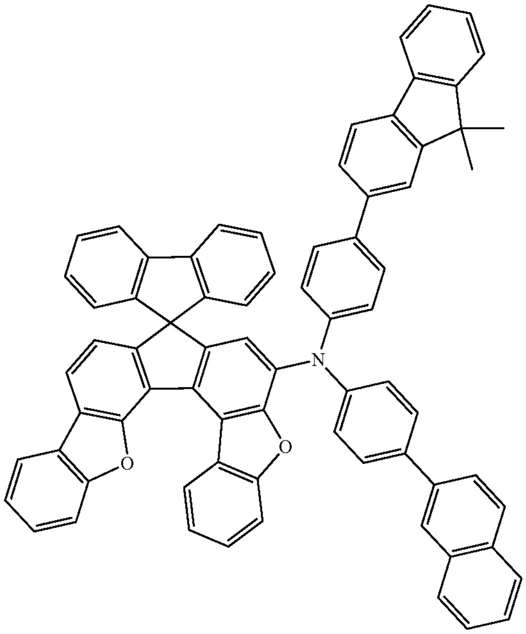
<Chemical Formula d199>
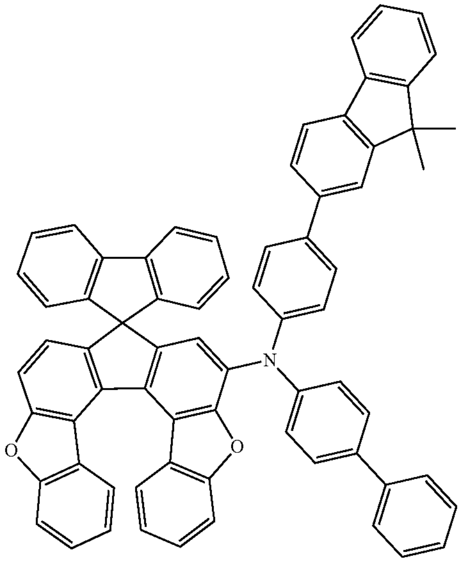
<Chemical Formula d200>
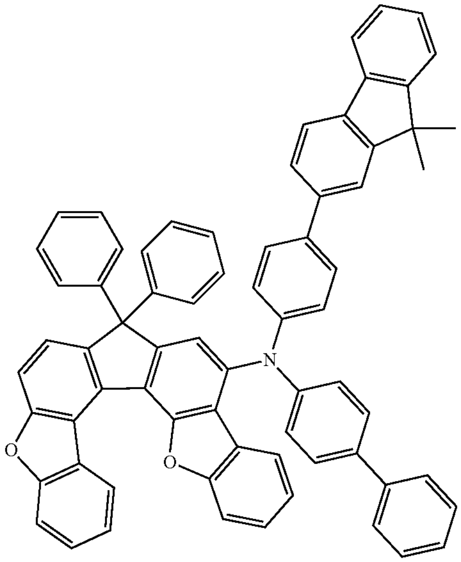

-continued
<Chemical Formula d201>
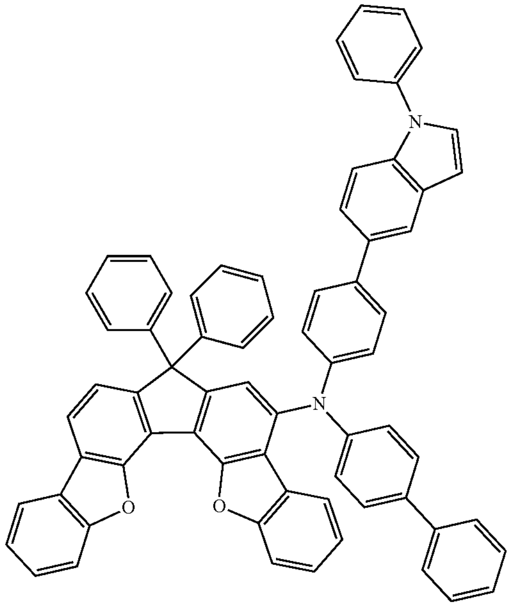
<Chemical Formula d202>
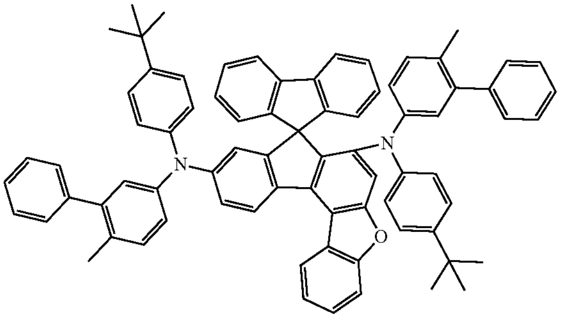
<Chemical Formula d203>
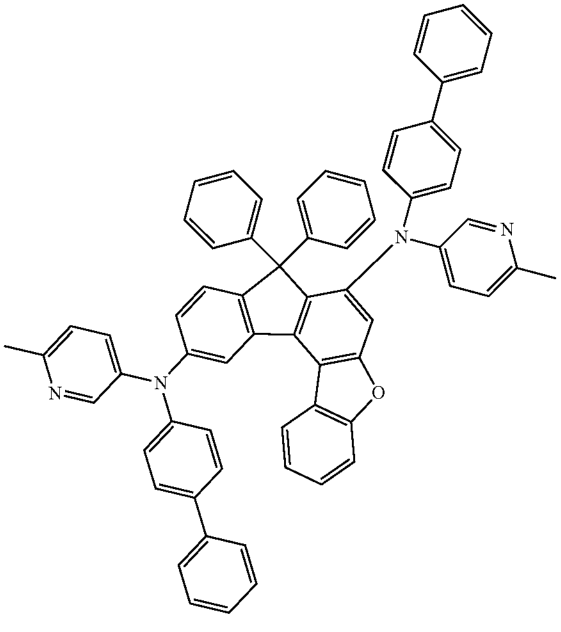
-continued
<Chemical Formula d204>
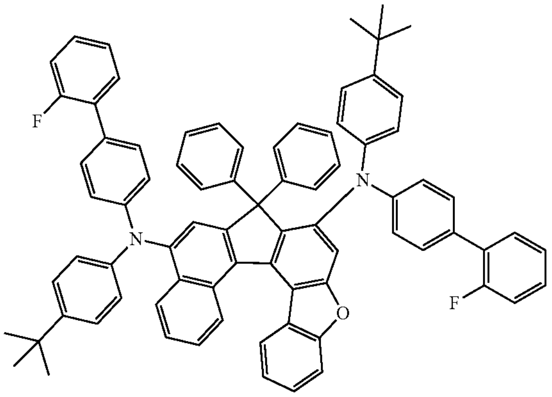
<Chemical Formula d205>
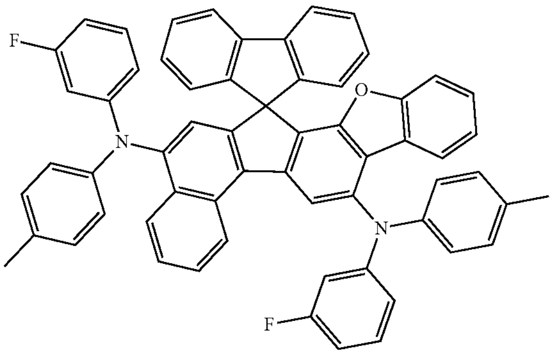
<Chemical Formula d206>
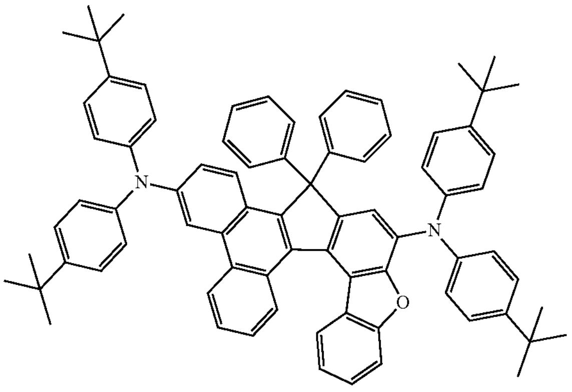
<Chemical Formula d207>
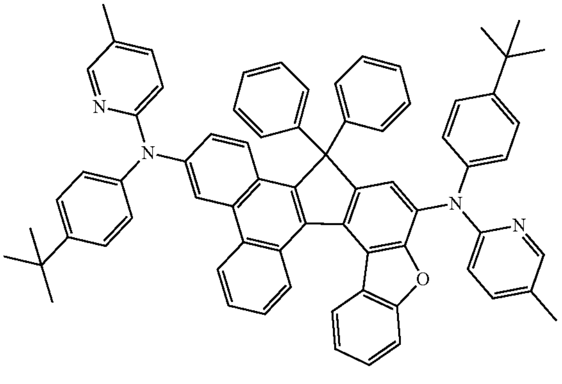

-continued
<Chemical Formula d208>
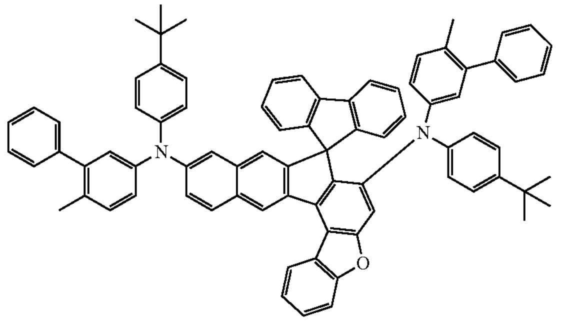
<Chemical Formula d209>
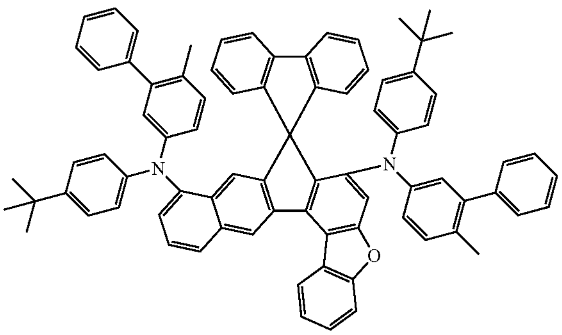
<Chemical Formula d210>
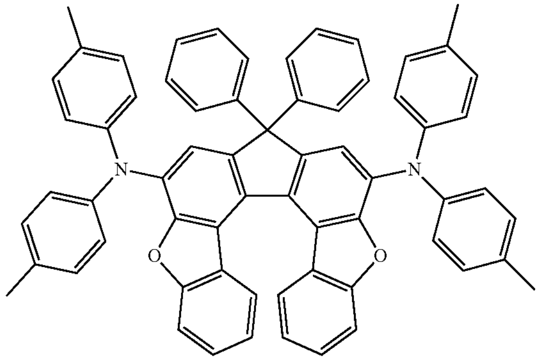
<Chemical Formula d211>
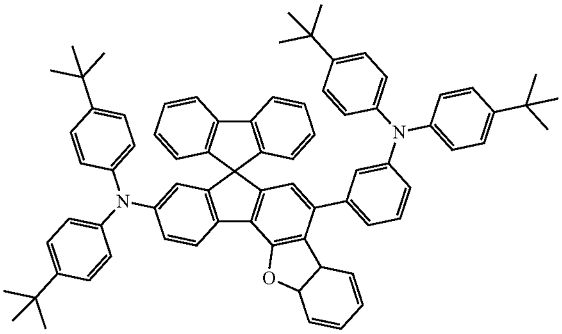
-continued
<Chemical Formula d212>
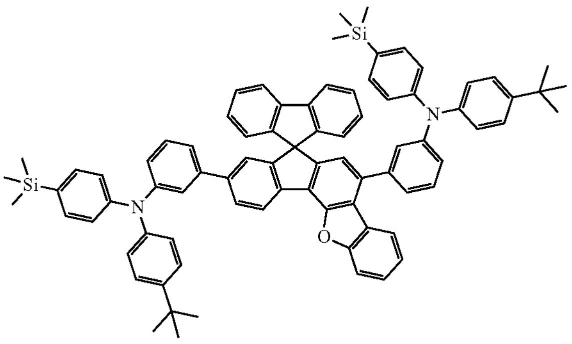
<Chemical Formula d213>
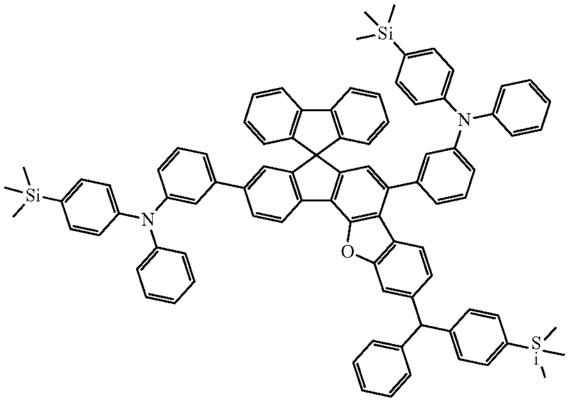
<Chemical Formula d214>
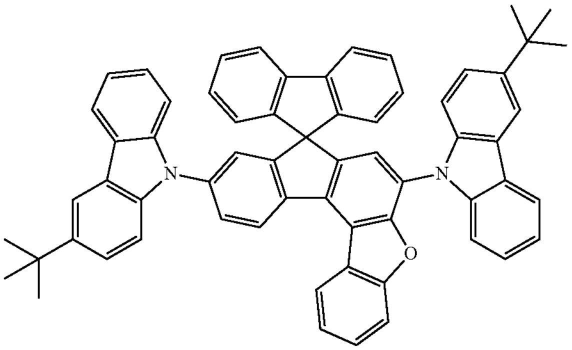
<Chemical Reaction d215>
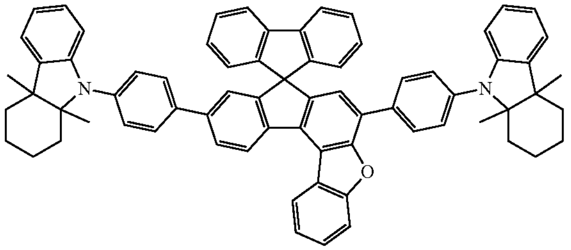

-continued
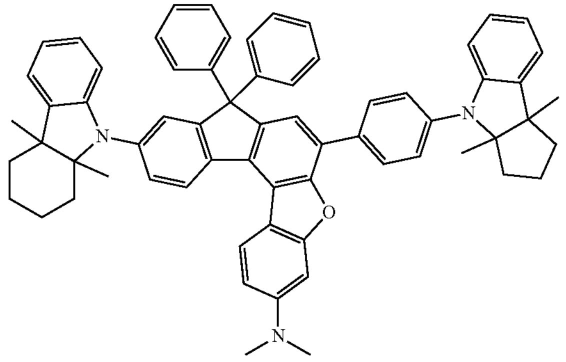
<CHemical Reaction d217>
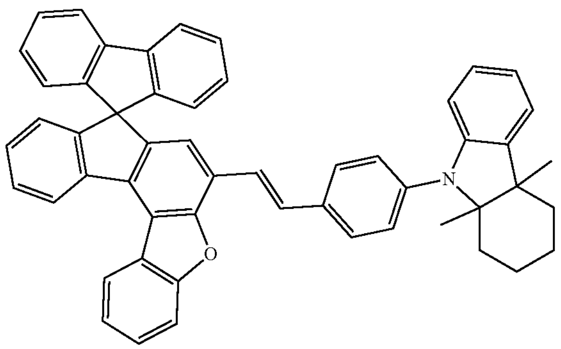
<Chemical Reaction d218>
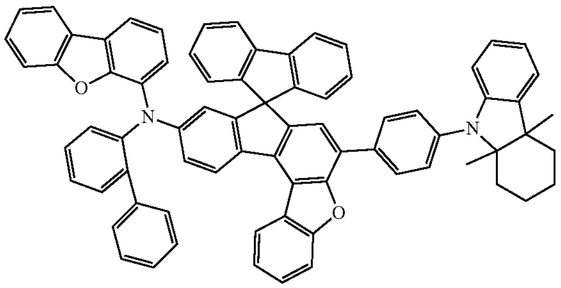
<Chemical Reaction d219>
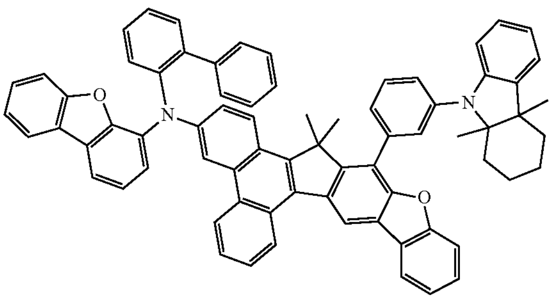
-continued
<Chemical Reaction d220>
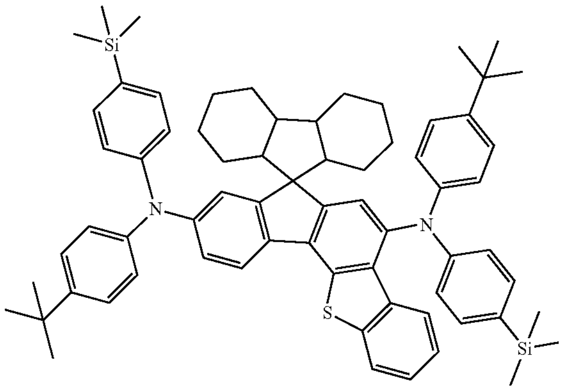
<Chemical Reaction d221>
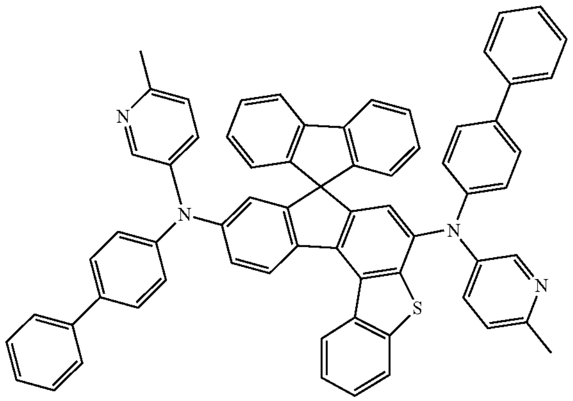
<Chemical Reaction d222>
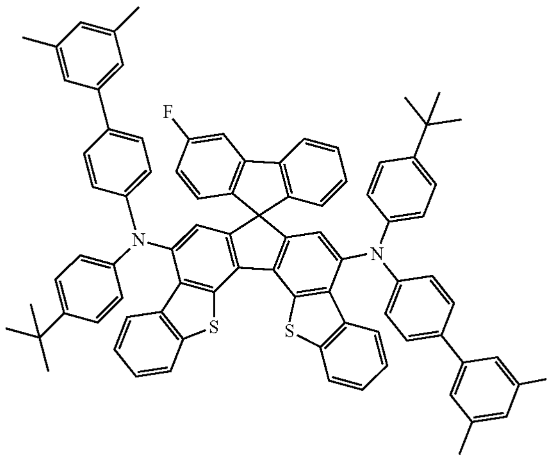

<Chemical Reaction d223>
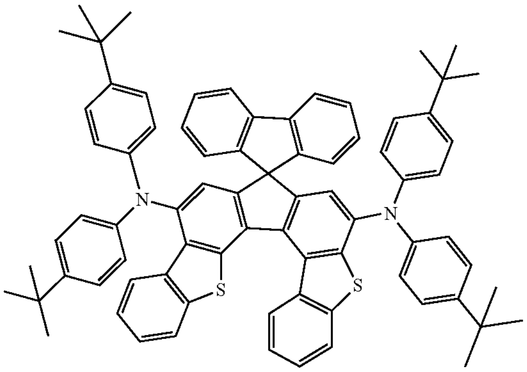
<Chemical Reaction d224>
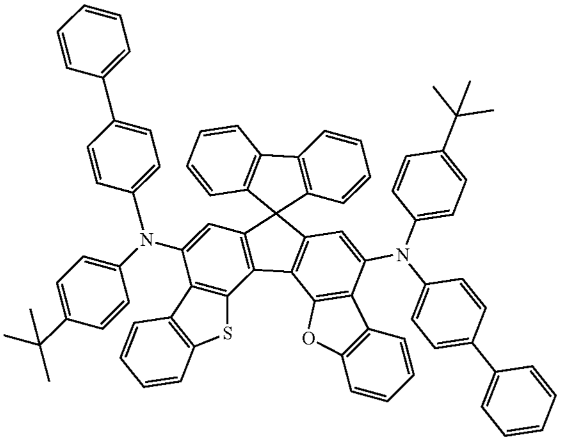
<Chemical Reaction d225>
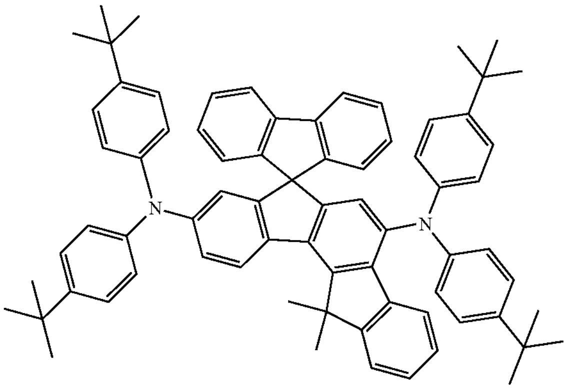
<Chemical Reaction d226>
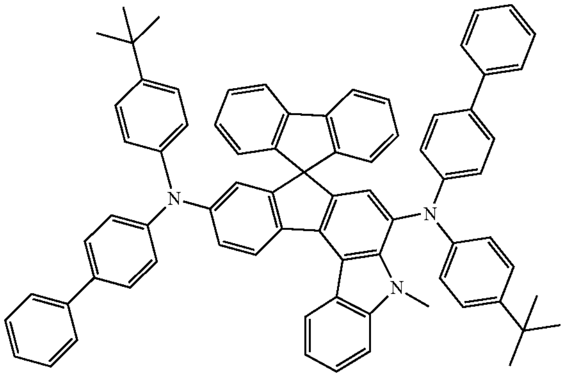
<Chemical Reaction d227>
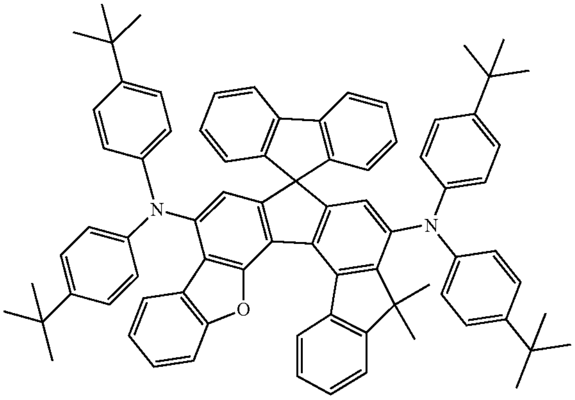
<Chemical Reaction d228>
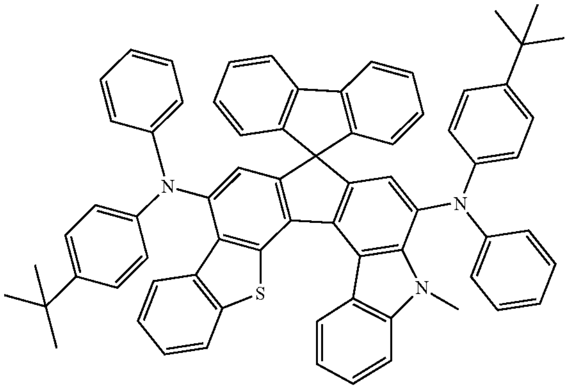

-continued
<Chemical Reaction d229>
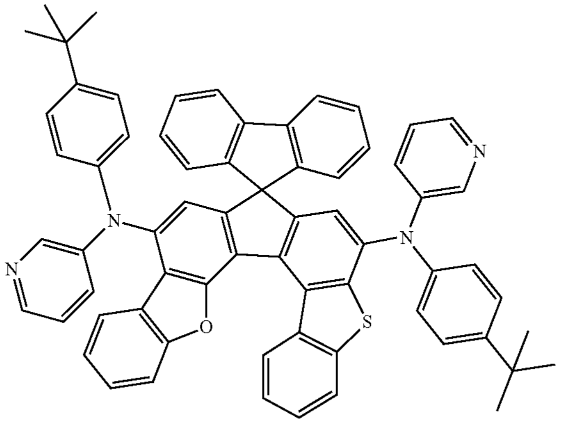
<Chemical Reaction d230>
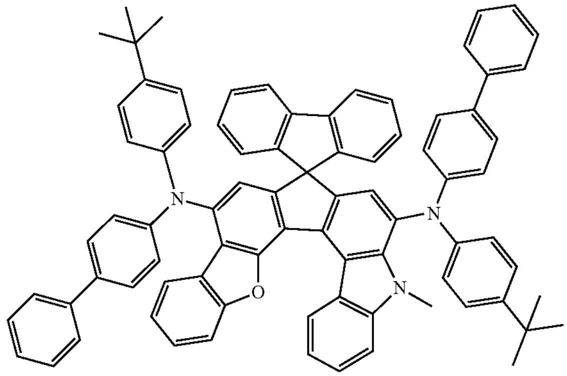
<Chemical Reaction d231>
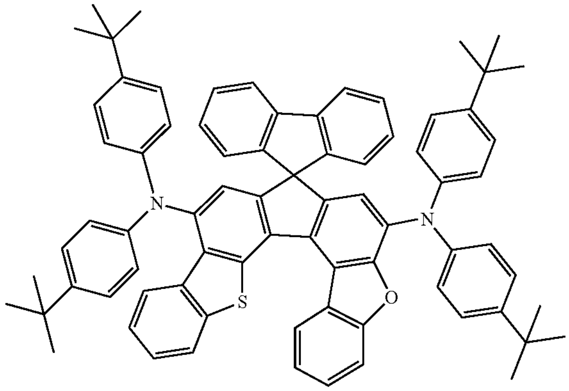
<Chemical Reaction d232>
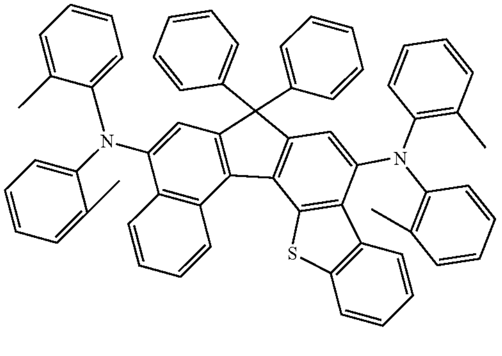
-continued
<Chemical Reaction d233>
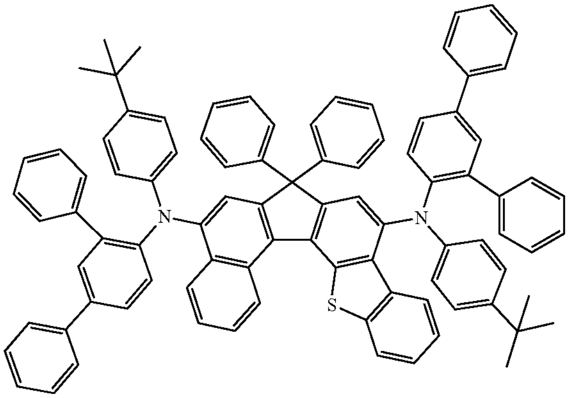
<Chemical Reaction d234>
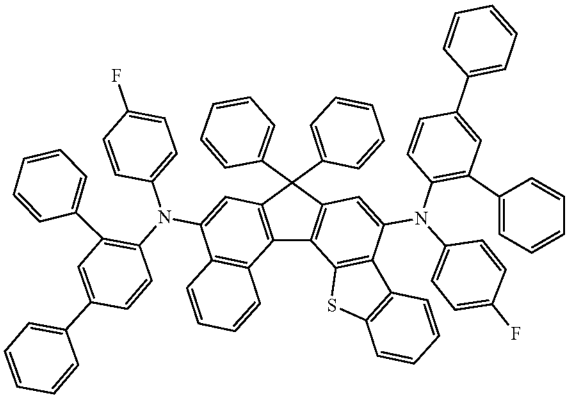
<Chemical Reaction d235>
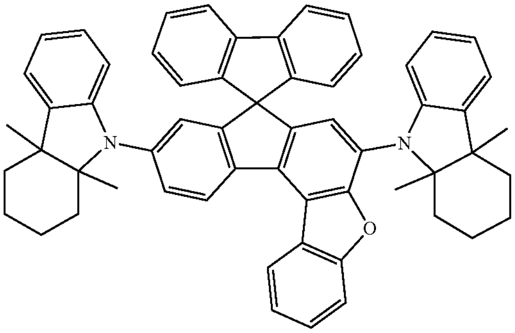
<Chemical Reaction d236>
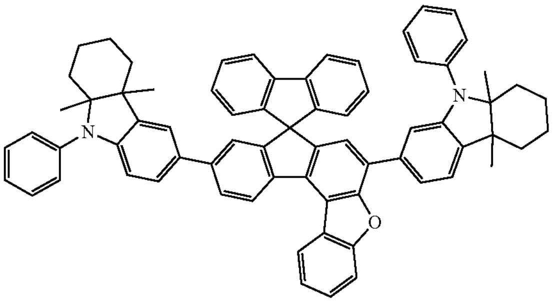

-continued
<Chemical Reaction d237>
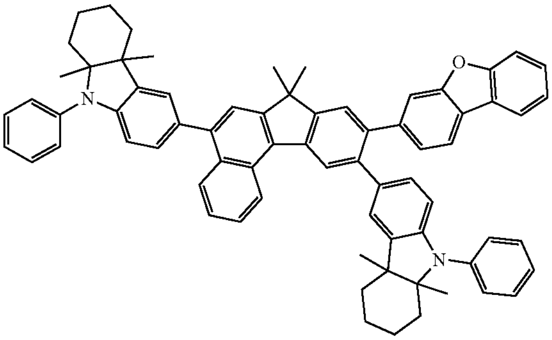
<Chemical Reaction d238>
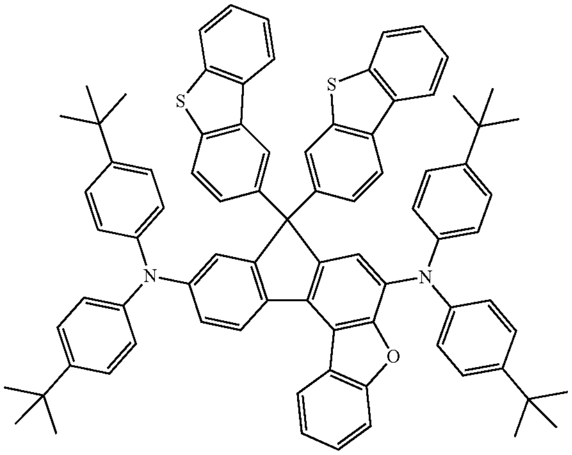
<Chemical Reaction d239>
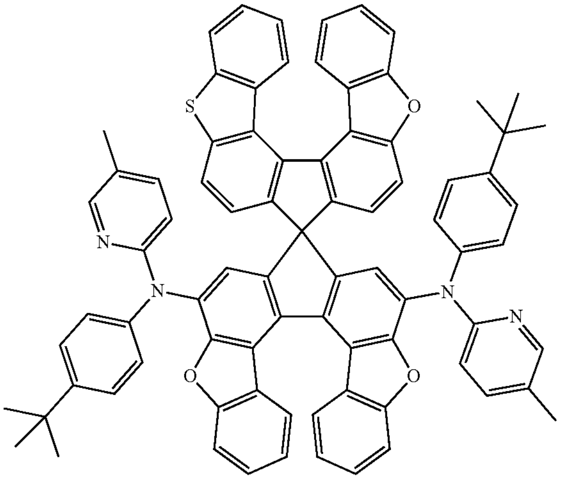
-continued
<Chemical Formula d240>
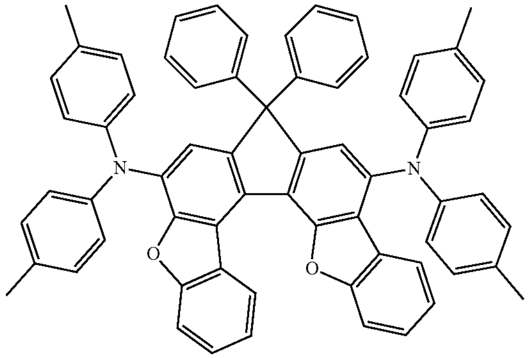
In addition, examples of the compound represented by Chemical Formula D3 as the dopant include the compounds of the following <Chemical Formula D 101> to <Chemical Formula D 130>:
<Chemical Formula D101>
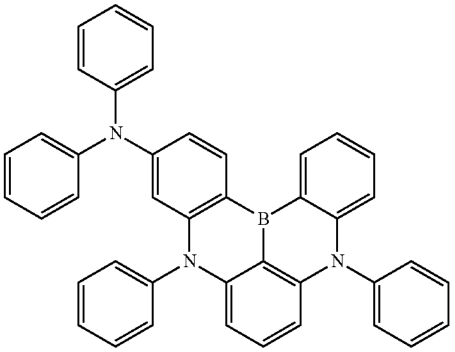
<Chemical Formula D102>
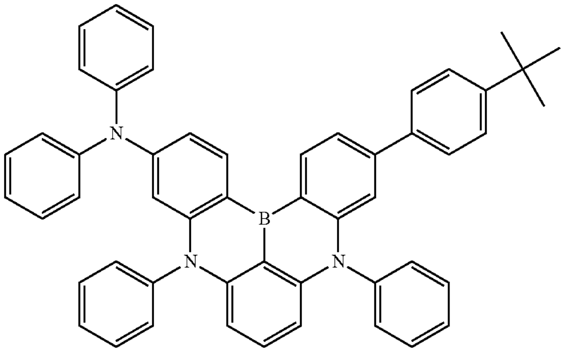
<Chemical Formula D103>
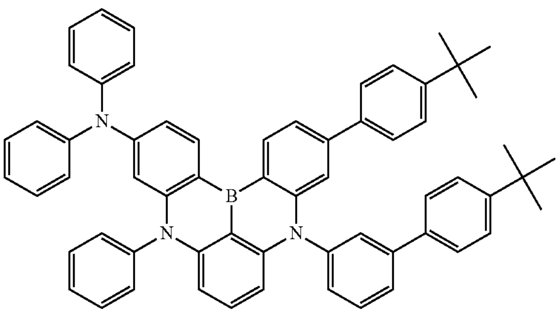

-continued
<Chemical Formula D104>
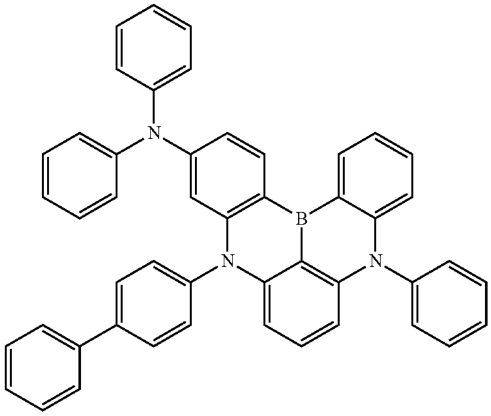
<Chemical Formula D105>
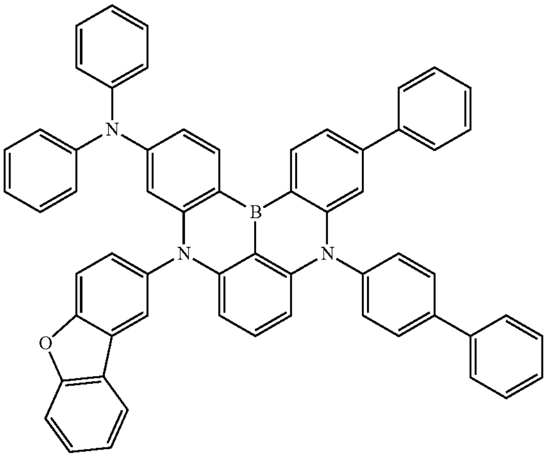
<Chemical Formula D106>
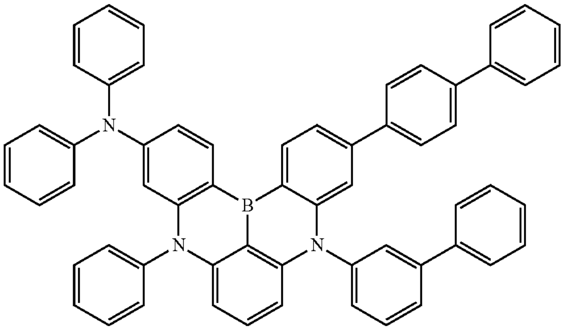
<Chemical Formula D107>
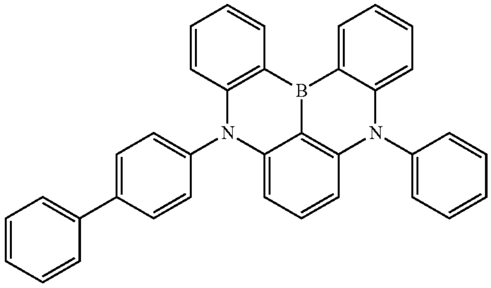
-continued
<Chemical Formula D108>
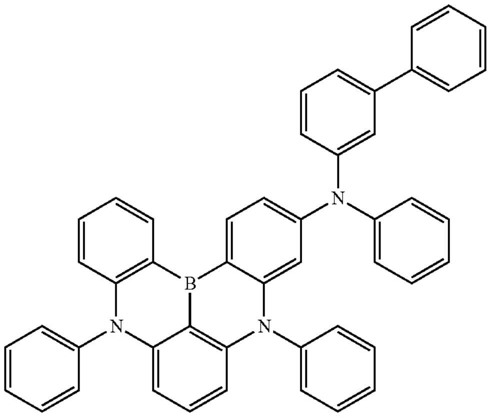
<Chemical Formula D109>
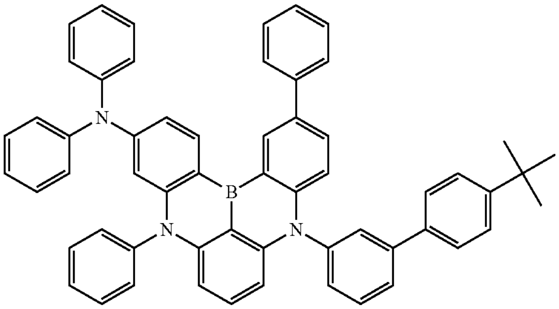
<Chemical Formula D110>
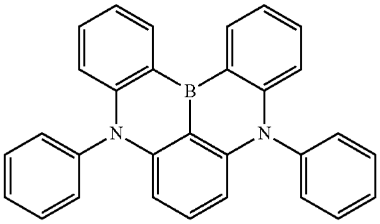
<Chemical Formula D111>
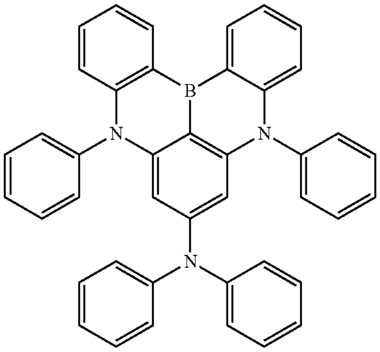

-continued
<Chemical Formula D112>
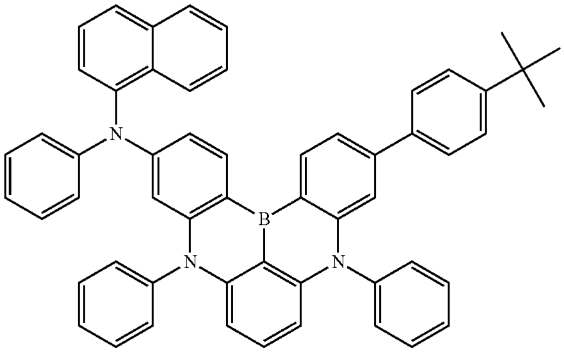
<Chemical Formula D113>
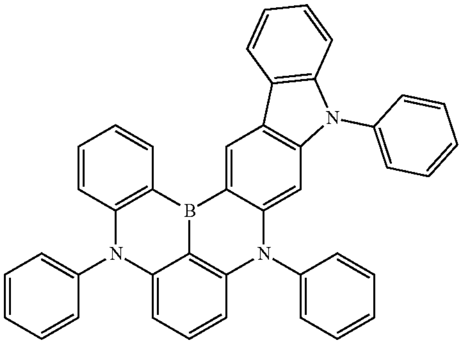
<Chemical Formula D114>
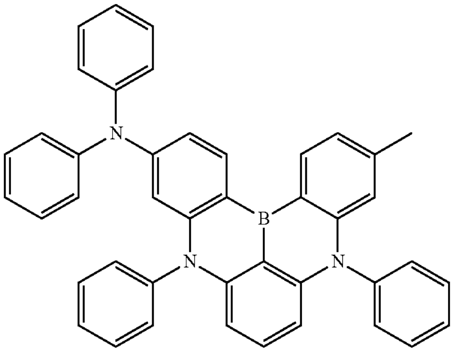
<Chemical Formula D115>
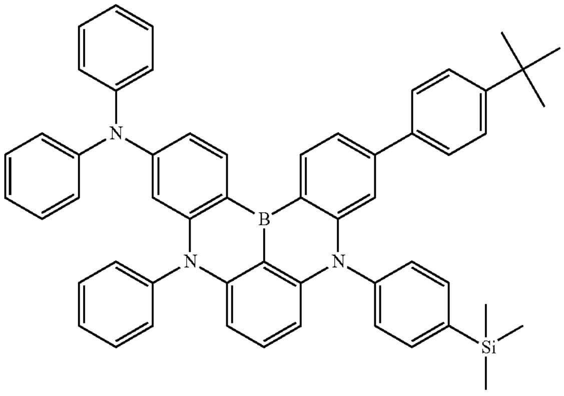
-continued
<Chemical Formula D116>
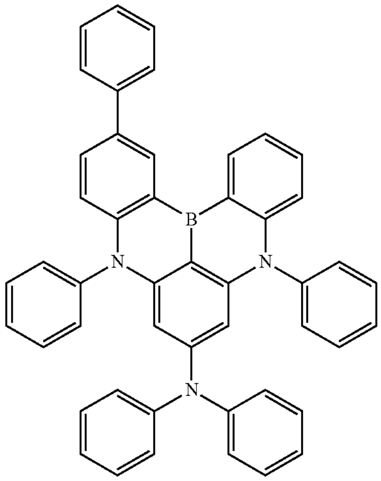
<Chemical Formula D117>
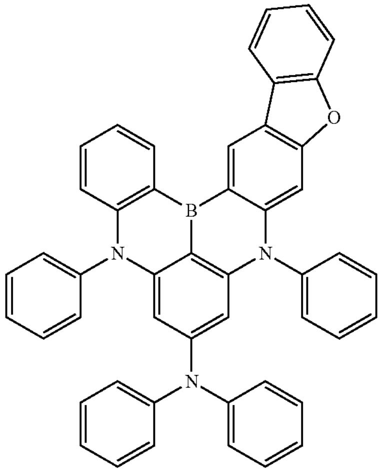
<Chemical Formula D118>
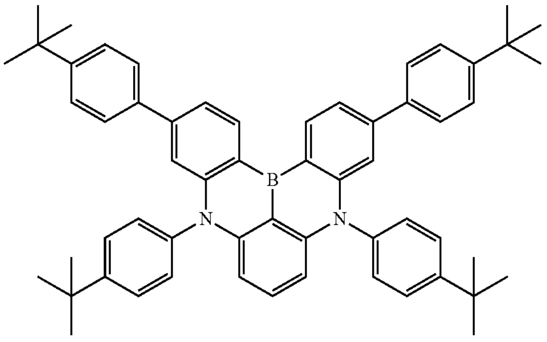

-continued
<Chemical Formula D119>
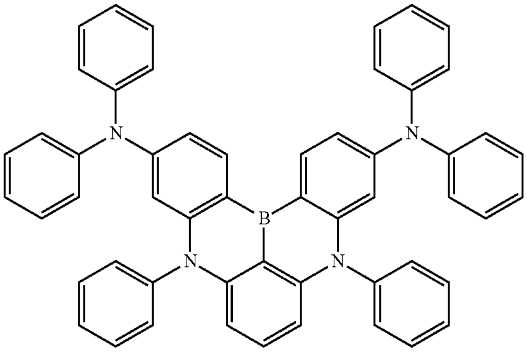
<Chemical Formula D120>
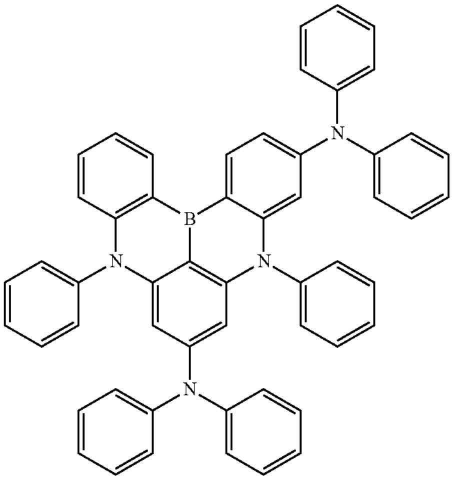
<Chemical Formula D121>
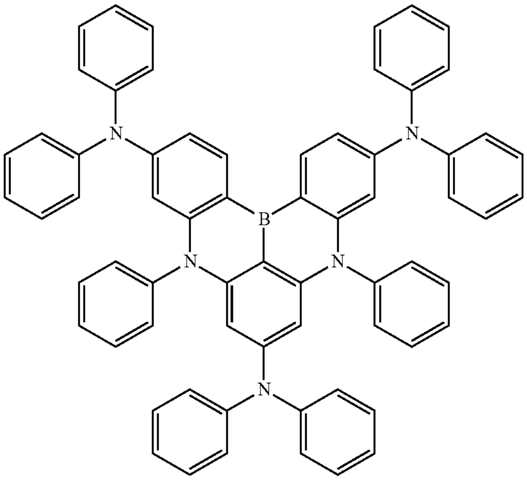
-continued
<Chemical Formula D122>
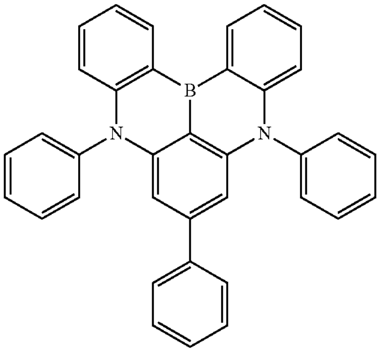
<Chemical Formula D123>
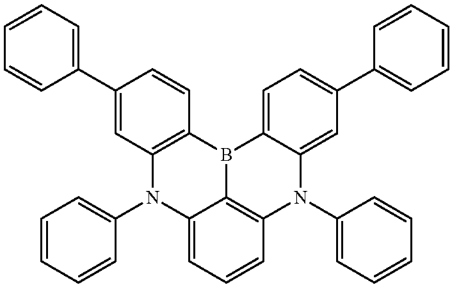
<Chemical Formula D124>
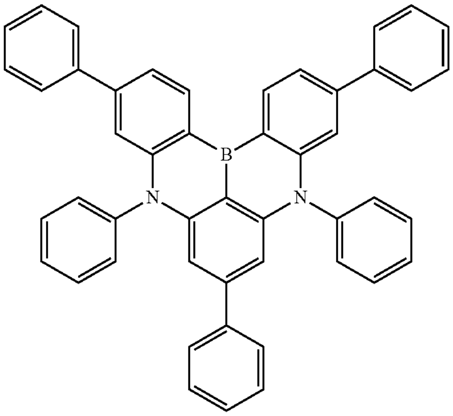
<Chemical Formula D125>
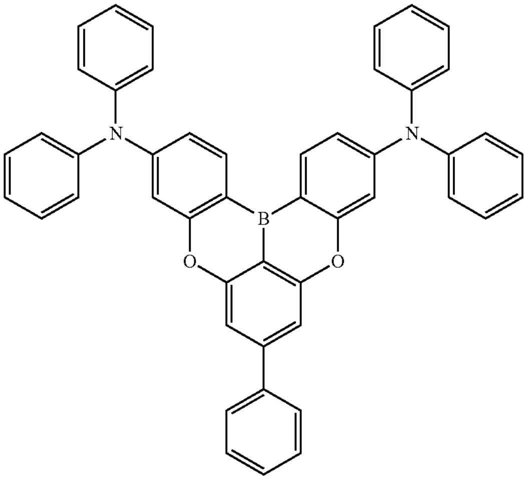

-continued
<Chemical Formula D126>
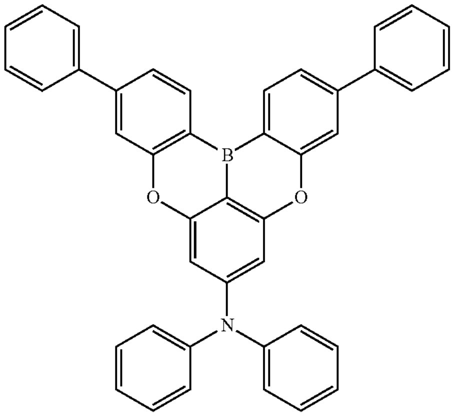
<Chemical Formula D127>
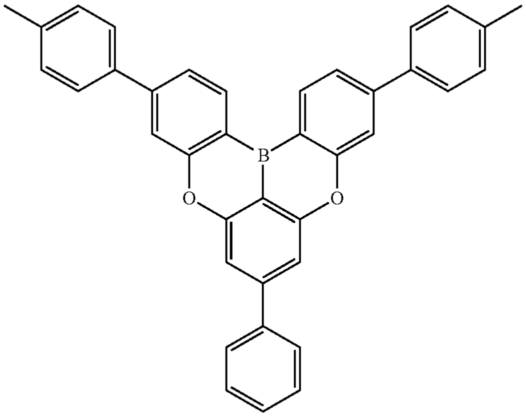
<Chemical Formula D128>
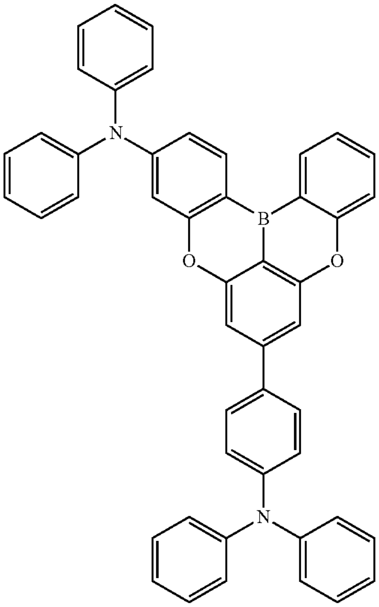
-continued
<Chemical Formula D129>
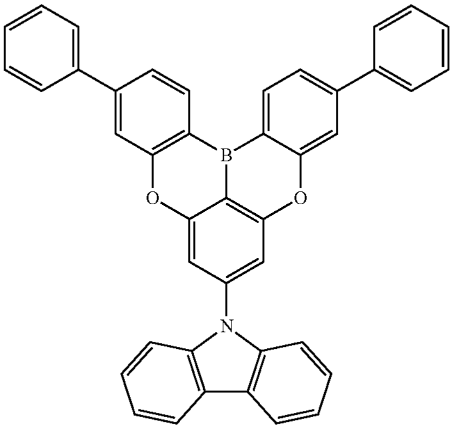
<Chemical Formula D130>
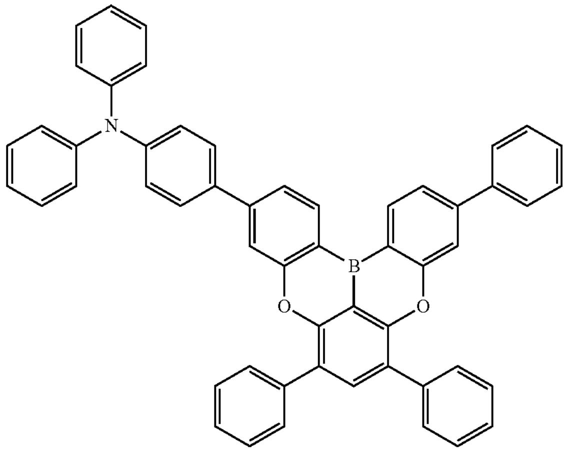
In addition, concrete examples of the compound represented by [Chemical Formula D4] or [Chemical Formula D5] include [Chemical Formula D201] to [Chemical Formula D281]:
[Chemical Formula D201]
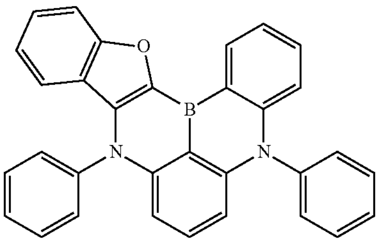
[Chemical Formula D202]
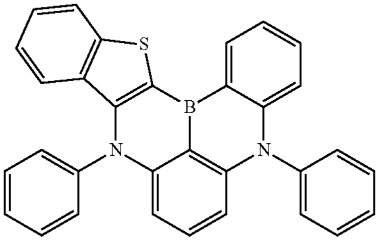

-continued
[Chemica Formua D203]
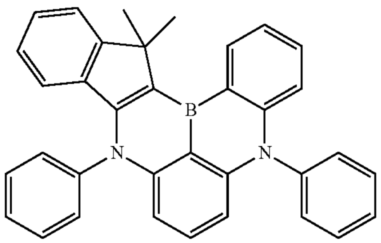
[Chemical Formula D204]
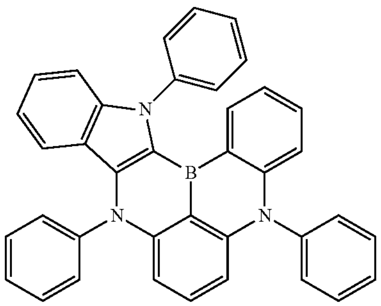
[Chemical Formula D205]
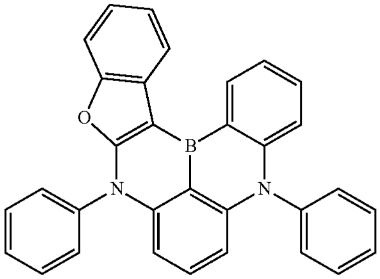
[Chemical Formula D206]
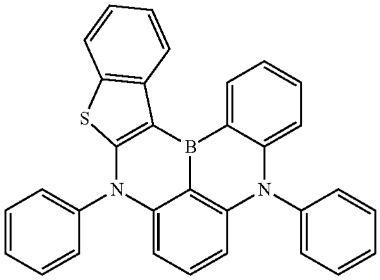
[Chemical Formula D207]
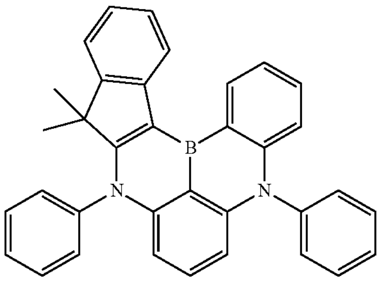
-continued
[Chemical Formula D208]
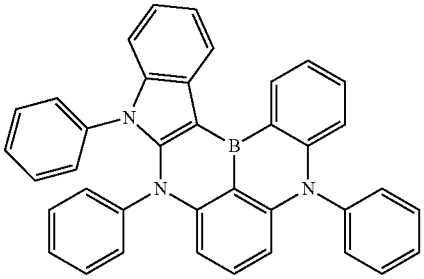
[Chemical Formula D209]
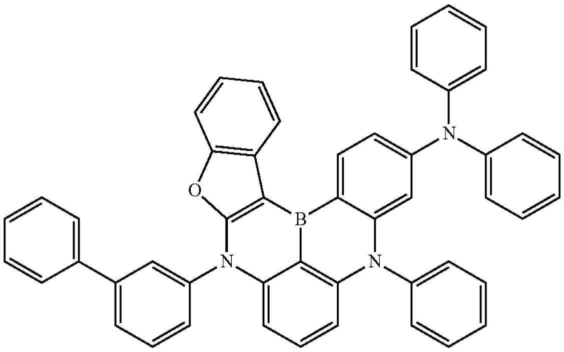
[Chemical Formula D210]
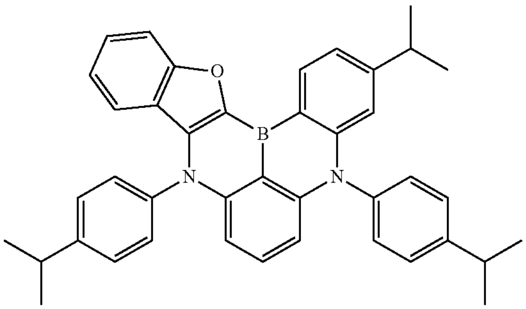
[Chemical Formula D211]
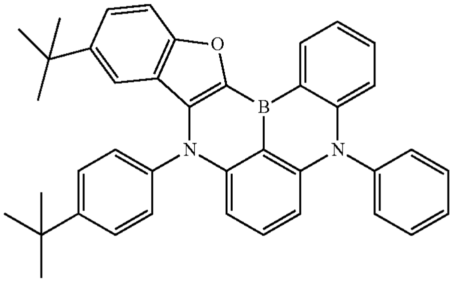

-continued
[Chemical Formula D212]
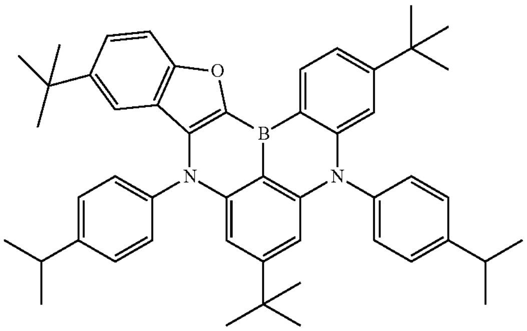
[Chemical Formula D213]
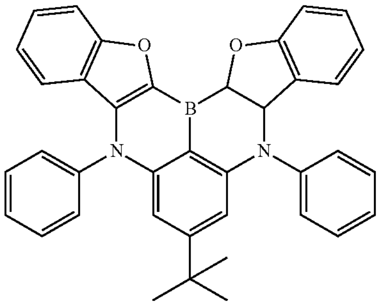
[Chemical Formmulla D214]
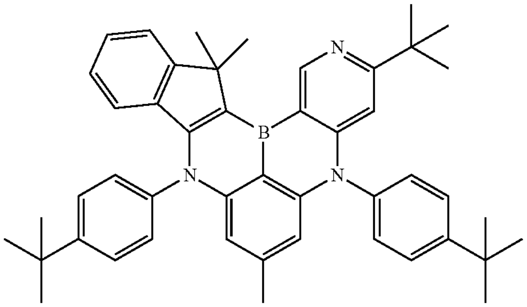
[Chemical Formula D215]
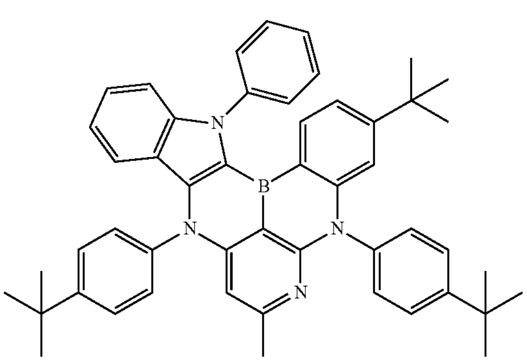
-continued
[Chemical Formula D216]
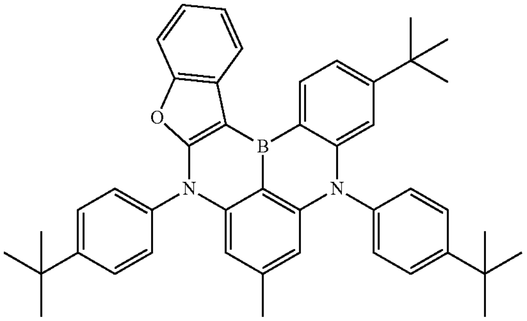
[Chemical Formula D217]
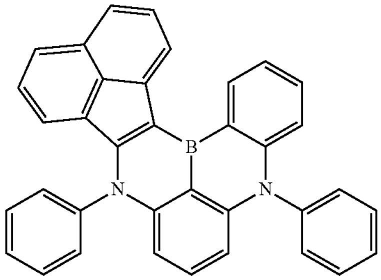
[Chemical Formula D218]
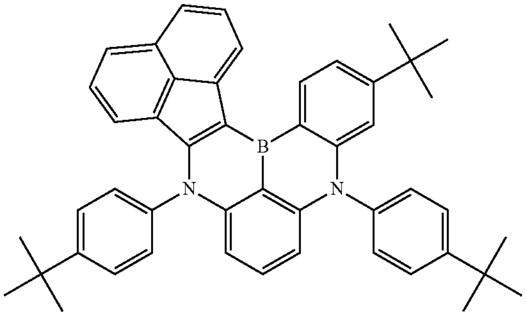
[Chemical Formula D219]
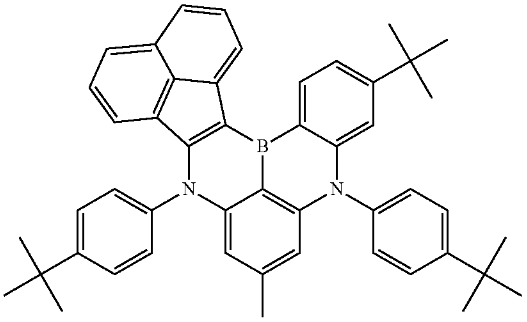

-continued
[Chemical Formula D220]
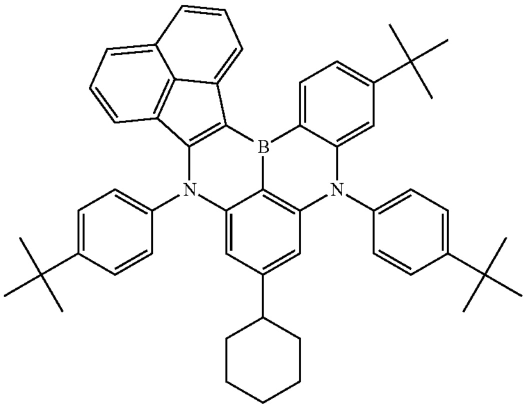
[Chemical Formula D221]
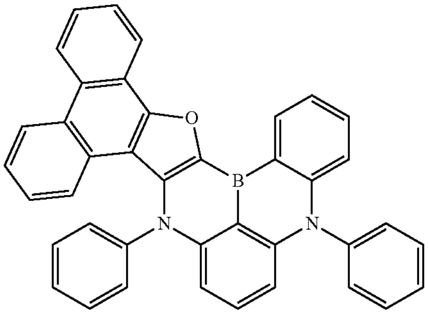
[Chemical Formula D222]
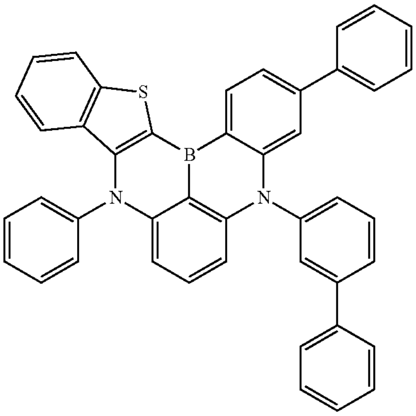
[Chemical Formula D223]
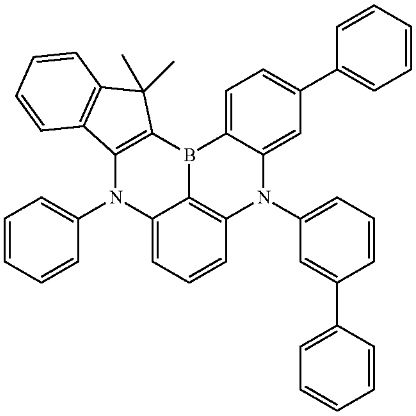
-continued
[Chemical Formula D224]
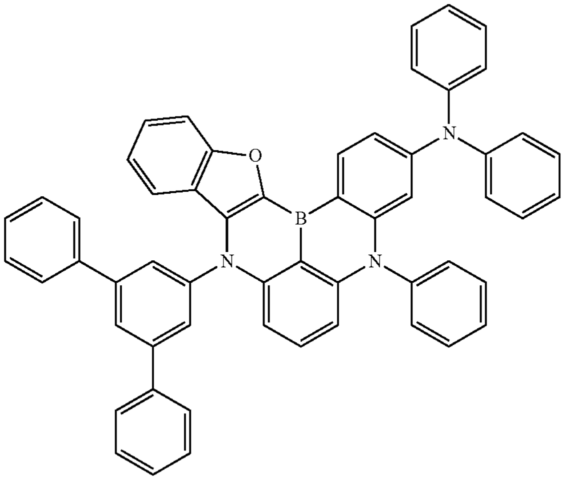
[Chemical Formula D225]
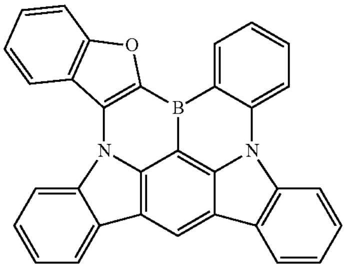
[Chemical Formula D226]
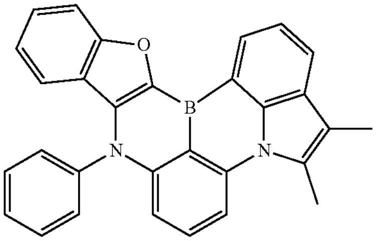
[Chemical Formula D227]
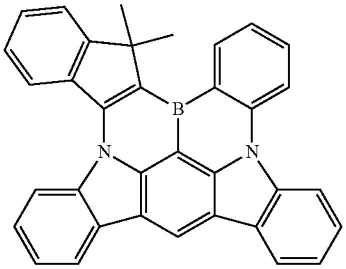

[Chemical Formula D228]
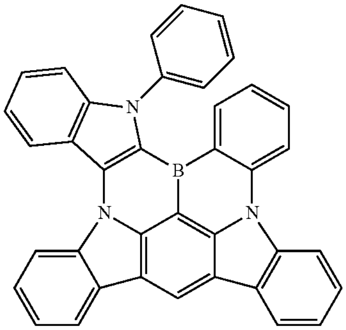
[Chemical Formula D229]
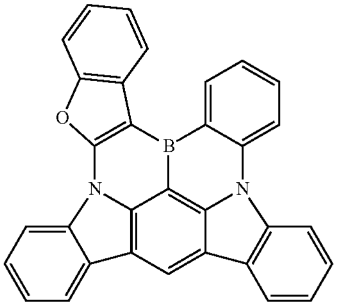
[Chemical Formula D230]
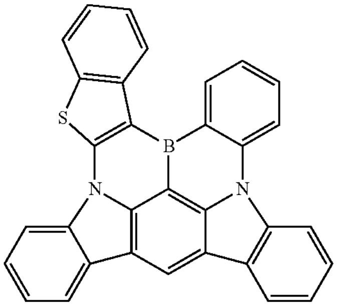
[Chemical Formula D231]
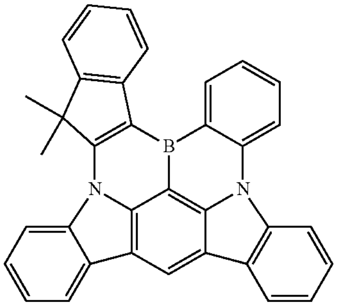
[Chemical Formula D232]
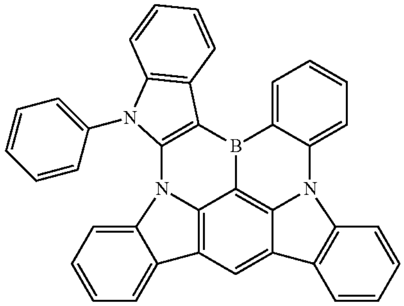
[Chemical Formula D233]
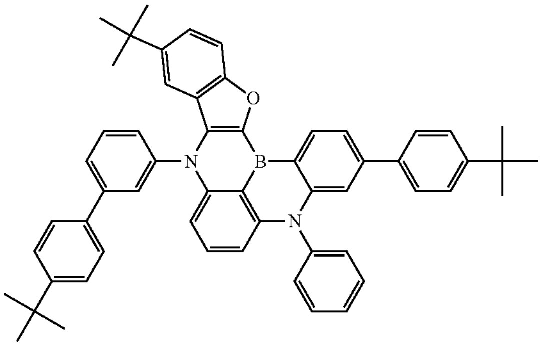
[Chemical Formula D234]
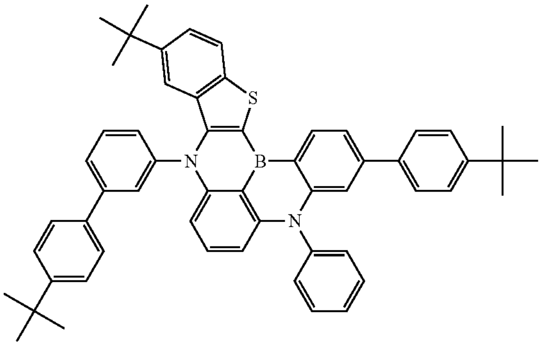
[Chemical Formula D235]
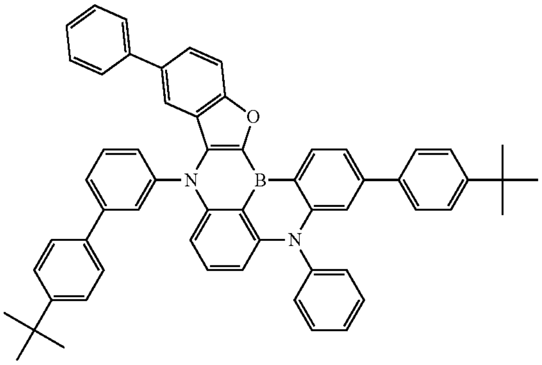
[Chemical Formula D236]
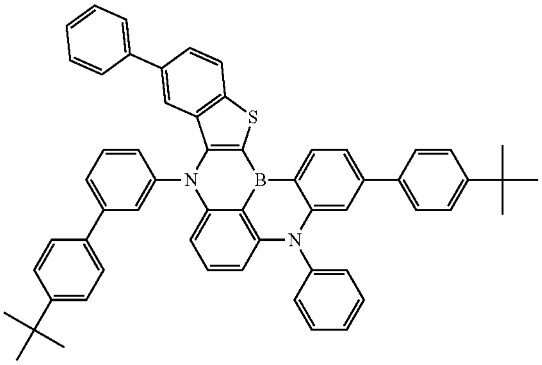

-continued
[Chemical Formula D237]
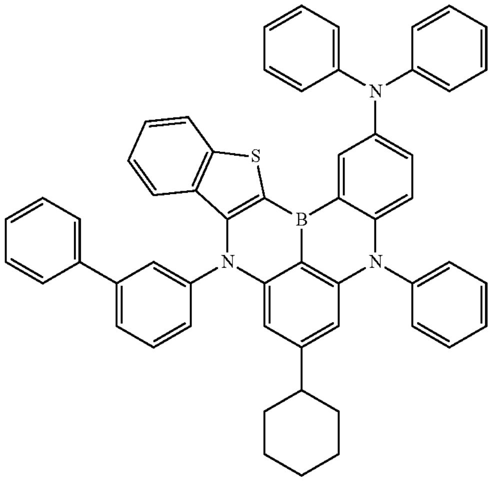
[Chemical Formula D238]
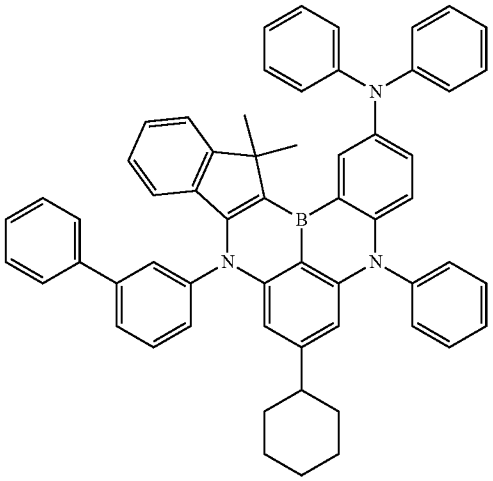
[Chemical Formula D239]
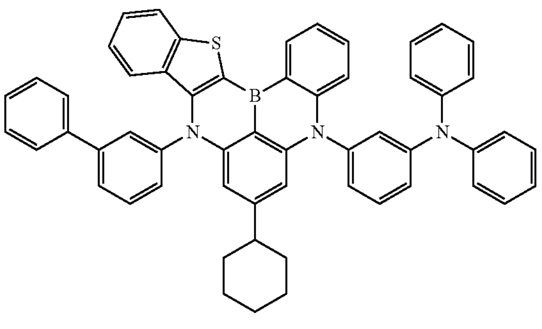
-continued
[Chemical Formula D240]
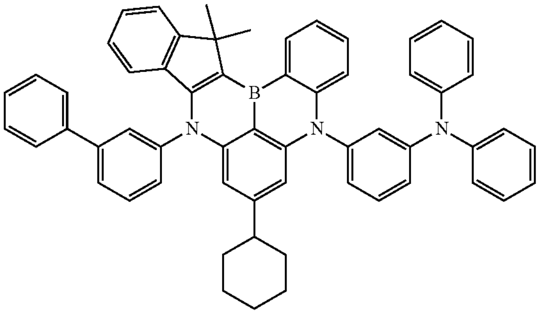
[Chemical Formula D241]
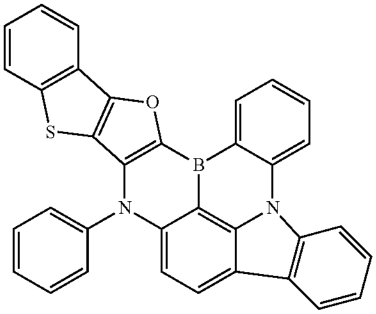
[Chemical Formula D242]
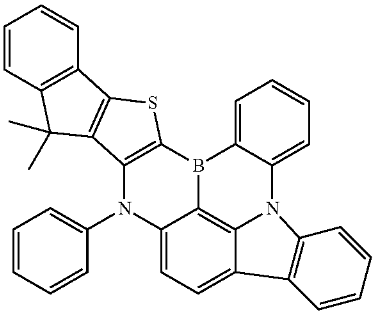
[Chemical Formula D243]
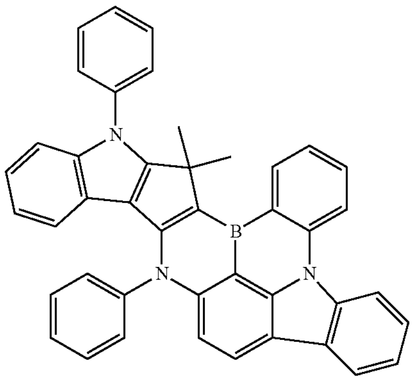

-continued
[Chemical Formula D244]
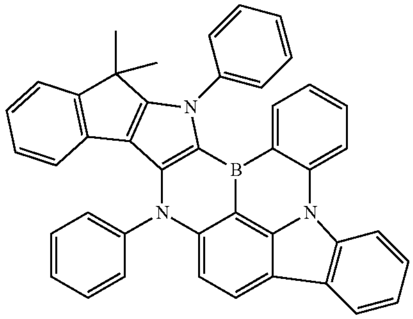
[Chemical Formula D245]
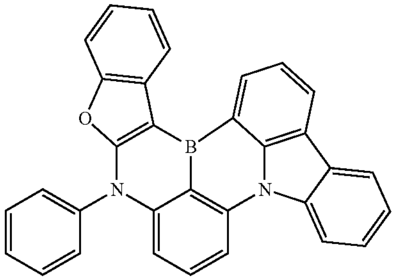
[Chemical Formula D246]
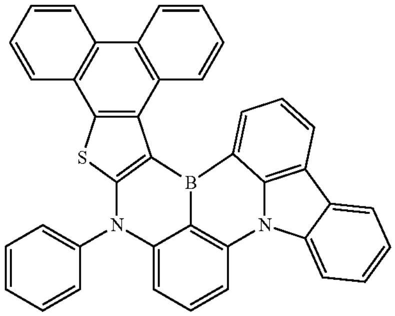
[Chemical ormula D247]
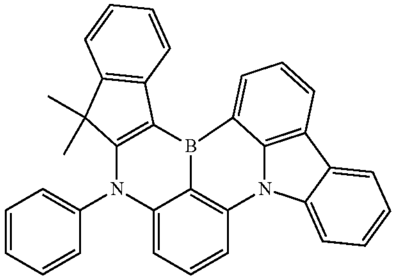
[Chemical Formula D248]
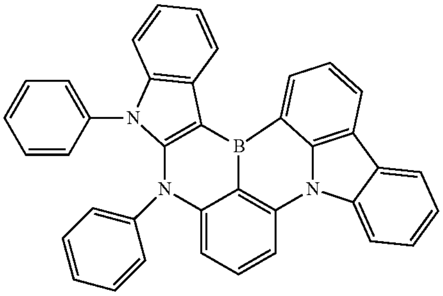
-continued
[Chemical Formula D249]
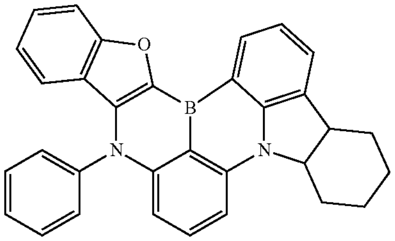
[Chemical Formula D250]
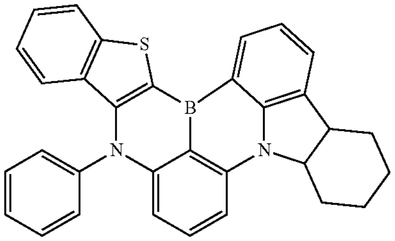
[Chemical Formula D251]
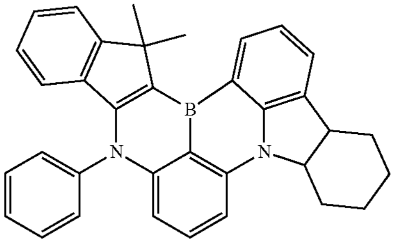
[Chemical Formula D252]
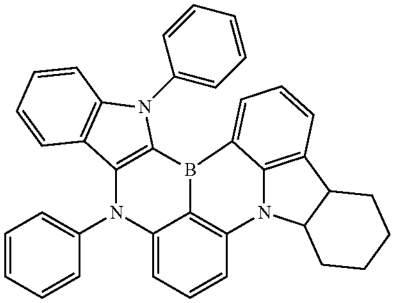
[Chemical Formula D253]
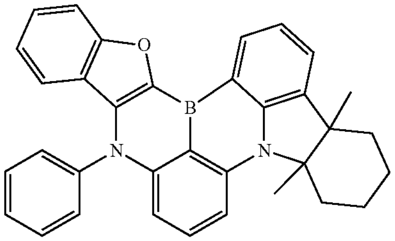

-continued
[Chemical Formula D254]
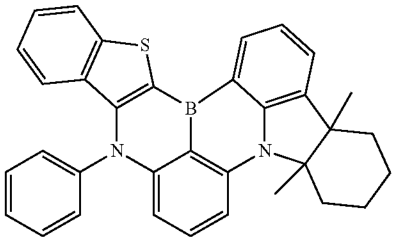
[Chemical Formula D255]
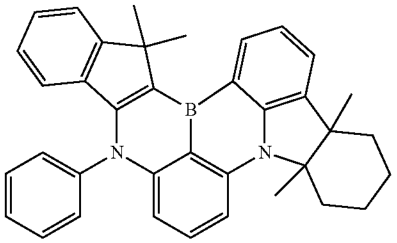
[Chemical Formula D256]
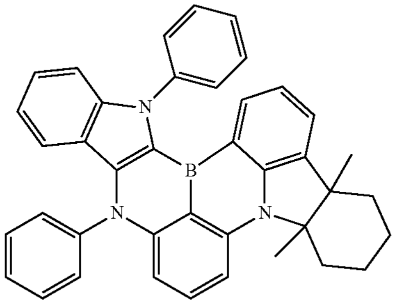
[Chemical Formula D257]
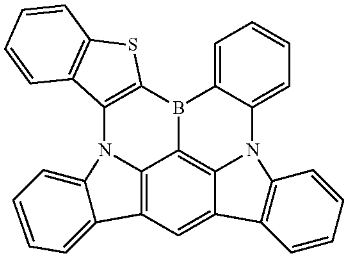
[Chemical Formula D258]
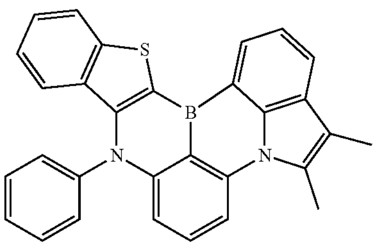
-continued
[Chemical Formula D259]
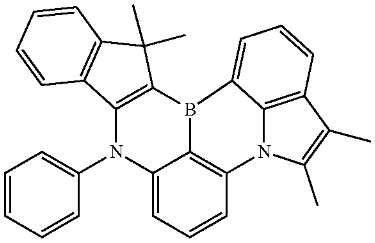
[Chemical Formula D260]
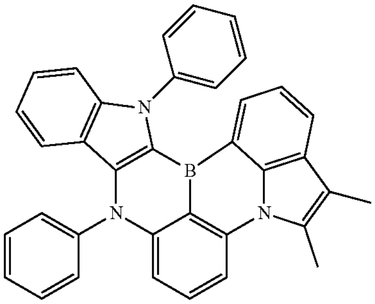
[[Chemical Formula D261]
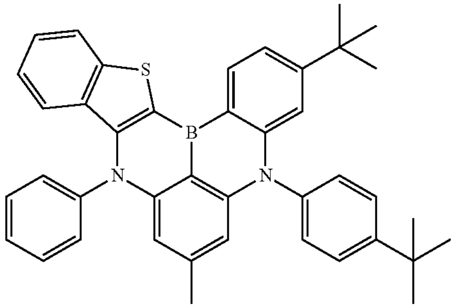
[Chemical Formula D262]
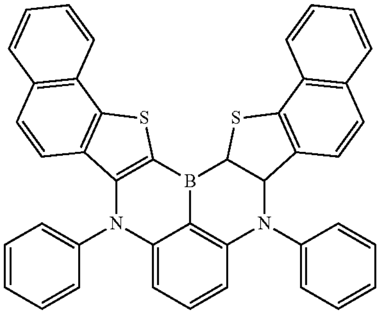
[Chemical Formula D263]
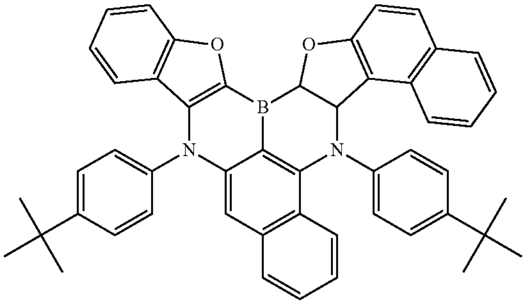

-continued
[Chemical Formula D264]
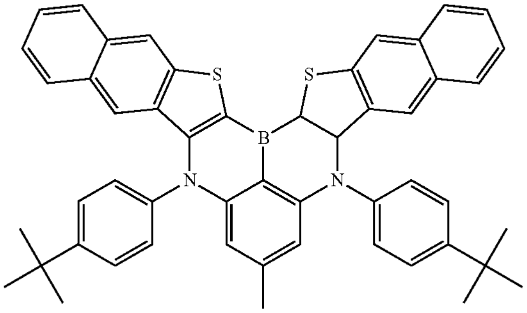
[Chemical Formula D265]
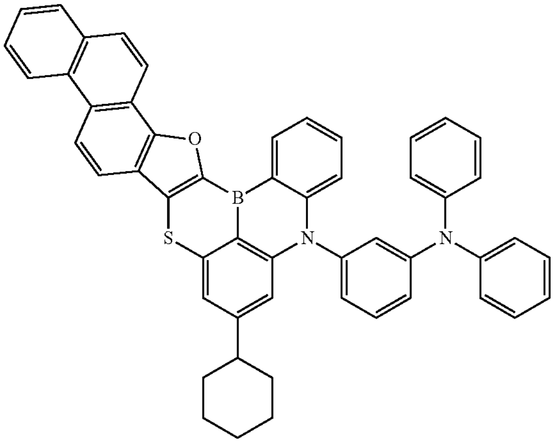
[Chemical Formula D266]
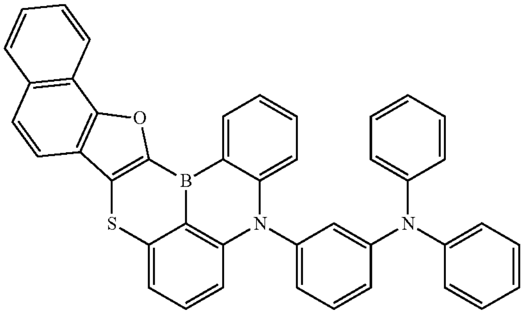
[Chemical Formula D267]
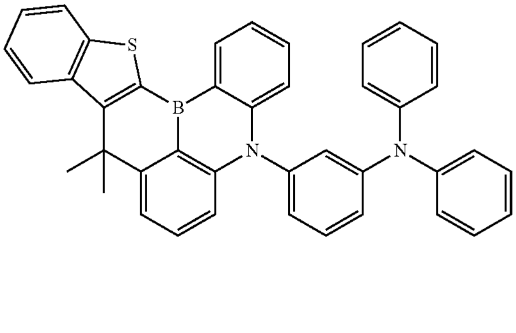
-continued
[Chemical Formula D268]
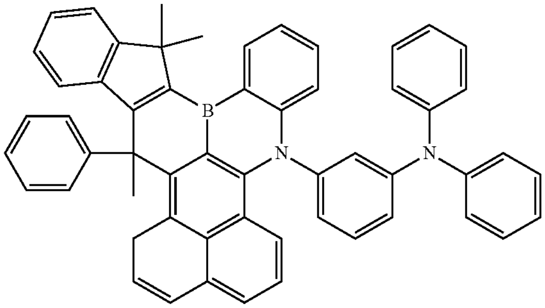
[Chemical Formula D269]
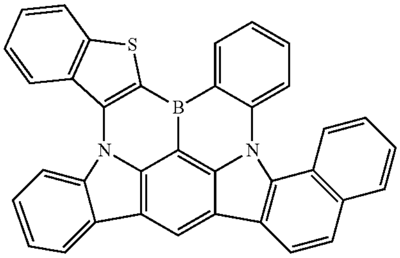
[Chemical Formula D270]
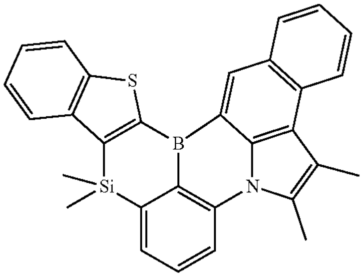
[Chemical Formula D271]
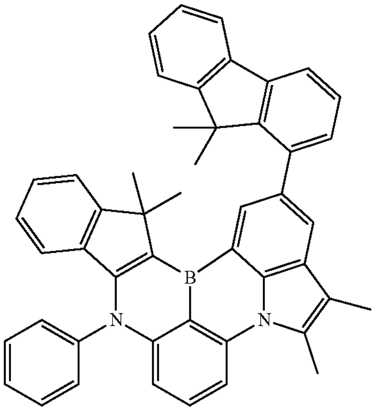
[Chemical Formula D272]
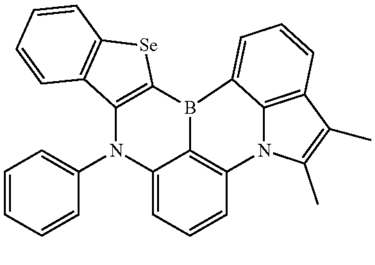

[Chemical Formula D273]
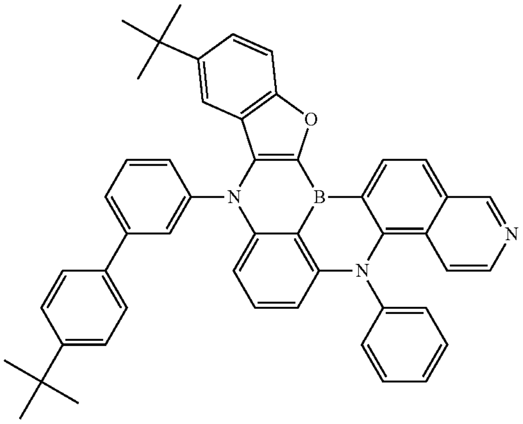
[Chemical Formula D274]
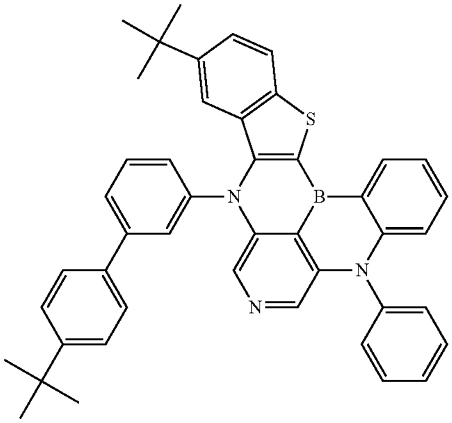
[Chemical Formula D275]
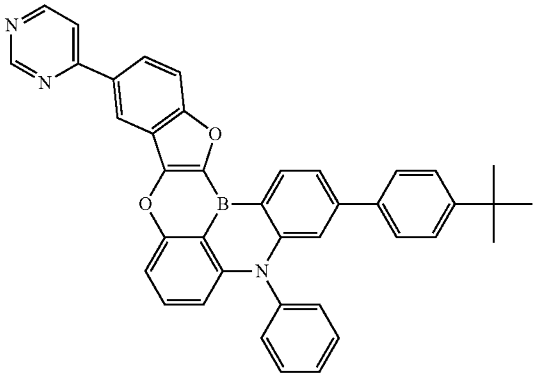
[Chemical Formula D276]
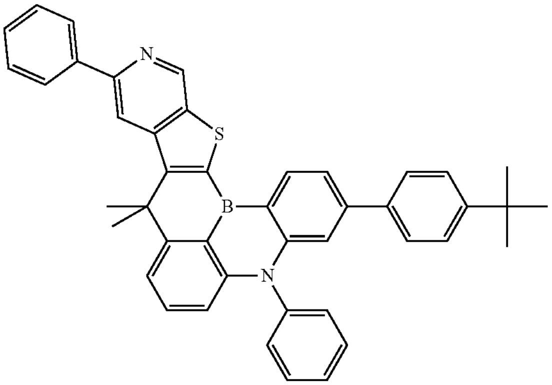
[Chemical Formula D277]
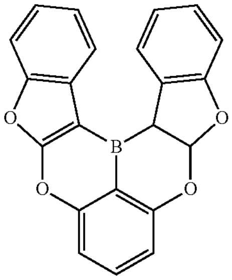
[Chemical Formula D278]
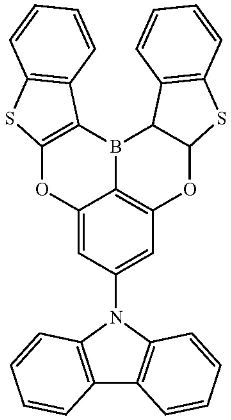
[Chemical Formula D279]
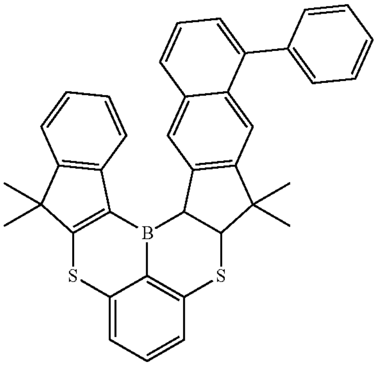

-continued
[Chemical FormulaD280]
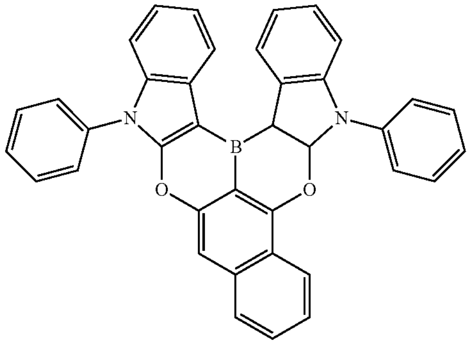
[Chemical Formula D281]
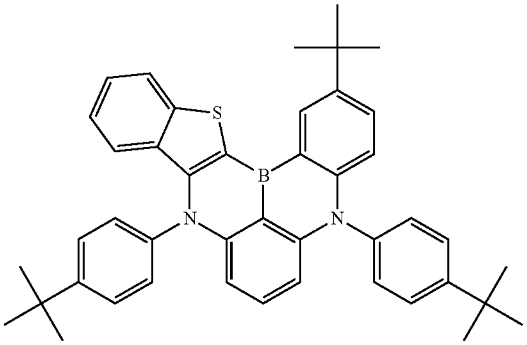
Concrete examples of the compounds represented by [Chemical Formula D6] to [Chemical Formula D8] include compounds of the following <Chemical Formula D301> to <Chemical Formula D432>:
<Compound 301>
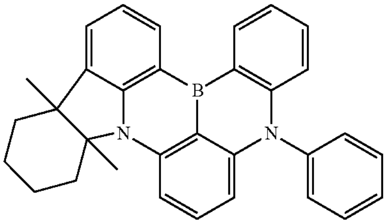
<Compound 302>
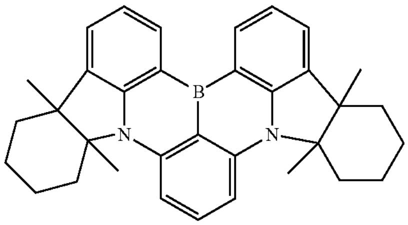
<Compound 303>
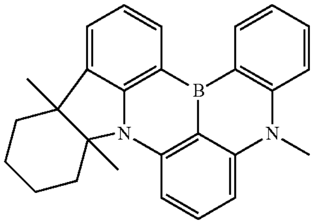
-continued
<Compound 304>
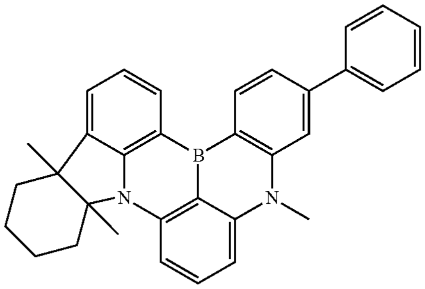
<Compound 305>
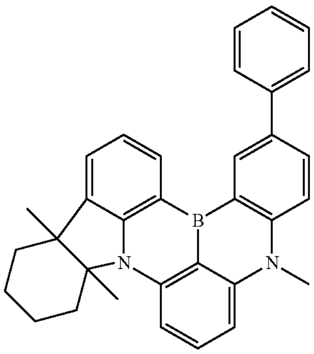
<Compound 306>
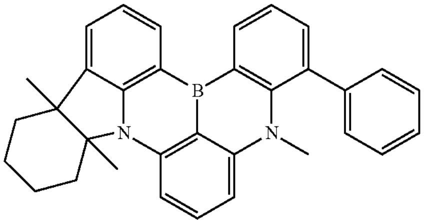
<Compound 307>
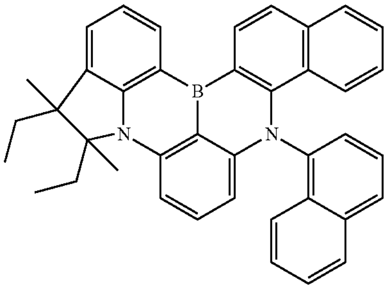
<Compound 308>
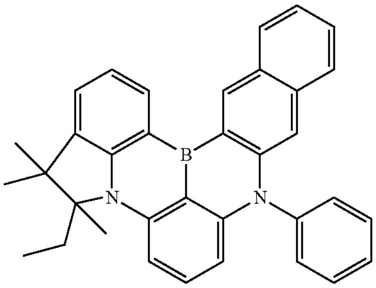

-continued
<Compound 309>
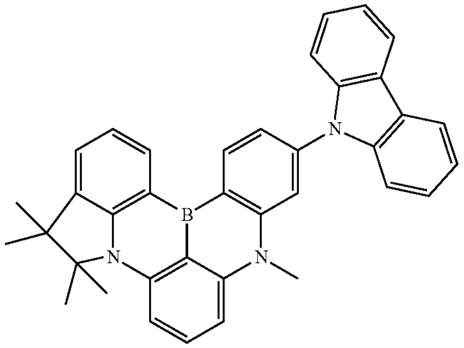
<Compound 310>
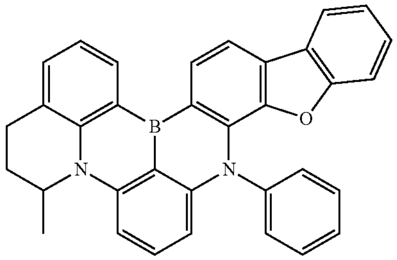
<Compound 311>
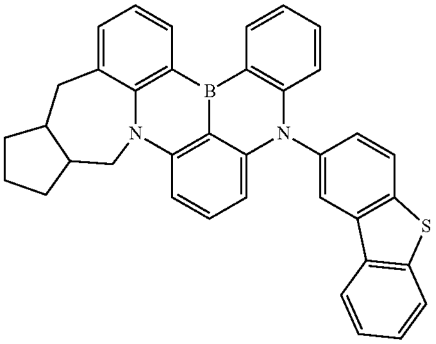
<Compound 312>
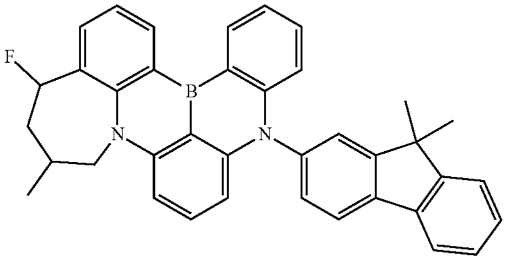
<Compound 313>
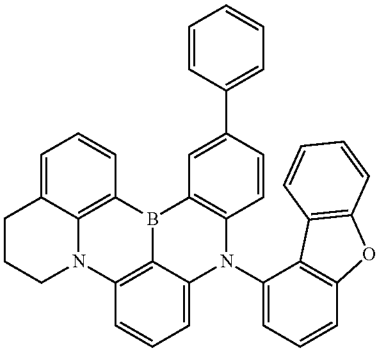
-continued
<Compound 314>
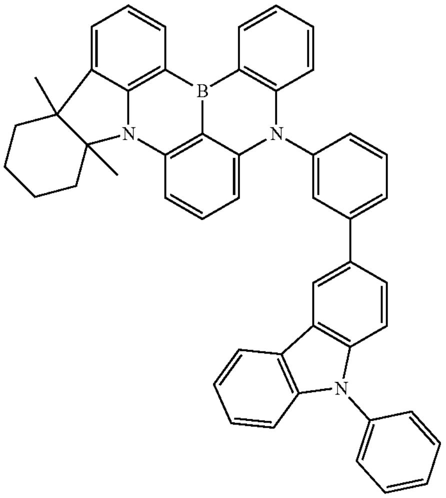
<Compound 315>
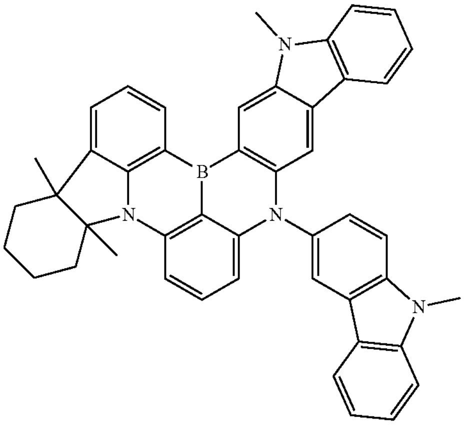
<Compound 316>
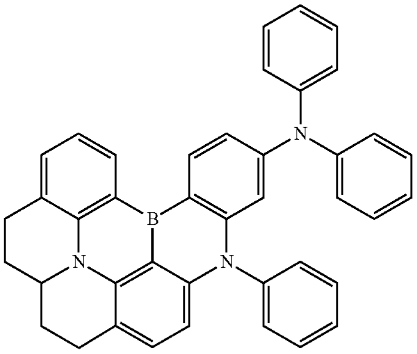

-continued
<Compound 317>
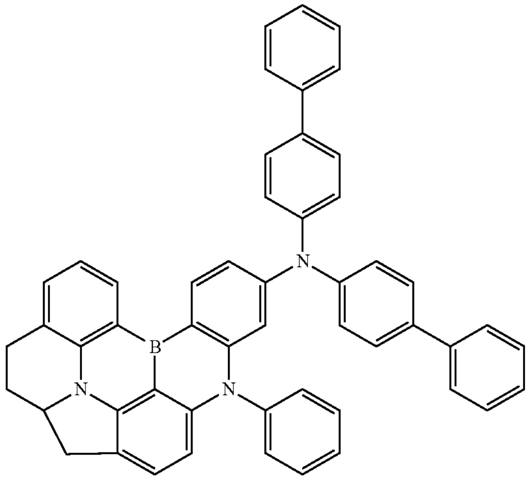
<Compound 318>
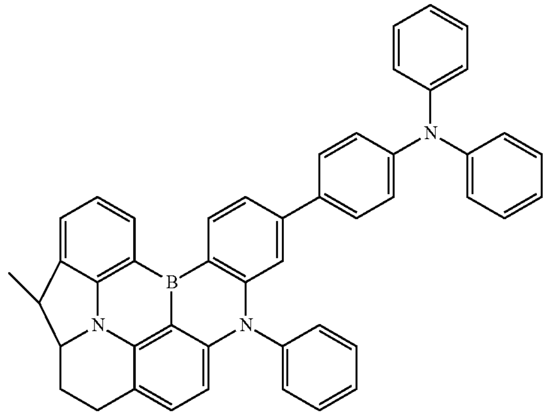
<Compound 319>
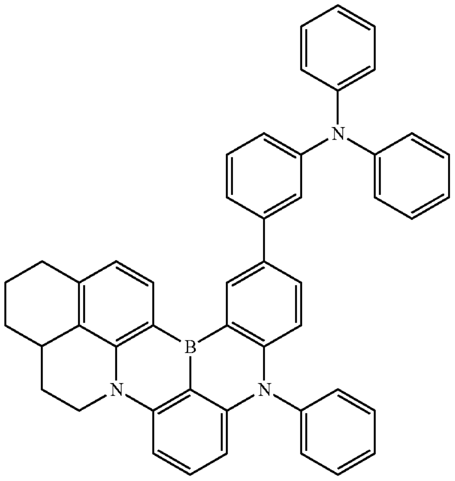
-continued
<Compound 320>
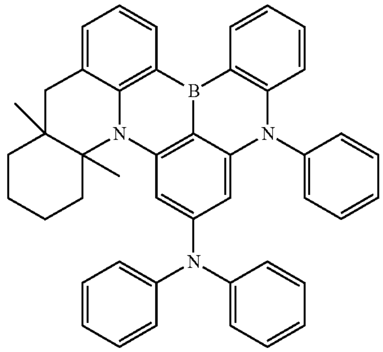
<Compound 321>
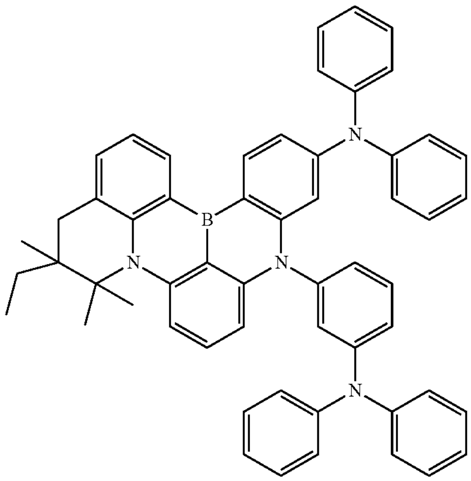
<Compound 322>
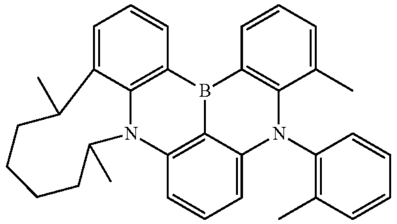
<Compound 323>
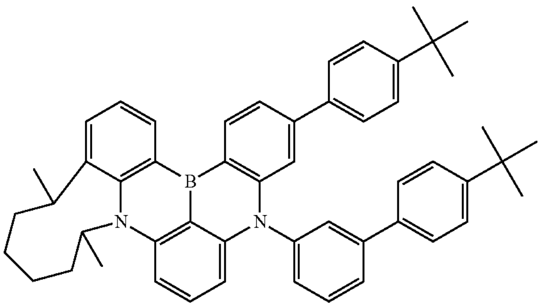

-continued
<Compound 324>
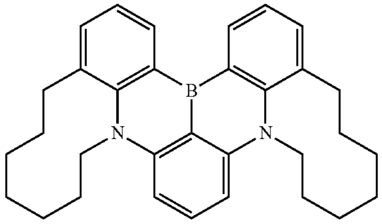
<Compound 325>
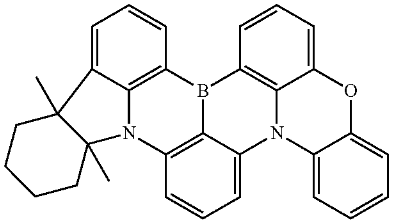
<Compound 326>
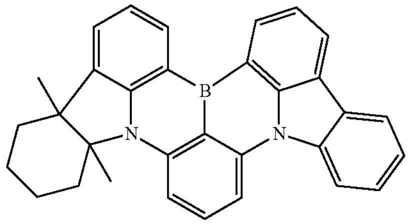
<Compound 327>
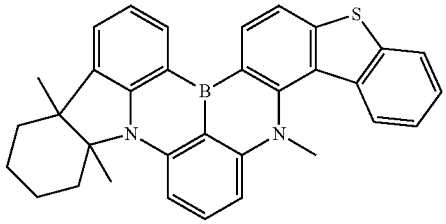
<Compound 328>
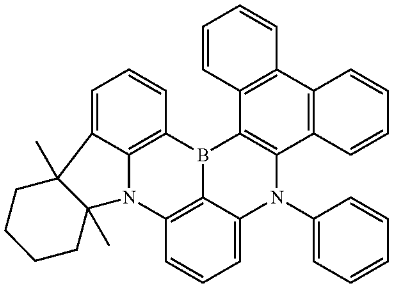
<Compound 329>
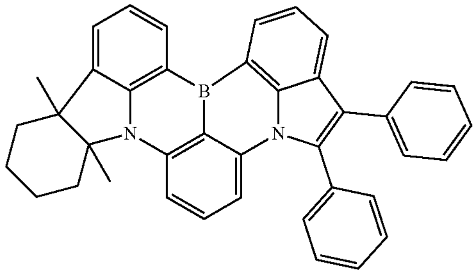
-continued
<Compound 330>
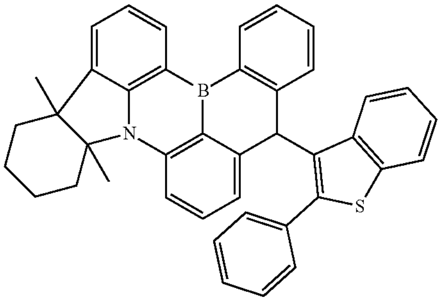
<Compound 331>
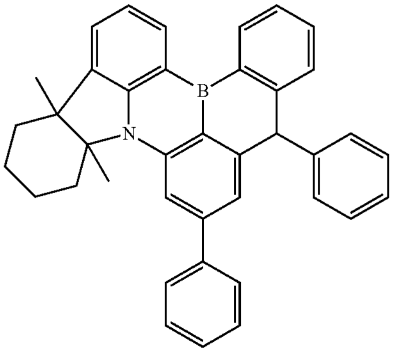
<Compund 332>
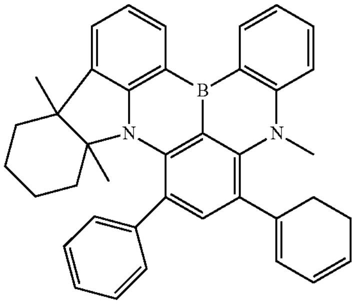
<Compund 333>
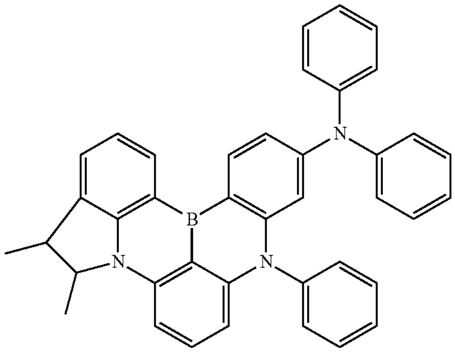

-continued
<Compound 334>
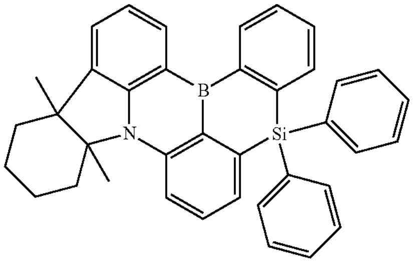
<Compound 335>
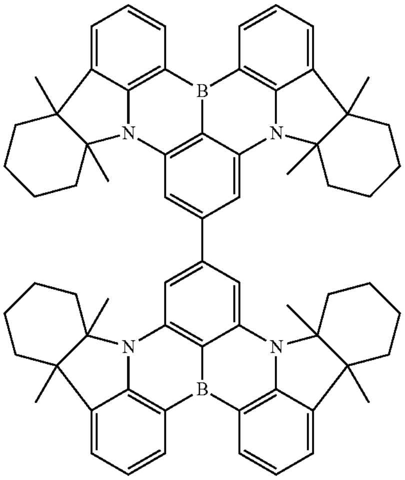
<Compound 336>
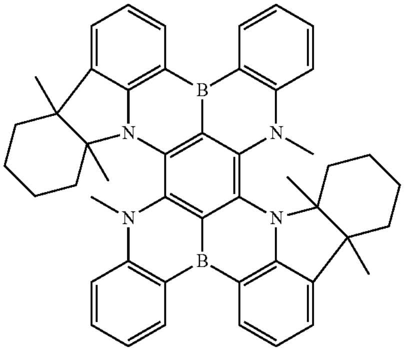
<Compound 337>
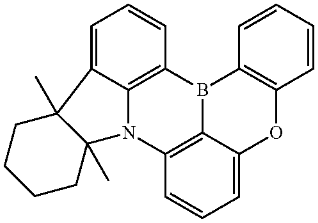
-continued
<Compound 338>
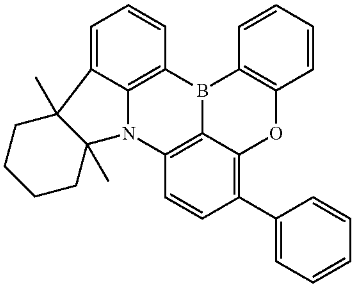
<Compound 339>
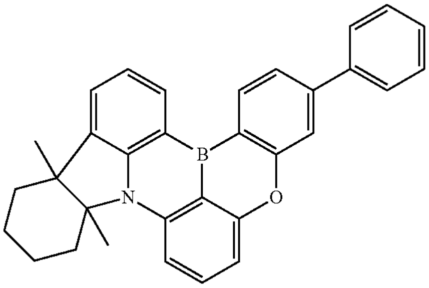
<Compound 340>
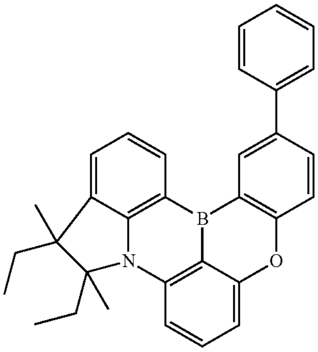
<Compound 341>
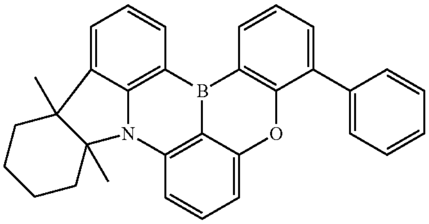
<Compound 342>
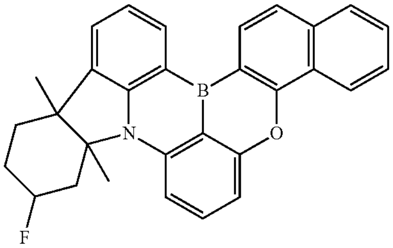

-continued
<Compound 343>
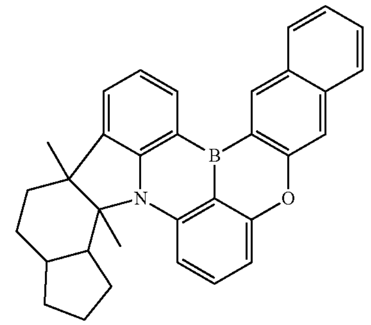
<Compound 344>
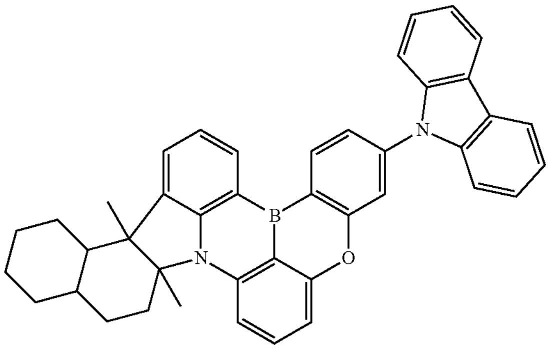
<Compound 345>
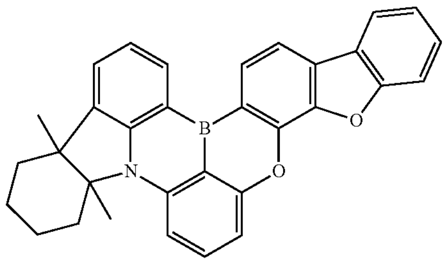
<Comound 346>
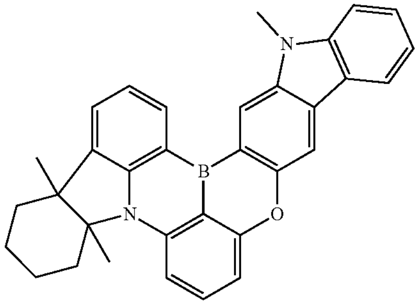
<Compound 347>
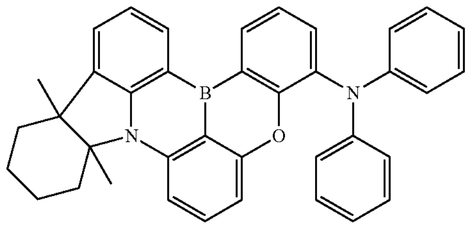
-continued
<Compound 348>
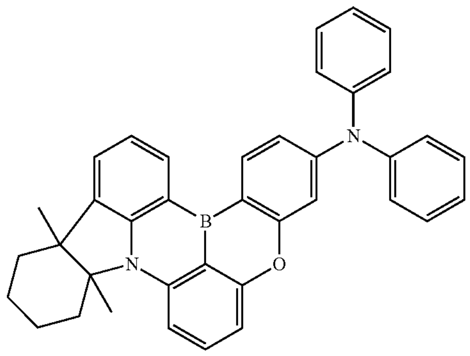
<Compound 349>
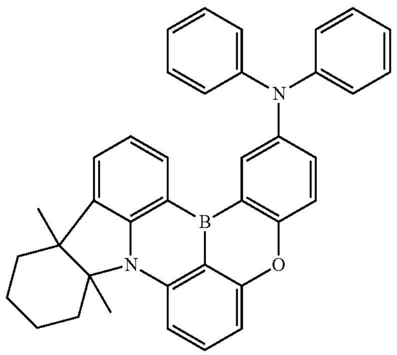
<Compound 350>
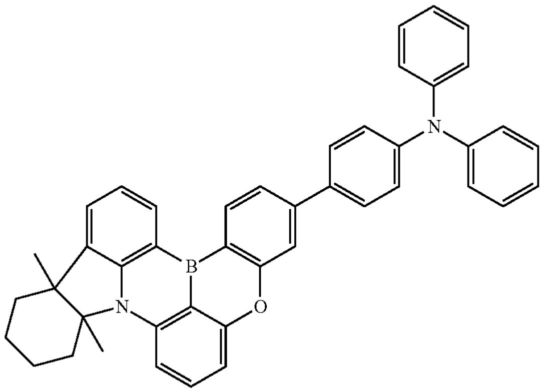

-continued
<Compound 351>
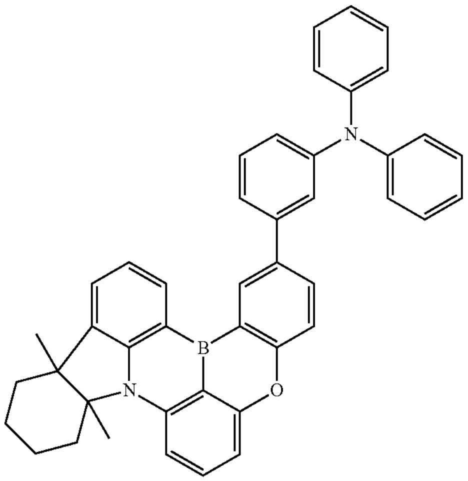
<Compound 352>
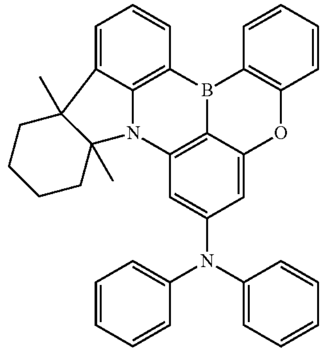
<Compound 353>
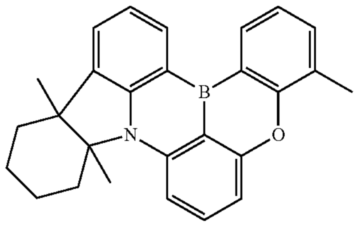
<Compound 354>
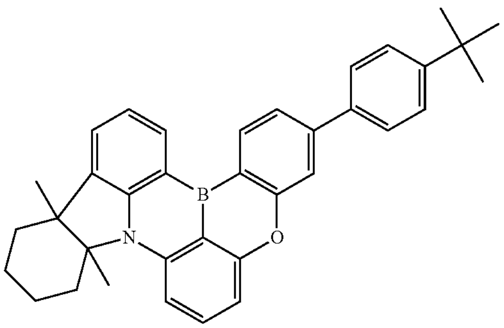
-continued
<Compound 355>
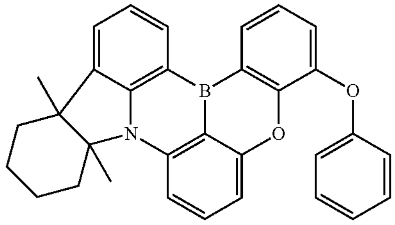
<Compound 356>
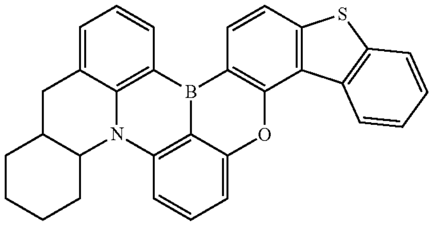
<Compound 357>
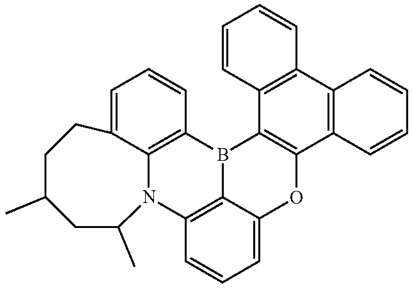
<Compound 358>
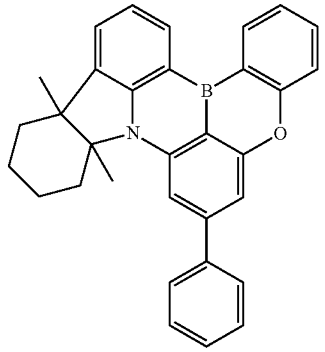
<Compound 359>
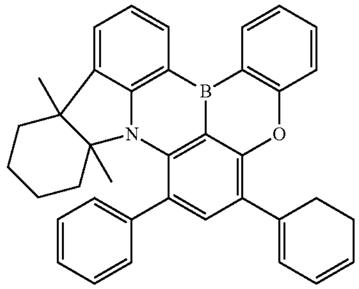

-continued
<Compound 360>
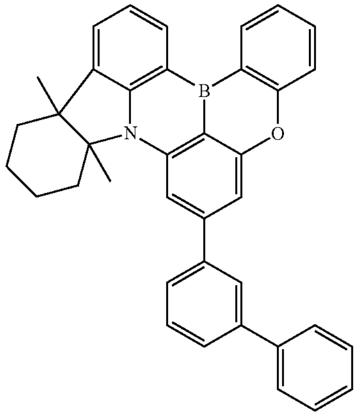
<Compound 361>
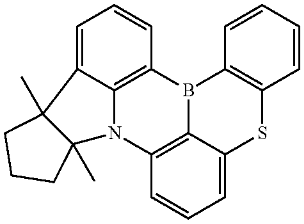
<Compound 362>
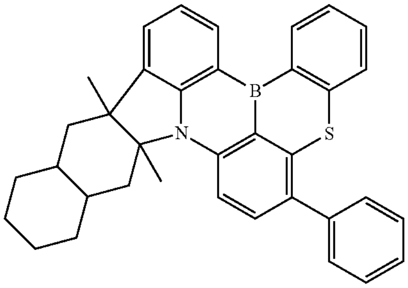
<Compound 363>
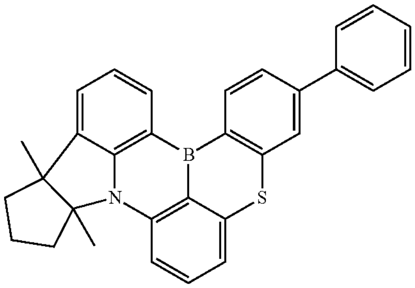
<Compound 364>
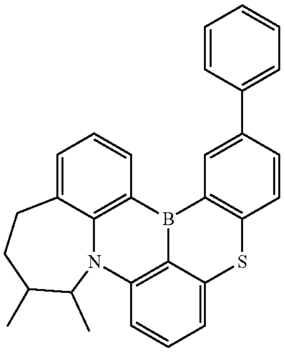
-continued
<Compound 365>
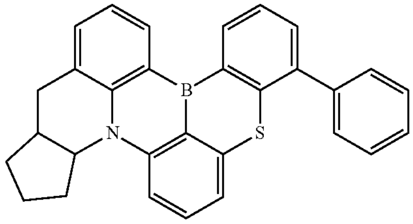
<Compound 366>
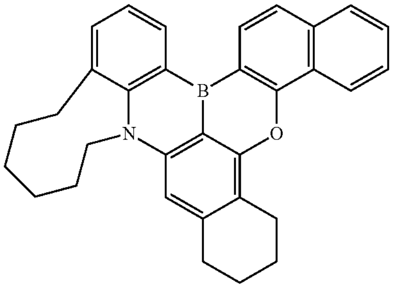
<Compound 367>
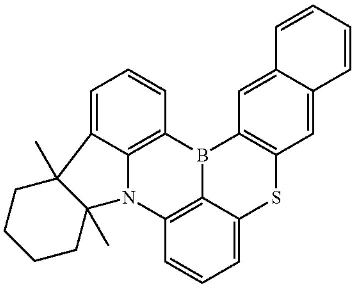
<Compound 368>
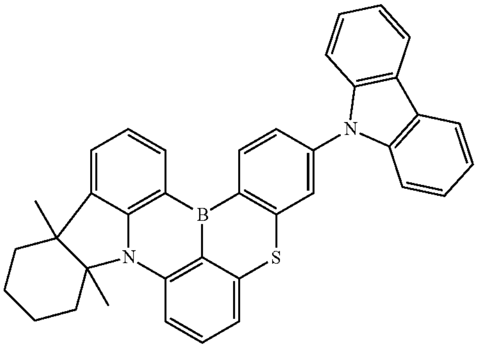
<Compound 369>
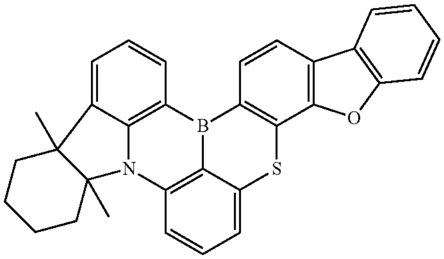

-continued
<Compound 370>
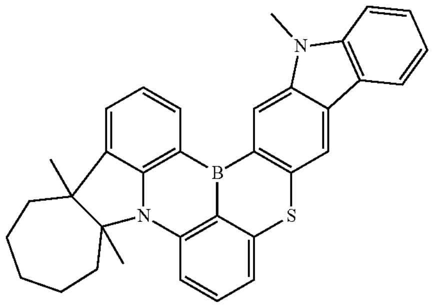
<Compound 371>
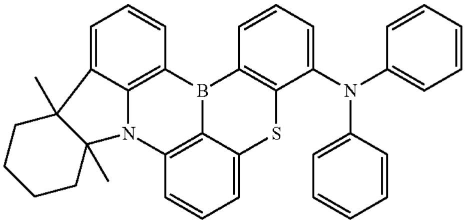
<Compound 372>
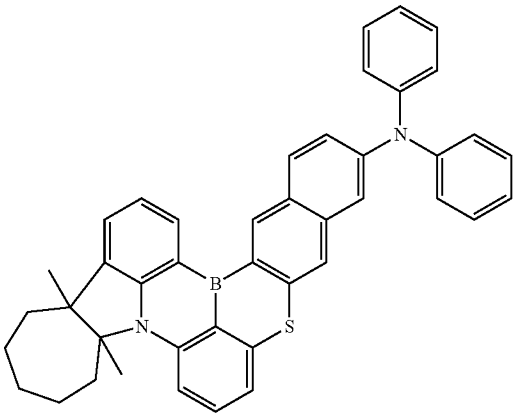
<Compound 373>
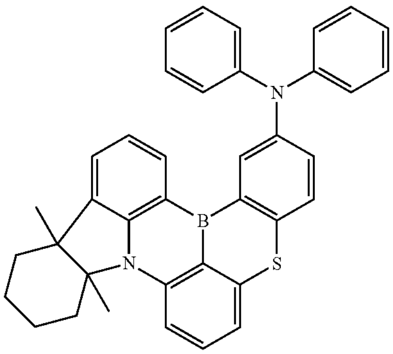
-continued
<Compound 374>
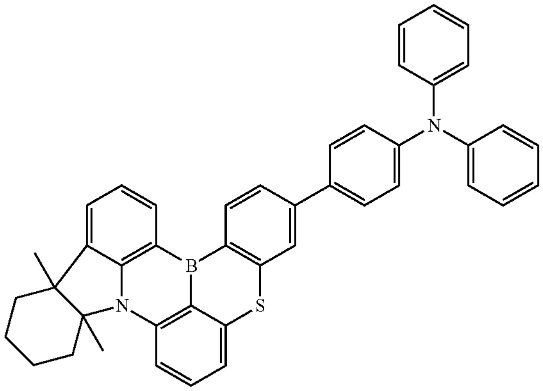
<Compound 375>
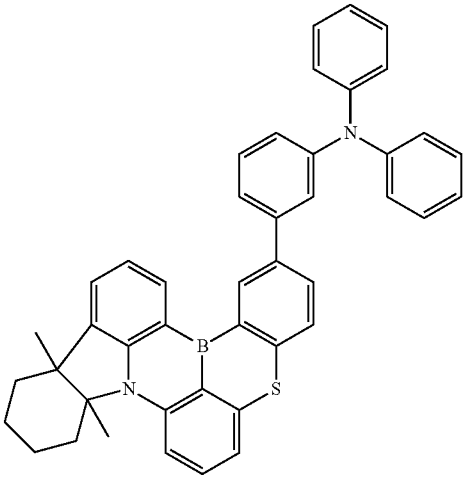
<Compound 376>
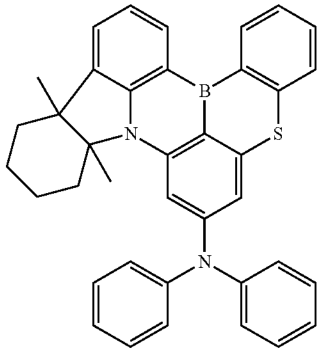
<Compound 377>
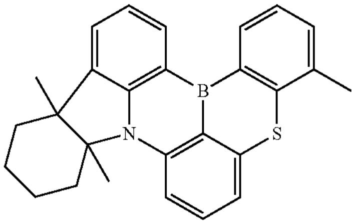

-continued
<Compound 378>
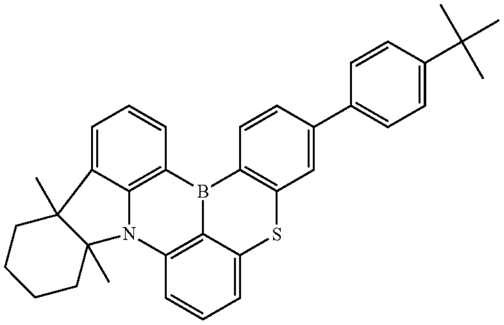
<Compound 379>
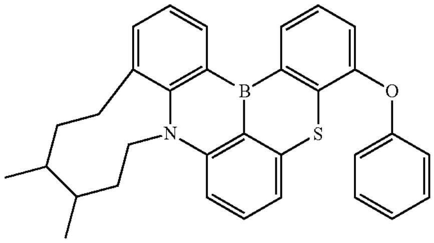
<Compound 380>
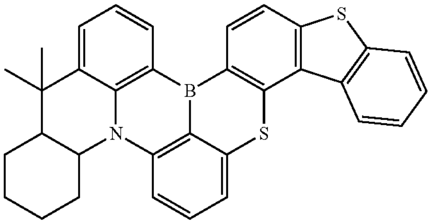
<Compound 381>
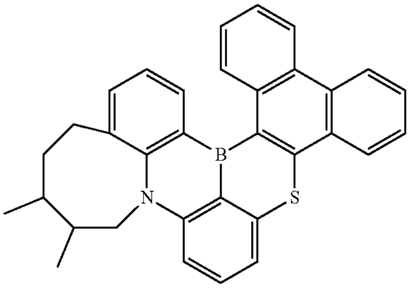
<Compound 382>
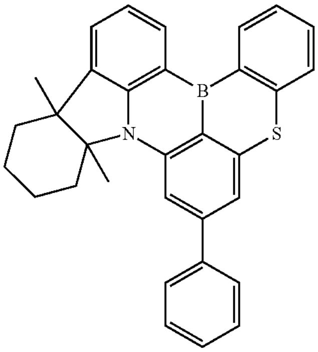
-continued
<Compopund 383>
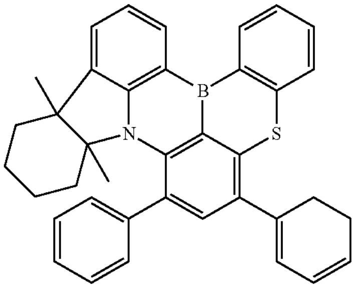
<Compound 384>
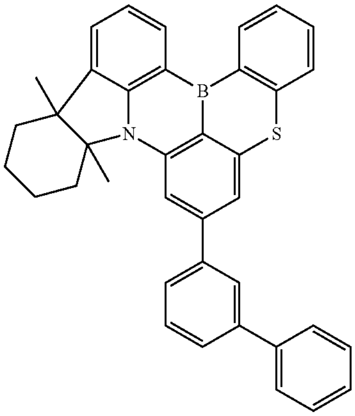
<Compound 385>
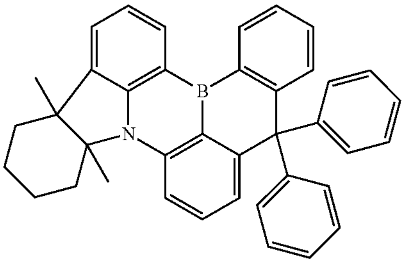
<Comopound 386>
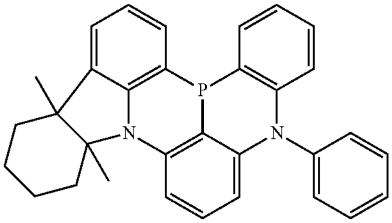
<Compound 387>
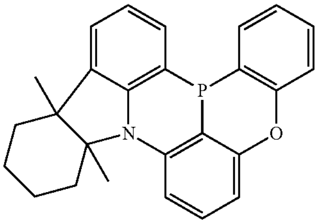

-continued
<Compound 388>
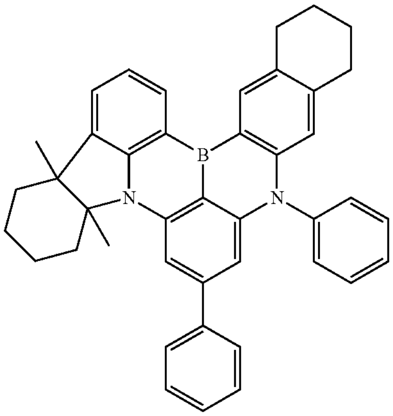
<Compound 389>
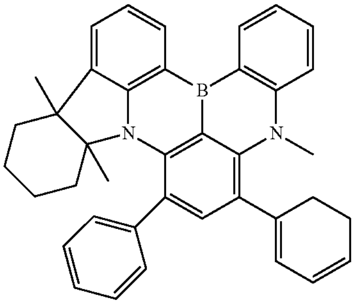
<Compound 390>
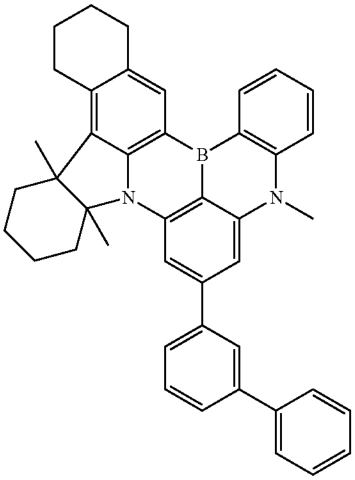
<Compound 391>
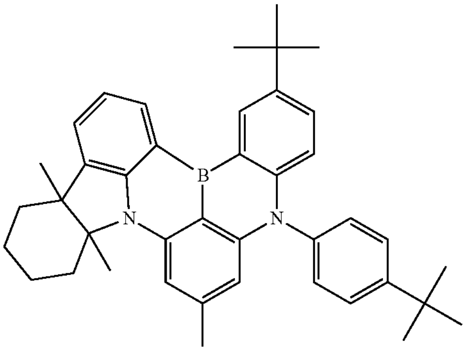
-continued
<Compound 392>
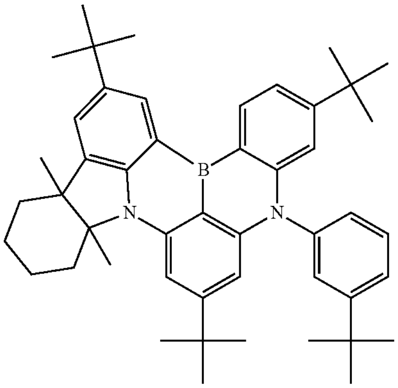
<Compound 393>
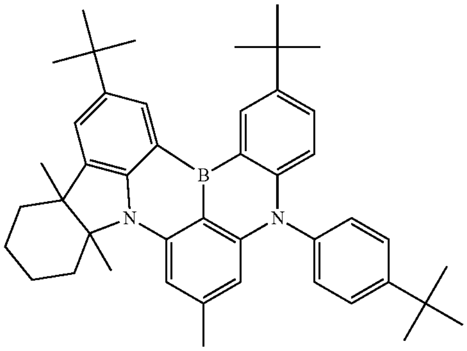
<Compound 394>
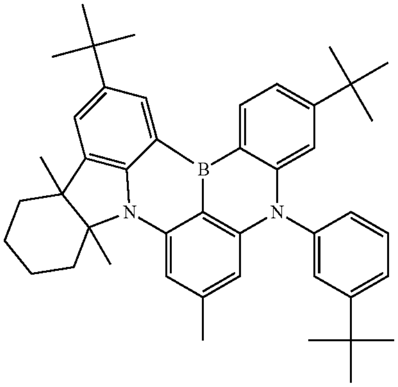
<Compound 395>
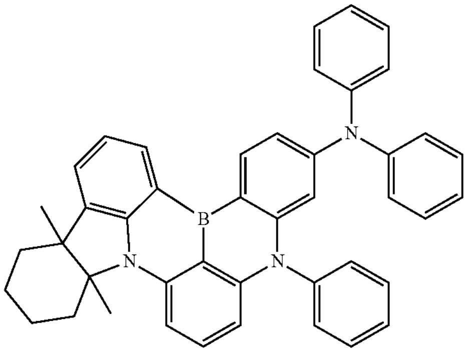

-continued
<Compound 396>
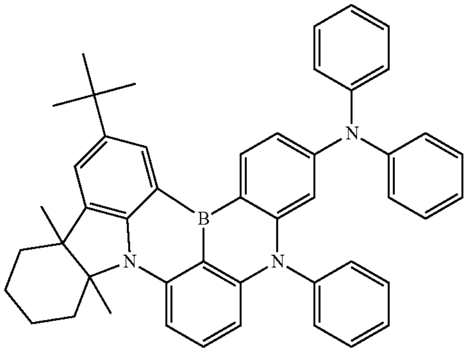
<Compound 397>
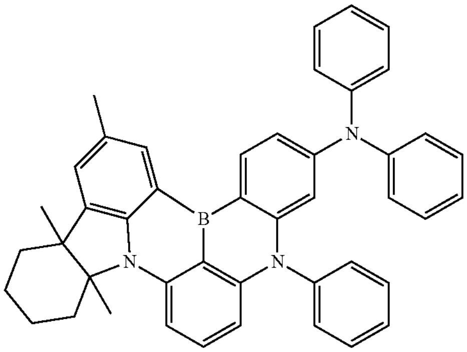
<Compound 398>
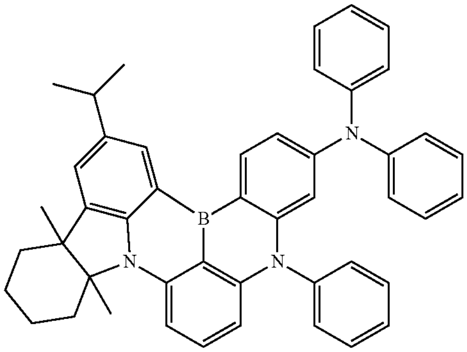
<Compound 399>
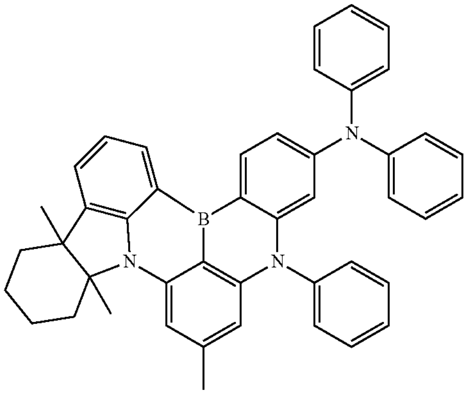
-continued
<Compound 400>
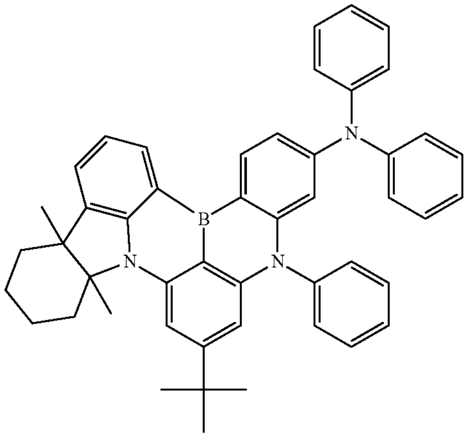
<Compound 401>
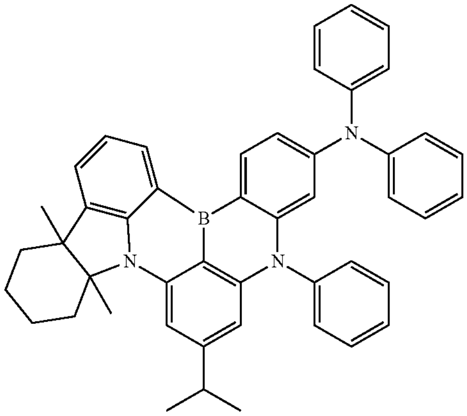
[Compound 402>
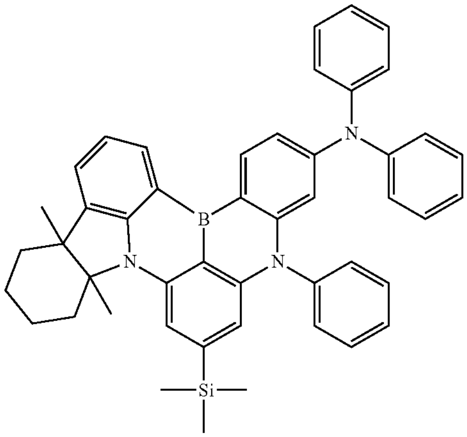

-continued
<Compound 403>
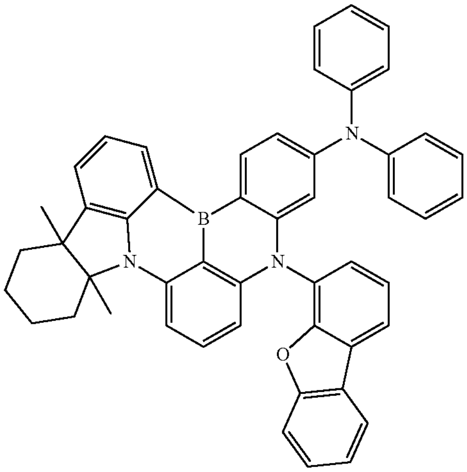
<Compound 404>
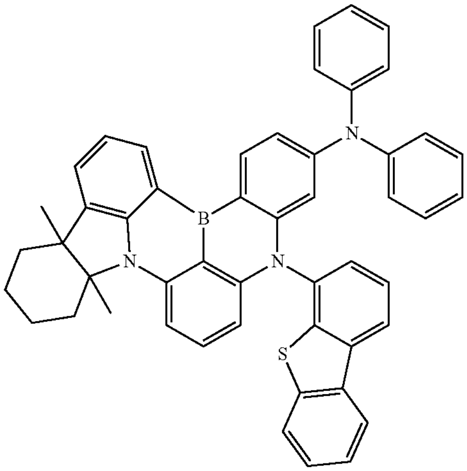
<Compoud 405>
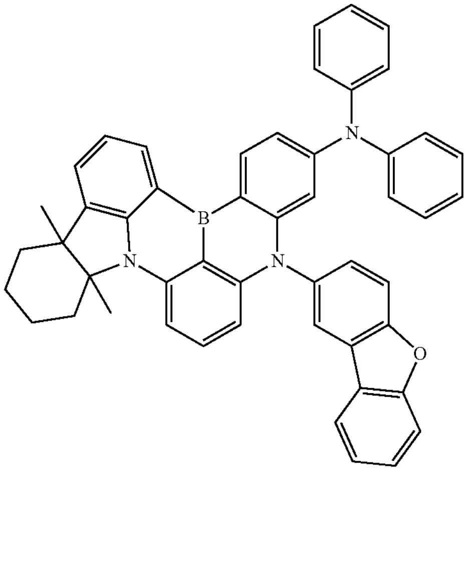
-continued
<Compound 406>
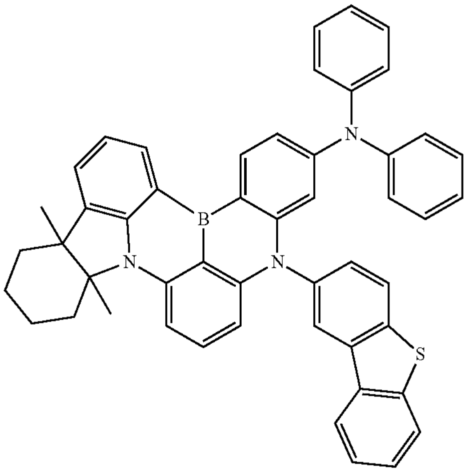
<Compound 407>
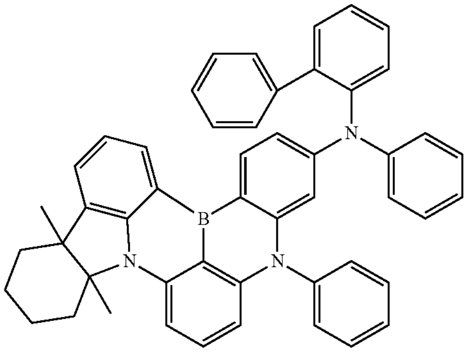
<Compound 408>
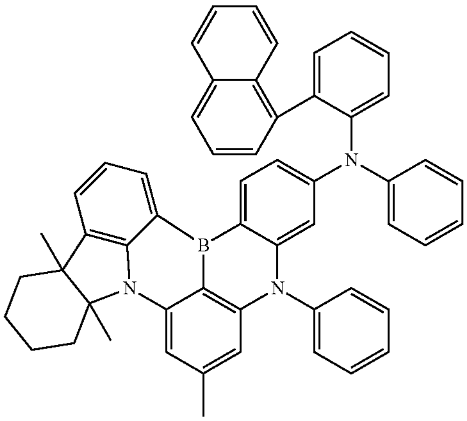

-continued
<Compound 409>
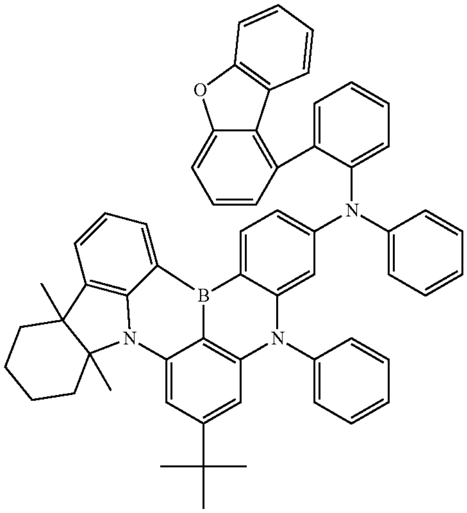
<Compound 410>
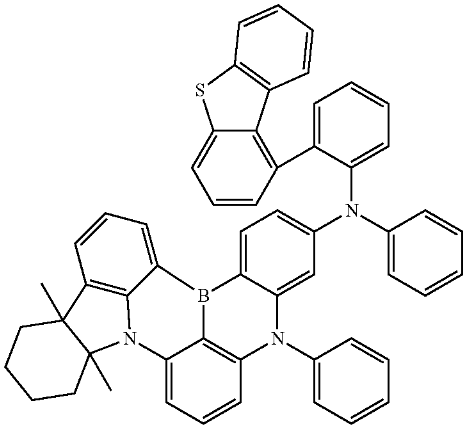
<Compound 411>
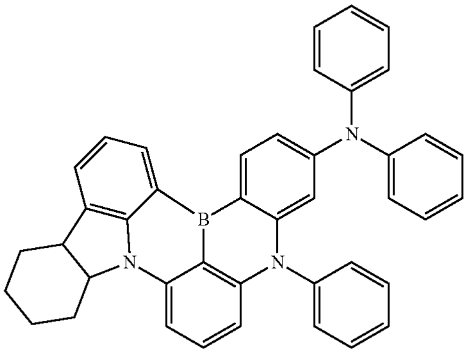
-continued
<Compound 412>
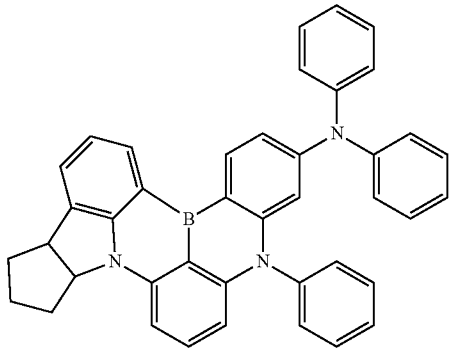
<Compound 413>
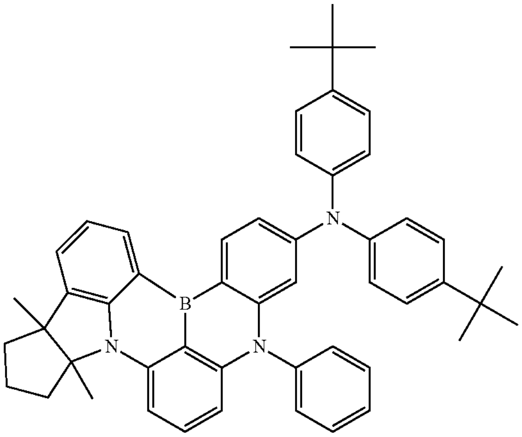
<Compound 414>
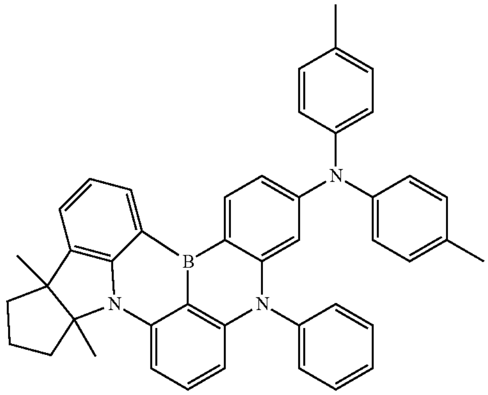
<Compound 415>
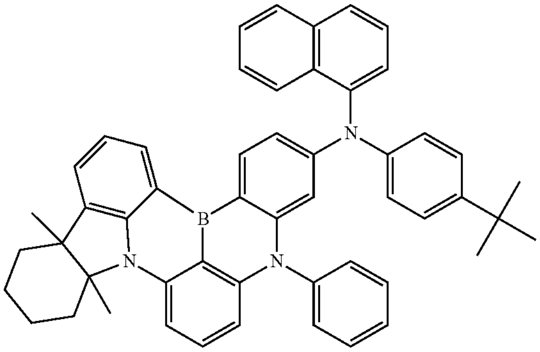

-continued
<Compound 416>
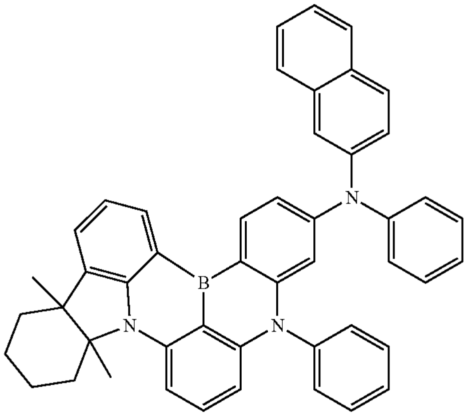
<Compound 417>
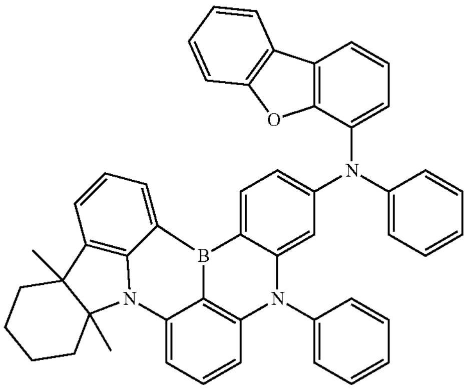
<Compound 418>
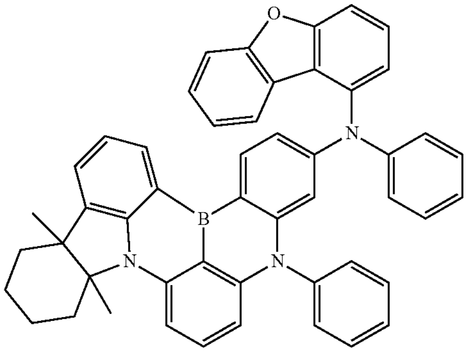
-continued
<Compound 419>
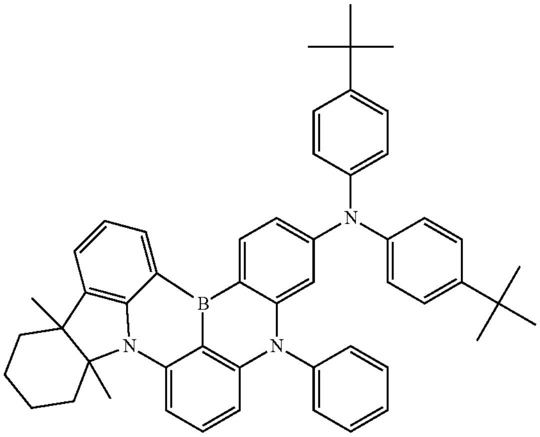
<Compound 420>
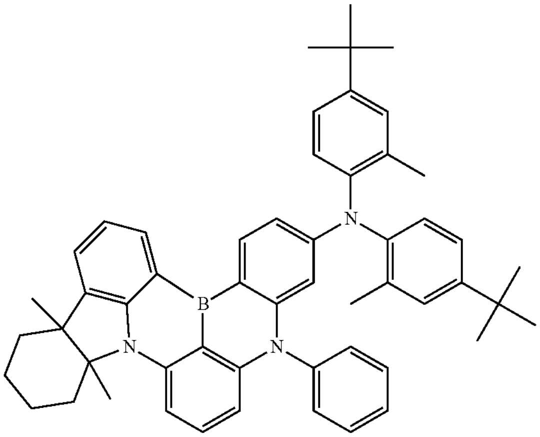
<Compound 421>
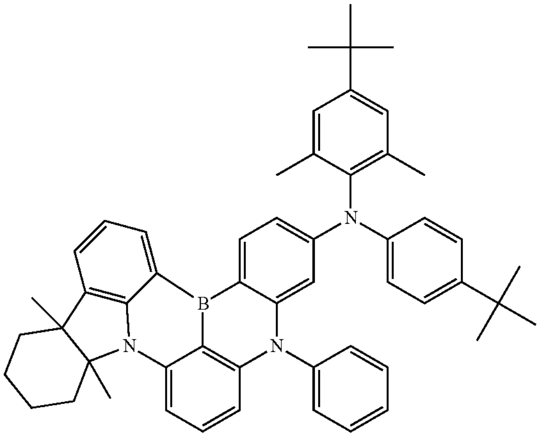

-continued
<Compound 422>
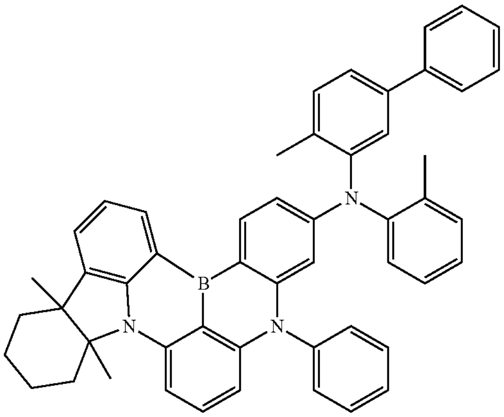
<Compound 423>
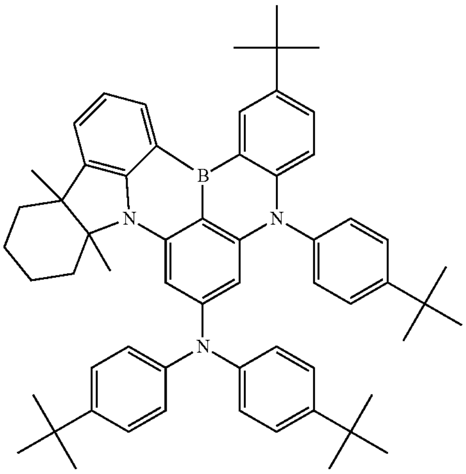
<Compound 424>
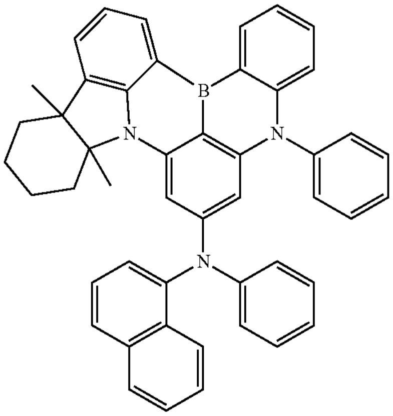
-continued
<Compound 425>
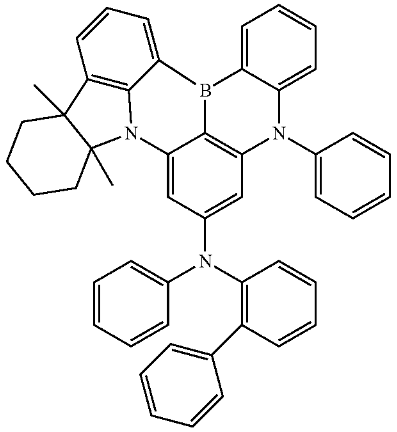
<Compound  426>
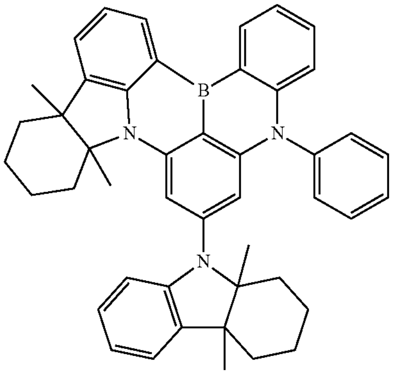
<Compoound 427>
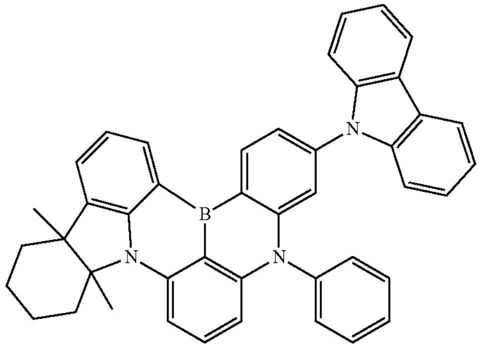
<Compound 428>
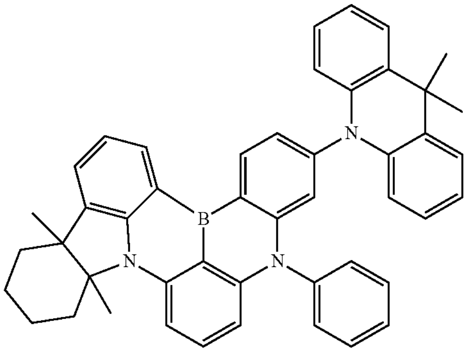

-continued

<Compound 429>

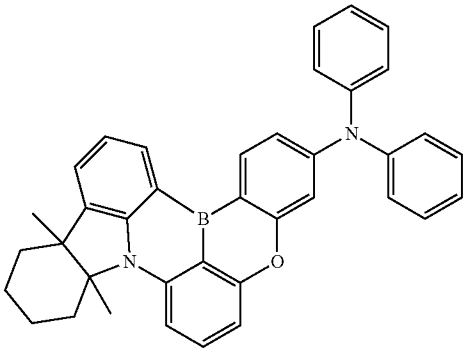

<Compound 430>

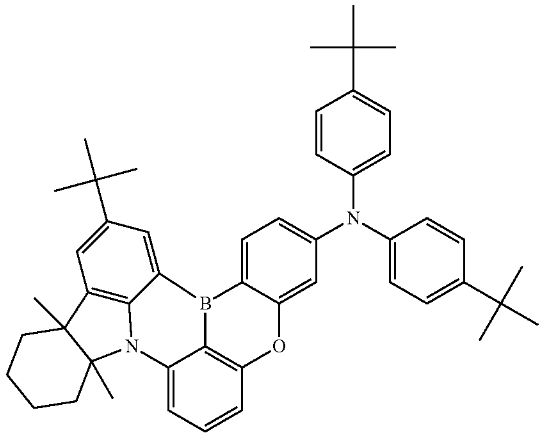

Compound 431>

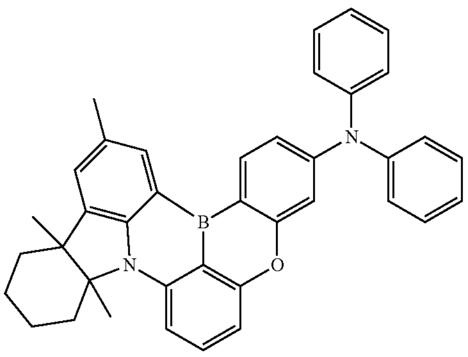

<Compound 432>

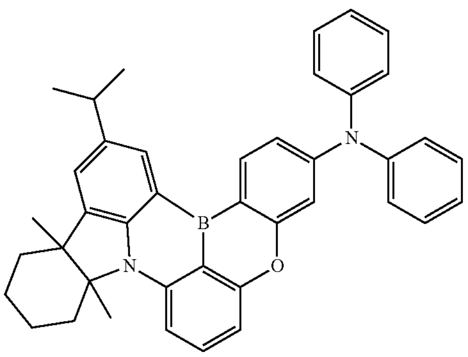

In a particular embodiment thereof, the present disclosure provides an organic light-emitting diode which includes: an anode as a first electrode; a cathode as a second electrode facing the first electrode; and a light-emitting layer interposed between the anode and the cathode, wherein the organic layer includes at least one of the anthracene derivaties represented by Chemical Formula A as a dopant in the light-emitting layer and at least one of the compounds represented by Chemical Formulas D1 to D8 as a dopant in the light-emitting layer. Having such structural characteristics, the organic light-emitting diode according to the present disclosure can be driven at a low voltage with high luminous efficiency.

The content of the dopant in the light-emitting layer may range from about 0.01 to 20 parts by weight, based on 100 parts by weight of the host, but is not limited thereto.

In addition to the above-mentioned dopants and hosts, the light-emitting layer may further include various hosts and dopant materials.

Below, the structure of the organic light-emitting diode according to the present disclosure is explained with reference to the drawing. FIGURE is a schematic cross-sectional view of the structure of an organic light-emitting diode according to an embodiment of the present disclosure. As shown in FIGURE, the organic light-emitting diode according to an embodiment of the present disclosure comprises an anode 20, a hole transport layer 40, an organic light-emitting layer 50 containing a host and a dopant, an electron transport layer 60, and a cathode 80, wherein the anode and the cathode serve as a first electrode and a second electrode, respectively, with the interposition of the hole transport layer between the anode and the light-emitting layer, and the electron transport layer between the light-emitting layer and the cathode.

Furthermore, the organic light-emitting diode according to an embodiment of the present disclosure may include a hole injection layer 30 between the anode 20 and the hole transport layer 40, and an electron injection layer 70 between the electron transport layer 60 and the cathode 80.

Reference is made to FIGURE with regard to the organic light emitting diode of the present disclosure and the fabrication thereof.

First, a substrate 10 is coated with an anode electrode material to form an anode 20. So long as it is used in a typical organic electroluminescence device, any substrate may be used as the substrate 10. Preferable is an organic substrate or transparent plastic substrate that exhibits excellent transparency, surface smoothness, ease of handling, and waterproofness. As the anode electrode material, indium tin oxide (ITO), indium zinc oxide (IZO), tin oxide (SnO2), or zinc oxide (ZnO), which are transparent and superior in terms of conductivity, may be used.

A hole injection layer material is applied on the anode 20 by thermal deposition in a vacuum or by spin coating to form a hole injection layer 30. Subsequently, thermal deposition in a vacuum or by spin coating may also be conducted to form a hole transport layer 40 with a hole transport layer material on the hole injection layer 30.

So long as it is typically used in the art, any material may be selected for the hole injection layer 30 without particular limitations thereto. Examples include, but are not limited to, 2-TNATA [4,4',4"-tris(2-naphthylphenyl-phenylamino)-triphenylamine], NPD [N,N'-di(1-naphthyl)-N,N'-diphenylbenzidine)], TPD [N,N'-diphenyl-N,N'-bis(3-methylphenyl)-1,1'-biphenyl-4,4'-diamine], DNTPD [N,N'-diphenyl-N,N'-bis-[4-(phenyl-m-tolyl-amino)-phenyl]-biphenyl-4,4'-dia mine], and HAT-CN (2,3,6,7,10,11-hexacyanohexaazatriphenylene).

Any material that is typically used in the art may be selected for the hole transport layer 40 without particular limitations thereto. Examples include, but are not limited to, N,N'-bis(3-methylphenyl)-N,N'-diphenyl-[1,1-biphenyl]-4,4'-diamine (TPD) and N,N'-di(naphthalen-1-yl)-N,N'-diphenylbenzidine (a-NPD).

In an embodiment of the present disclosure, an electron blocking layer may be additionally disposed on the hole transport layer. Functioning to prevent the electrons injected from the electron injection layer from entering the hole transport layer from the light-emitting layer, the electron blocking layer is adapted to increase the life span and luminous efficiency of the diode. The electron blocking layer may be formed at a suitable position between the light emitting layer and the hole injection layer. Particularly, the electron blocking layer may be formed between the light emitting layer and the hole transport layer.

Next, the light-emitting layer 50 may be deposited on the hole transport layer 40 or the electron blocking layer by deposition in a vacuum or by spin coating.

Herein, the light-emitting layer may contain a host and a dopant and the materials are as described above.

In some embodiments of the present disclosure, the light-emitting layer particularly ranges in thickness from 50 to 2,000 Å.

Meanwhile, the electron transport layer 60 is applied on the light-emitting layer by deposition in a vacuum and spin coating.

A material for use in the electron transport layer 60 functions to stably carry the electrons injected from the electron injection electrode (cathode), and may be an electron transport material known in the art. Examples of the electron transport material known in the art include quinoline derivatives, particularly, tris(8-quinolinolate)aluminum ($Alq_3$), Liq, TAZ, BAlq, beryllium bis(benzoquinolin-10-olate) (Bebq2), Compound 201, Compound 202, BCP, and oxadiazole derivatives such as PBD, BMD, and BND, but are not limited thereto:

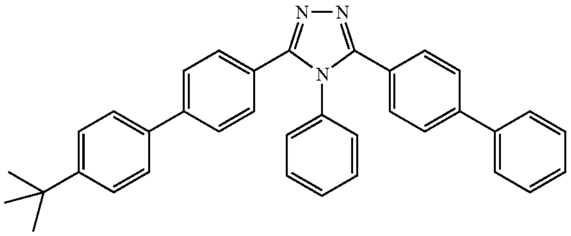

TAZ

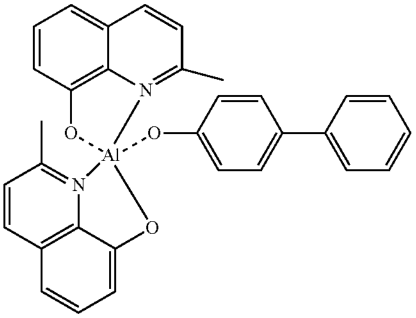

BAlq

-continued

<Compound 201>

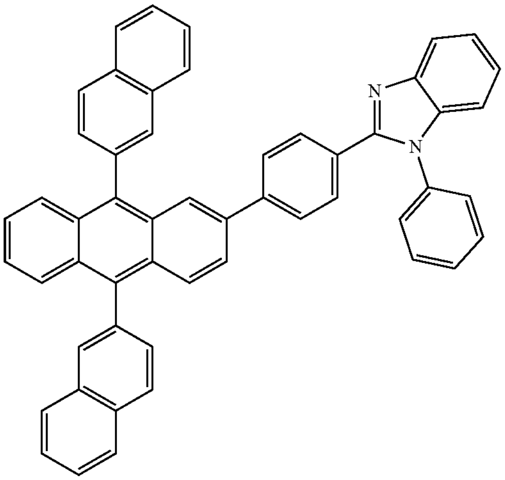

<Compound 202>

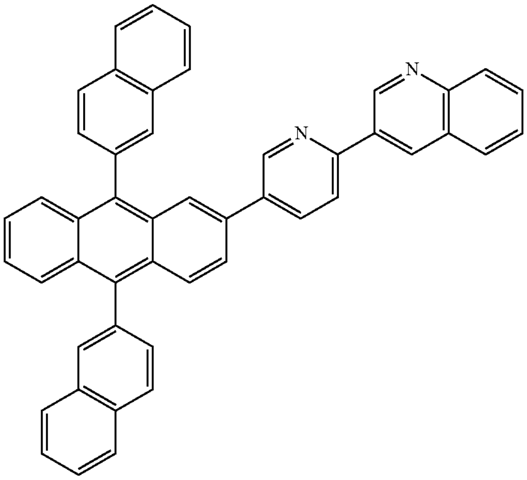

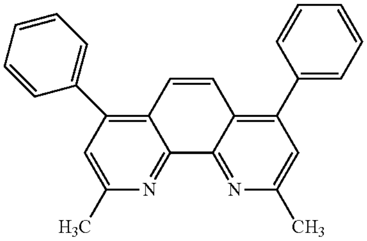

BCP

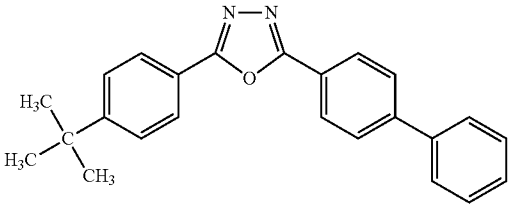

PBD

-continued

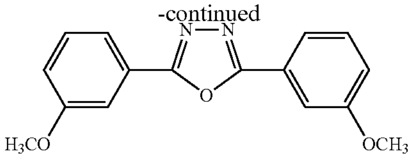

BMD

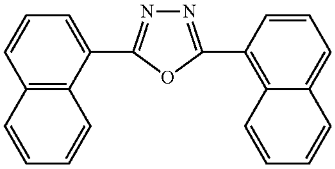

BND

In the organic light emitting diode of the present disclosure, an electron injection layer (EIL) 70 that functions to facilitate electron injection from the cathode may be deposited on the electron transport layer 60. The material for the EIL is not particularly limited.

Any material that is conventionally used in the art can be available for the electron injection layer 70 without particular limitations. Examples include CsF, NaF, LiF, $Li_2O$, and BaO. Deposition conditions for the electron injection layer may vary, depending on compounds used, but may be generally selected from condition scopes that are almost the same as for the formation of hole injection layers.

The electron injection layer 70 may range in thickness from about 1 Å to about 100 Å, and particularly from about 3 Å to about 90 Å. Given the thickness range for the electron injection layer, the diode can exhibit satisfactory electron injection properties without actually elevating a driving voltage.

In order to facilitate electron injection, the cathode 80 may be made of a material having a small work function, such as metal or metal alloy such as lithium (Li), magnesium (Mg), calcium (Ca), an alloy aluminum (Al) thereof, aluminum-lithium (Al—Li), magnesium-indium (Mg—In), and magnesium-silver (Mg—Ag). Alternatively, ITO or IZO may be employed to form a transparent cathode for an organic light-emitting diode.

Moreover, the organic light-emitting diode of the present disclosure may further comprise a light-emitting layer containing a blue, green, or red luminescent material that emits radiations in the wavelength range of 380 nm to 800 nm. That is, the light-emitting layer in the present disclosure has a multi-layer structure wherein the blue, green, or red luminescent material may be a fluorescent material or a phosphorescent material.

Furthermore, at least one selected from among the layers may be deposited using a single-molecule deposition process or a solution process.

Here, the deposition process is a process by which a material is vaporized in a vacuum or at a low pressure and deposited to form a layer, and the solution process is a method in which a material is dissolved in a solvent and applied for the formation of a thin film by means of inkjet printing, roll-to-roll coating, screen printing, spray coating, dip coating, spin coating, etc.

Also, the organic light-emitting diode of the present disclosure may be applied to a device selected from among flat display devices, flexible display devices, monochrome or grayscale flat illumination devices, and monochrome or grayscale flexible illumination devices.

A better understanding of the present disclosure may be obtained through the following examples which are set forth to illustrate, but are not to be construed as limiting the present invention.

EXAMPLES

Synthesis Example 1: Synthesis of Compound 12

Synthesis Example 1-(1): Synthesis of Intermediate 1-a

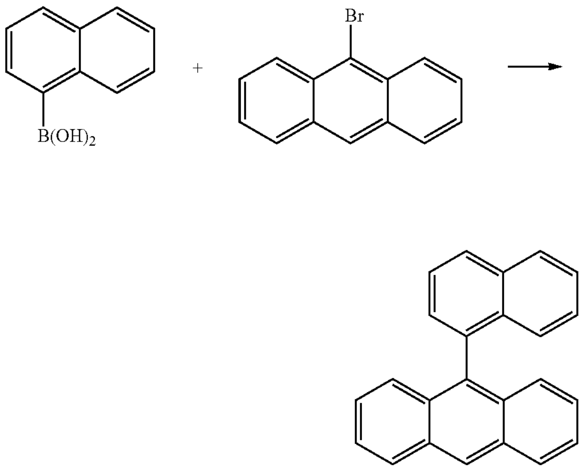

<Intermediate 1-a>

In a 1-L flask filled with nitrogen gas, 1-naphthalene boronic acid (20.1 g, 0.117 mol), 9-bromoanthracene (25 g, 0.097 mol), tetrakis(triphenylphosphine)palladium (0.8 g, 0.005 mol), potassium carbonate (26.9 g, 0.194 mol), toluene (125 ml), ethanol (125 ml), and water (50 ml) were stirred together under reflux. After completion of the reaction, an excess of methanol was poured into the flask. The precipitates thus formed were filtered and dissolved in toluene. Silica gel filtration was followed by vacuum concentration. The concentrate was added with methanol to give a precipitate which was then filtered to afford <Intermediate 1-a> (24 g, 81%).

Synthesis Example 1-(2): Synthesis of Intermediate 1-b

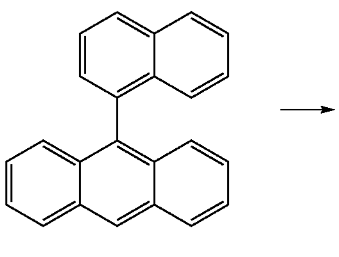

-continued

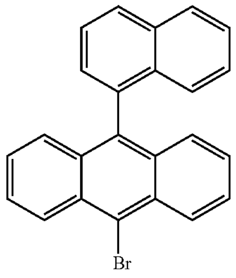

<Intermediate 1-b>

In a 1-L flask, <Intermediate 1-a> (24 g, 0.079 mol) and dichloromethane (208 ml) were stirred together at 0° C. A dilution of bromine (13.9 g, 0.087 mol) in dichloromethane (120 ml) was dropwise added before elevating the temperature to room temperature. After completion of the reaction, the reaction mixture was added with water (200 ml). The organic layer thus formed was extracted. The addition of methanol gave precipitates which were then filtered to afford <Intermediate 1-b> (28.2 g, 93%).

Synthesis Example 1-(3): Synthesis of Intermediate 1-c

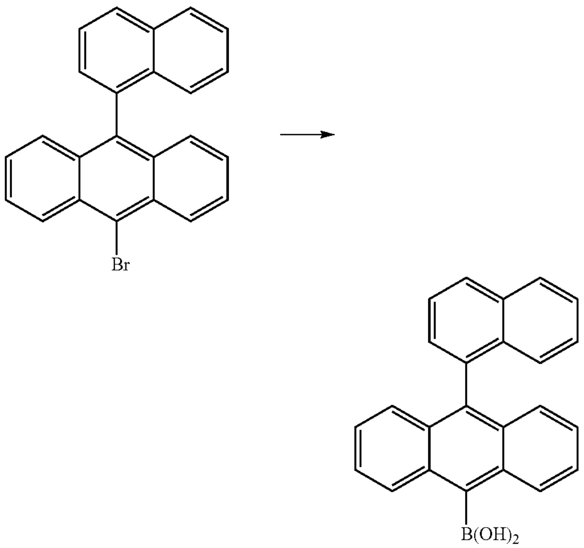

<Intermediate 1-c>

<Intermediate 1-b> (28.2 g, 0.074 mol) and tetrahydrofuran (225.6 ml) in a 1-L flask, were stirred at −78° C. under a nitrogen atmosphere in a reactor. Butyl lithium (1.6 M) (50.6 ml) was dropwise added and the mixture was stirred at the same temperature. Drops of trimethyl borate (12 ml) were added and the rection mixture was heated to room temperature and stirred for 2 hours. After completion of the reaction, 2 M aqeuous hydrochloric acid solution (200 ml) was added to the reaction mixture which was then stirred and added with ethyl acetate (100 ml). The organic layer thus formed was extracted and concentrated in a vacuum. Crystallization in an excess of heptane gave precipitates which were filtered to afford <Intermediate 1-c> (19.5 g, 76%).

Synthesis Example 1-(4): Synthesis of Intermediate 1-d

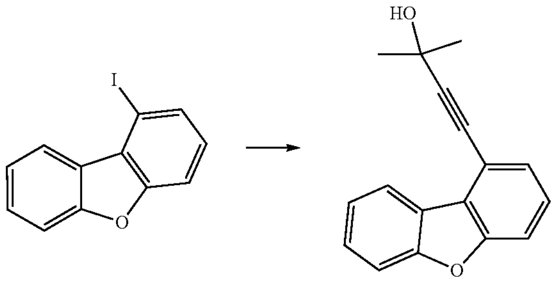

<Intermediate 1-d>

In a 500-ml flask, 1-iododibenzofuran (25 g, 0.085 mol), tetrakis(triphenylphosphine)palladium (0.98 g, 0.001 mol), and triethyl amine (250 ml) were stirred together at room temperature, followed by drops of 2-methyl-3-butyn-2-ol (7.2 g, 0.085 mol) (8.3 ml). After completion of the reaction, an excess of heptane was added to the reaction mixture and the organic layer thus formed was concentrated in a vacuum to afford <Intermediate 1-d> (15.3 g, 72%).

Synthesis Example 1-(5): Synthesis of Intermediate 1-e

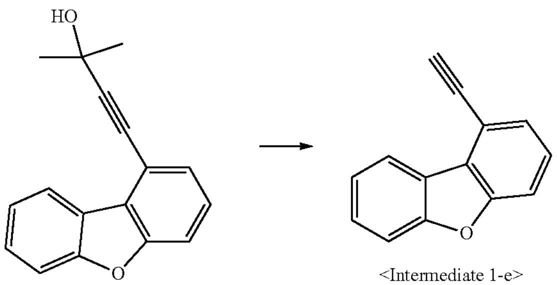 [SMILES: CC(C)(O)C#Cc1cccc2oc3ccccc3c12 ; C#Cc1cccc2oc3ccccc3c12]

<Intermediate 1-e>

A 300-ml flask containing <Intermediate 1-d> (15.3 g, 0.061 mol) and toluene (100 ml) was heated to 70-75° C. under a nitrogen atmosphere in a reactor. Tetrabutylammonium hydroxide (1.59 g, 0.0061 mol) (6.1 ml) was added and stirred. The reaction was terminated with 2 M aqueous hydrochloric acid solution. For extraction, ethyl acetate was added and the organic layer thus formed was concentrated in a vacuum. Isolation by column chromatography afforded <Intermediate 1-e> (10.6 g, 90%).

Synthesis Example 1-(6): Synthesis of Intermediate 1-f

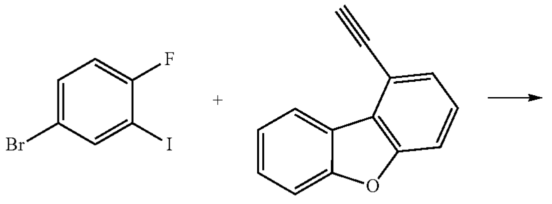

-continued

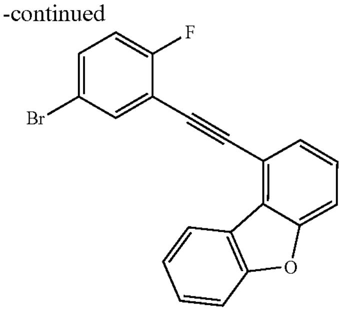

<Intermediate 1-f>

In a 300-ml flask, 1-bromo-4-fluoro-3-iodobenzene (17.8 g, 0.059 mol), tetrakis(triphenylphosphine)palladium (0.68 g, 0.001 mol), copper iodide (0.56 g, 0.003 mol), and triethyl amine (178 ml) were stirred at room temperature and then, <Intermediate 1-e> (10.6 g, 0.059 mol) was added dropwise thereto. After completion of the reaction, an excess of heptane was added to the reaction mixture which was filtered. The organic layer was concentrated in a vacuum. Crystallization in heptane gave precipitates which were filtered to afford <Intermediate 1-f> (18.3 g, 85%).

Synthesis Example 1-(7): Synthesis of Intermediate 1-g

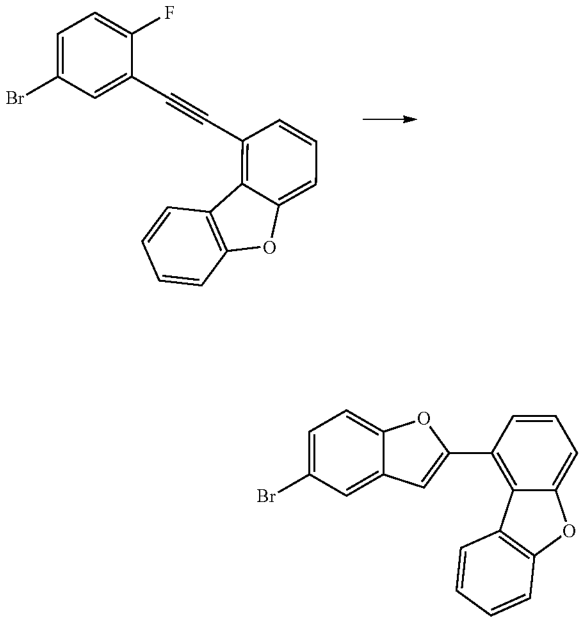

<Intermediate 1-g>

In a 500-ml flask, a mixture of <Intermediate 1-f> (18.3 g, 0.0501 mol), copper iodide (0.95 g, 0.00501 mol), potassium hydroxide (10.065 g, 0.0276 mol), potassium iodide (1.664 g, 0.01 mol), and dimethyl sulfoxide (183 ml) was heated to 80-90° C. and stirred. After completion of the reaction, the organic layer was concentrated in a vacuum and separation by column chromatography afforded <Intermediate 1-g> (13.4 g, 74%).

Synthesis Example 1-(8): Synthesis of Compound 12

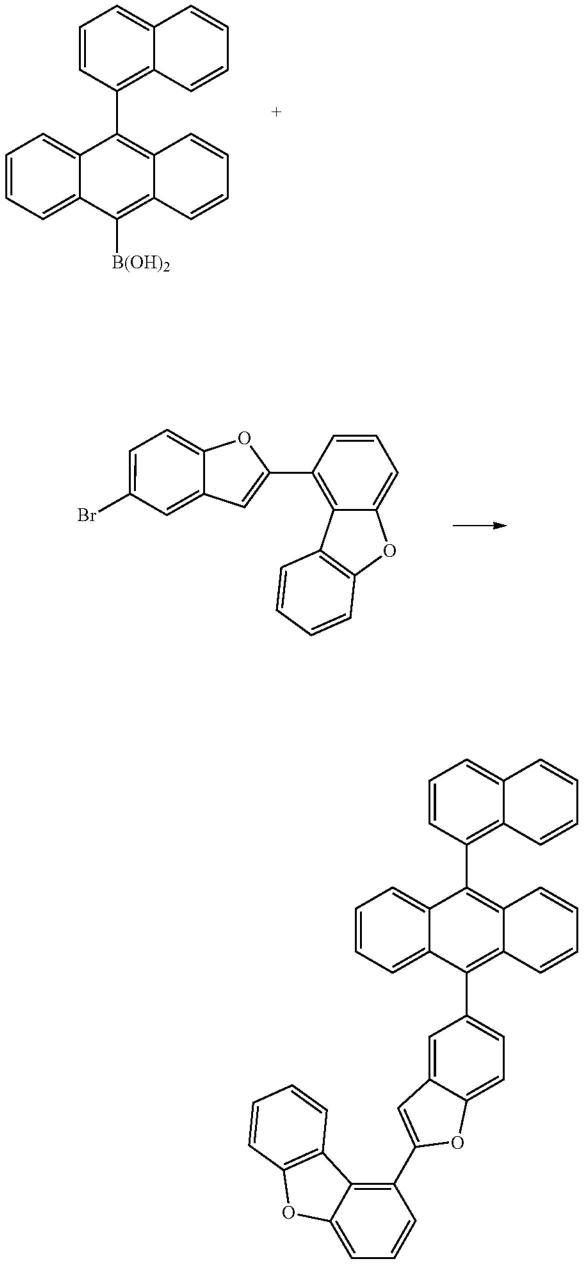

<Compound 12>

In a 500-ml flask, <Intermediate 1-c> (16.7 g, 0.048 mol), <Intermediate 1-g> (13.4 g, 0.037 mol), tetrakis(triphenylphosphine)palladium (0.85 g, 0.001 mol), potassium carbonate (10.2 g, 0.074 mol), toluene (67 ml), ethanol (67 ml), and water (27 ml) were stirred together under reflux. After completion of the reaction, an excess of methanol was poured to form a solid which was then dissolved in toluene. Silica gel filtration of the solution was followed by concentrating the organic layer in a vacuum. Recrystallization in toluene and acetone afforded <Compound 12> (13.7 g, 63%).

MS (MALDI-TOF): m/z 586.19 [M+]

Synthesis Example 2: Synthesis of Compound 33

Synthesis Example 2-(1): Synthesis of Intermediate 2-a

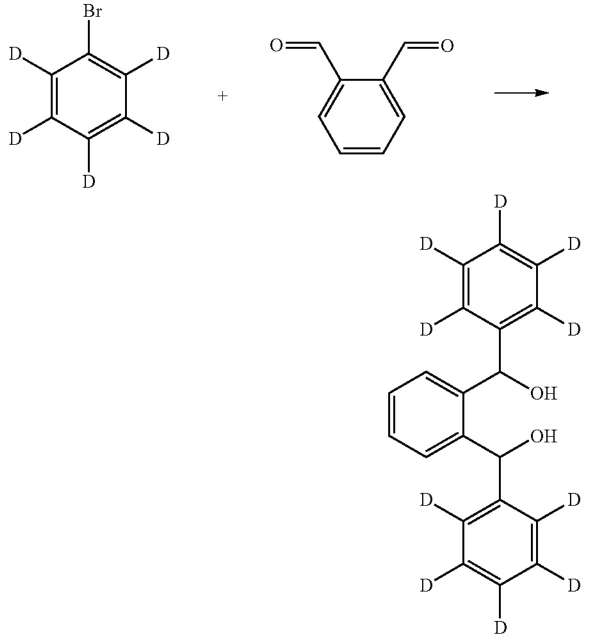

<Intermediate 2-a>

A 2-L flask containing bromophenyl-D5 (79.73 g, 0.49 mol) and tetrahydrofuran (797 ml) was chilled to −78° C. under a nitrogen atmosphere in a reactor. Drops of 1.6 M butyl lithium (307.5 ml, 0.49 mol) were added. Phthalaldehyde (30 g, 0.22 mol) was added little by little and stirred at room temperature for 2 hours. The reaction was terminated by adding water (500 ml). Following extraction with ethyl acetate and water, the organic layer was separated and concentrated in a vacuum to afford <Intermediate 2-a> (52 g, 77%).

Synthesis Example 2-(2): Synthesis of Intermediate 2-b

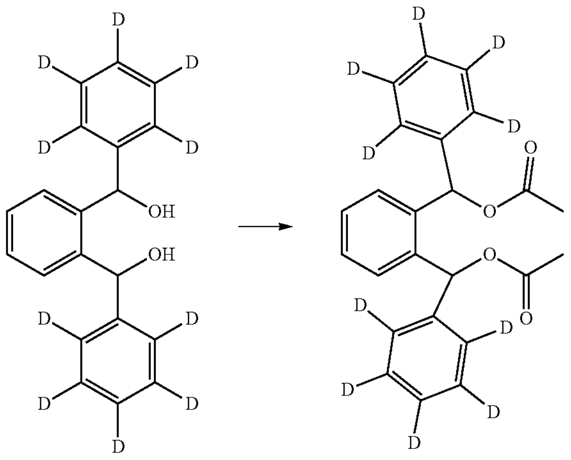

<Intermediate 2-b>

In a 2-L flask, <Intermediate 2-a> (52 g, 0.173 mol), dichloromethane (520 ml), acetic anhydride (70.68 g, 0.692 mol), and triethyl amine (105.1 g, 1.039 mol) were stirred together at 0° C. To the reactor was added little by little 4-dimethylaminopyridine (4.23 g, 0.035 mol), followed by stirring the mixture at room temperature. After completion of the reaction, water (500 ml) was added for extraction. The organic layer thus formed was separated and concentrated in a vacuum to afford <Intermediate 2-b> (61.5 g, 92%).

Synthesis Example 2-(3): Synthesis of Intermediate 2-c

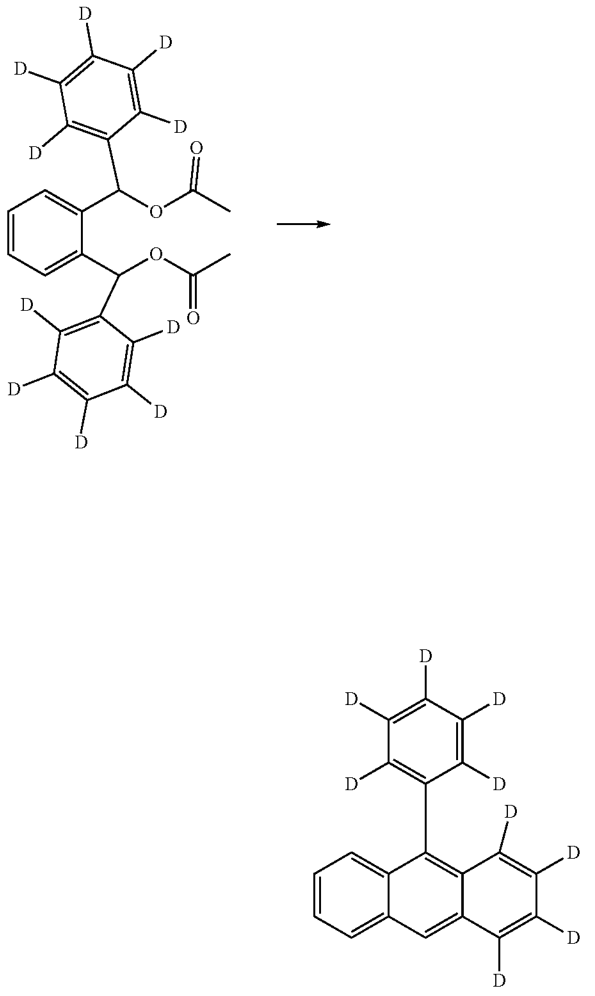

<Intermediate 2-c>

In a 2-L flask, <Intermediate 2-b> (61.5 g, 0.16 mol) and dichloromethane (615 ml) were stirred and then together sulfuric acid (1.7 ml, 0.032 mol). After completion of the reaction, the reaction mixture was stirred with water (600 ml) for extraction. The organic layer thus formed was separated and concentrated in a vacuum. The addition of an excess of methanol formed precipitates which were filtered to afford <Intermediate 2-c> (37.4 g, 89%).

Synthesis Example 2-(4): Synthesis of Intermediate 2-d

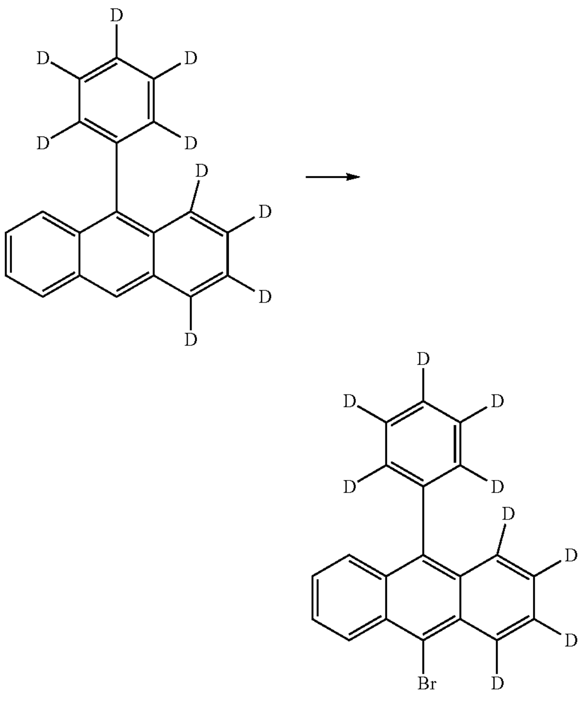

<Intermediate 2-d>

In a 1-L flask, <Intermediate 2-c> (37.4 g, 0.142 mol) and dichloromethane (374 ml) were stirred together. To this mixture were added drops of solution of N-bromosuccinimide (26.54 g, 0.149 mol) in dimethylformaldehyde (39.8 ml). After completion of the reaction, an excess of methanol was poured and the solid thus formed was filtered. Isolation by column chromatography afforded <Intermediate 2-d> (35.2 g, 72%).

Synthesis Example 2-(5): Synthesis of Intermediate 2-e

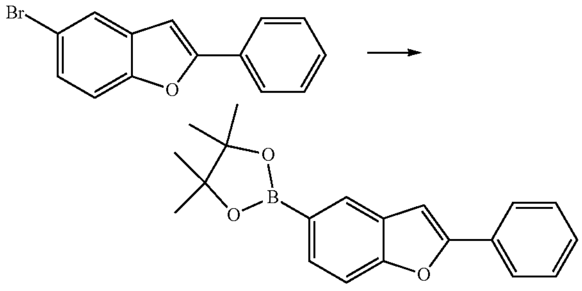

<Intermediate 2-e>

In a 500-ml flask, 5-bromo-2-phenylbenzofuran (30 g, 0.11 mol), bis(pinacolato)diboron (33.5 g, 0.132 mol), palladium(II) dichloride (diphenylphosphinoferocene) (2.69 g, 0.003 mol), potassium acetate (32.34 g, 0.33 mol), and toluene (300 ml) were stirred together under reflux. After completion of the reaction, the reaction mixture was concentrated in a vacuum and isolation by column chromatography afforded <Intermediate 2-e> (28.6 g, 81%).

Synthesis Example 2-(6): Synthesis of Compound 33

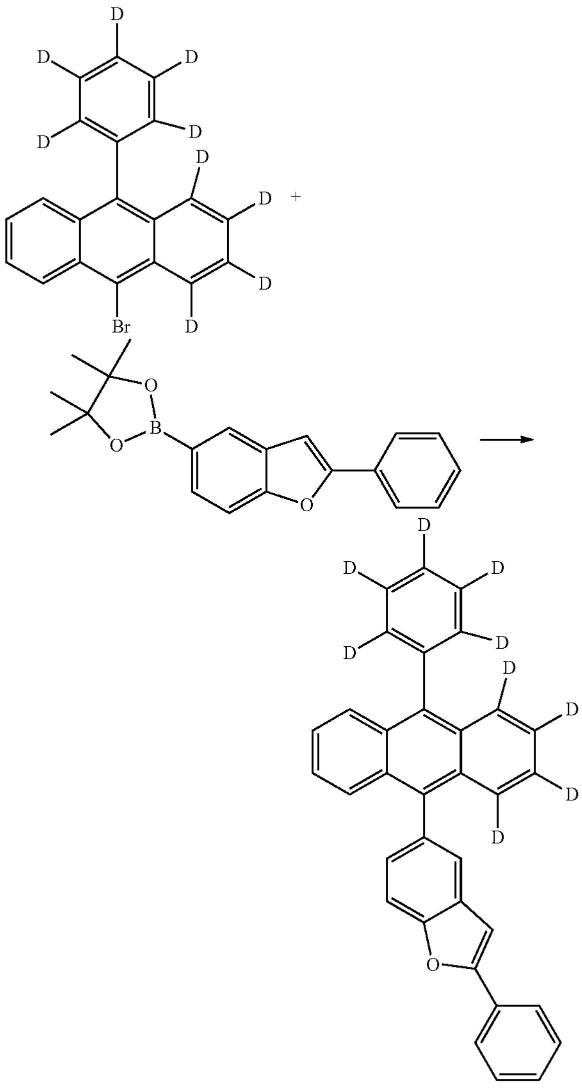

<Compound 33>

In a 300-mL flask, <Intermediate 2-d> (10.0 g, 0.029 mol), <Intermediate 2-e> (10.3 g, 0.032 mol), palladium(II) dichloride (diphenylphosphinoferocene) (0.48 g, 0.001 mol), sodium bicarbonate (4.91 g, 0.058 mol), tetrahydrofuran (120 ml), and water (40 ml) were stirred under reflux. After completion of the reaction, the reaction mixture was cooled to room temperature and an excess of methanol was poured. The precipitates thus formed were filtered and recrystallized in toluene and acetone to afford <Compound 33> (7.2 g, 54%).

MS (MALDI-TOF): m/z 455.22 [M+]

Synthesis Example 3: Synthesis of Compound 40

Synthesis Example 3-(1): Synthesis of Intermediate 3-a

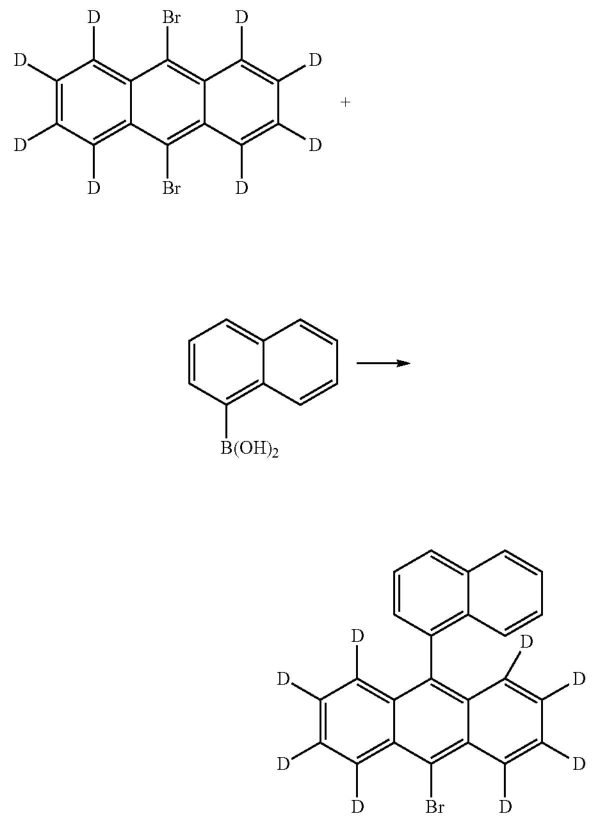

<Intermediate 3-a>

In a 500-ml flask, 1-naphthalene boronic acid (12.2 g, 0.071 mol), 9,10-dibromoanthracene (25 g, 0.073 mol), tetrakis(triphenylphosphine)palladium (1.68 g, 0.001 mol), potassium carbonate (20.08 g, 0.145 mol), toluene (125 ml), ethanol (125 ml), and water (50 ml) were refluxed under a nitrogen atmosphere. An excess of methanol was poured and the precipitates thus formed were filtered to afford <Intermediate 3-a> (18.2 g, 64%).

Synthesis Example 3-(2): Synthesis of Intermediate 3-b

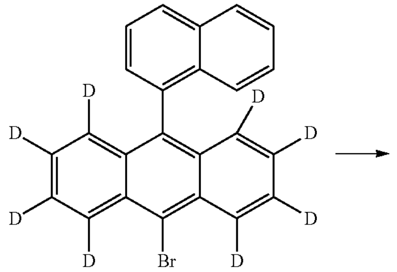

-continued

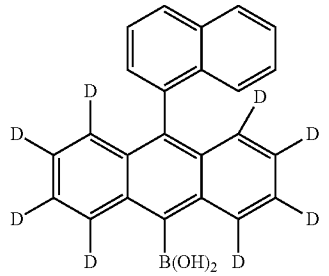

<Intermediate 3-b>

In a 1-L flask, <Intermediate 3-a> (18.2 g, 0.047 mol) and tetrahydrofuran (145.6 ml) were stirred together at −78° C. under a nitrogen atmosphere. Butyl lithium (1.6 M) (32 ml) was dropwise added, followed by stirring for 1 hour at the same temperature. Then, drops of trimethyl borate (8 ml) added before stirring at room temperature for 2 hours. After completion of the reaction, 2 M aqueous hydrochloric acid solution (100 ml) was poured and ethyl acetate (50 ml) was added for extraction. After vacuum concentration, an excess of heptane was added to form precipitates which were filtered to afford <Intermediate 3-b> (12.4 g, 75%).

Synthesis Example 3-(3): Synthesis of Intermediate 3-c

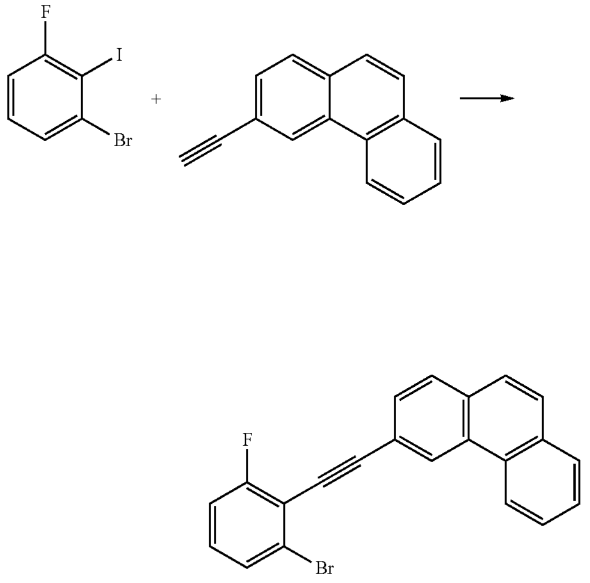

<Intermediate 3-c>

In a 500-ml flask, 1-bromo-3-fluoro-2-iodobenzene (30 g, 0.100 mol), tetrakis(triphenylphosphine)palladium (1.15 g, 0.001 mol), copper iodide (0.95 g, 0.005 mol), and triethyl amine (300 ml) were stirred at room temperature before adding drops of 3-ethinylphenanthrene (20.2 g, 0.100 mol) thereto. After completion of the reaction, an excess of heptane was poured and filtration was conducted. The organic layer was concentrated in a vacuum to afford <Intermediate 3-c> (31.6 g, 84%).

Synthesis Example 3-(4): Synthesis of Intermediate 3-d

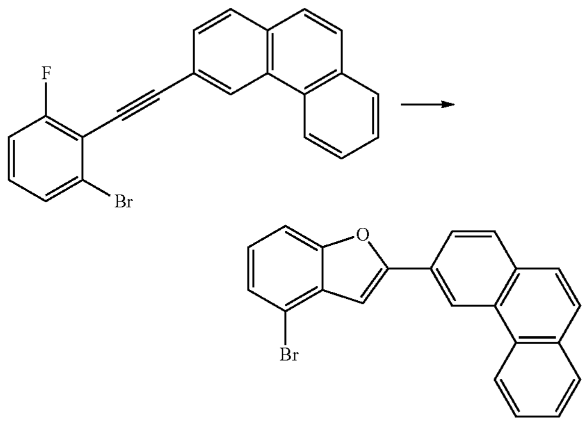

<Intermediate 3-d>

In a 500-ml flask, <Intermediate 3-c> (31.6 g, 0.0842 mol), copper iodide (1.604 g, 0.0084 mol), potassium hydroxide (17.38 g, 0.046 mol), potassium iodide (2.796 g, 0.0168 mol), and dimethyl sulfoxide (316 ml) were stirred together at 80-90° C. After completion of the reaction, the organic layer was concentrated in a vacuum and purified by column chromatography to afford <Intermediate 3-d> (24.9 g, 79%).

Synthesis Example 3-(5): Synthesis of Compound 40

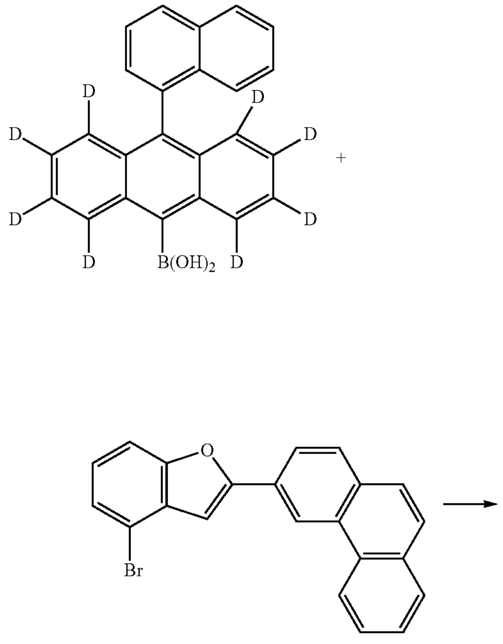

-continued

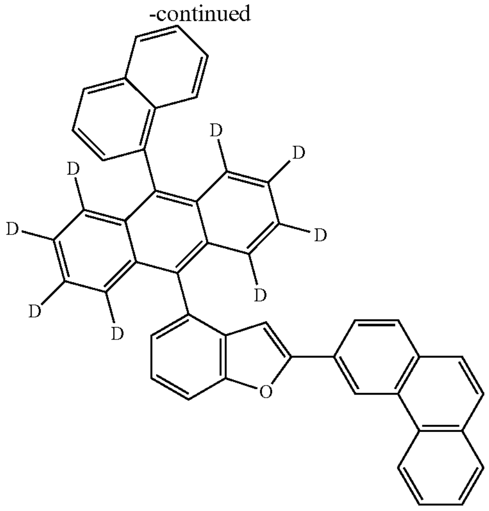

<Compound 40>

In a 500-ml flask, <Intermediate 3-b> (11.5 g, 0.032 mol), <Intermediate 3-d> (10.0 g, 0.027 mol), tetrakis(triphenylphosphine)palladium (0.62 g, 0.00054 mol), potassium carbonate (7.4 g, 0.054 mol), toluene (80 ml), ethanol (40 ml), and water (30 ml) were stirred together under reflux. After completion of the reaction, an excess of methanol was poured. The precipitate thus formed was filtered and recrystallized in toluene and acetone to afford <Compound 40> (9.7 g, 60%).

MS (MALDI-TOF): m/z 604.26 [M+]

Synthesis Example 4: Synthesis of Compound 58

Synthesis Example 4-(1): Synthesis of Intermediate 4-a

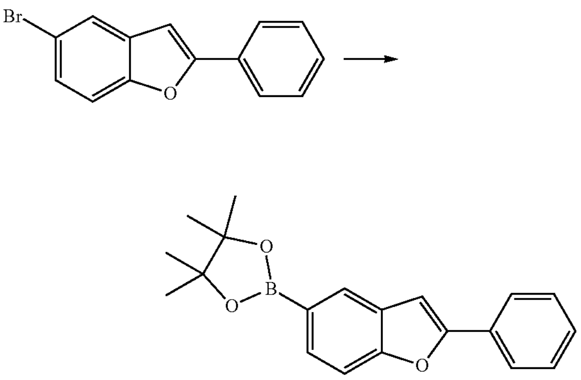

<Intermediate 4-a>

In a 1-L flask, 5-bromo-2-phenylbenzofuran (50 g, 0.183 mol), bis(pinacolato)diboron (55.8 g, 0.220 mol), palladium (II)dichloride (diphenylphosphinoferocene) (4.49 g, 0.005 mol), potassium acetate (53.9 g, 0.549 mol), and toluene (500 ml) were stirred together under reflux. After completion of the reaction, concentration in a vacuum was conducted and isolation by column chromatography according <Intermediate 4-a> (47.1 g, 80%).

Synthesis Example 4-(2): Synthesis of Intermediate 4-b

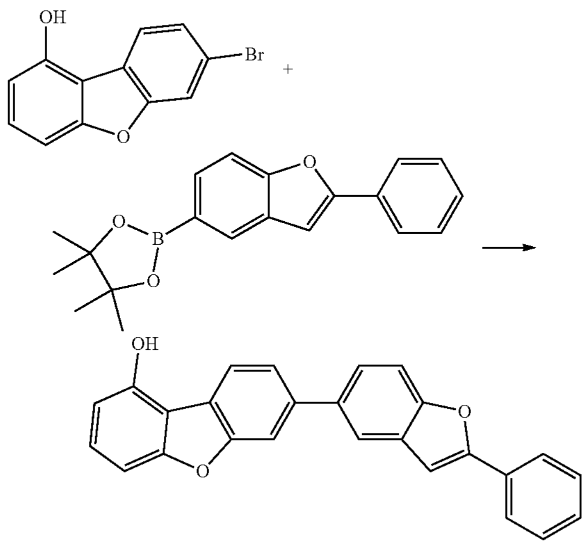

<Intermediate 4-b>

In a 1-L flask, <Intermediate 4-a> (47.1 g, 0.147 mol), 7-bromo-1-hydroxydibenzofuran (35.0 g, 0.133 mol), palladium(II)dichloride (diphenylphosphinoferocene) (2.17 g, 0.003 mol), sodium bicarbonate (22.35 g, 0.266 mol), tetrahydrofuran (420 ml), and water (140 ml) were stirred together under reflux. After completion of the reaction, the reaction mixture was cooled to room temperature and added with dichloromethane. The precipitate thus formed was filtered to afford <Intermediate 4-b> (41.5 g, 83%).

Synthesis Example 4-(3): Synthesis of Intermediate 4-c

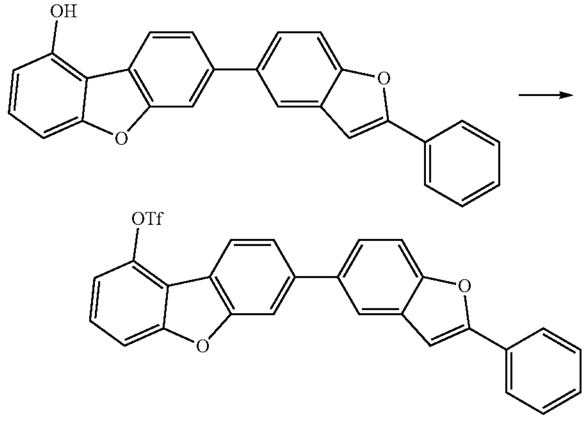

<Intermediate 4-c>

In a 1-L flask, <Intermediate 4-b> (41.5 g, 0.11 mol), pyridine (17.44 g, 0.220 mol) (17.8 ml), and dichloromethane (415 ml) were stirred together at 0° C. under a nitrogen atmosphere. Trifluoromethane sulfonic anhydride (46.7 g, 0.165 mol) (28 ml) was added dropwise, followed by stirring at room temperature. The reaction was terminated with water, and the organic layer was concentrated in a vacuum to afford <Intermediate 4-c> (48.2 g, 86%).

Synthesis Example 4-(4): Synthesis of Intermediate 4-d

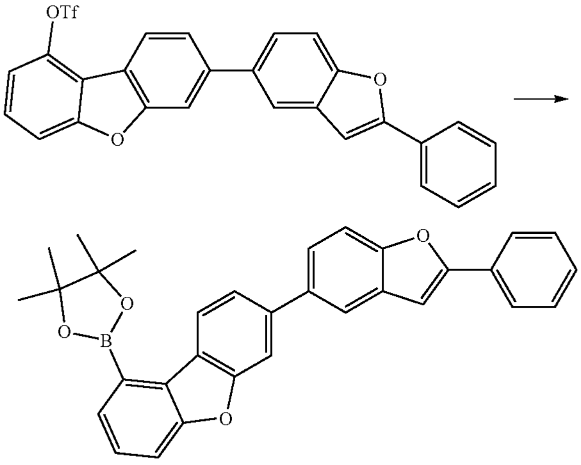

<Intermediate 4-d>

In a 1-L flask, <Intermediate 4-c> (48.2 g, 0.095 mol), bis(pinacolato)diboron (28.9 g, 0.114 mol), palladium(II) dichloride (diphenylphosphinoferocene) (2.32 g, 0.003 mol), potassium acetate (27.91 g, 0.284 mol), and toluene (482 ml) was stirred together under reflux. After completion of the reaction, the reaction mixture was filtered and the filtrate was concentrated in a vacuum. Purification by column chromatography afforded <Intermediate 4-d> (37.2 g, 81%).

Synthesis Example 4-(5): Synthesis of <Compound 58>

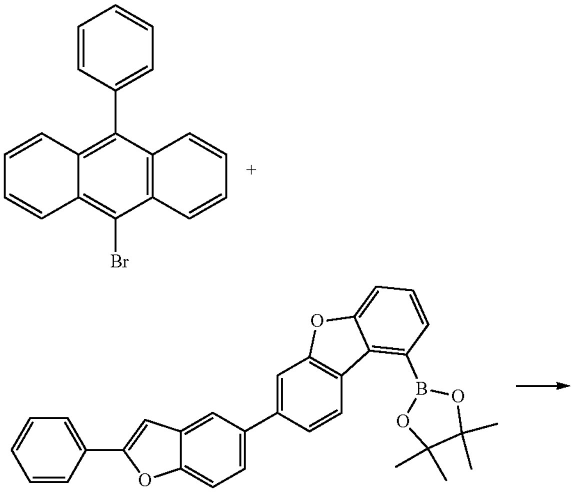

-continued

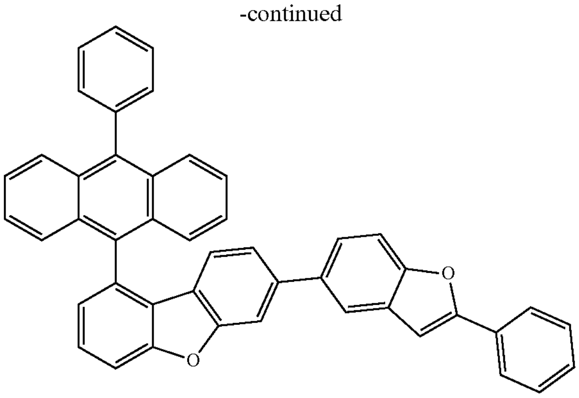

<Compound 58>

In a 300-mL flask, 9-bromo-10-phenylanthracene (10.0 g, 0.030 mol), <Intermediate 4-d> (16.1 g, 0.033 mol), palladium(II)dichloride (diphenylphosphinoferocene) (0.49 g, 0.001 mol), sodium bicarbonate (5.04 g, 0.06 mol), tetrahydrofuran (120 ml), and water (40 ml) were stirred together under reflux. After completion of the reaction, an excess of methanol was added to the reaction mixture at room temperature to form a precipitate. Filtration and recrystallization in toluene and acetone afforded <Compound 58> (12.7 g, 69%).

MS (MALDI-TOF): m/z 612.21 [M+]

Synthesis Example 5: Synthesis of Compound 45

Synthesis Example 5-(1): Synthesis of Intermediate 5-a

<Intermediate 5-a>

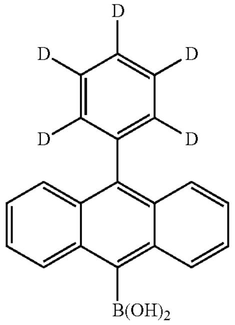

The same procedures as in Synthesis Examples 1-(1) to 1-(3) were carried out, with the exception of using phenylboronic acid (D5) instead of 1-naphthalene boronic acid used in Synthesis Example 1-(1), to afford <Intermediate 5-a>. (yield 70%)

Synthesis Example 5-(2): Synthesis of <Compound 45>

The same procedure as in Synthesis Example 1-(8) was carried out, with the exception of using <Intermediate 5-a> and 4-bromo-2-phenylbenzofuran instead of <Intermediate 1-c> and <Intermediate 1-g>, respectively, to afford <Compound 45>. (yield 60%)

MS (MALDI-TOF): m/z 451.20 [M+]

Synthesis Example 6: Synthesis of Compound 111

Synthesis Example 6-(1): Synthesis of Intermediate 6-a

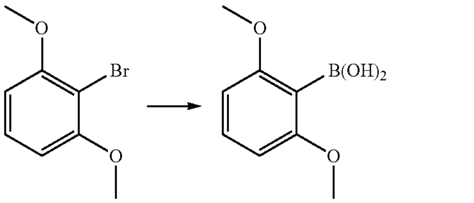

<Intermediate 6-a>

In a 1-L round bottom flask, 2-bromo-1,3-dimethoxybenzene (50 g, 230 mmol) was dissolved in tetrahydrofuran (400 ml) under a nitrogen atmosphere. The solution was chilled to −78° C. and added with drops of n-butyl lithium (167 ml, 280 mmol). At the same temperature, the solution was stirred for 2 hours. Addition of trimethyl borate (36 ml, 320 mmol) was followed by stirring overnight at room temperature. After completion of the reaction, the reaction mixture was acidified as 2N HCl was slowly added thereto. The reaction mixture was subjected to extraction with water and ethyl acetate and the organic layer thus formed was separated and dried over magnesium sulfate. The residue was concentrated in a vacuum and recrystallized in heptane and toluene to afford <Intermediate 6-a> (20.8 g, 50%).

Synthesis Example 6-(2): Synthesis of Intermediate 6-b

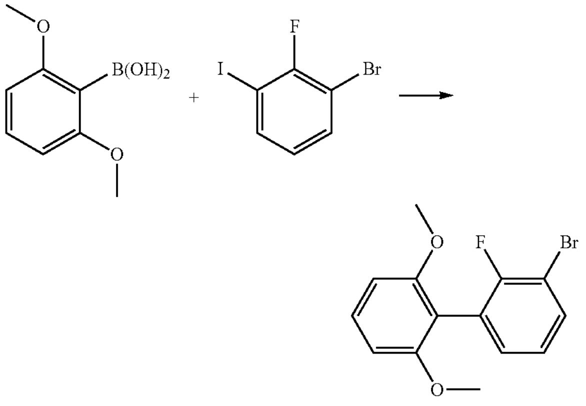

<Intermediate 6-b>

To a 500-ml round bottom flask were added <Intermediate 1-a> (20.8 g, 110 mmol), 1-bromo-2-fluoro-3-iodobenzene (28.7 g, 95 mmol), tetrakis(triphenylphosphine)palladium (33 g, 29 mmol), and sodium carbonate (30.3 g, 290 mmol) and then toluene (200 ml), ethanol (60 ml), and water (60 ml). The reactor was heated to 80° C. and the mixture was stirred for 12 hours. After completion of the reaction, the reactor was cooled to room temperature at which extraction was conducted with ethyl acetate. The organic layer thus obtained was concentrated in a vacuum. Purification by column chromatography afforded <Intermediate 6-b> (22.3 g, 63%).

Synthesis Example 6-(3): Synthesis of Intermediate 6-c

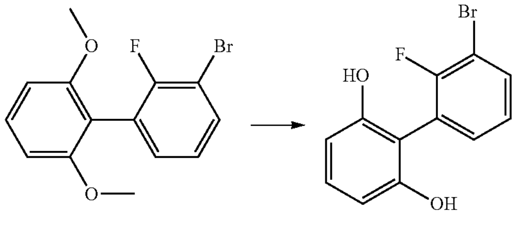

<Intermediate 6-c>

In a 500-ml round bottom flask, <Intermediate 6-b> (16.5 g, 53 mmol), hydrobromic acid (48 ml, 260 mmol), and acetic acid (100 ml) were stirred together for 12 hour. After completion of the reaction, the reaction mixture was cooled to room temperature and stirred together with water. Extraction was conducted with water and ethyl acetate. The organic layer thus formed was separated and concentrated in a vacuum. Recrystallization in heptane was followed by filtration and drying to afford <Intermediate 6-c> (13.5 g, 90%).

Synthesis Example 6-(4): Synthesis of Intermediate 6-d

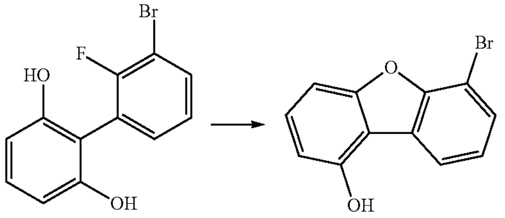

<Intermediate 6-d>

In a 500-ml round bottom flask, <Intermediate 6-c> (14.1 g, 50 mmol), potassium carbonate (20.7 g, 150 mmol), and N-methyl-2-pyrrolidone (112 ml) were stirred together for 12 hours. After completion of the reaction, the reaction mixture was cooled to room temperature. Extraction with water and ethyl acetate formed an organic layer which was concentrated in a vacuum and subjected to recrystallization in heptane to afford <Intermediate 6-d> (10.5 g, 80%).

Synthesis Example 6-(5): Synthesis of Intermediate 6-e

<Intermediate 6-e>

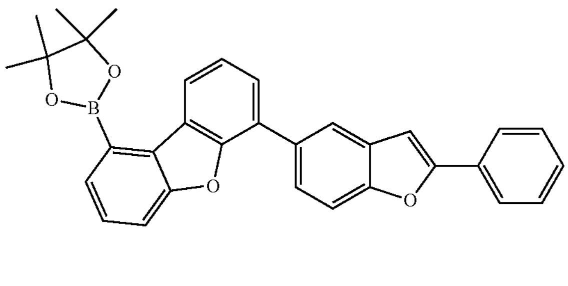

The same procedures as in Synthesis Examples 4-(2) to 4-(4) were carried out, with the exception of using <Intermediate 6-d> instead of 7-bromo-1-hydroxydibenzofuran in Synthesis Example 4-(2), to afford <Intermediate 6-e>. (yield 80%)

Synthesis Example 6-(6): Synthesis of <Compound 111>

The same procedures as in Synthesis Example 2-(6) was carried out, with the exception of using <Intermediate 6-e> instead of <Intermediate 2-e>, to afford <Compound 111>. (yield 55%)

MS (MALDI-TOF): m/z 621.27 [M+]

Preparation Examples: Dopant Compounds

Synthesis Example 7: Synthesis of [BD1]

Synthesis Example 7-(1): Synthesis of Intermediate 7-a

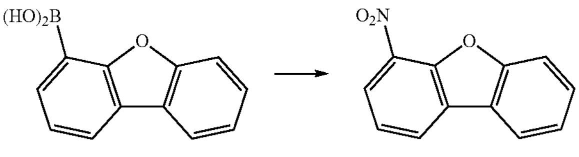

<Intermediate 7-a>

In a 1-L flask, 4-dibenzofuran boronic acid (85.0 g, 0.401 mol), bismuth (III) nitrate pentahydrate (99.2 g, 0.200 mol), and toluene (400 ml) were stirred together at 70° C. for 3 hours under a nitrogen atmosphere. After completion of the reaction, the reaction mixture was cooled to room temperature and the precipitate thus formed was washed with toluene to afford <Intermediate 7-a> (61.5 g, 72%).

Synthesis Example 7-(2): Synthesis of Intermediate 7-b

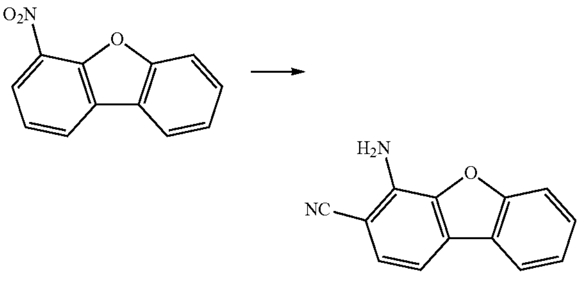

<Intermediate 7-b>

In a 2-L flask, ethyl cyanoacetate (202.9 g, 1.794 mol) and dimethyl formamide (500 ml) were added with potassium hydroxide (67.10 g, 1.196 mol) and potassium cyanide (38.95 g, 0.598 mol) and then with dimethyl formamide (200 ml) before being stirred together at room temperature. The reaction solution was added little by little with <Intermediate 7-a> (127.5 g, 0.737 mol) and then stirred 50° C. for 72 hours. After completion of the reaction, an aqueous sodium hydroxide solution (25%, 200 ml) was added for stirring under reflux. After three hours of stirring, the reaction mixture was cooled to room temperature and subjected to extraction with ethyl acetate and water. The organic layer thus formed was isolated, concentrated in a vacuum, and purified through column chromatography to afford <Intermediate 7-b> (20.0 g, 16%).

Synthesis Example 7-(3): Synthesis of Intermediate 7-c

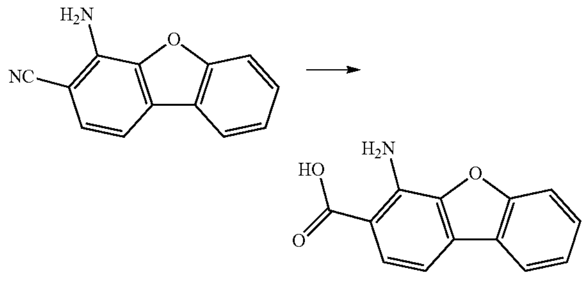

<Intermediate 7-c>

In a 2-L flask, <Intermediate 7-b> (20.0 g, 0.096 mol), ethanol (600 ml), and an aqueous potassium hydroxide solution (142.26 g, 2.53 mol, 170 ml) were stirred together for 12 hours under reflux. After completion of the reaction, the reaction mixture was cooled to room temperature. It was acidified with 6 N HCl (400 ml). The solid thus formed was stirred for 20 minutes and then filtered. The filtrate was washed with ethanol to afford <Intermediate 7-c> (17.0 g, 88%).

Synthesis Example 7-(4): Synthesis of Intermediate 7-d

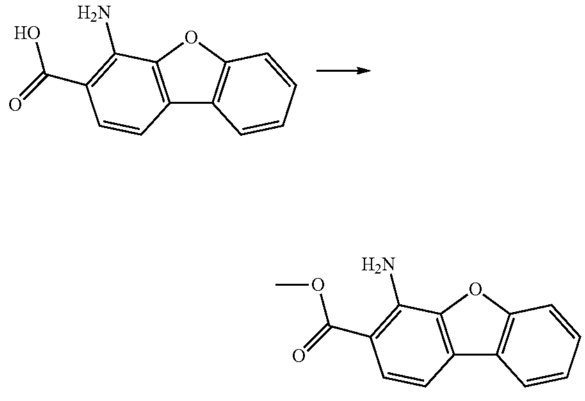

<Intermediate 7-d>

In a 2-L flask, <Intermediate 7-c> (17.0 g, 0.075 mol) and sulfuric acid (15 ml) were stirred together for 72 hours under reflux. After completion of the reaction, the reaction mixture was cooled to room temperature and subjected to extraction with ethyl acetate and water. The organic layer thus formed was isolated and washed with an aqueous sodium hydrogen carbonate. The organic layer was concentrated and added with an excess of methanol. Filtration afforded <Intermediate 7-d> as a solid (14.0 g, 78%).

Synthesis Example 7-(5): Synthesis of Intermediate 7-e

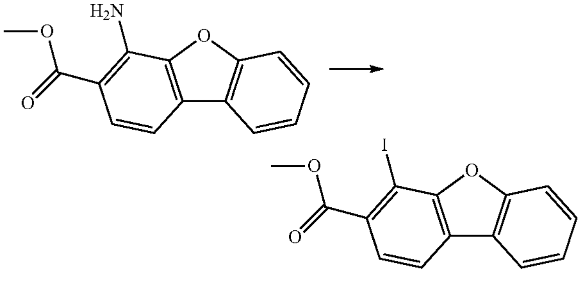

<Intermediate 7-e>

In a 500-mL flask, <Intermediate 7-d> (14.0 g, 0.058 mol), HCl (20 ml), and water (100 ml) were stirred at 0° C. for 1 hour. At the same temperature, an aqueous sodium nitrite solution (7.4 g, 0.116 mol, 50 ml) was added dropwise, followed by stirring for 1 hour. An aqueous potassium iodide (30.0 g, 0.180 mol, 100 ml) was added dropwise, taking care that the temperature of the reaction solution did not exceed 5° C. Stirring was conducted at room temperature for 5 hours. After completion of the reaction, the reaction mixture was washed with an aqueous sodium thiosulfate and subjected to extraction with ethyl acetate and water. The organic layer was concentrated in a vacuum and purified through column chromatography to afford <Intermediate 7-e> (9.1 g, 48%).

Synthesis Example 7-(6): Synthesis of Intermediate 7-f

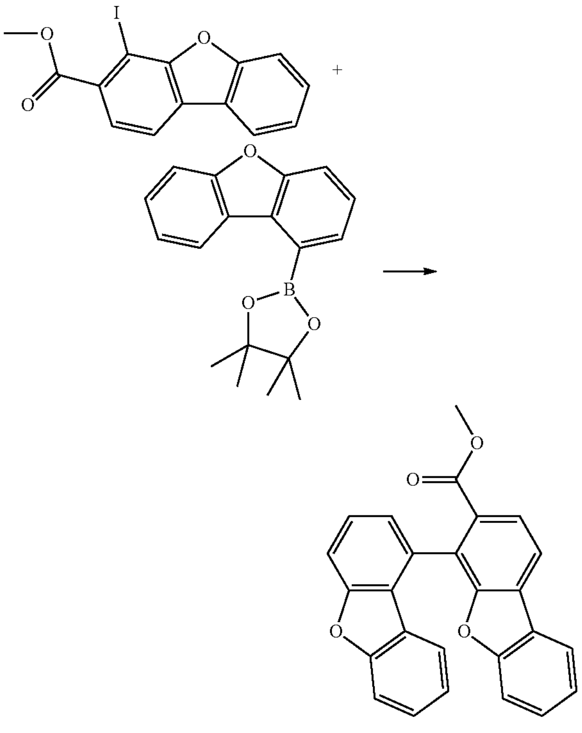

<Intermediate 7-f>

Into a 250-mL flask were added <Intermediate 7-e> (9.3 g, 25 mmol), 1-dibenzofuran boronic acid ((8.3 g, 28 mmol), tetrakis(triphenylphosphine)palladium (0.6 g, 0.05 mmol), and potassium carbonate (6.7 g, 50 mmol), followed by toluene (50 mL), tetrahydrofuran (50 mL), and water (20 mL). The reactor was heated to 80° C. at which the mixture was stirred for 10 hours. After completion of the reaction, the reactor was cooled to room temperature and the reaction mixture was subjected to extraction with ethyl acetate. The organic layer thus formed was isolated, concentrated in a vacuum, and purified through column chromatography to afford <Intermediate 7-f>. (5.3 g, 52%)

Synthesis Example 7-(7): Synthesis of Intermediate 7-g

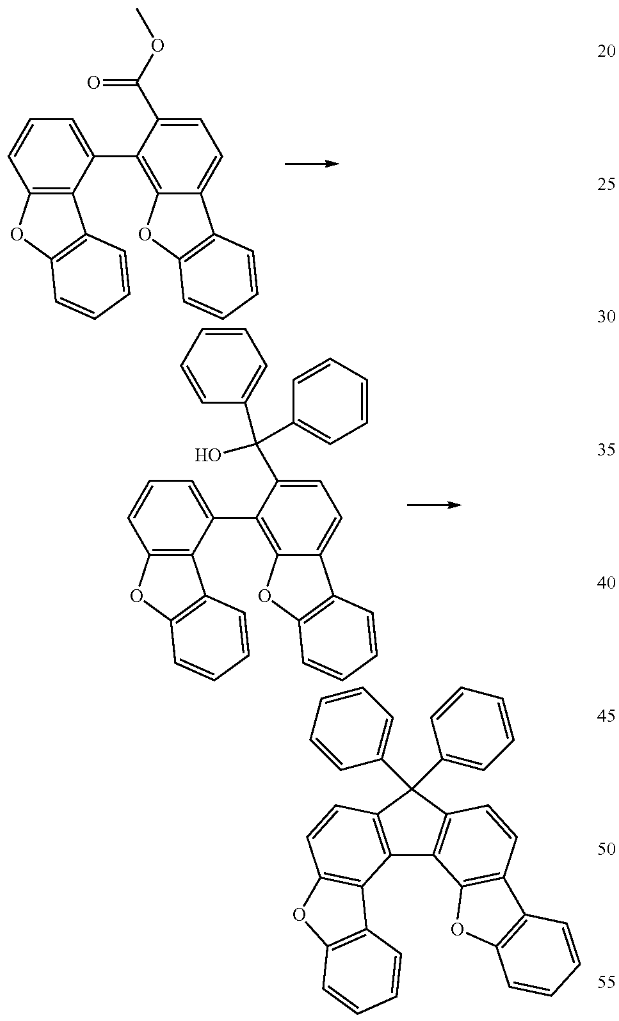

<Intermediate 7-g>

In a 500-mL flask, bromobenzene (25.5 g, 0.163 mol) and tetrahydrofuran (170 ml) were chilled to −78° C. under a nitrogen atmosphere. To this chilled solution, drops of n-butyl lithium (1.6 M, 95.6 ml, 0.153 mol) were added. Following stirring at the same temperature for 1 hour, the solution was added with <Intermediate 7-f> (20.0 g, 0.051 mol) and stirred at room temperature for 3 hours. After completion of the reaction, the reaction mixture was added with water (50 ml), stirred for 30 minutes, and subjected to extraction with ethyl acetate and water. The organic layer thus formed was isolated and concentrated in a vacuum. The concentrate was added with acetic acid (200 ml) and HCl (1 ml) and stirred at 80° C. After completion of the reaction, the reaction mixture was filtered and washed with methanol to afford <Intermediate 7-g> (20.0 g, 78%).

Synthesis Example 7-(8): Synthesis of Intermediate 7-h

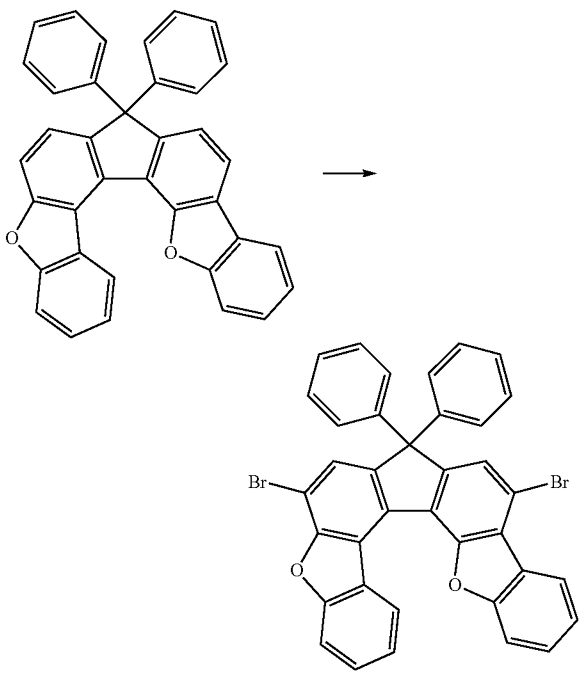

<Intermediate 7-h>

In a 100-mL flask, <Intermediate 7-g> (20 g, 58 mmol) and dichloromethane (40 ml) were stirred at room temperature. A dilution of bromine (5.8 ml, 116 mmol) in chloromethane (10 ml) was added dropwise and stirred at room temperature for 8 hours. After completion of the reaction, acetone (20 ml) was added to the reaction vessel and stirred again. The solid thus formed was filtered and washed with acetone. Recrystallization in monochlorobenzene afforded <Intermediate 7-h>. (15.8 g, 55%)

Synthesis Example 7-(9): Synthesis of [BD 1]

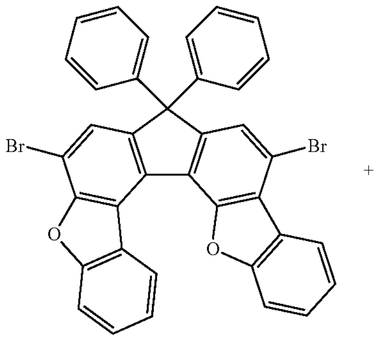

-continued

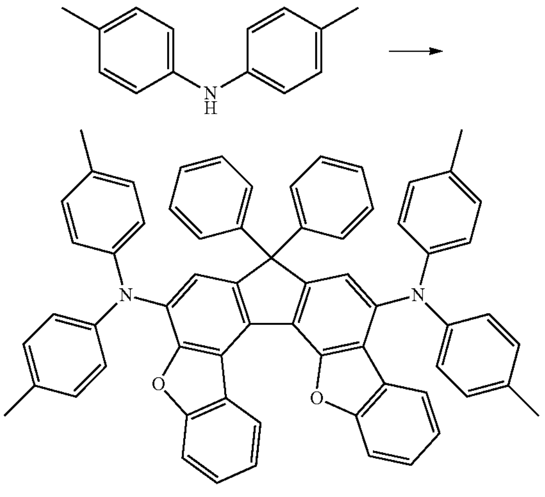

[BD 1]

In a 100-mL flask, <Intermediate 7-h> (4.0 g, 0.006 mol), di-p-tolyl amine (3.2 g, 0.016 mol), palladium (II) acetate (0.08 g, 0.4 mmol), sodium tert-butoxide (3.2 g, 0.032 mol), tri-tert-butyl phosphine (0.08 g, 0.4 mmol), and toluene (50 ml) were stirred together for 2 hours under reflux. After completion of the reaction, the reaction mixture was cooled to room temperature and subjected to extraction with dichloromethane and water. The organic layer thus formed was isolated, dried over magnesium sulfate, and concentrated in a vacuum. Following isolation through column chromatography, recrystallization in dichloromethane and acetone afforded [BD 1]. (2.1 g, 41%)

MS (MALDI-TOF): m/z 888.37 [M+]

Synthesis Example 8: Synthesis of [BD 2]

Synthesis Example 8-(1): Synthesis of Intermediate 8-a

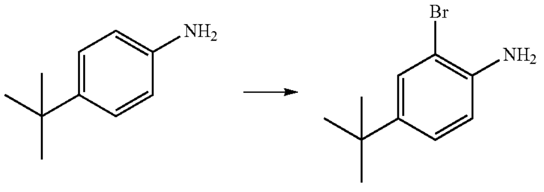

<Intermediate 8-a>

In a 1-L reactor, a solution of 4-tert-butyl aniline (40 g, 236 mmol) in methylene chloride (400 mL) was stirred at 0° C. Subsequently, N-bromosuccinimide (42 g, 236 mmol) was slowly added to the reactor. The temperature was raised to the room temperature before stirring for 4 hours. After completion of the reaction, $H_2O$ was dropwise added at room temperature and extraction with methylene chloride was conducted. The organic layer thus formed was concentrated. Purification through column chromatography afforded <Intermediate 8-a> (48 g, 80%).

Synthesis Example 8-(2): Synthesis of <Intermediate 8-b>

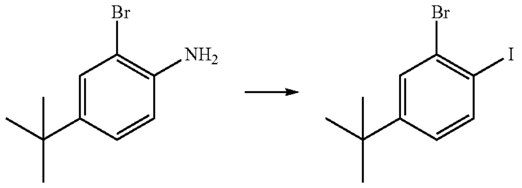

<Intermediate 8-b>

In a 2-L reactor, <Intermediate 8-a> (80 g, 351 mmol) and water (450 mL) were stirred together. Sulfuric acid (104 mL) was added. At 0° C., a solution of sodium nitrite (31.5 g, 456 mmol) in water (240 mL) was added dropwise and stirred for 2 hours. A solution of potassium iodide (116.4 g, 701 mmol) in water (450 mL) was added dropwise at 0° C. and then stirred at room temperature for 6 hours. After completion of the reaction, an aqueous sodium thiosulfate solution was added at room temperature and stirred. The organic layer thus formed was concentrated, followed by isolation through column chromatography to afford <Intermediate 8-b> (58 g, 51%).

Synthesis Example 8-(3): Synthesis of <Intermediate 8-c>

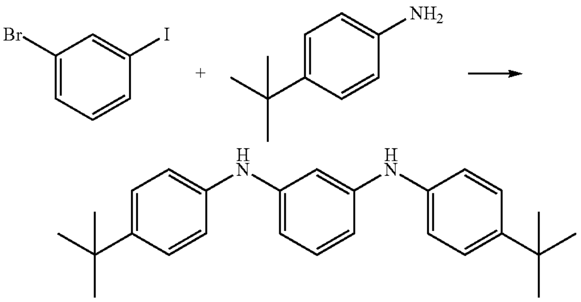

<Intermediate 8-c>

In a 1-L reactor, 1-bromo-5-iodobenzene (50.1 g, 177 mmol), 4-tert-butyl aniline (58 g, 389 mmol), palladium acetate (1.6 g, 7 mmol), sodium tert-butoxide (51 g, 530 mmol), bis(diphenylphosphino)-1,1'-binaphthyl (4.4 g, 7 mmol), and toluene (500 mL) were stirred together for 24 hours under reflux. After completion of the reaction, the reaction mixture was filtrated. The filtrate was concentrated and purified through column chromatography to afford <Intermediate 8-c> (52.8 g, 80%).

Synthesis Example 8-(4): Synthesis of <Intermediate 8-d>

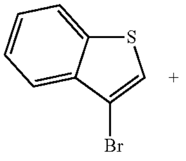

-continued

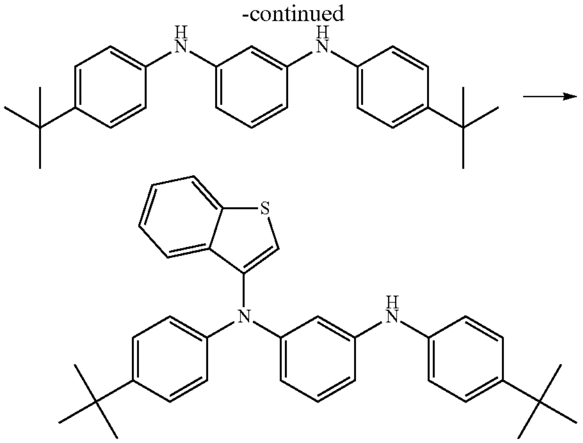

<Intermediate 8-d>

In a 250-mL reactor, <Intermediate 8-c> (36.5 g, 98 mmol), 3-bromobenzothiophene (20.9 g, 98 mmol), palladium acetate (0.5 g, 2 mmol), sodium tert-butoxide (18.9 g, 196 mmol), tri-tert-butylphosphine (0.8 g, 4 mmol), and toluene (200 mL) were stirred together for 5 hours under reflux. After completion of the reaction, the rection mixture was filtrated and the filtrate was purified by column chromatography to afford <Intermediate 8-d> (35.6 g, 72%).

Synthesis Example 8-5: Synthesis of <Intermediate 8-e>

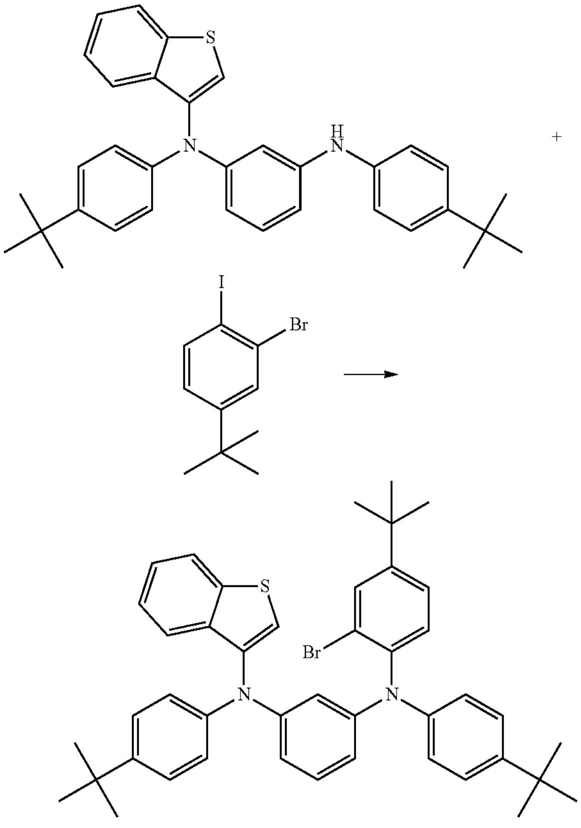

<Intermediate 8-e>

The same procedure as in Synthesis Example 8-(4) was carried out, with the exception of using <Intermediate 8-d> and 2-bromo-4-tert-butyl-1-iodobenzene instead of <Intermediate 8-c> and 3-bromobenzothiophene, respectively, to afford <Intermediate 8-e>. (yield 67%) Synthesis Example 8-(6): Synthesis of [BD 2]

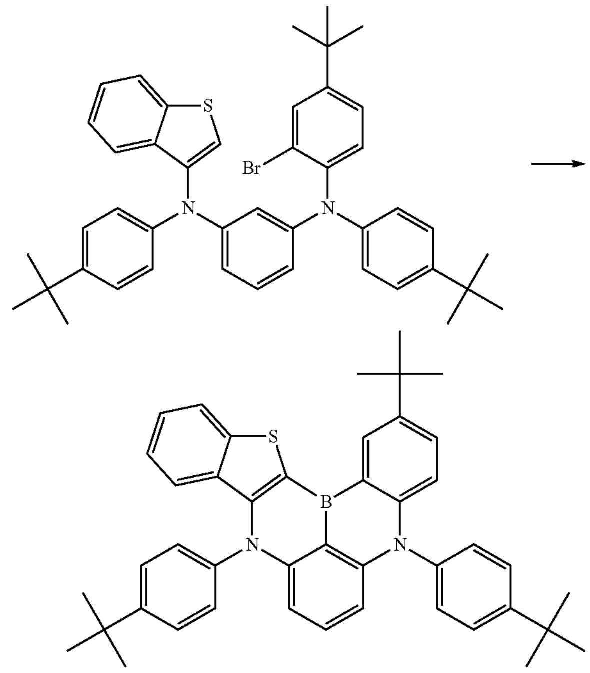

<BD 2>

In a 300-mL reaction, <Intermediate 8-e> (16.5 g, 23 mmol) and tert-butyl benzene (120 mL) were added with drops of n-butyl lithium (42.5 mL, 68 mmol) at −78° C., followed by stirring at 60° C. for 3 hours. At the same temperature, heptane was purged with nitrogen. Addition of drops of boron tribromide (11.3 g, 45 mmol) at −78° C., stirring at room temperature for one hour, addition of drops of N,N-diisopropylethyl amine (5.9 g, 45 mmol) at 0° C., and stirring at 120° C. for 2 hours were conducted in that order. After completion of the reaction, an aqueous sodium acetate solution was added at room temperature. Extraction with ethyl acetate was followed by concentrating the organic layer. Purification through column chromatography afforded <BD 2> (2.2 g, 15%).

MS (MALDI-TOF): m/z 644.34 [M+]

Examples 1 TO 4: Fabrication of Organic Light-Emitting Diodes

An ITO glass substrate was patterned to have a translucent area of 2 mm×2 mm and cleansed. The ITO glass was mounted in a vacuum chamber that was then set to have a base pressure of 1×10−7 torr. On the ITO glass substrate, films were sequentially formed of 2-TNATA (400 Å) and a-NPD (200 Å). Subsequently, a light-emitting layer (250 Å) was formed of the compound of the present disclosure as a host and [BD1] (3 wt %) as a dopant. Then, [Chemical Formula E-1] was deposited to form an electron transport layer (300 Å) on which an electron injection layer of was formed of Liq (10 Å) and then covered with an Al layer (1000 Å) to fabricate an organic light-emitting diode. The organic light-emitting diodes thus obtained were measured at 10 mA/cm2 for luminescence properties:

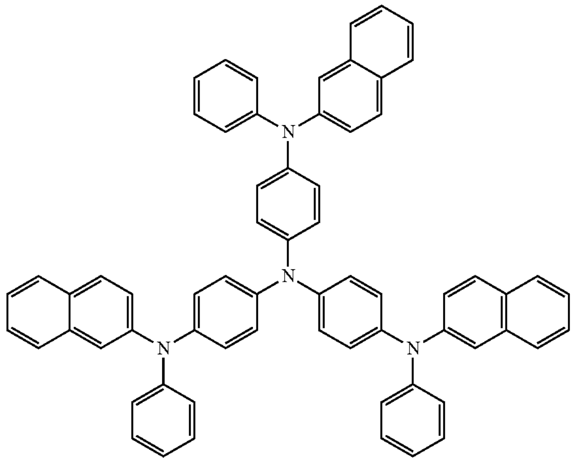

[2-TNATA]

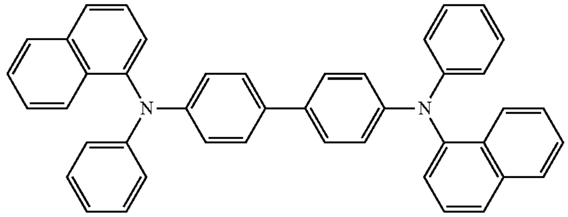

[α-NPD]

[BD1]

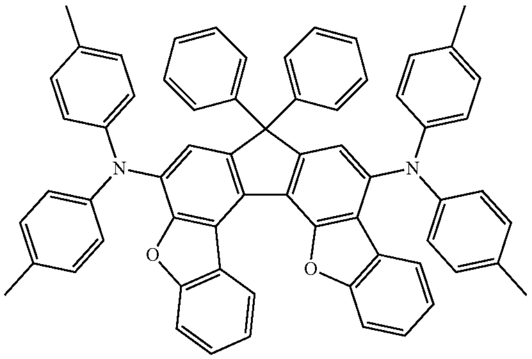

-continued

[Chemical Formula E-1]

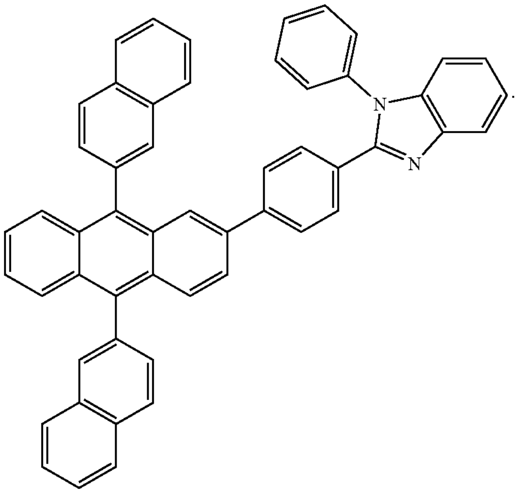

Examples 5 to 7

Organic light-emitting diodes were fabricated in the same manner as in Example, with the exception that the compounds listed in Table 2 were employed instead of the compounds used as hosts while [BD2] was used as a dopant. The structure of [BD2] is as follows:

[BD2]

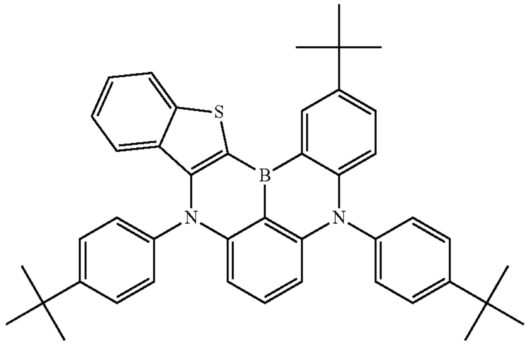

Comparative Examples 1 to 3

Organic light emitting diodes were fabricated in the same manner as in the Example 1, with the exception of using [BH1] to [BH3] as hosts instead of the compounds according to the present disclosure. The luminescence properties of the organic light-emitting diodes thus obtained was measured at 10 mA/cm2. Structures of compounds [BH1] to [BH3] are as follows:

[BH1]

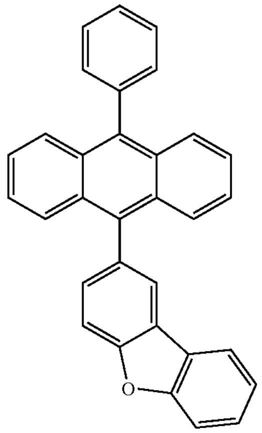

[BH2]

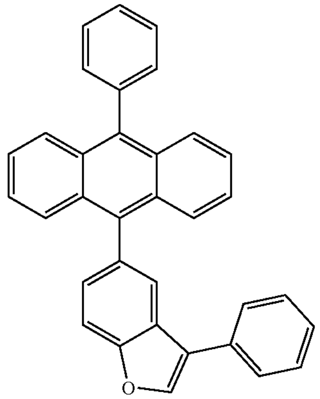

[BH3]

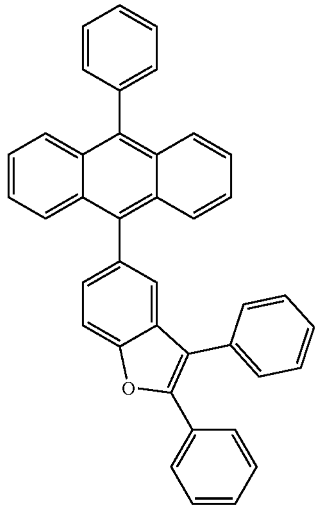

Comparative Examples 4 to 6

Organic light-emitting diodes were fabricated in the same manner as in Examples 1 to 3, with the exception of using [BD2] as a dopant, instead of [BD1]. The luminescence properties of the organic light-emitting diodes were measured at 10 mA/cm2.

TABLE 1

| | Host | Current Density ($mA/cm^2$) | Volt. (V) | External quantum efficiency (%) |
|---|---|---|---|---|
| Example 1 | Compound 12 | 10 | 3.8 | 9.1 |
| Example 2 | Compound 33 | 10 | 3.6 | 10.1 |
| Example 3 | Compound 40 | 10 | 3.7 | 9.8 |
| Example 4 | Compound 58 | 10 | 3.8 | 9.5 |
| C. Example 1 | BH1 | 10 | 3.9 | 7.5 |
| C. Example 2 | BH2 | 10 | 4.0 | 8.0 |
| C. Example 3 | BH3 | 10 | 4.0 | 7.8 |

TABLE 2

| | Host | Current Density ($mA/cm^2$) | Volt. (V) | External quantum efficiency (%) |
|---|---|---|---|---|
| Example 5 | Compound 33 | 10 | 3.6 | 12.2 |
| Example 6 | Compound 45 | 10 | 3.7 | 12.0 |
| Example 7 | Compound 111 | 10 | 3.6 | 10.6 |
| C. Example 4 | BH1 | 10 | 3.8 | 8.0 |
| C. Example 5 | BH2 | 10 | 3.9 | 8.5 |
| C. Example 6 | BH3 | 10 | 3.9 | 8.2 |

As can be understood from the data of Tables 1 and 2, the characteristics of low driving voltage and high luminous efficiency were generally improved in balance in the light-emitting diodes in which the light-emitting layers were prepared with the anthracene compounds according to the present disclosure, compared to conventional organic light-emitting diodes, so that the light-emitting diodes of the present disclosure are highly industrially applicable.

INDUSTRIAL APPLICABILITY

The organic light-emitting diode in which the light-emitting layer is prepared with the anthracene compound according to the present disclosure exhibits a balanced improvement in low driving voltage and high luminous efficiency characteristics, compared to conventional organic light-emitting diodes. With such improved characteristics, the organic light-emitting diode of the present disclosure can find advantageous applications in the related industries.

The invention claimed is:

1. An anthracene compound represented by the following Chemical Formula A:

[Chemial Formula A]

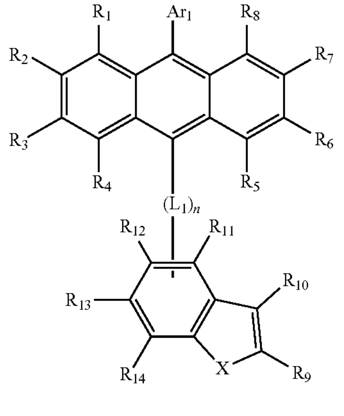

wherein, $Ar_1$ is a substituted or unsubstituted aryl of 6 to 18 carbon atoms or a substituted or unsubstituted heteroaryl of 2 to 18 carbon atoms, $R_1$ to $R_8$ and $R_{11}$ to $R_{14}$, which are same or different, are each independently selected from a hydrogen atom, a deuterium atom, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkylsilyl of 1 to 30 carbon atoms, a substituted or unsubstituted arylsilyl of 6 to 30 carbon atoms, a cyano, and a halogen, one of $R_{11}$ to $R_{14}$ being a single bond to $L_1$, $R_9$ is any one selected from a substituted or unsubstituted alkyl of 1 to 30 carbon atoms, a substituted or unsubstituted cycloalkyl of 3 to 30 carbon atoms, a substituted or unsubstituted aryl of 6 to 18 carbon atoms, and a substituted or unsubstituted heteroaryl of 2 to 18 carbon atoms, $R_{10}$ is a hydrogen atom or a deuterium atom, X is an oxygen atom (O) or a sulfur atom (S), $L_1$, which functions as a linker, is a single bond or any one selected from a substituted or unsubstituted arylene of 6 to 20 carbon atoms, and a substituted or unsubstituted heteroarylene of 2 to 20 carbon atoms, and n is an integer of 1 to 3 wherein when n is 2 or more, the corresponding $L_1$'s are same or different, the anthracene compound represented by Chemical Formula A includes at least one deuterium atom, wherein the term "substituted" in the expression "substituted or unsubstituted" used for compounds of Chemical Formula A means having at least one substituent selected from the group consisting of a deuterium atom, a cyano, a halogen, a nitro, an alkyl of 1 to 24 carbon atoms, a halogenated alkyl of 1 to 24 carbon atoms, cycloalkyl of 3 to 30 carbon atoms, an aryl of 6 to 24 carbon atoms, an arylalkyl of 7 to 24 carbon atoms, an alkylaryl of 7 to 24 carbon atoms, a heteroaryl of 2 to 24 carbon atoms, an alkylsilyl of 1 to 24 carbon atoms, and an arylsilyl of 6 to 24 carbon atoms.

2. The anthracene compound of claim 1, wherein the anthracene compound represented by Chemical Formula A is an anthracene compound represented by the following [Chemical Formula A-1] or [Chemical Formula A-2]:

[Chemical Formula A-1]

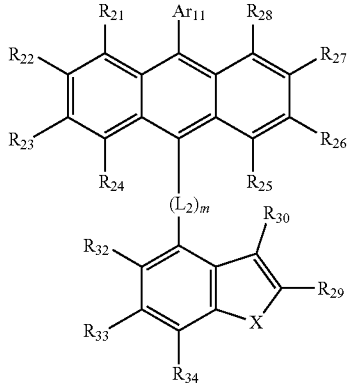

-continued

[Chemical Formula A-2]

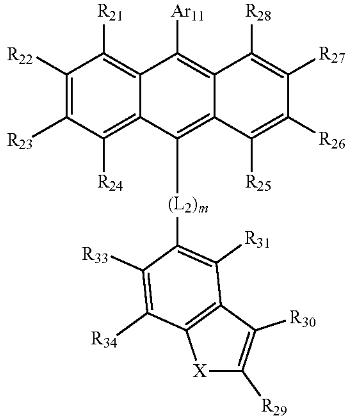

wherein, $Ar_{11}$ is a substituted or unsubstituted aryl of 6 to 18 carbon atoms or a substituted or unsubstituted heteroaryl of 2 to 18 carbon atoms, $R_{21}$ to $R_{28}$ and $R_{31}$ to $R_{34}$, which are same or different, are each independently any one selected from a hydrogen atom, a deuterium atom, a substituted or unsubstituted alkyl of 1 to 15 carbon atoms, a substituted or unsubstituted cycloalkyl of 3 to 15 carbon atoms, a substituted or unsubstituted aryl of 6 to 18 carbon atoms, a substituted or unsubstituted heteroaryl of 2 to 18 carbon atoms, a substituted or unsubstituted alkylsilyl of 1 to 15 carbon atoms, a substituted or unsubstituted arylsilyl of 6 to 18 carbon atoms, a cyano, and a halogen, $R_{29}$ is any one selected from a substituted or unsubstituted alkyl of 1 to 15 carbon atoms, a substituted or unsubstituted cycloalkyl of 3 to 15 carbon atoms, a substituted or unsubstituted aryl of 6 to 18 carbon atoms, and a substituted or unsubstituted heteroaryl of 2 to 18 carbon atoms, $R_{30}$ is a hydrogen atom or a deuterium atom, X is an oxygen atom (O) or a sulfur atom (S), $L_2$ is a single bond or any one selected from a substituted or unsubstituted arylene of 6 to 20 carbon atoms, and a substituted or unsubstituted heteroarylene of 2 to 20 carbon atoms, and m is an integer of 1 to 3 wherein when m is 2 or higher, the corresponding $L_2$'s are same or different, wherein the term "substituted" in the expression "substituted or unsubstituted" is as defined above.

3. The anthracene compound of claim 1, wherein $R_1$ to $R_8$ in Chemical Formula A are same or different and each independently a hydrogen atom or a deuterium atom.

4. The anthracene compound of claim 1, wherein $Ar_1$ in Chemical Formula A is a substituted or unsubstituted aryl of 6 to 18 carbon atoms.

5. The anthracene compound of claim 4, wherein $Ar_1$ in Chemical Formula A is a substituted aryl of 6 to 18 carbon atoms having as a substituent thereon any one selected from a deuterium atom, a phenyl, and a naphthyl or an unsubstituted aryl of 6 to 18 carbon atoms.

6. The anthracene compound of claim 4, wherein $Ar_1$ in Chemical Formula A is any one selected from a substituted or unsubstituted phenyl, a substituted or unsubstituted naphthyl, a substituted or unsubstituted biphenyl, a substituted or unsubstituted anthracenyl, a substituted or unsubstituted phenanthrenyl, and a substituted or unsubstituted fluorenyl.

7. The anthracene compound of claim 1, wherein Li in Chemical Formula A is a single bond or a substituted or unsubstituted arylene of 6 to 18 carbon atoms.

8. The anthracene compound of claim 1, wherein Li in Chemical Formula A is any one selected from compounds represented by the following Structural Formulas 11 to 17:

[Structural Formula 11]

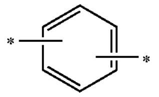

[Structural Formula 12]

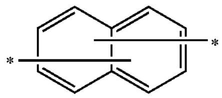

[Structural Formula 13]

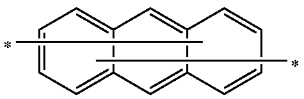

[Structural Formula 14]

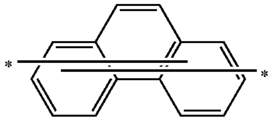

[Structural Formula 15]

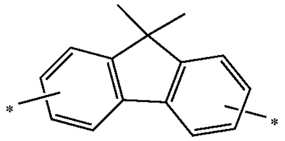

[Structural Formula 16]

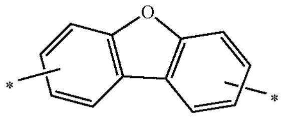

[Structural Formula 17]

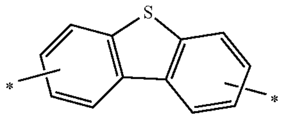

wherein each of the unsubstituted carbon atoms of the aromatic ring moiety can be bound with a hydrogen atom or a deuterium atom.

9. The anthracene compound of claim 1, wherein $R_9$ in Chemical Formula A is a substituted or unsubstituted aryl of 6 to 18 carbon atoms or a substituted or unsubstituted heteroaryl of 2 to 18 carbon atoms.

10. The anthracene compound of claim 9, wherein $R_9$ in Chemical Formula A is any one selected from a substituted or unsubstituted phenyl, a substituted or unsubstituted naphthyl, a substituted or unsubstituted biphenyl, a substituted or unsubstituted anthracenyl, a substituted or unsubstituted phenanthrenyl, a substituted or unsubstituted fluorenyl, a substituted or unsubstituted benzofuran, a substituted or unsubstituted benzothiophene, a substituted or unsubstituted dibenzofuran, and a substituted or unsubstituted dibenzothiophene.

11. The anthracene compound of claim 1, wherein the anthracene compound represented by Chemical Formula A is any one selected from the following [Compound 16] to [Compound 34], [Compound 40], [Compound 45] to [Compound 52], [Compound 60], [Compound 68], [Compound 69], [Compound 76] to [Compound 81], [Compound 85] to [Compound 87], [Compound 90] to [Compound 93], [Compound 95] to [Compound 97], [Compound 99] to [Compound 102], and [Compound 104] to [Compound 111]:

[Compound 16]

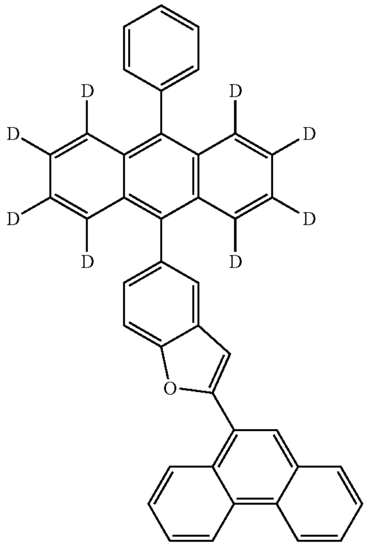

[Compound 17]

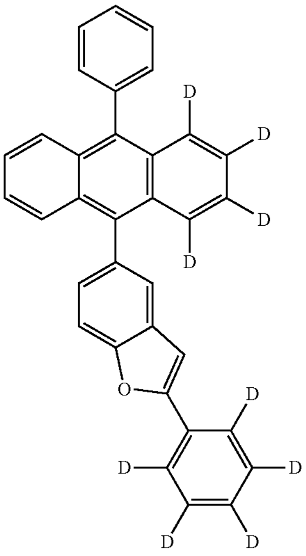

-continued
[Compound 18]
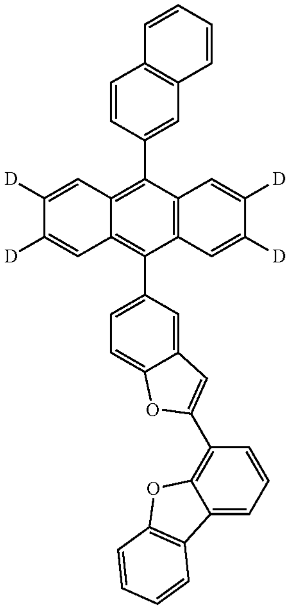
[Compound 19]
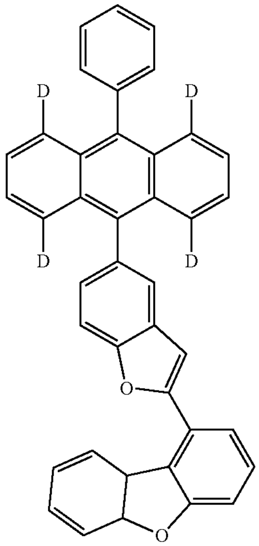
-continued
[Compound 20]
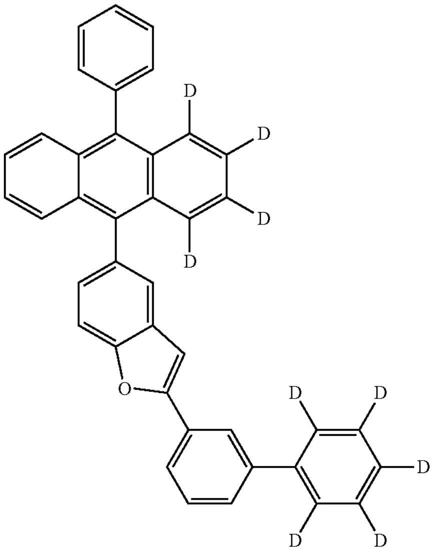
[Compound 21]
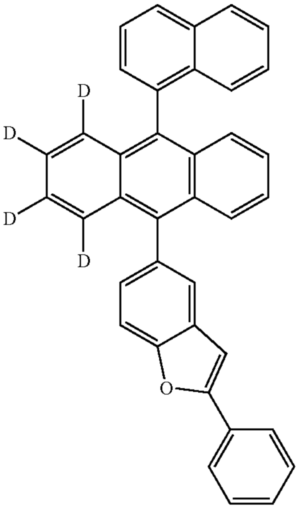
[Compound 22]
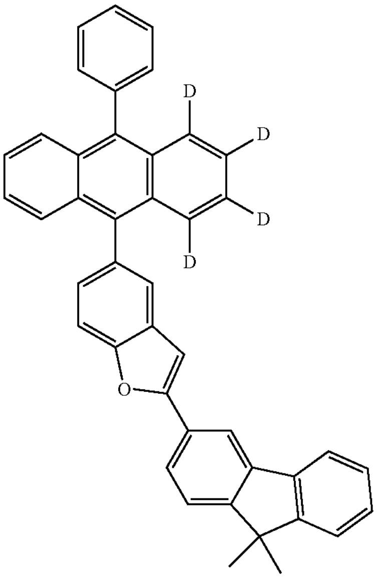

-continued
[Compound 23]
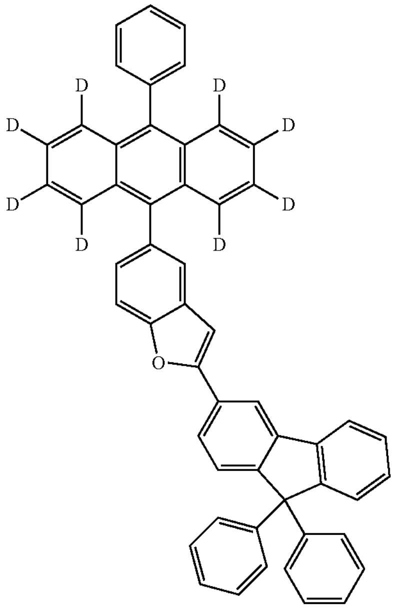
[Compound 24]
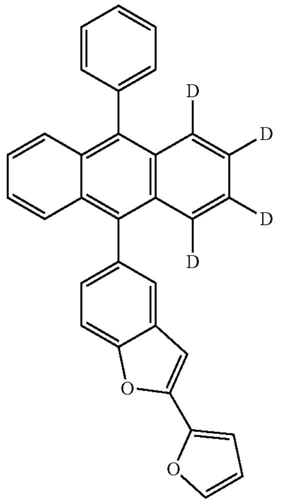
-continued
[Compound 25]
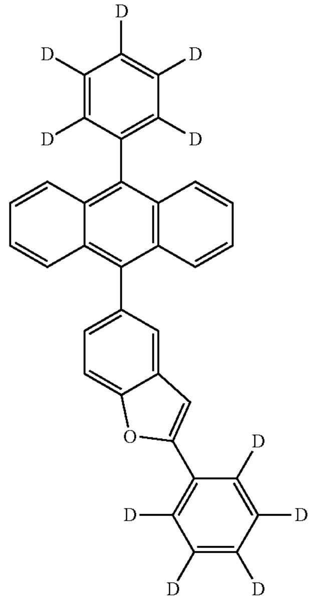
[Compound 26]
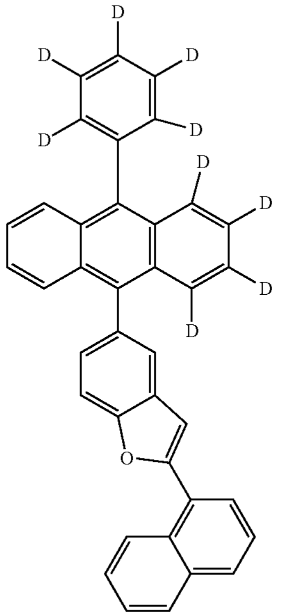

-continued
[Compound 27]
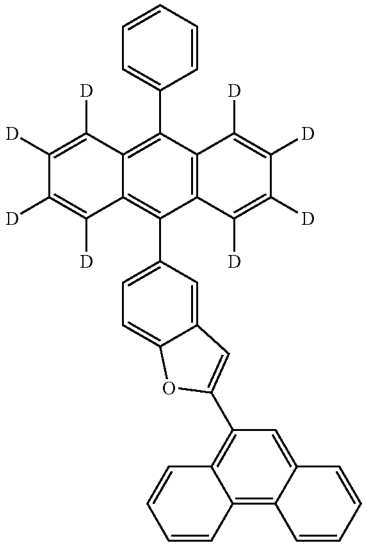
[Compound 28]
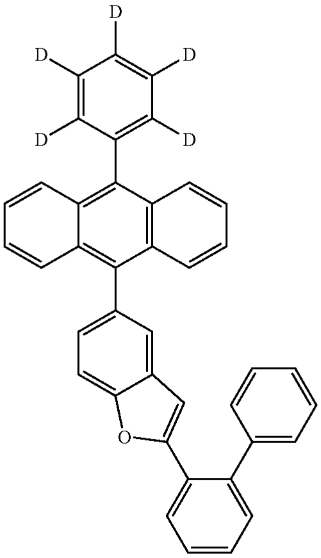
-continued
[Compound 29]
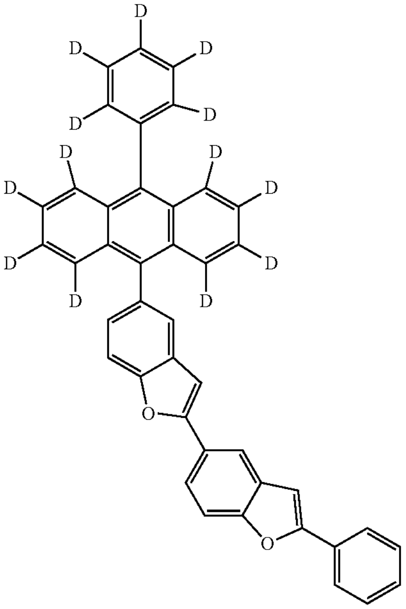
[Compound 30]
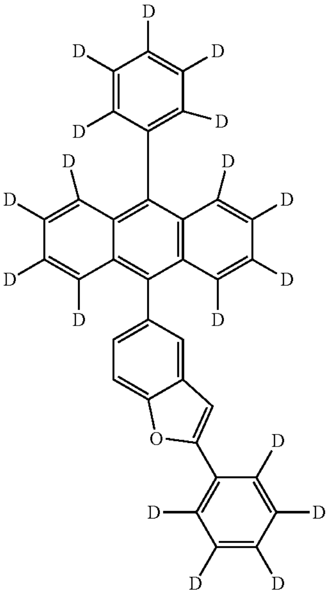

-continued
[Compound 31]
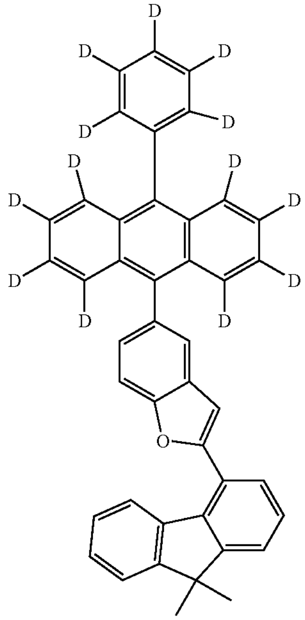
[Compound 32]
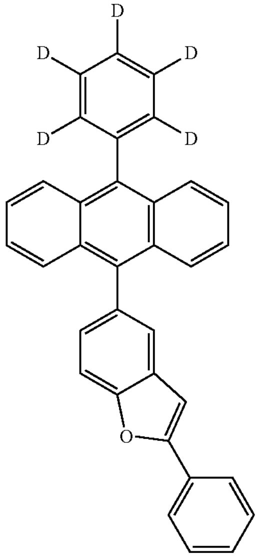
-continued
[Compound 33]
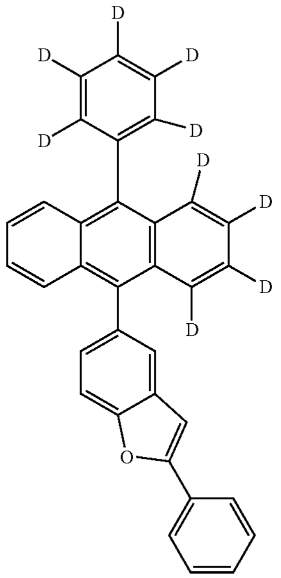
[Compound 34]
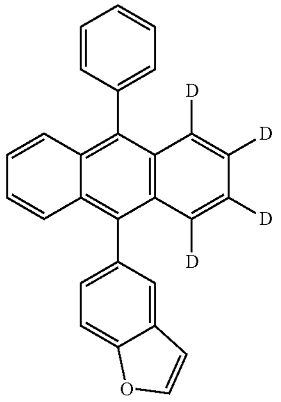
[Compound 40]
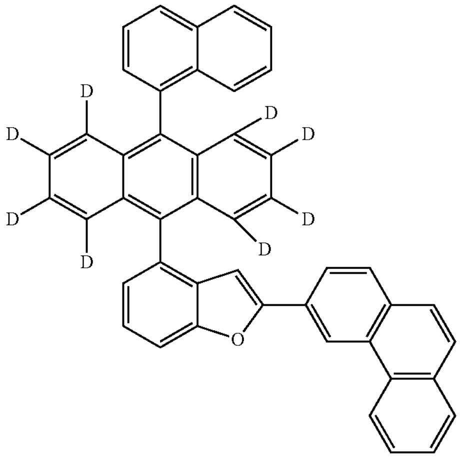

-continued
[Compound 45]
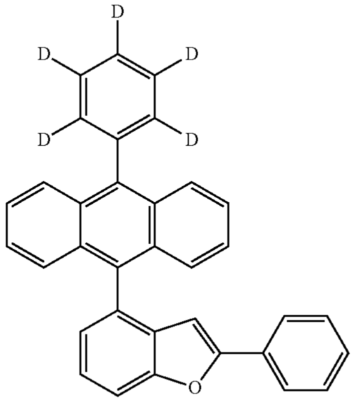
[Compound 46]
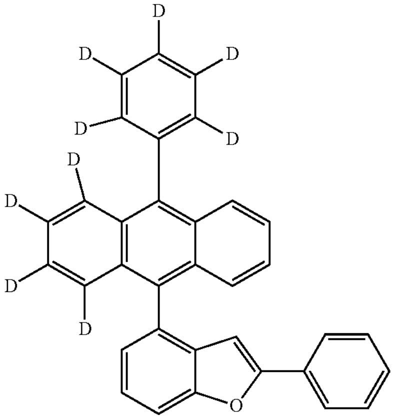
[Compound 47]
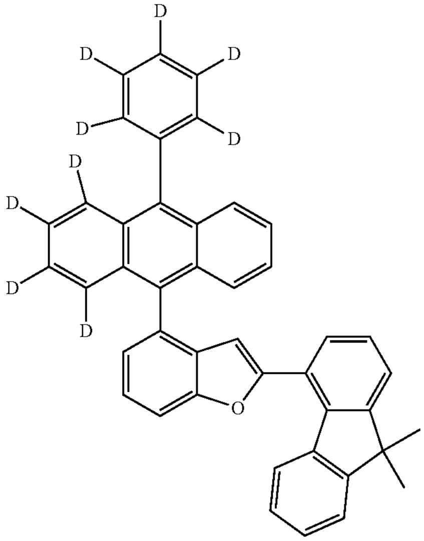
-continued
[Compound 48]
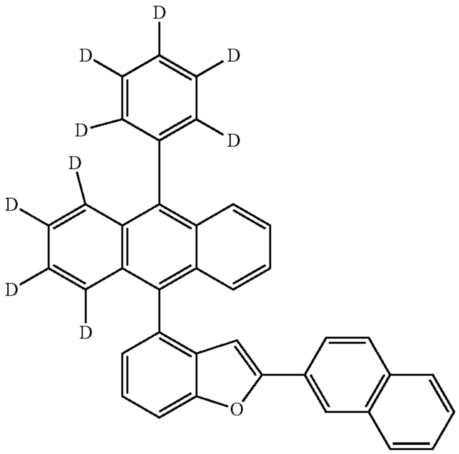
[Compound 49]
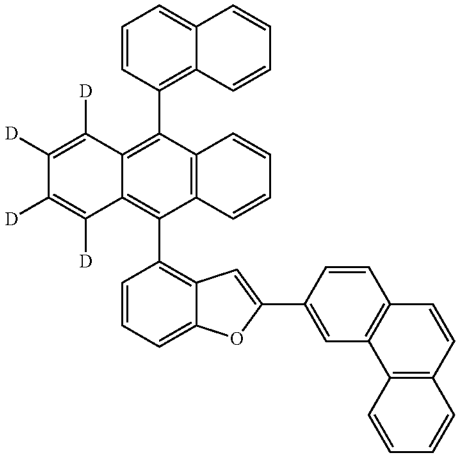
[Compound 50]
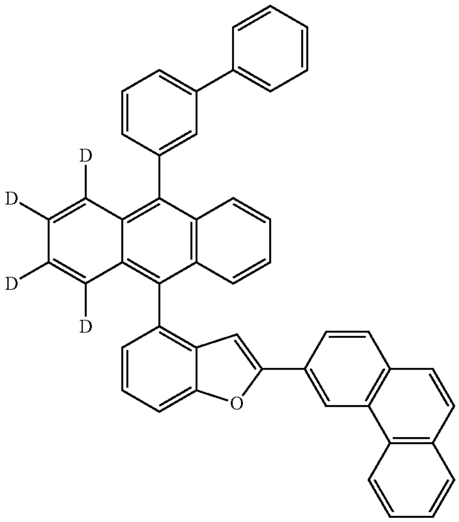

-continued
[Compound 51]
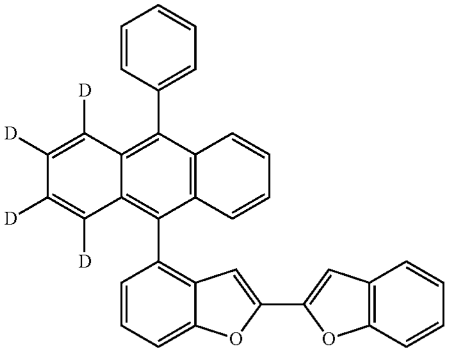
[Compound 52]
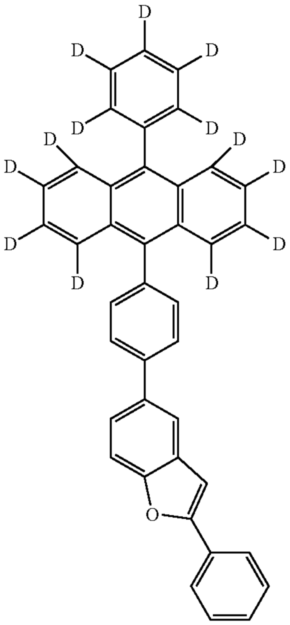
[Compound 60]
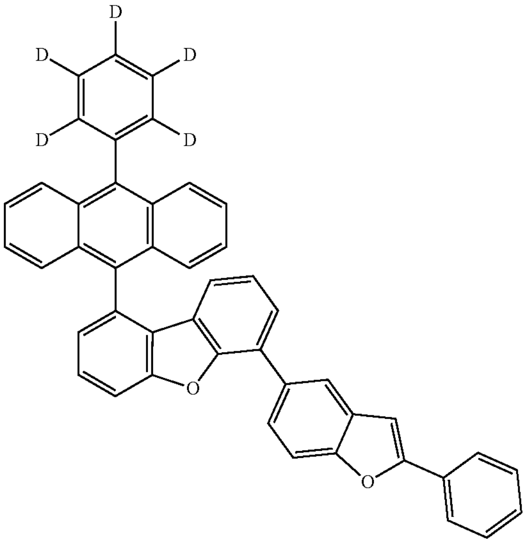
-continued
[Compound 68]
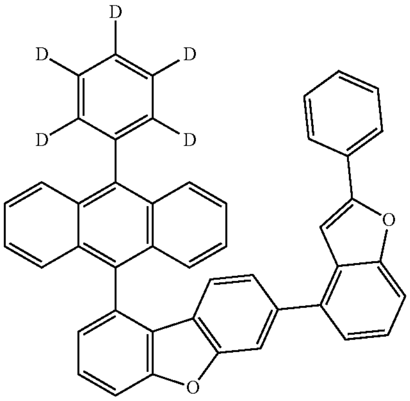
[Compound 69]
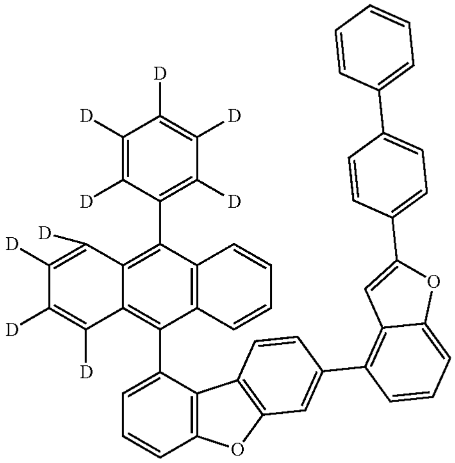
[Compound 76]
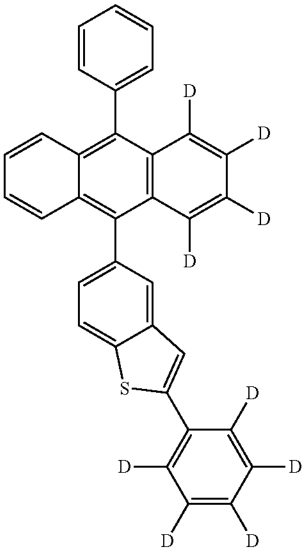

-continued
[Compound 77]
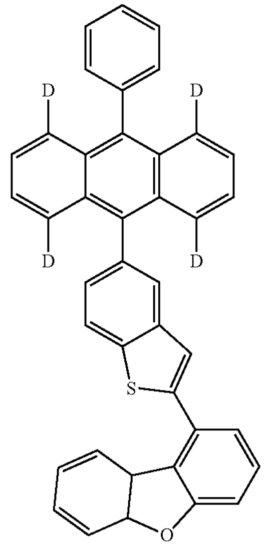
[Compound 78]
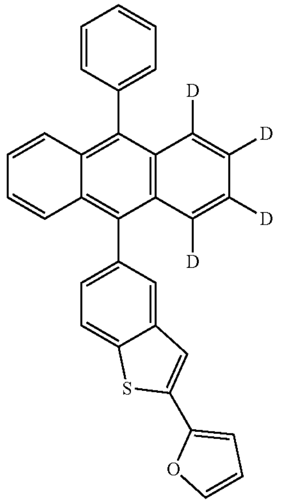
[Compound 79]
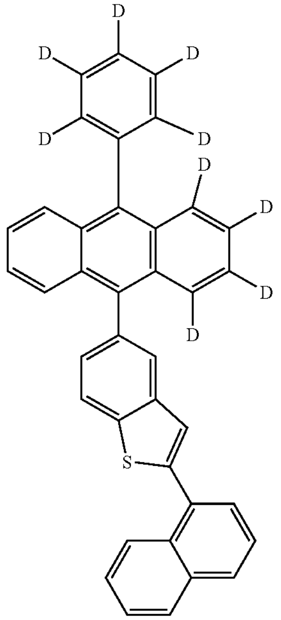
-continued
[Compound 80]
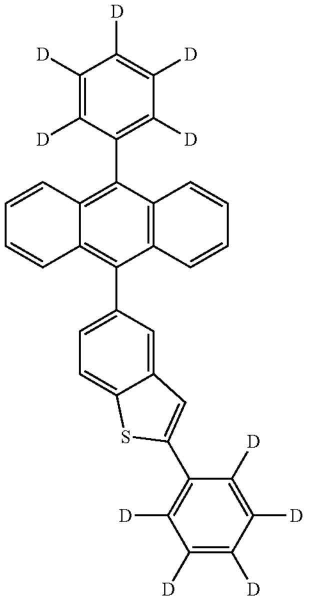
[Compound 81]
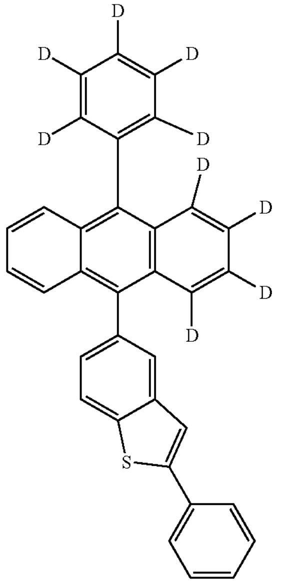
[Compound 85]
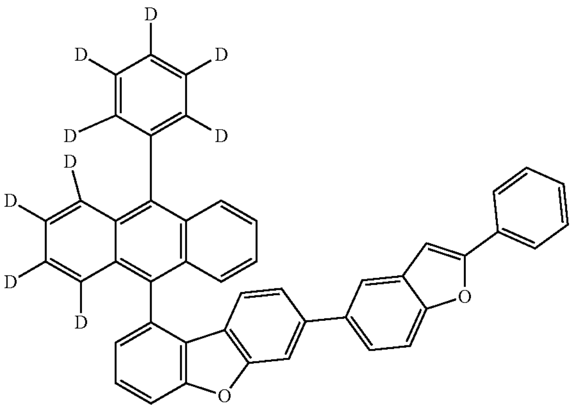

-continued
[Compound 86]
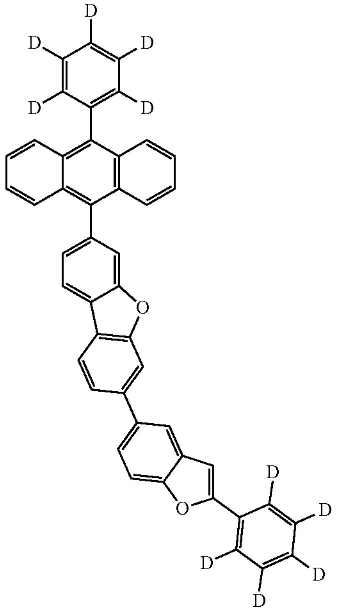
[Compound 87]
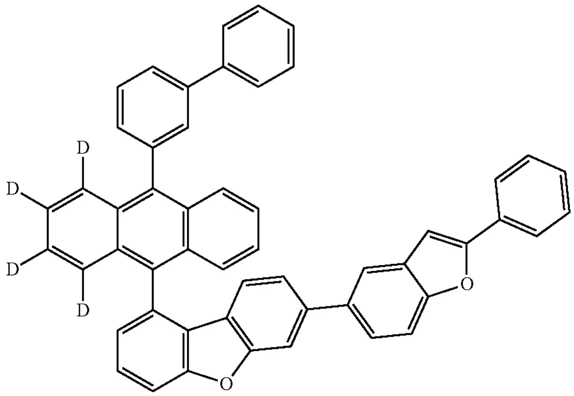
[Compound 90]
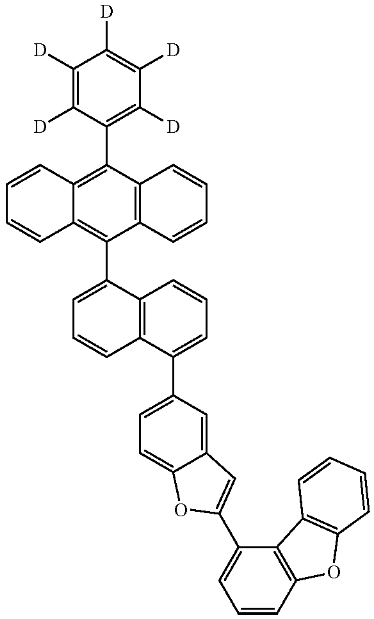
-continued
[Compound 91]
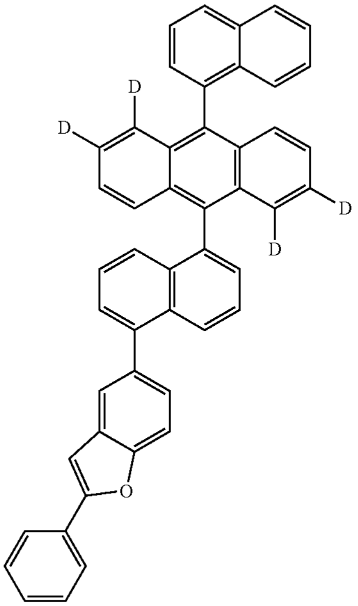
[Compound 92]
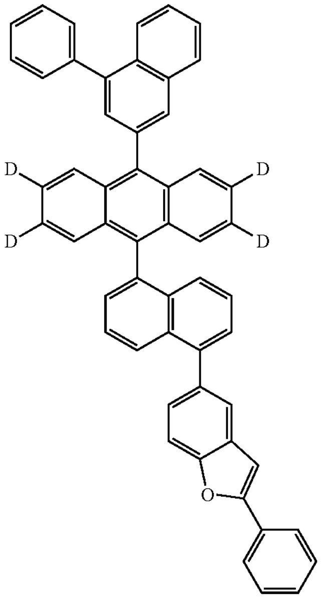

-continued
[Compound 93]
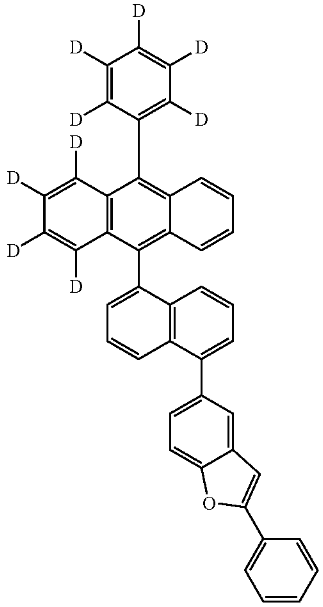
[Compound 95]
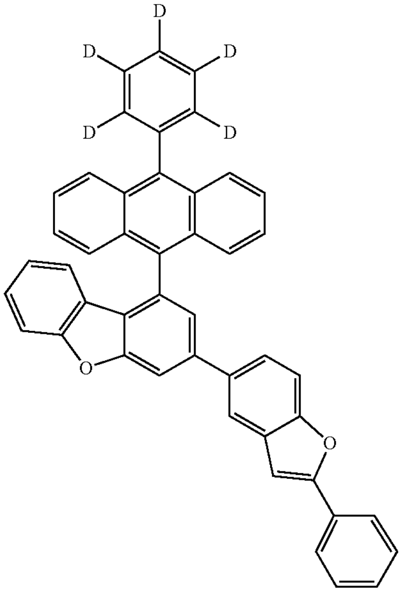
-continued
[Compound 96]
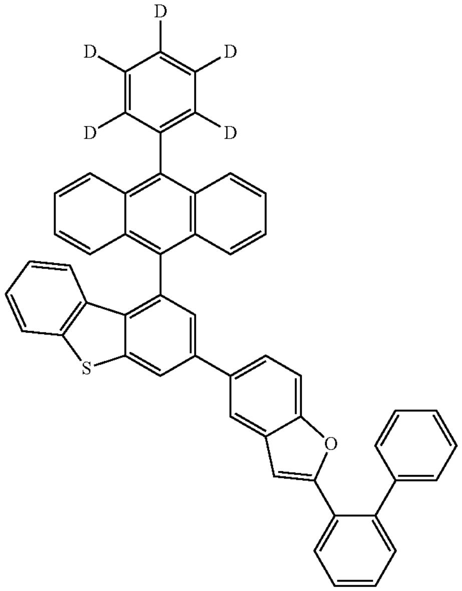
[Compound 97]
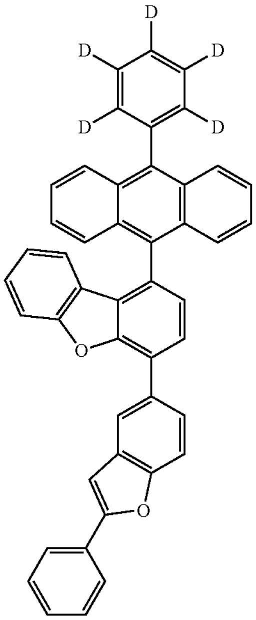

-continued
[Compound 99]
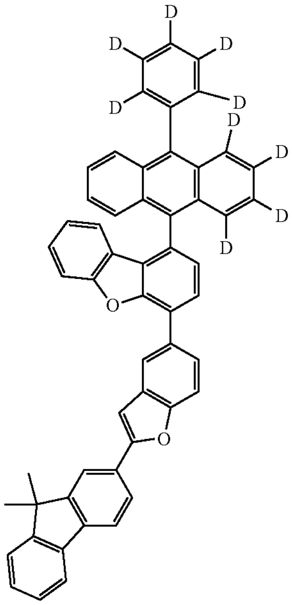
[Compound 100]
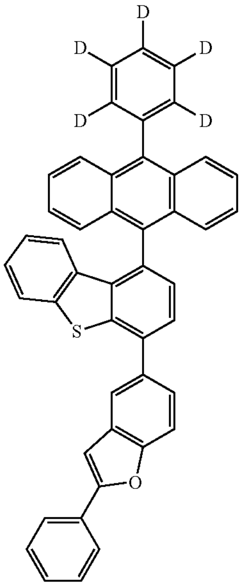
-continued
[Compound 101]
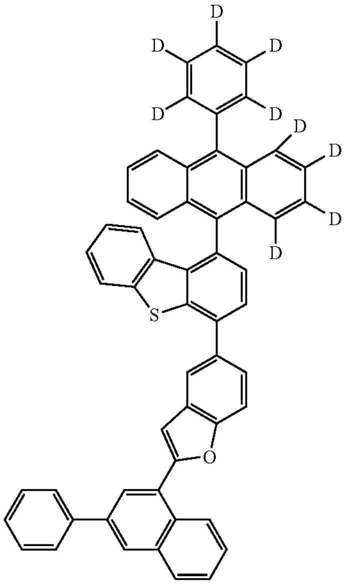
[Compound 102]
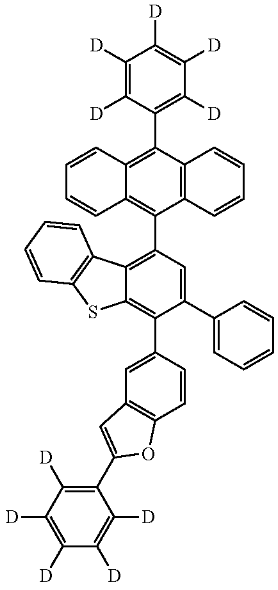

[Compound 104]
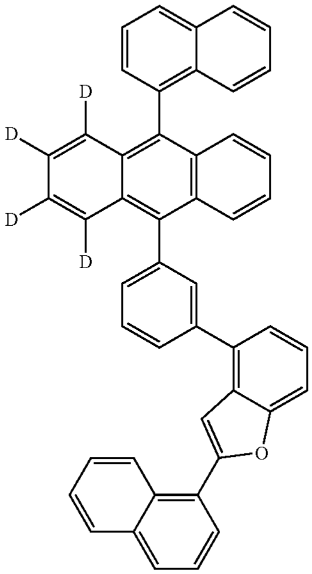
[Compound 105]
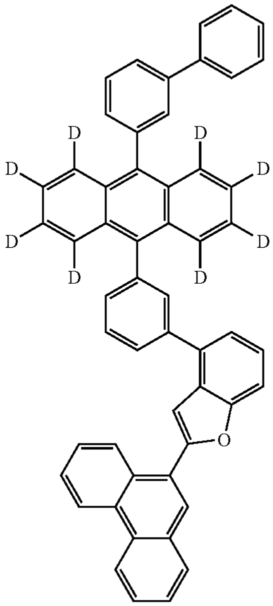
[Compound 106]
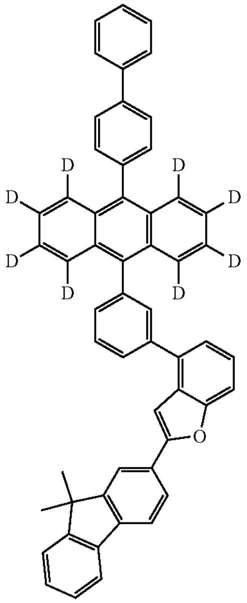
[Compound 107]
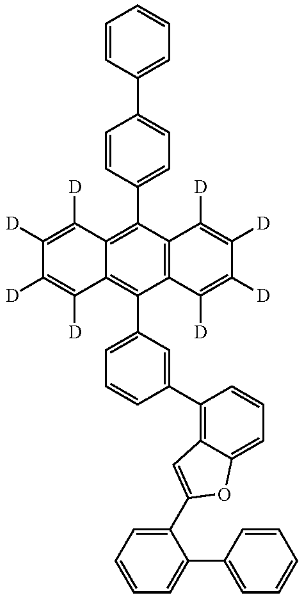

-continued

[Compound 108]

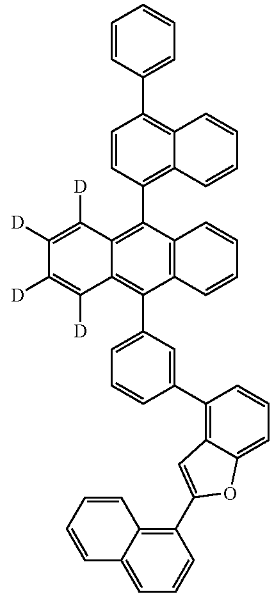

[Compound 109]

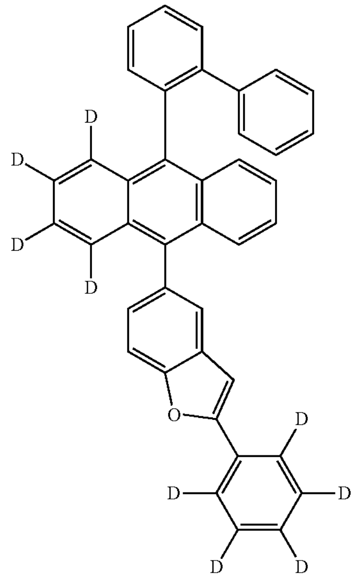

[Compound 110]

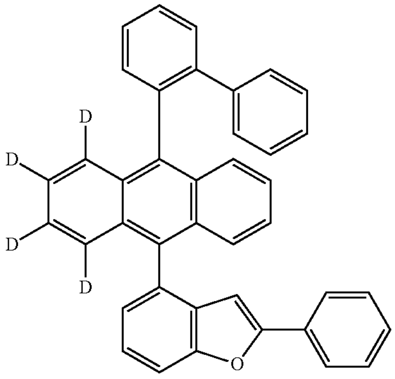

-continued

[Compound 111]

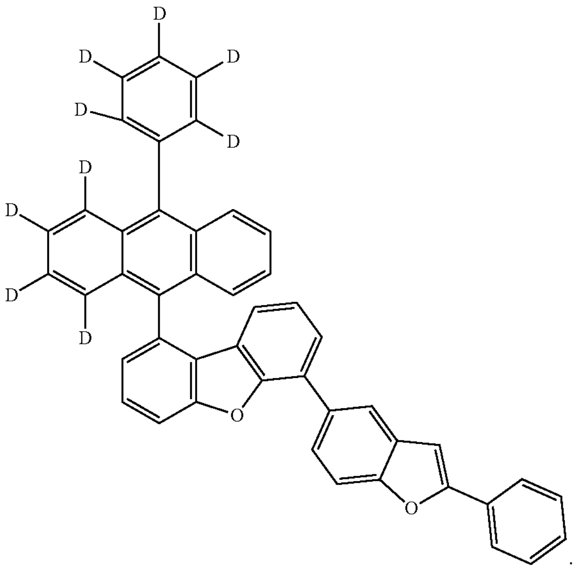

12. An organic light-emitting diode, comprising:

a first electrode;

a second electrode facing the first electrode; and an organic layer interposed between the first electrode and the second electrode wherein the organic layer comprises the anthracene compound of claim 1.

13. The organic light-emitting diode of claim 12, wherein the organic light-emitting diode comprises at least one of a hole injection layer, a hole transport layer, a functional layer capable of both hole injection and hole transport, an electron blocking layer, a light emitting layer, an electron transport layer, an electron injection layer, and a capping layer.

14. The organic light-emitting diode of claim 12, wherein the organic layer interposed between the first electrode and the second electrode comprises a light-emitting layer composed of a host and a dopant, and the anthracene compound represented by Chemical Formula A is used as the host.

15. A device comprising the organic light-emitting diode of claim 12, wherein the device is selected from among a flat display device; a flexible display device;

a monochrome or grayscale flat illumination; and a monochrome or grayscale flexible illumination device.

* * * * *